(12) United States Patent
Harris et al.

(10) Patent No.: US 10,314,587 B2
(45) Date of Patent: Jun. 11, 2019

(54) SURGICAL STAPLE CARTRIDGE WITH IMPROVED STAPLE DRIVER CONFIGURATIONS

(71) Applicant: Ethicon Endo-Surgery, LLC, Guaynabo, PR (US)

(72) Inventors: Jason L. Harris, Lebanon, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 642 days.

(21) Appl. No.: 14/843,168

(22) Filed: Sep. 2, 2015

(65) Prior Publication Data

US 2017/0056011 A1 Mar. 2, 2017

(51) Int. Cl.
*A61B 17/068* (2006.01)
*A61B 17/10* (2006.01)
*A61B 17/072* (2006.01)

(52) U.S. Cl.
CPC .......... *A61B 17/105* (2013.01); *A61B 17/068* (2013.01); *A61B 17/07207* (2013.01); *A61B 2017/07228* (2013.01); *A61B 2017/07271* (2013.01); *A61B 2017/07278* (2013.01)

(58) Field of Classification Search
CPC .......... A61B 2017/07228; A61B 2017/07271; A61B 2017/07278
USPC ..................................................... 227/175.1
See application file for complete search history.

(56) References Cited

U.S. PATENT DOCUMENTS

| | | | |
|---|---|---|---|
| 66,052 | A | 6/1897 | Smith |
| 662,587 | A | 11/1900 | Blake |
| 670,748 | A | 3/1901 | Weddeler |
| 951,393 | A | 3/1910 | Hahn |
| 1,306,107 | A | 6/1919 | Elliott |
| 1,314,601 | A | 9/1919 | McCaskey |

(Continued)

FOREIGN PATENT DOCUMENTS

| | | |
|---|---|---|
| AU | 2008207624 A1 | 3/2009 |
| AU | 2010214687 A1 | 9/2010 |

(Continued)

OTHER PUBLICATIONS

"Biomedical Coatings," Fort Wayne Metals, Research Products Corporation, obtained online at www.fwmetals.com on Jun. 21, 2010 (1 page).

(Continued)

*Primary Examiner* — Chelsea E Stinson

(57) ABSTRACT

A surgical staple driver array configured for operable use with a surgical staple cartridge. A distal staple driver is slidably supportable in the surgical staple cartridge and is configured to operably support a distal surgical staple thereon that is oriented in a distal direction. At least one intermediate staple driver is configured to be slidably supported in the surgical staple cartridge adjacent the distal staple driver. Each intermediate staple driver is configured to operably support a first surgical staple that is oriented in a first direction, a second surgical staple that is oriented in a second direction and a third surgical staple that is oriented in a third direction. A proximal staple driver is slidably supported adjacent a proximal most one of the intermediate staple drivers. The proximal staple driver is configured to operably support a proximal surgical staple thereon.

20 Claims, 47 Drawing Sheets

(56) References Cited

U.S. PATENT DOCUMENTS

| | | |
|---|---|---|
| 1,677,337 A | 7/1928 | Grove |
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,441,096 A | 5/1948 | Happe |
| 2,475,322 A | 7/1949 | Horton et al. |
| 2,526,902 A | 10/1950 | Rublee |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,499,591 A | 3/1970 | Green |
| 3,551,987 A | 1/1971 | Wilkinson |
| 3,583,393 A | 6/1971 | Takahashi |
| 3,662,939 A | 5/1972 | Bryan |
| 3,717,294 A | 2/1973 | Green |
| 3,799,151 A | 3/1974 | Fukaumi et al. |
| RE28,932 E | 8/1976 | Noiles et al. |
| 4,060,089 A | 11/1977 | Noiles |
| 4,106,446 A | 8/1978 | Yamada et al. |
| 4,108,211 A | 8/1978 | Tanaka |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |
| 4,305,539 A | 12/1981 | Korolkov et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,454,887 A | 6/1984 | Kruger |
| 4,467,805 A | 8/1984 | Fukuda |
| 4,473,077 A | 9/1984 | Noiles et al. |
| 4,475,679 A | 10/1984 | Fleury, Jr. |
| 4,485,816 A | 12/1984 | Krumme |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| D286,180 S | 10/1986 | Korthoff |
| D286,441 S | 10/1986 | Korthoff et al. |
| D286,442 S | 10/1986 | Korthoff et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |

(56) References Cited

U.S. PATENT DOCUMENTS

| | | |
|---|---|---|
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,787,387 A | 11/1988 | Burbank, III et al. |
| 4,790,225 A | 12/1988 | Moody et al. |
| 4,802,478 A | 2/1989 | Powell |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,873,977 A | 10/1989 | Avant et al. |
| 4,874,122 A | 10/1989 | Froelich et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,951,860 A | 8/1990 | Peters et al. |
| 4,955,898 A | 9/1990 | Matsutani et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A | 7/1991 | Pruitt |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |
| 5,053,047 A | 10/1991 | Yoon |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,009 A | 2/1992 | Green |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| D327,323 S | 6/1992 | Hunt |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,200,280 A | 4/1993 | Karasa |
| 5,201,746 A | 4/1993 | Shichman |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,440 A | 8/1993 | Hlavacek |
| 5,239,981 A | 8/1993 | Anapliotis |

(56) References Cited

U.S. PATENT DOCUMENTS

| | | |
|---|---|---|
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| D348,930 S | 7/1994 | Olson |
| 5,329,923 A | 7/1994 | Lundquist |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,403,043 A | 4/1995 | Smet |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,409,498 A | 4/1995 | Braddock et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |

(56) References Cited

U.S. PATENT DOCUMENTS

| | | |
|---|---|---|
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |

(56) References Cited

U.S. PATENT DOCUMENTS

| | | |
|---|---|---|
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| D381,077 S | 7/1997 | Hunt |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |

(56) References Cited

U.S. PATENT DOCUMENTS

| | | |
|---|---|---|
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| D416,089 S | 11/1999 | Barton et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,010,054 A | 1/2000 | Johnson et al. |
| 6,010,513 A | 1/2000 | Tormala et al. |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,097 A | 5/2000 | Oi et al. |
| 6,063,098 A | 5/2000 | Houser et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,148 A | 9/2000 | Ravo et al. |
| 6,117,158 A | 9/2000 | Measamer et al. |

(56) References Cited

U.S. PATENT DOCUMENTS

| | | |
|---|---|---|
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,194 B1 | 1/2001 | Morton |
| 6,179,195 B1 | 1/2001 | Adams et al. |
| 6,179,776 B1 | 1/2001 | Adams et al. |
| 6,179,849 B1 | 1/2001 | Yencho et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,117 B1 | 6/2001 | Blatter |
| 6,249,076 B1 | 6/2001 | Madden et al. |
| 6,250,532 B1 | 6/2001 | Green et al. |
| 6,258,107 B1 | 7/2001 | Balazs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,383,958 B1 | 5/2002 | Swanson et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,447,518 B1 | 9/2002 | Krause et al. |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,478,210 B2 | 11/2002 | Adams et al. |
| 6,482,200 B2 | 11/2002 | Shippert |
| 6,485,490 B2 | 11/2002 | Wampler et al. |
| 6,485,503 B2 | 11/2002 | Jacobs et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |

(56) References Cited

U.S. PATENT DOCUMENTS

| | | |
|---|---|---|
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,588,643 B2 | 7/2003 | Bolduc et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |

(56) References Cited

U.S. PATENT DOCUMENTS

| | | |
|---|---|---|
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,858,005 B2 | 2/2005 | Ohline et al. |
| RE38,708 E | 3/2005 | Bolanos et al. |
| D502,994 S | 3/2005 | Blake, III |
| 6,861,142 B1 | 3/2005 | Wilkie et al. |
| 6,863,668 B2 | 3/2005 | Gillespie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,899,538 B2 | 5/2005 | Matoba |
| 6,905,057 B2 | 6/2005 | Swayze et al. |
| 6,905,497 B2 | 6/2005 | Truckai et al. |
| 6,908,472 B2 | 6/2005 | Wiener et al. |
| 6,911,033 B2 | 6/2005 | de Guillebon et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| D509,297 S | 9/2005 | Wells |
| D509,589 S | 9/2005 | Wells |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,731 B2 | 1/2006 | Haytayan |
| 6,990,796 B2 | 1/2006 | Schnipke et al. |
| 6,994,708 B2 | 2/2006 | Manzo |
| 6,995,729 B2 | 2/2006 | Govari et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |

(56) References Cited

U.S. PATENT DOCUMENTS

| | | |
|---|---|---|
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,202,653 B2 | 4/2007 | Pai |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,213,736 B2 | 5/2007 | Wales et al. |
| 7,214,224 B2 | 5/2007 | Goble |
| 7,214,232 B2 | 5/2007 | Bowman et al. |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,267,682 B1 | 9/2007 | Bender et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,293,685 B2 | 11/2007 | Ehrenfels et al. |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,730 B2 | 6/2008 | Uchikubo |
| 7,388,217 B2 | 6/2008 | Buschbeck et al. |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |

(56) References Cited

U.S. PATENT DOCUMENTS

| | | |
|---|---|---|
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| D605,762 S | 12/2009 | Nalagatla et al. |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,457 B2 | 1/2010 | Stefanchik et al. |
| 7,648,519 B2 | 1/2010 | Lee et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,686,201 B2 | 3/2010 | Csiky |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,106 B2 | 4/2010 | Schenberger et al. |

(56) References Cited

U.S. PATENT DOCUMENTS

| | | |
|---|---|---|
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,037 B2 | 8/2010 | Odom |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,838,789 B2 | 11/2010 | Stoffers et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,623 B2 | 12/2010 | Griffin et al. |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,563 B2 | 2/2011 | Cummins |
| 7,891,531 B1 | 2/2011 | Ward |
| 7,891,532 B2 | 2/2011 | Mastri et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,895 B2 | 3/2011 | Boudreaux et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese et al. |
| 7,905,902 B2 | 3/2011 | Huitema et al. |
| 7,909,191 B2 | 3/2011 | Baker et al. |

(56) References Cited

U.S. PATENT DOCUMENTS

| | | |
|---|---|---|
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,918,867 B2 | 4/2011 | Dana et al. |
| 7,918,873 B2 | 4/2011 | Cummins |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,931,660 B2 | 4/2011 | Aranyi et al. |
| 7,931,695 B2 | 4/2011 | Ringeisen |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,301 B2 | 5/2011 | Sater |
| 7,942,303 B2 | 5/2011 | Shah |
| 7,942,890 B2 | 5/2011 | D'Agostino et al. |
| 7,944,175 B2 | 5/2011 | Mori et al. |
| 7,946,453 B2 | 5/2011 | Voegele et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,954,688 B2 | 6/2011 | Argentine et al. |
| 7,955,257 B2 | 6/2011 | Frasier et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Francischelli et al. |
| 7,963,964 B2 | 6/2011 | Santilli et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,980,443 B2 | 7/2011 | Scheib et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,993,360 B2 | 8/2011 | Hacker et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,511 B2 | 8/2011 | Brock et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,034,363 B2 | 10/2011 | Li et al. |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,047,236 B2 | 11/2011 | Perry |
| 8,048,503 B2 | 11/2011 | Farnsworth et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,061,576 B2 | 11/2011 | Cappola |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,033 B2 | 12/2011 | Milliman et al. |
| 8,070,035 B2 | 12/2011 | Holsten et al. |
| 8,070,743 B2 | 12/2011 | Kagan et al. |
| 8,075,571 B2 | 12/2011 | Vitali et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,085,013 B2 | 12/2011 | Wei et al. |
| 8,087,563 B2 | 1/2012 | Milliman et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,100,872 B2 | 1/2012 | Patel |
| 8,102,278 B2 | 1/2012 | Deck et al. |
| 8,105,350 B2 | 1/2012 | Lee et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,766 B2 | 2/2012 | Bauman et al. |
| 8,123,767 B2 | 2/2012 | Bauman et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,136,713 B2 | 3/2012 | Hathaway et al. |
| 8,140,417 B2 | 3/2012 | Shibata |
| 8,141,762 B2 | 3/2012 | Bedi et al. |
| 8,141,763 B2 | 3/2012 | Milliman |
| 8,146,790 B2 | 4/2012 | Milliman |
| 8,147,485 B2 | 4/2012 | Wham et al. |
| 8,152,041 B2 | 4/2012 | Kostrzewski |
| 8,157,145 B2 | 4/2012 | Shelton, IV et al. |
| 8,157,148 B2 | 4/2012 | Scirica |

(56) References Cited

U.S. PATENT DOCUMENTS

| | | |
|---|---|---|
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,180,458 B2 | 5/2012 | Kane et al. |
| 8,181,840 B2 | 5/2012 | Milliman |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,206,291 B2 | 6/2012 | Fischvogt et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,225,980 B1 | 7/2012 | Rivera |
| 8,226,715 B2 | 7/2012 | Hwang et al. |
| 8,227,946 B2 | 7/2012 | Kim |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,257,634 B2 | 9/2012 | Scirica |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,281,974 B2 | 10/2012 | Hessler et al. |
| 8,285,367 B2 | 10/2012 | Hyde et al. |
| 8,286,845 B2 | 10/2012 | Perry et al. |
| 8,286,846 B2 | 10/2012 | Smith et al. |
| 8,287,561 B2 | 10/2012 | Nunez et al. |
| 8,292,147 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,314 B2 | 12/2012 | Blier |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,348,123 B2 | 1/2013 | Scirica et al. |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,787 B2 | 2/2013 | Brown et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |

(56) References Cited

U.S. PATENT DOCUMENTS

| | | |
|---|---|---|
| 8,387,848 B2 | 3/2013 | Johnson et al. |
| 8,388,633 B2 | 3/2013 | Rousseau et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,973 B1 | 3/2013 | Hausen |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,945 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,222 B2 | 4/2013 | Whitfield et al. |
| 8,409,223 B2 | 4/2013 | Sorrentino et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,908 B1 | 4/2013 | Beardsley |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,892 B2 | 4/2013 | Bindra et al. |
| 8,430,898 B2 | 4/2013 | Wiener et al. |
| 8,439,246 B1 | 5/2013 | Knodel |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,502 B2 | 6/2013 | Zergiebel |
| 8,469,973 B2 | 6/2013 | Meade et al. |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,475,491 B2 | 7/2013 | Milo |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,491,603 B2 | 7/2013 | Yeung et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,556,151 B2 | 10/2013 | Viola |
| 8,556,918 B2 | 10/2013 | Bauman et al. |
| 8,556,935 B1 | 10/2013 | Knodel et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,263 B2 | 11/2013 | Mueller |
| 8,579,176 B2 | 11/2013 | Smith et al. |
| 8,579,178 B2 | 11/2013 | Holsten et al. |
| 8,579,937 B2 | 11/2013 | Gresham |
| 8,579,938 B2 | 11/2013 | Heinrich et al. |
| 8,584,919 B2 | 11/2013 | Hueil et al. |
| 8,585,721 B2 | 11/2013 | Kirsch |
| 8,590,760 B2 | 11/2013 | Cummins et al. |
| 8,590,762 B2 * | 11/2013 | Hess ............... A61B 17/07207 227/175.1 |
| 8,590,764 B2 | 11/2013 | Hartwick et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,814 B2 | 2/2014 | Werneth et al. |
| 8,662,370 B2 | 3/2014 | Takei |

(56) References Cited

U.S. PATENT DOCUMENTS

| | | |
|---|---|---|
| 8,663,192 B2 | 3/2014 | Hester et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,951 B2 | 3/2014 | Smith et al. |
| 8,678,263 B2 | 3/2014 | Viola |
| 8,679,093 B2 | 3/2014 | Farra |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,211 B2 | 4/2014 | Zemlok et al. |
| 8,708,213 B2 | 4/2014 | Shelton, IV et al. |
| 8,714,429 B2 | 5/2014 | Demmy |
| 8,720,766 B2 | 5/2014 | Hess et al. |
| 8,721,630 B2 | 5/2014 | Ortiz et al. |
| 8,721,646 B2 | 5/2014 | Fox |
| 8,721,666 B2 | 5/2014 | Schroeder et al. |
| 8,727,197 B2 | 5/2014 | Hess et al. |
| 8,728,119 B2 | 5/2014 | Cummins |
| 8,728,120 B2 | 5/2014 | Blier |
| 8,733,612 B2 | 5/2014 | Ma |
| 8,733,613 B2 | 5/2014 | Huitema et al. |
| 8,733,614 B2 | 5/2014 | Ross et al. |
| 8,734,478 B2 | 5/2014 | Widenhouse et al. |
| D706,927 S | 6/2014 | Cheney et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,287 B2 | 6/2014 | Mak et al. |
| 8,757,465 B2 | 6/2014 | Woodard, Jr. et al. |
| 8,757,467 B2 | 6/2014 | Racenet et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,312 B1 | 7/2014 | Knodel et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,800,837 B2 | 8/2014 | Zemlok |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,801,732 B2 | 8/2014 | Harris et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,808,294 B2 | 8/2014 | Fox et al. |
| 8,808,311 B2 | 8/2014 | Heinrich et al. |
| 8,808,325 B2 | 8/2014 | Hess et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,632 B2 | 9/2014 | Swensgard |
| 8,834,498 B2 | 9/2014 | Byrum et al. |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,852,185 B2 | 10/2014 | Twomey |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,049 B2 | 10/2014 | Amid et al. |
| 8,870,050 B2 | 10/2014 | Hodgkinson |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,888,792 B2 | 11/2014 | Harris et al. |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,287 B2 | 12/2014 | Racenet et al. |
| 8,905,977 B2 | 12/2014 | Shelton et al. |
| 8,911,426 B2 | 12/2014 | Coppeta et al. |
| 8,911,471 B2 | 12/2014 | Spivey et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,955,732 B2 | 2/2015 | Zemlok et al. |
| 8,956,390 B2 | 2/2015 | Shah et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,967,443 B2 | 3/2015 | McCuen |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,337 B2 | 3/2015 | Whitfield et al. |

(56) References Cited

U.S. PATENT DOCUMENTS

| | | |
|---|---|---|
| 8,968,355 B2 | 3/2015 | Malkowski et al. |
| 8,968,358 B2 | 3/2015 | Reschke |
| 8,973,803 B2 | 3/2015 | Hall et al. |
| 8,973,804 B2 | 3/2015 | Hess et al. |
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,422 B2 | 3/2015 | Spivey et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,061 B2 | 4/2015 | Williams et al. |
| 9,004,339 B1 | 4/2015 | Park |
| 9,005,230 B2 | 4/2015 | Yates et al. |
| 9,005,243 B2 | 4/2015 | Stopek et al. |
| 9,010,608 B2 | 4/2015 | Casasanta, Jr. et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,017,331 B2 | 4/2015 | Fox |
| 9,023,014 B2 | 5/2015 | Chowaniec et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,120 B2 | 6/2015 | Swarup et al. |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,060,769 B2 | 6/2015 | Coleman et al. |
| 9,060,770 B2 | 6/2015 | Shelton, IV et al. |
| 9,060,894 B2 | 6/2015 | Wubbeling |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,089,330 B2 | 7/2015 | Widenhouse et al. |
| 9,095,339 B2 | 8/2015 | Moore et al. |
| 9,095,362 B2 | 8/2015 | Dachs, II et al. |
| 9,096,033 B2 | 8/2015 | Holop et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,870 B2 | 8/2015 | Viola |
| 9,113,874 B2 | 8/2015 | Shelton, IV et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,125,649 B2 | 9/2015 | Bruewer et al. |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,138,225 B2 | 9/2015 | Huang et al. |
| 9,138,226 B2 | 9/2015 | Racenet et al. |
| 9,149,274 B2 | 10/2015 | Spivey et al. |
| 9,149,325 B2 | 10/2015 | Worrell et al. |
| 9,168,038 B2 | 10/2015 | Shelton, IV et al. |
| 9,168,039 B1 | 10/2015 | Knodel |
| 9,179,911 B2 | 11/2015 | Morgan et al. |
| 9,179,912 B2 | 11/2015 | Yates et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,143 B2 | 11/2015 | Timm et al. |
| 9,192,380 B2 | 11/2015 | Racenet et al. |
| 9,192,384 B2 | 11/2015 | Bettuchi |
| 9,198,661 B2 | 12/2015 | Swensgard |
| 9,198,662 B2 | 12/2015 | Barton et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,923 B2 | 12/2015 | Manzo et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,019 B2 | 12/2015 | Schmid et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,237,891 B2 | 1/2016 | Shelton, IV |
| 9,237,892 B2 | 1/2016 | Hodgkinson |
| 9,241,714 B2 | 1/2016 | Timm et al. |
| 9,265,500 B2 | 2/2016 | Sorrentino et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,464 B2 | 3/2016 | Shelton, IV et al. |
| 9,295,466 B2 | 3/2016 | Hodgkinson et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,314,246 B2 | 4/2016 | Shelton, IV et al. |
| 9,314,247 B2 | 4/2016 | Shelton, IV et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |

(56) References Cited

U.S. PATENT DOCUMENTS

| | | |
|---|---|---|
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,082 B2 | 5/2016 | Wei et al. |
| 9,345,477 B2 | 5/2016 | Anim et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,351,731 B2 | 5/2016 | Carter et al. |
| 9,358,003 B2 | 6/2016 | Hall et al. |
| 9,358,005 B2 | 6/2016 | Shelton, IV et al. |
| 9,358,015 B2 | 6/2016 | Sorrentino et al. |
| 9,364,219 B2 | 6/2016 | Olson et al. |
| 9,364,220 B2 | 6/2016 | Williams |
| 9,364,229 B2 | 6/2016 | D'Agostino et al. |
| 9,364,230 B2 | 6/2016 | Shelton, IV et al. |
| 9,364,233 B2 | 6/2016 | Alexander, III et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,393,015 B2 | 7/2016 | Laurent et al. |
| 9,393,018 B2 | 7/2016 | Wang et al. |
| 9,398,911 B2 | 7/2016 | Auld |
| 9,402,604 B2 | 8/2016 | Williams et al. |
| 9,402,626 B2 | 8/2016 | Ortiz et al. |
| 9,402,628 B2 | 8/2016 | Beardsley |
| 9,408,604 B2 | 8/2016 | Shelton, IV et al. |
| 9,408,606 B2 | 8/2016 | Shelton, IV |
| 9,408,622 B2 | 8/2016 | Stulen et al. |
| 9,414,838 B2 | 8/2016 | Shelton, IV et al. |
| 9,414,880 B2 | 8/2016 | Monson et al. |
| 9,421,014 B2 | 8/2016 | Ingmanson et al. |
| 9,427,223 B2 | 8/2016 | Park et al. |
| 9,433,411 B2 | 9/2016 | Racenet et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,651 B2 | 9/2016 | Smith et al. |
| 9,445,813 B2 | 9/2016 | Shelton, IV et al. |
| 9,451,956 B2 | 9/2016 | Balbierz et al. |
| 9,451,958 B2 | 9/2016 | Shelton, IV et al. |
| 9,463,260 B2 | 10/2016 | Stopek |
| 9,468,438 B2 | 10/2016 | Baber et al. |
| 9,480,476 B2 | 11/2016 | Aldridge et al. |
| 9,480,492 B2 | 11/2016 | Aranyi et al. |
| 9,486,213 B2 | 11/2016 | Altman et al. |
| 9,486,214 B2 | 11/2016 | Shelton, IV |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,498,215 B2 | 11/2016 | Duque et al. |
| 9,498,219 B2 | 11/2016 | Moore et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,517,063 B2 | 12/2016 | Swayze et al. |
| 9,517,068 B2 | 12/2016 | Shelton, IV et al. |
| 9,522,029 B2 | 12/2016 | Yates et al. |
| 9,545,258 B2 | 1/2017 | Smith et al. |
| 9,549,732 B2 | 1/2017 | Yates et al. |
| 9,549,735 B2 | 1/2017 | Shelton, IV et al. |
| 9,554,794 B2 | 1/2017 | Baber et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,572,574 B2 | 2/2017 | Shelton, IV et al. |
| 9,572,577 B2 | 2/2017 | Lloyd et al. |
| 9,574,644 B2 | 2/2017 | Parihar |
| 9,585,657 B2 | 3/2017 | Shelton, IV et al. |
| 9,585,658 B2 | 3/2017 | Shelton, IV |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,074 B2 | 3/2017 | Felder et al. |
| 9,597,075 B2 | 3/2017 | Shelton, IV et al. |
| 9,597,080 B2 | 3/2017 | Milliman et al. |
| 9,603,595 B2 | 3/2017 | Shelton, IV et al. |
| 9,603,598 B2 | 3/2017 | Shelton, IV et al. |
| 9,603,991 B2 | 3/2017 | Shelton, IV et al. |
| 9,610,080 B2 | 4/2017 | Whitfield et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,629 B2 | 4/2017 | Leimbach et al. |
| 9,629,814 B2 | 4/2017 | Widenhouse et al. |
| 9,642,620 B2 | 5/2017 | Baxter, III et al. |
| 9,649,110 B2 | 5/2017 | Parihar et al. |
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,624 B2 | 5/2017 | Shelton, IV et al. |
| 9,662,110 B2 | 5/2017 | Huang et al. |
| 9,662,131 B2 | 5/2017 | Omori et al. |
| 9,668,729 B2 | 6/2017 | Williams et al. |
| 9,668,732 B2 | 6/2017 | Patel et al. |
| 9,675,344 B2 | 6/2017 | Combrowski et al. |
| 9,675,351 B2 | 6/2017 | Hodgkinson et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,681,870 B2 | 6/2017 | Baxter, III et al. |
| 9,681,873 B2 | 6/2017 | Smith et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,236 B2 | 6/2017 | Leimbach et al. |
| 9,687,237 B2 | 6/2017 | Schmid et al. |
| 9,690,362 B2 | 6/2017 | Leimbach et al. |
| 9,693,772 B2 | 7/2017 | Ingmanson et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,317 B2 | 7/2017 | Aronhalt et al. |
| 9,700,319 B2 | 7/2017 | Motooka et al. |
| 9,700,321 B2 | 7/2017 | Shelton, IV et al. |
| 9,706,991 B2 | 7/2017 | Hess et al. |
| 9,707,043 B2 | 7/2017 | Bozung |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,096 B2 | 8/2017 | Thompson et al. |
| 9,724,098 B2 | 8/2017 | Baxter, III et al. |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,733,663 B2 | 8/2017 | Leimbach et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,928 B2 | 8/2017 | Shelton, IV et al. |
| 9,743,929 B2 | 8/2017 | Leimbach et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,757,123 B2 | 9/2017 | Giordano et al. |

(56) References Cited

U.S. PATENT DOCUMENTS

| | | |
|---|---|---|
| 9,757,124 B2 | 9/2017 | Schellin et al. |
| 9,757,128 B2 | 9/2017 | Baber et al. |
| 9,757,130 B2 | 9/2017 | Shelton, IV |
| 9,763,662 B2 | 9/2017 | Shelton, IV et al. |
| 9,770,245 B2 | 9/2017 | Swayze et al. |
| 9,775,608 B2 | 10/2017 | Aronhalt et al. |
| 9,775,609 B2 | 10/2017 | Shelton, IV et al. |
| 9,775,613 B2 | 10/2017 | Shelton, IV et al. |
| 9,775,614 B2 | 10/2017 | Shelton, IV et al. |
| 9,782,169 B2 | 10/2017 | Kimsey et al. |
| 9,788,834 B2 | 10/2017 | Schmid et al. |
| 9,788,836 B2 | 10/2017 | Overmyer et al. |
| 9,795,379 B2 | 10/2017 | Leimbach et al. |
| 9,795,381 B2 | 10/2017 | Shelton, IV |
| 9,795,382 B2 | 10/2017 | Shelton, IV |
| 9,795,384 B2 | 10/2017 | Weaner et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,820,738 B2 | 11/2017 | Lytle, IV et al. |
| 9,820,741 B2 | 11/2017 | Kostrzewski |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,833,236 B2 | 12/2017 | Shelton, IV et al. |
| 9,833,238 B2 | 12/2017 | Baxter, III et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,425 B2 | 12/2017 | Zergiebel et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,873 B2 | 12/2017 | Shelton, IV |
| 9,848,875 B2 | 12/2017 | Aronhalt et al. |
| 9,861,359 B2 | 1/2018 | Shelton, IV et al. |
| 9,861,361 B2 | 1/2018 | Aronhalt et al. |
| 9,867,612 B2 | 1/2018 | Parihar et al. |
| 9,867,613 B2 | 1/2018 | Marczyk et al. |
| 9,867,618 B2 | 1/2018 | Hall et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,877,721 B2 | 1/2018 | Schellin et al. |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,342 B2 | 2/2018 | Shelton, IV et al. |
| 9,901,343 B2 | 2/2018 | Vold et al. |
| 9,907,620 B2 | 3/2018 | Shelton, IV et al. |
| 9,913,642 B2 | 3/2018 | Leimbach et al. |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,918,704 B2 | 3/2018 | Shelton, IV et al. |
| 9,918,716 B2 | 3/2018 | Baxter, III et al. |
| 9,918,717 B2 | 3/2018 | Czernik |
| 9,924,942 B2 | 3/2018 | Swayze et al. |
| 9,924,944 B2 | 3/2018 | Shelton, IV et al. |
| 9,924,947 B2 | 3/2018 | Shelton, IV et al. |
| 9,924,961 B2 | 3/2018 | Shelton, IV et al. |
| 9,931,118 B2 | 4/2018 | Shelton, IV et al. |
| 9,943,309 B2 | 4/2018 | Shelton, IV et al. |
| 9,943,310 B2 | 4/2018 | Harris et al. |
| 9,962,158 B2 | 5/2018 | Hall et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,980,713 B2 | 5/2018 | Aronhalt et al. |
| 9,980,729 B2 | 5/2018 | Moore et al. |
| 9,987,000 B2 | 6/2018 | Shelton, IV et al. |
| 9,987,006 B2 | 6/2018 | Morgan et al. |
| 9,987,011 B2 | 6/2018 | Williams et al. |
| 9,987,095 B2 | 6/2018 | Chowaniec et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 9,999,426 B2 | 6/2018 | Moore et al. |
| 9,999,431 B2 | 6/2018 | Shelton, IV et al. |
| 10,004,497 B2 | 6/2018 | Overmyer et al. |
| 10,004,498 B2 | 6/2018 | Morgan et al. |
| 10,004,501 B2 | 6/2018 | Shelton, IV et al. |
| 10,004,505 B2 | 6/2018 | Moore et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| D826,405 S | 8/2018 | Shelton, IV et al. |
| 10,039,529 B2 | 8/2018 | Kerr et al. |
| 10,045,769 B2 | 8/2018 | Aronhalt et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,104 B2 | 8/2018 | Shelton, IV et al. |
| 10,058,317 B2 | 8/2018 | Fan et al. |
| 10,058,327 B2 | 8/2018 | Weisenburgh, II et al. |
| 10,058,963 B2 | 8/2018 | Shelton, IV et al. |
| 10,064,621 B2 | 9/2018 | Kerr et al. |
| 10,064,624 B2 | 9/2018 | Shelton, IV et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,080,552 B2 | 9/2018 | Nicholas et al. |
| 10,085,748 B2 | 10/2018 | Morgan et al. |
| 10,098,642 B2 | 10/2018 | Baxter, III et al. |
| 10,111,679 B2 | 10/2018 | Baber et al. |
| 10,117,649 B2 | 11/2018 | Baxter, III et al. |
| 10,117,652 B2 | 11/2018 | Schmid et al. |
| 10,123,798 B2 | 11/2018 | Baxter, III et al. |
| 10,123,799 B2 | 11/2018 | Zergiebel et al. |
| 10,130,352 B2 | 11/2018 | Widenhouse et al. |
| 10,130,363 B2 | 11/2018 | Huitema et al. |

(56) References Cited

U.S. PATENT DOCUMENTS

| | | |
|---|---|---|
| 10,130,366 B2 | 11/2018 | Shelton, IV et al. |
| 10,135,242 B2 | 11/2018 | Baber et al. |
| 10,136,887 B2 | 11/2018 | Shelton, IV et al. |
| 10,136,890 B2 | 11/2018 | Shelton, IV et al. |
| 2001/0025183 A1 | 9/2001 | Shahidi |
| 2002/0022836 A1 | 2/2002 | Goble et al. |
| 2002/0029036 A1 | 3/2002 | Goble et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0134811 A1 | 9/2002 | Napier et al. |
| 2002/0143340 A1 | 10/2002 | Kaneko |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0139741 A1 | 7/2003 | Goble et al. |
| 2003/0153908 A1 | 8/2003 | Goble et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044364 A1 | 3/2004 | DeVries et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010213 A1 | 1/2005 | Stad et al. |
| 2005/0032511 A1 | 2/2005 | Malone et al. |
| 2005/0033352 A1 | 2/2005 | Zepf et al. |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0124855 A1 | 6/2005 | Jaffe et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0154258 A1 | 7/2005 | Tartaglia et al. |
| 2005/0154406 A1 | 7/2005 | Bombard et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0245965 A1 | 11/2005 | Orban, III et al. |
| 2005/0246881 A1 | 11/2005 | Kelly et al. |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0283188 A1 | 12/2005 | Loshakove et al. |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100649 A1 | 5/2006 | Hart |
| 2006/0180634 A1 | 8/2006 | Shelton et al. |
| 2006/0185682 A1 | 8/2006 | Marczyk |
| 2006/0201989 A1 | 9/2006 | Ojeda |
| 2006/0212071 A1 | 9/2006 | Ginn et al. |
| 2006/0252993 A1 | 11/2006 | Freed et al. |
| 2006/0289602 A1 | 12/2006 | Wales et al. |
| 2006/0291981 A1 | 12/2006 | Viola et al. |
| 2007/0010838 A1 | 1/2007 | Shelton et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0073341 A1 | 3/2007 | Smith et al. |
| 2007/0078484 A1 | 4/2007 | Talarico et al. |
| 2007/0084897 A1 | 4/2007 | Shelton et al. |
| 2007/0093869 A1 | 4/2007 | Bloom et al. |
| 2007/0102472 A1 | 5/2007 | Shelton |
| 2007/0106113 A1 | 5/2007 | Ravo |
| 2007/0106317 A1 | 5/2007 | Shelton et al. |
| 2007/0135686 A1 | 6/2007 | Pruitt et al. |
| 2007/0135803 A1 | 6/2007 | Belson |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |

(56) References Cited

U.S. PATENT DOCUMENTS

| | | |
|---|---|---|
| 2007/0203510 A1 | 8/2007 | Bettuchi |
| 2007/0208359 A1 | 9/2007 | Hoffman |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2008/0003196 A1 | 1/2008 | Jonn et al. |
| 2008/0015598 A1 | 1/2008 | Prommersberger |
| 2008/0021278 A1 | 1/2008 | Leonard et al. |
| 2008/0023522 A1 * | 1/2008 | Olson ............ A61B 17/07207 227/175.1 |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0051833 A1 | 2/2008 | Gramuglia et al. |
| 2008/0065153 A1 | 3/2008 | Allard et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Livneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0183193 A1 | 7/2008 | Omori et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0255413 A1 | 10/2008 | Zemlok et al. |
| 2008/0262654 A1 | 10/2008 | Omori et al. |
| 2008/0287944 A1 | 11/2008 | Pearson et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0020958 A1 | 1/2009 | Soul |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0090763 A1 | 4/2009 | Zemlok et al. |
| 2009/0092651 A1 | 4/2009 | Shah et al. |
| 2009/0099579 A1 | 4/2009 | Nentwick et al. |
| 2009/0099876 A1 | 4/2009 | Whitman |
| 2009/0119011 A1 | 5/2009 | Kondo et al. |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177201 A1 | 7/2009 | Soltz et al. |
| 2009/0177226 A1 | 7/2009 | Reinprecht et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2009/0247901 A1 | 10/2009 | Zimmer |
| 2009/0255974 A1 | 10/2009 | Viola |
| 2009/0270895 A1 | 10/2009 | Churchill et al. |
| 2009/0292283 A1 | 11/2009 | Odom |
| 2009/0308907 A1 | 12/2009 | Nalagatla et al. |
| 2009/0318957 A1 | 12/2009 | Viola et al. |
| 2010/0016888 A1 | 1/2010 | Calabrese et al. |
| 2010/0023024 A1 | 1/2010 | Zeiner et al. |
| 2010/0023052 A1 | 1/2010 | Heinrich et al. |
| 2010/0036370 A1 | 2/2010 | Mirel et al. |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0100124 A1 | 4/2010 | Calabrese et al. |
| 2010/0133316 A1 | 6/2010 | Lizee et al. |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0179022 A1 | 7/2010 | Shirokoshi |
| 2010/0191262 A1 | 7/2010 | Harris et al. |
| 2010/0193566 A1 | 8/2010 | Scheib et al. |
| 2010/0204717 A1 | 8/2010 | Knodel |
| 2010/0222901 A1 | 9/2010 | Swayze et al. |
| 2010/0249497 A1 | 9/2010 | Peine et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0312261 A1 | 12/2010 | Suzuki et al. |
| 2010/0331856 A1 | 12/2010 | Carlson et al. |
| 2011/0006101 A1 | 1/2011 | Hall et al. |
| 2011/0011916 A1 | 1/2011 | Levine |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0046667 A1 | 2/2011 | Culligan et al. |
| 2011/0060363 A1 | 3/2011 | Hess et al. |
| 2011/0082538 A1 | 4/2011 | Dahlgren et al. |
| 2011/0087276 A1 | 4/2011 | Bedi et al. |
| 2011/0114697 A1 | 5/2011 | Baxter, III et al. |
| 2011/0121049 A1 | 5/2011 | Malinouskas et al. |
| 2011/0125176 A1 | 5/2011 | Yates et al. |
| 2011/0137340 A1 | 6/2011 | Cummins |
| 2011/0147433 A1 | 6/2011 | Shelton, IV et al. |
| 2011/0163146 A1 | 7/2011 | Ortiz et al. |
| 2011/0174861 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016413 A1 | 1/2012 | Timm et al. |
| 2012/0029272 A1 | 2/2012 | Shelton, IV et al. |
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080497 A1 | 4/2012 | White et al. |
| 2012/0080498 A1 | 4/2012 | Shelton, IV et al. |
| 2012/0125792 A1 | 5/2012 | Cassivi |
| 2012/0130421 A1 | 5/2012 | Hafez et al. |

(56) References Cited

U.S. PATENT DOCUMENTS

| | | |
|---|---|---|
| 2012/0175398 A1 | 7/2012 | Sandborn et al. |
| 2012/0234895 A1 | 9/2012 | O'Connor et al. |
| 2012/0234897 A1 | 9/2012 | Shelton, IV et al. |
| 2012/0248169 A1 | 10/2012 | Widenhouse et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2013/0012983 A1 | 1/2013 | Kleyman |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0087597 A1 | 4/2013 | Shelton, IV et al. |
| 2013/0098970 A1 | 4/2013 | Racenet et al. |
| 2013/0116669 A1 | 5/2013 | Shelton, IV et al. |
| 2013/0131651 A1 | 5/2013 | Strobl et al. |
| 2013/0153636 A1 | 6/2013 | Shelton, IV et al. |
| 2013/0153641 A1 | 6/2013 | Shelton, IV et al. |
| 2013/0172929 A1* | 7/2013 | Hess .................. F16B 15/00 606/219 |
| 2013/0175317 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0214025 A1 | 8/2013 | Zemlok et al. |
| 2013/0214030 A1 | 8/2013 | Aronhalt et al. |
| 2013/0233906 A1 | 9/2013 | Hess et al. |
| 2013/0256373 A1 | 10/2013 | Schmid et al. |
| 2013/0256379 A1 | 10/2013 | Schmid et al. |
| 2013/0256380 A1 | 10/2013 | Schmid et al. |
| 2013/0261661 A1 | 10/2013 | Piraka |
| 2013/0270322 A1 | 10/2013 | Scheib et al. |
| 2013/0317305 A1 | 11/2013 | Stevenson et al. |
| 2013/0324981 A1 | 12/2013 | Smith et al. |
| 2013/0324982 A1 | 12/2013 | Smith et al. |
| 2013/0334280 A1 | 12/2013 | Krehel et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0014705 A1 | 1/2014 | Baxter, III |
| 2014/0018832 A1 | 1/2014 | Shelton, IV |
| 2014/0048580 A1 | 2/2014 | Merchant et al. |
| 2014/0103098 A1 | 4/2014 | Choi et al. |
| 2014/0107640 A1 | 4/2014 | Yates et al. |
| 2014/0151433 A1 | 6/2014 | Shelton, IV et al. |
| 2014/0158747 A1 | 6/2014 | Measamer et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0224857 A1 | 8/2014 | Schmid |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0284371 A1 | 9/2014 | Morgan et al. |
| 2014/0291378 A1 | 10/2014 | Shelton, IV et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0305991 A1 | 10/2014 | Parihar et al. |
| 2014/0309666 A1 | 10/2014 | Shelton, IV et al. |
| 2014/0330161 A1 | 11/2014 | Swayze et al. |
| 2015/0008248 A1 | 1/2015 | Giordano et al. |
| 2015/0053737 A1 | 2/2015 | Leimbach et al. |
| 2015/0053742 A1 | 2/2015 | Shelton, IV et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083781 A1 | 3/2015 | Giordano et al. |
| 2015/0083782 A1 | 3/2015 | Scheib et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0144679 A1 | 5/2015 | Scirica et al. |
| 2015/0150620 A1 | 6/2015 | Miyamoto et al. |
| 2015/0173744 A1 | 6/2015 | Shelton, IV et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0182220 A1 | 7/2015 | Yates et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0231409 A1 | 8/2015 | Racenet et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0280384 A1 | 10/2015 | Leimbach et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297219 A1 | 10/2015 | Shelton, IV et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0313594 A1 | 11/2015 | Shelton, IV et al. |
| 2015/0327864 A1 | 11/2015 | Hodgkinson et al. |
| 2015/0335328 A1 | 11/2015 | Shelton, IV et al. |
| 2015/0342607 A1 | 12/2015 | Shelton, IV et al. |
| 2015/0374368 A1 | 12/2015 | Swayze et al. |
| 2015/0374369 A1 | 12/2015 | Yates et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |

(56) References Cited

U.S. PATENT DOCUMENTS

| | | |
|---|---|---|
| 2016/0000431 A1 | 1/2016 | Giordano et al. |
| 2016/0000437 A1 | 1/2016 | Giordano et al. |
| 2016/0000438 A1 | 1/2016 | Swayze et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015391 A1 | 1/2016 | Shelton, IV et al. |
| 2016/0051257 A1 | 2/2016 | Shelton, IV et al. |
| 2016/0058443 A1 | 3/2016 | Yates et al. |
| 2016/0066913 A1 | 3/2016 | Swayze et al. |
| 2016/0074040 A1 | 3/2016 | Widenhouse et al. |
| 2016/0089137 A1 | 3/2016 | Hess et al. |
| 2016/0089142 A1 | 3/2016 | Harris et al. |
| 2016/0089146 A1 | 3/2016 | Harris et al. |
| 2016/0089147 A1 | 3/2016 | Harris et al. |
| 2016/0089149 A1 | 3/2016 | Harris et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0166256 A1 | 6/2016 | Baxter, III et al. |
| 2016/0174969 A1 | 6/2016 | Kerr et al. |
| 2016/0174972 A1 | 6/2016 | Shelton, IV et al. |
| 2016/0174974 A1 | 6/2016 | Schmid et al. |
| 2016/0174984 A1 | 6/2016 | Smith et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192933 A1 | 7/2016 | Shelton, IV |
| 2016/0192936 A1 | 7/2016 | Leimbach et al. |
| 2016/0192996 A1 | 7/2016 | Spivey et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199089 A1 | 7/2016 | Hess et al. |
| 2016/0199956 A1 | 7/2016 | Shelton, IV et al. |
| 2016/0206310 A1 | 7/2016 | Shelton, IV |
| 2016/0206314 A1 | 7/2016 | Scheib et al. |
| 2016/0220248 A1 | 8/2016 | Timm et al. |
| 2016/0220249 A1 | 8/2016 | Shelton, IV et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249909 A1 | 9/2016 | Shelton, IV et al. |
| 2016/0249910 A1 | 9/2016 | Shelton, IV et al. |
| 2016/0249911 A1 | 9/2016 | Timm et al. |
| 2016/0249915 A1 | 9/2016 | Beckman et al. |
| 2016/0249916 A1 | 9/2016 | Shelton, IV et al. |
| 2016/0249917 A1 | 9/2016 | Beckman et al. |
| 2016/0249918 A1 | 9/2016 | Shelton, IV et al. |
| 2016/0249922 A1 | 9/2016 | Morgan et al. |
| 2016/0249927 A1 | 9/2016 | Beckman et al. |
| 2016/0256071 A1 | 9/2016 | Shelton, IV et al. |
| 2016/0256154 A1 | 9/2016 | Shelton, IV et al. |
| 2016/0256156 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256185 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0270780 A1 | 9/2016 | Hall et al. |
| 2016/0270789 A1 | 9/2016 | Gupta et al. |
| 2016/0287249 A1 | 10/2016 | Alexander, III et al. |
| 2016/0287250 A1 | 10/2016 | Shelton, IV et al. |
| 2016/0287251 A1 | 10/2016 | Shelton, IV et al. |
| 2016/0287253 A1 | 10/2016 | Shelton, IV et al. |
| 2016/0338702 A1 | 11/2016 | Ehrenfels et al. |
| 2016/0367255 A1 | 12/2016 | Wise et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0055991 A1 | 3/2017 | Kang |
| 2017/0055997 A1 | 3/2017 | Swayze et al. |
| 2017/0055998 A1 | 3/2017 | Baxter, III et al. |
| 2017/0055999 A1 | 3/2017 | Baxter, III et al. |
| 2017/0056000 A1 | 3/2017 | Nalagatla et al. |
| 2017/0056001 A1 | 3/2017 | Shelton, IV et al. |
| 2017/0056002 A1 | 3/2017 | Nalagatla et al. |
| 2017/0056004 A1 | 3/2017 | Shelton, IV et al. |
| 2017/0056005 A1 | 3/2017 | Shelton, IV et al. |
| 2017/0056006 A1 | 3/2017 | Shelton, IV et al. |
| 2017/0056007 A1 | 3/2017 | Eckert et al. |
| 2017/0056008 A1 | 3/2017 | Shelton, IV et al. |
| 2017/0056012 A1 | 3/2017 | Harris et al. |
| 2017/0056013 A1 | 3/2017 | Harris et al. |
| 2017/0056014 A1 | 3/2017 | Harris et al. |
| 2017/0056015 A1* | 3/2017 | Harris ............... A61B 17/105 |
| 2017/0095250 A1 | 4/2017 | Kostrzewski et al. |
| 2017/0105727 A1 | 4/2017 | Scheib et al. |
| 2017/0105728 A1 | 4/2017 | Scheib et al. |
| 2017/0105731 A1 | 4/2017 | Scheib et al. |
| 2017/0231633 A1 | 8/2017 | Marczyk et al. |
| 2017/0245856 A1 | 8/2017 | Baxter, III et al. |
| 2017/0245857 A1 | 8/2017 | Shelton, IV et al. |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367698 A1 | 12/2017 | Shelton, IV et al. |
| 2017/0367699 A1 | 12/2017 | Shelton, IV et al. |
| 2018/0103948 A1 | 4/2018 | Baxter, III et al. |
| 2018/0110513 A1 | 4/2018 | Baxter, III et al. |
| 2018/0110517 A1 | 4/2018 | Baxter, III et al. |
| 2018/0168585 A1 | 6/2018 | Shelton, IV et al. |
| 2018/0168586 A1 | 6/2018 | Shelton, IV et al. |
| 2018/0168600 A1 | 6/2018 | Shelton, IV et al. |
| 2018/0168617 A1 | 6/2018 | Shelton, IV et al. |
| 2018/0168643 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |

FOREIGN PATENT DOCUMENTS

| | | |
|---|---|---|
| AU | 2011218702 B2 | 6/2013 |
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CA | 2795323 A1 | 5/2014 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |

(56) References Cited

FOREIGN PATENT DOCUMENTS

| | | | |
|---|---|---|---|
| CN | 2868212 Y | 2/2007 |
| CN | 1960679 A | 5/2007 |
| CN | 101011286 A | 8/2007 |
| CN | 101095621 A | 1/2008 |
| CN | 101111196 A | 1/2008 |
| CN | 101137402 A | 3/2008 |
| CN | 101507620 A | 8/2009 |
| CN | 101507622 A | 8/2009 |
| CN | 101507623 A | 8/2009 |
| CN | 101507625 A | 8/2009 |
| CN | 101507628 A | 8/2009 |
| CN | 101675898 A | 3/2010 |
| CN | 101683280 A | 3/2010 |
| CN | 101028205 B | 1/2011 |
| CN | 101934098 A | 1/2011 |
| CN | 201949071 U | 8/2011 |
| CN | 101336835 B | 9/2011 |
| CN | 102188270 A | 9/2011 |
| CN | 101779977 B | 12/2011 |
| CN | 101534723 B | 1/2012 |
| CN | 101310680 B | 4/2012 |
| CN | 202397539 U | 8/2012 |
| CN | 101317782 B | 10/2012 |
| CN | 101541251 A | 11/2012 |
| CN | 101507633 B | 2/2013 |
| CN | 101023879 B | 3/2013 |
| CN | 101327137 B | 6/2013 |
| CN | 101401736 B | 6/2013 |
| CN | 202982106 U | 6/2013 |
| CN | 101332110 B | 7/2013 |
| CN | 101683281 B | 1/2014 |
| CN | 103648408 A | 3/2014 |
| CN | 203777011 U | 8/2014 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 4228909 A1 | 3/1994 |
| DE | 9412228 U1 | 9/1994 |
| DE | 19509116 A1 | 9/1996 |
| DE | 19707373 C1 | 2/1998 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 202004012389 U1 | 9/2004 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 4/1985 |
| EP | 0156774 A2 | 10/1985 |
| EP | 0050554 B1 | 1/1986 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0379721 B1 | 9/1993 |
| EP | 0277959 B1 | 10/1993 |
| EP | 0233940 B1 | 11/1993 |
| EP | 0261230 B1 | 11/1993 |
| EP | 0324636 B1 | 3/1994 |
| EP | 0591946 A1 | 4/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0639349 A2 | 2/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0676173 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0541987 B1 | 7/1996 |
| EP | 0667119 B1 | 7/1996 |
| EP | 0737446 A1 | 10/1996 |
| EP | 0741996 B1 | 11/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0623312 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 B1 | 9/1999 |
| EP | 0843906 B1 | 3/2000 |
| EP | 0552050 B1 | 5/2000 |
| EP | 0833592 B1 | 5/2000 |
| EP | 0795298 B1 | 6/2000 |
| EP | 0832605 B1 | 6/2000 |
| EP | 0484677 B2 | 7/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |

(56) References Cited

FOREIGN PATENT DOCUMENTS

| | | | |
|---|---|---|---|
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1058177 | A1 | 12/2000 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 0768840 | B1 | 12/2001 |
| EP | 0908152 | B1 | 1/2002 |
| EP | 0717959 | B1 | 2/2002 |
| EP | 0872213 | B1 | 5/2002 |
| EP | 0862386 | B1 | 6/2002 |
| EP | 0949886 | B1 | 9/2002 |
| EP | 1238634 | A2 | 9/2002 |
| EP | 0858295 | B1 | 12/2002 |
| EP | 0656188 | B1 | 1/2003 |
| EP | 0717960 | B1 | 2/2003 |
| EP | 1284120 | A1 | 2/2003 |
| EP | 1287788 | A1 | 3/2003 |
| EP | 0717966 | B1 | 4/2003 |
| EP | 0869742 | B1 | 5/2003 |
| EP | 0829235 | B1 | 6/2003 |
| EP | 0887046 | B1 | 7/2003 |
| EP | 1323384 | A2 | 7/2003 |
| EP | 0852480 | B1 | 8/2003 |
| EP | 0891154 | B1 | 9/2003 |
| EP | 0813843 | B1 | 10/2003 |
| EP | 0873089 | B1 | 10/2003 |
| EP | 0856326 | B1 | 11/2003 |
| EP | 1374788 | A1 | 1/2004 |
| EP | 0814712 | B1 | 2/2004 |
| EP | 1402837 | A1 | 3/2004 |
| EP | 0705570 | B1 | 4/2004 |
| EP | 0959784 | B1 | 4/2004 |
| EP | 1407719 | A2 | 4/2004 |
| EP | 1411626 | A2 | 4/2004 |
| EP | 1086713 | B1 | 5/2004 |
| EP | 0996378 | B1 | 6/2004 |
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1453432 | A2 | 9/2004 |
| EP | 1459695 | A1 | 9/2004 |
| EP | 1254636 | B1 | 10/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1496805 | A2 | 1/2005 |
| EP | 1256318 | B1 | 2/2005 |
| EP | 1520521 | A1 | 4/2005 |
| EP | 1520522 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 0906764 | B1 | 12/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621143 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1230899 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1736105 | A1 | 12/2006 |
| EP | 1011494 | B1 | 1/2007 |
| EP | 1479346 | B1 | 1/2007 |
| EP | 1484024 | B1 | 1/2007 |
| EP | 1749485 | A1 | 2/2007 |
| EP | 1754445 | A2 | 2/2007 |
| EP | 1759812 | A1 | 3/2007 |
| EP | 1767157 | A1 | 3/2007 |
| EP | 1767163 | A1 | 3/2007 |
| EP | 1563792 | B1 | 4/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1563793 | B1 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1815950 | A1 | 8/2007 |
| EP | 1330991 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1917929 | A1 | 5/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |

(56) References Cited

FOREIGN PATENT DOCUMENTS

| | | |
|---|---|---|
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1980214 A2 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000101 A2 | 12/2008 |
| EP | 2000102 A2 | 12/2008 |
| EP | 2005894 A2 | 12/2008 |
| EP | 2005897 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110083 A2 | 10/2009 |
| EP | 2110084 A2 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1762190 B8 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 2165664 A2 | 3/2010 |
| EP | 1566150 B1 | 4/2010 |
| EP | 1813206 B1 | 4/2010 |
| EP | 2184014 A2 | 5/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 B1 | 3/2011 |
| EP | 1884201 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 1728475 B1 | 8/2011 |
| EP | 2353545 A1 | 8/2011 |
| EP | 2361562 A1 | 8/2011 |
| EP | 1936253 B1 | 10/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2397079 A1 | 12/2011 |
| EP | 2399538 A2 | 12/2011 |
| EP | 1785102 B1 | 1/2012 |
| EP | 2415416 A1 | 2/2012 |
| EP | 2090253 B1 | 3/2012 |
| EP | 2430986 A2 | 3/2012 |
| EP | 2444008 A2 | 4/2012 |
| EP | 1347638 B1 | 5/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486860 A2 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 2191778 B1 | 12/2012 |
| EP | 1884206 B1 | 3/2013 |
| EP | 2090238 B1 | 4/2013 |
| EP | 1806103 B1 | 5/2013 |
| EP | 2586380 A1 | 5/2013 |
| EP | 1982657 B1 | 7/2013 |

(56) References Cited

FOREIGN PATENT DOCUMENTS

| | | |
|---|---|---|
| EP | 2614782 A2 | 7/2013 |
| EP | 2090234 B1 | 9/2013 |
| EP | 2633830 A1 | 9/2013 |
| EP | 2090244 B1 | 10/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 2713902 A1 | 4/2014 |
| EP | 1772105 B1 | 5/2014 |
| EP | 2759267 A2 | 7/2014 |
| EP | 2777528 A2 | 9/2014 |
| EP | 2777538 A2 | 9/2014 |
| EP | 2446835 B1 | 1/2015 |
| EP | 2891460 A1 | 7/2015 |
| EP | 2923660 A2 | 9/2015 |
| EP | 2371296 B1 | 8/2016 |
| EP | 2116192 B1 | 3/2017 |
| EP | 3135208 A2 | 3/2017 |
| EP | 2621364 B1 | 6/2017 |
| EP | 3005956 B1 | 9/2017 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S4711908 Y1 | 5/1972 |
| JP | S5033988 U | 4/1975 |
| JP | S56112235 A | 9/1981 |
| JP | S58500053 A | 1/1983 |
| JP | S58501360 A | 8/1983 |
| JP | S59174920 A | 10/1984 |
| JP | S60100955 A | 6/1985 |
| JP | S60212152 A | 10/1985 |
| JP | S6198249 A | 5/1986 |
| JP | S61502036 A | 9/1986 |
| JP | S62170011 U | 10/1987 |
| JP | S6359764 A | 3/1988 |
| JP | S63147449 A | 6/1988 |
| JP | S63203149 A | 8/1988 |
| JP | H02279149 A | 11/1990 |
| JP | H0312126 A | 1/1991 |
| JP | H04215747 A | 8/1992 |
| JP | H04131860 U | 12/1992 |
| JP | H0584252 A | 4/1993 |
| JP | H05123325 A | 5/1993 |
| JP | H05212039 A | 8/1993 |
| JP | H067357 U | 1/1994 |
| JP | H0630945 A | 2/1994 |
| JP | H0654857 A | 3/1994 |
| JP | H0663054 A | 3/1994 |
| JP | H0626812 U | 4/1994 |
| JP | H06121798 A | 5/1994 |
| JP | H06125913 A | 5/1994 |
| JP | H06197901 A | 7/1994 |
| JP | H06237937 A | 8/1994 |
| JP | H06327684 A | 11/1994 |
| JP | H079622 U | 2/1995 |
| JP | H0731623 A | 2/1995 |
| JP | H0747070 A | 2/1995 |
| JP | H0751273 A | 2/1995 |
| JP | H07124166 A | 5/1995 |
| JP | H07163574 A | 6/1995 |
| JP | H07171163 A | 7/1995 |
| JP | H07255735 A | 10/1995 |
| JP | H07285089 A | 10/1995 |
| JP | H0833641 A | 2/1996 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08336540 A | 12/1996 |
| JP | H08336544 A | 12/1996 |
| JP | H09501081 A | 2/1997 |
| JP | H09501577 A | 2/1997 |
| JP | H09164144 A | 6/1997 |
| JP | H10113352 A | 5/1998 |
| JP | H10118090 A | 5/1998 |
| JP | H10512469 A | 12/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001046384 A | 2/2001 |
| JP | 2001087272 A | 4/2001 |
| JP | 2001514541 A | 9/2001 |
| JP | 2001276091 A | 10/2001 |
| JP | 2001286477 A | 10/2001 |
| JP | 2001517473 A | 10/2001 |
| JP | 2002051974 A | 2/2002 |
| JP | 2002085415 A | 3/2002 |
| JP | 2002143078 A | 5/2002 |
| JP | 2002204801 A | 7/2002 |
| JP | 2002528161 A | 9/2002 |
| JP | 2002314298 A | 10/2002 |
| JP | 2002369820 A | 12/2002 |
| JP | 2003000603 A | 1/2003 |
| JP | 2003500153 A | 1/2003 |
| JP | 2003504104 A | 2/2003 |
| JP | 2003135473 A | 5/2003 |
| JP | 2003148903 A | 5/2003 |
| JP | 2003164066 A | 6/2003 |
| JP | 2003521301 A | 7/2003 |
| JP | 2003523251 A | 8/2003 |
| JP | 2003523254 A | 8/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2004524076 A | 8/2004 |
| JP | 2004531280 A | 10/2004 |
| JP | 2004532084 A | 10/2004 |
| JP | 2004532676 A | 10/2004 |
| JP | 2004329624 A | 11/2004 |
| JP | 2004337617 A | 12/2004 |
| JP | 2004344662 A | 12/2004 |
| JP | 2004344663 A | 12/2004 |
| JP | 2005013573 A | 1/2005 |
| JP | 2005028147 A | 2/2005 |
| JP | 2005028148 A | 2/2005 |
| JP | 2005028149 A | 2/2005 |
| JP | 2005505309 A | 2/2005 |
| JP | 2005505322 A | 2/2005 |
| JP | 2005505334 A | 2/2005 |
| JP | 2005080702 A | 3/2005 |
| JP | 2005103280 A | 4/2005 |
| JP | 2005103281 A | 4/2005 |
| JP | 2005103293 A | 4/2005 |
| JP | 2005511131 A | 4/2005 |
| JP | 2005511137 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |

(56) References Cited

FOREIGN PATENT DOCUMENTS

| | | |
|---|---|---|
| JP | 2005131212 A | 5/2005 |
| JP | 2005137423 A | 6/2005 |
| JP | 2005137919 A | 6/2005 |
| JP | 2005144183 A | 6/2005 |
| JP | 2005152416 A | 6/2005 |
| JP | 2005516714 A | 6/2005 |
| JP | 2005521109 A | 7/2005 |
| JP | 2005523105 A | 8/2005 |
| JP | 2005524474 A | 8/2005 |
| JP | 2005296412 A | 10/2005 |
| JP | 2005328882 A | 12/2005 |
| JP | 2005335432 A | 12/2005 |
| JP | 2005342267 A | 12/2005 |
| JP | 2006034975 A | 2/2006 |
| JP | 2006034977 A | 2/2006 |
| JP | 2006034978 A | 2/2006 |
| JP | 2006034980 A | 2/2006 |
| JP | 2006506106 A | 2/2006 |
| JP | 2006510879 A | 3/2006 |
| JP | 2006187649 A | 7/2006 |
| JP | 2006218297 A | 8/2006 |
| JP | 2006223872 A | 8/2006 |
| JP | 2006281405 A | 10/2006 |
| JP | 2006289064 A | 10/2006 |
| JP | 2006334412 A | 12/2006 |
| JP | 2006334417 A | 12/2006 |
| JP | 2006346445 A | 12/2006 |
| JP | 2007000634 A | 1/2007 |
| JP | 2007050253 A | 3/2007 |
| JP | 2007061628 A | 3/2007 |
| JP | 3906843 B2 | 4/2007 |
| JP | 2007083051 A | 4/2007 |
| JP | 2007098130 A | 4/2007 |
| JP | 2007105481 A | 4/2007 |
| JP | 2007117725 A | 5/2007 |
| JP | 2007130471 A | 5/2007 |
| JP | 2007130479 A | 5/2007 |
| JP | 3934161 B2 | 6/2007 |
| JP | 2007203049 A | 8/2007 |
| JP | 2007203051 A | 8/2007 |
| JP | 2007203055 A | 8/2007 |
| JP | 2007203057 A | 8/2007 |
| JP | 2007524435 A | 8/2007 |
| JP | 2007222615 A | 9/2007 |
| JP | 2007229448 A | 9/2007 |
| JP | 4001860 B2 | 10/2007 |
| JP | 2007252916 A | 10/2007 |
| JP | 2007307373 A | 11/2007 |
| JP | 2007325922 A | 12/2007 |
| JP | 2008068073 A | 3/2008 |
| JP | 2008206967 A | 9/2008 |
| JP | 2008212637 A | 9/2008 |
| JP | 2008212638 A | 9/2008 |
| JP | 2008220956 A | 9/2008 |
| JP | 2008237881 A | 10/2008 |
| JP | 2008259860 A | 10/2008 |
| JP | 2008264535 A | 11/2008 |
| JP | 2008283459 A | 11/2008 |
| JP | 2009006137 A | 1/2009 |
| JP | 2009502351 A | 1/2009 |
| JP | 2009502352 A | 1/2009 |
| JP | 2009022742 A | 2/2009 |
| JP | 2009506799 A | 2/2009 |
| JP | 2009507526 A | 2/2009 |
| JP | 2009072599 A | 4/2009 |
| JP | 2009090113 A | 4/2009 |
| JP | 2009106752 A | 5/2009 |
| JP | 2009189836 A | 8/2009 |
| JP | 2009189837 A | 8/2009 |
| JP | 2009189838 A | 8/2009 |
| JP | 2009201998 A | 9/2009 |
| JP | 2009536082 A | 10/2009 |
| JP | 2009261944 A | 11/2009 |
| JP | 2009268908 A | 11/2009 |
| JP | 2009539420 A | 11/2009 |
| JP | 2009291604 A | 12/2009 |
| JP | 2010504808 A | 2/2010 |
| JP | 2010504809 A | 2/2010 |
| JP | 2010504846 A | 2/2010 |
| JP | 2010505524 A | 2/2010 |
| JP | 2010069310 A | 4/2010 |
| JP | 2010075695 A | 4/2010 |
| JP | 2010088876 A | 4/2010 |
| JP | 2010098844 A | 4/2010 |
| JP | 4461008 B2 | 5/2010 |
| JP | 4549018 B2 | 9/2010 |
| JP | 2010214166 A | 9/2010 |
| JP | 2010540192 A | 12/2010 |
| JP | 4783373 B2 | 9/2011 |
| JP | 2011524199 A | 9/2011 |
| JP | 5140421 B2 | 2/2013 |
| JP | 5162595 B2 | 3/2013 |
| JP | 2013128791 A | 7/2013 |
| JP | 5333899 B2 | 11/2013 |
| KR | 20110003229 A | 1/2011 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-8202824 A1 | 9/1982 |
| WO | WO-8602254 A1 | 4/1986 |
| WO | WO-9115157 A1 | 10/1991 |
| WO | WO-9220295 A1 | 11/1992 |
| WO | WO-9221300 A1 | 12/1992 |
| WO | WO-9308755 A1 | 5/1993 |
| WO | WO-9313718 A1 | 7/1993 |
| WO | WO-9314690 A1 | 8/1993 |
| WO | WO-9315648 A1 | 8/1993 |
| WO | WO-9315850 A1 | 8/1993 |
| WO | WO-9319681 A1 | 10/1993 |
| WO | WO-9400060 A1 | 1/1994 |
| WO | WO-9411057 A1 | 5/1994 |
| WO | WO-9412108 A1 | 6/1994 |
| WO | WO-9417737 A1 | 8/1994 |
| WO | WO-9418893 A1 | 9/1994 |
| WO | WO-9420030 A1 | 9/1994 |
| WO | WO-9422378 A1 | 10/1994 |
| WO | WO-9423659 A1 | 10/1994 |
| WO | WO-9424943 A1 | 11/1994 |
| WO | WO-9424947 A1 | 11/1994 |
| WO | WO-9502369 A1 | 1/1995 |
| WO | WO-9503743 A1 | 2/1995 |
| WO | WO-9506817 A1 | 3/1995 |
| WO | WO-9509576 A1 | 4/1995 |
| WO | WO-9509577 A1 | 4/1995 |
| WO | WO-9514436 A1 | 6/1995 |
| WO | WO-9517855 A1 | 7/1995 |
| WO | WO-9518383 A1 | 7/1995 |
| WO | WO-9518572 A1 | 7/1995 |
| WO | WO-9519739 A1 | 7/1995 |
| WO | WO-9520360 A1 | 8/1995 |

(56) References Cited

FOREIGN PATENT DOCUMENTS

| | | |
|---|---|---|
| WO | WO-9523557 A1 | 9/1995 |
| WO | WO-9524865 A1 | 9/1995 |
| WO | WO-9525471 A3 | 9/1995 |
| WO | WO-9526562 A1 | 10/1995 |
| WO | WO-9529639 A1 | 11/1995 |
| WO | WO-9604858 A1 | 2/1996 |
| WO | WO-9618344 A2 | 6/1996 |
| WO | WO-9619151 A1 | 6/1996 |
| WO | WO-9619152 A1 | 6/1996 |
| WO | WO-9620652 A1 | 7/1996 |
| WO | WO-9621119 A1 | 7/1996 |
| WO | WO-9622055 A1 | 7/1996 |
| WO | WO-9623448 A1 | 8/1996 |
| WO | WO-9624301 A1 | 8/1996 |
| WO | WO-9627337 A1 | 9/1996 |
| WO | WO-9631155 A1 | 10/1996 |
| WO | WO-9635464 A1 | 11/1996 |
| WO | WO-9639085 A1 | 12/1996 |
| WO | WO-9639086 A1 | 12/1996 |
| WO | WO-9639087 A1 | 12/1996 |
| WO | WO-9639088 A1 | 12/1996 |
| WO | WO-9639089 A1 | 12/1996 |
| WO | WO-9700646 A1 | 1/1997 |
| WO | WO-9700647 A1 | 1/1997 |
| WO | WO-9701989 A1 | 1/1997 |
| WO | WO-9706582 A1 | 2/1997 |
| WO | WO-9710763 A1 | 3/1997 |
| WO | WO-9710764 A1 | 3/1997 |
| WO | WO-9711648 A2 | 4/1997 |
| WO | WO-9711649 A1 | 4/1997 |
| WO | WO-9715237 A1 | 5/1997 |
| WO | WO-9724073 A1 | 7/1997 |
| WO | WO-9724993 A1 | 7/1997 |
| WO | WO-9730644 A1 | 8/1997 |
| WO | WO-9734533 A1 | 9/1997 |
| WO | WO-9737598 A1 | 10/1997 |
| WO | WO-9739688 A2 | 10/1997 |
| WO | WO-9801080 A1 | 1/1998 |
| WO | WO-9817180 A1 | 4/1998 |
| WO | WO-9822154 A2 | 5/1998 |
| WO | WO-9827880 A1 | 7/1998 |
| WO | WO-9830153 A1 | 7/1998 |
| WO | WO-9847436 A1 | 10/1998 |
| WO | WO-9858589 A1 | 12/1998 |
| WO | WO-9902090 A1 | 1/1999 |
| WO | WO-9903407 A1 | 1/1999 |
| WO | WO-9903408 A1 | 1/1999 |
| WO | WO-9903409 A1 | 1/1999 |
| WO | WO-9912483 A1 | 3/1999 |
| WO | WO-9912487 A1 | 3/1999 |
| WO | WO-9912488 A1 | 3/1999 |
| WO | WO-9915086 A1 | 4/1999 |
| WO | WO-9915091 A1 | 4/1999 |
| WO | WO-9923933 A2 | 5/1999 |
| WO | WO-9923959 A1 | 5/1999 |
| WO | WO-9925261 A1 | 5/1999 |
| WO | WO-9929244 A1 | 6/1999 |
| WO | WO-9934744 A1 | 7/1999 |
| WO | WO-9945849 A1 | 9/1999 |
| WO | WO-9948430 A1 | 9/1999 |
| WO | WO-9951158 A1 | 10/1999 |
| WO | WO-0024322 A1 | 5/2000 |
| WO | WO-0024330 A1 | 5/2000 |
| WO | WO-0041638 A1 | 7/2000 |
| WO | WO-0048506 A1 | 8/2000 |
| WO | WO-0053112 A2 | 9/2000 |
| WO | WO-0054653 A1 | 9/2000 |
| WO | WO-0057796 A1 | 10/2000 |
| WO | WO-0064365 A1 | 11/2000 |
| WO | WO-0072762 A1 | 12/2000 |
| WO | WO-0072765 A1 | 12/2000 |
| WO | WO-0078222 A1 | 12/2000 |
| WO | WO-0103587 A1 | 1/2001 |
| WO | WO-0105702 A1 | 1/2001 |
| WO | WO-0110482 A1 | 2/2001 |
| WO | WO-0135845 A1 | 5/2001 |
| WO | WO-0154594 A1 | 8/2001 |
| WO | WO-0158371 A1 | 8/2001 |
| WO | WO-0162158 A2 | 8/2001 |
| WO | WO-0162161 A1 | 8/2001 |
| WO | WO-0162162 A1 | 8/2001 |
| WO | WO-0162163 A1 | 8/2001 |
| WO | WO-0162164 A2 | 8/2001 |
| WO | WO-0162169 A2 | 8/2001 |
| WO | WO-0178605 A2 | 10/2001 |
| WO | WO-0180757 A2 | 11/2001 |
| WO | WO-0191646 A1 | 12/2001 |
| WO | WO-0200121 A1 | 1/2002 |
| WO | WO-0207608 A2 | 1/2002 |
| WO | WO-0207618 A1 | 1/2002 |
| WO | WO-0217799 A1 | 3/2002 |
| WO | WO-0219920 A1 | 3/2002 |
| WO | WO-0219932 A1 | 3/2002 |
| WO | WO-0226143 A1 | 4/2002 |
| WO | WO-0230297 A2 | 4/2002 |
| WO | WO-0232322 A2 | 4/2002 |
| WO | WO-0236028 A1 | 5/2002 |
| WO | WO-0243571 A2 | 6/2002 |
| WO | WO-02058568 A1 | 8/2002 |
| WO | WO-02060328 A1 | 8/2002 |
| WO | WO-02065933 A2 | 8/2002 |
| WO | WO-02067785 A2 | 9/2002 |
| WO | WO-02080781 A2 | 10/2002 |
| WO | WO-02085218 A2 | 10/2002 |
| WO | WO-02087586 A1 | 11/2002 |
| WO | WO-02098302 A1 | 12/2002 |
| WO | WO-03000138 A2 | 1/2003 |
| WO | WO-03001329 A2 | 1/2003 |
| WO | WO-03001986 A2 | 1/2003 |
| WO | WO-03013363 A1 | 2/2003 |
| WO | WO-03013372 A2 | 2/2003 |
| WO | WO-03015604 A2 | 2/2003 |
| WO | WO-03020106 A2 | 3/2003 |
| WO | WO-03020139 A2 | 3/2003 |
| WO | WO-03024339 A1 | 3/2003 |
| WO | WO-03030743 A2 | 4/2003 |
| WO | WO-03037193 A1 | 5/2003 |
| WO | WO-03055402 A1 | 7/2003 |
| WO | WO-03057048 A1 | 7/2003 |
| WO | WO-03057058 A1 | 7/2003 |
| WO | WO-03063694 A1 | 8/2003 |
| WO | WO-03077769 A1 | 9/2003 |
| WO | WO-03079911 A1 | 10/2003 |
| WO | WO-03082126 A1 | 10/2003 |
| WO | WO-03086206 A1 | 10/2003 |
| WO | WO-03088845 A2 | 10/2003 |
| WO | WO-03047436 A3 | 11/2003 |
| WO | WO-03090630 A2 | 11/2003 |
| WO | WO-03094743 A1 | 11/2003 |
| WO | WO-03094745 A1 | 11/2003 |
| WO | WO-03094746 A1 | 11/2003 |
| WO | WO-03094747 A1 | 11/2003 |
| WO | WO-03101313 A1 | 12/2003 |
| WO | WO-03105698 A2 | 12/2003 |
| WO | WO-03105702 A2 | 12/2003 |
| WO | WO-2004004578 A1 | 1/2004 |
| WO | WO-2004006980 A2 | 1/2004 |
| WO | WO-2004011037 A2 | 2/2004 |
| WO | WO-2004014238 A2 | 2/2004 |
| WO | WO-03079909 A3 | 3/2004 |
| WO | WO-2004019769 A1 | 3/2004 |
| WO | WO-2004019803 A1 | 3/2004 |
| WO | WO-2004021868 A2 | 3/2004 |
| WO | WO-2004028585 A2 | 4/2004 |
| WO | WO-2004030554 A1 | 4/2004 |
| WO | WO-2004032754 A2 | 4/2004 |
| WO | WO-2004032760 A2 | 4/2004 |
| WO | WO-2004032762 A1 | 4/2004 |
| WO | WO-2004032763 A2 | 4/2004 |
| WO | WO-2004032783 A1 | 4/2004 |
| WO | WO-2004034875 A2 | 4/2004 |
| WO | WO-2004047626 A1 | 6/2004 |
| WO | WO-2004047653 A2 | 6/2004 |
| WO | WO-2004049956 A2 | 6/2004 |

(56) References Cited

FOREIGN PATENT DOCUMENTS

| | | |
|---|---|---|
| WO | WO-2004050971 A2 | 6/2004 |
| WO | WO-2004052426 A2 | 6/2004 |
| WO | WO-2004056276 A1 | 7/2004 |
| WO | WO-2004056277 A1 | 7/2004 |
| WO | WO-2004058079 A2 | 7/2004 |
| WO | WO-2004062516 A1 | 7/2004 |
| WO | WO-2004064600 A2 | 8/2004 |
| WO | WO-2004078050 A2 | 9/2004 |
| WO | WO-2004078051 A2 | 9/2004 |
| WO | WO-2004078236 A2 | 9/2004 |
| WO | WO-2004086987 A1 | 10/2004 |
| WO | WO-2004096015 A2 | 11/2004 |
| WO | WO-2004096057 A2 | 11/2004 |
| WO | WO-2004103157 A2 | 12/2004 |
| WO | WO-2004105593 A1 | 12/2004 |
| WO | WO-2004105621 A1 | 12/2004 |
| WO | WO-2004112618 A2 | 12/2004 |
| WO | WO-2004112652 A2 | 12/2004 |
| WO | WO-2005027983 A2 | 3/2005 |
| WO | WO-2005037329 A2 | 4/2005 |
| WO | WO-2005042041 A1 | 5/2005 |
| WO | WO-2005044078 A2 | 5/2005 |
| WO | WO-2005055846 A1 | 6/2005 |
| WO | WO-2005072634 A2 | 8/2005 |
| WO | WO-2005078892 A1 | 8/2005 |
| WO | WO-2005079675 A2 | 9/2005 |
| WO | WO-2005087128 A1 | 9/2005 |
| WO | WO-2005096954 A2 | 10/2005 |
| WO | WO-2005112806 A2 | 12/2005 |
| WO | WO-2005112808 A1 | 12/2005 |
| WO | WO-2005115251 A1 | 12/2005 |
| WO | WO-2005115253 A2 | 12/2005 |
| WO | WO-2005117735 A1 | 12/2005 |
| WO | WO-2005122936 A1 | 12/2005 |
| WO | WO-2006023486 A1 | 3/2006 |
| WO | WO-2006023578 A2 | 3/2006 |
| WO | WO-2006027014 A1 | 3/2006 |
| WO | WO-2006028314 A1 | 3/2006 |
| WO | WO-2006044490 A2 | 4/2006 |
| WO | WO-2006044581 A2 | 4/2006 |
| WO | WO-2006044810 A2 | 4/2006 |
| WO | WO-2006049852 A2 | 5/2006 |
| WO | WO-2006051252 A1 | 5/2006 |
| WO | WO-2006059067 A1 | 6/2006 |
| WO | WO-2006083748 A1 | 8/2006 |
| WO | WO-2006085389 A1 | 8/2006 |
| WO | WO-2006092563 A1 | 9/2006 |
| WO | WO-2006092565 A1 | 9/2006 |
| WO | WO-2006115958 A1 | 11/2006 |
| WO | WO-2006125940 A1 | 11/2006 |
| WO | WO-2006132992 A2 | 12/2006 |
| WO | WO-2007002180 A2 | 1/2007 |
| WO | WO-2007016290 A2 | 2/2007 |
| WO | WO-2007018898 A2 | 2/2007 |
| WO | WO-2007059233 A2 | 5/2007 |
| WO | WO-2007074430 A1 | 7/2007 |
| WO | WO-2007089603 A2 | 8/2007 |
| WO | WO-2007098220 A2 | 8/2007 |
| WO | WO-2007121579 A1 | 11/2007 |
| WO | WO-2007129121 A1 | 11/2007 |
| WO | WO-2007131110 A2 | 11/2007 |
| WO | WO-2007137304 A2 | 11/2007 |
| WO | WO-2007139734 A2 | 12/2007 |
| WO | WO-2007142625 A2 | 12/2007 |
| WO | WO-2007145825 A2 | 12/2007 |
| WO | WO-2007146987 A2 | 12/2007 |
| WO | WO-2007147439 A1 | 12/2007 |
| WO | WO-2008020964 A2 | 2/2008 |
| WO | WO-2008021969 A2 | 2/2008 |
| WO | WO-2008039237 A1 | 4/2008 |
| WO | WO-2008039249 A1 | 4/2008 |
| WO | WO-2008039270 A1 | 4/2008 |
| WO | WO-2008045383 A2 | 4/2008 |
| WO | WO-2008057281 A2 | 5/2008 |
| WO | WO-2008070763 A1 | 6/2008 |
| WO | WO-2008089404 A2 | 7/2008 |
| WO | WO-2008101080 A1 | 8/2008 |
| WO | WO-2008101228 A2 | 8/2008 |
| WO | WO-2008103797 A2 | 8/2008 |
| WO | WO-2008109125 A1 | 9/2008 |
| WO | WO-2008112912 A2 | 9/2008 |
| WO | WO-2008118728 A1 | 10/2008 |
| WO | WO-2008124748 A1 | 10/2008 |
| WO | WO-2009005969 A2 | 1/2009 |
| WO | WO-2009022614 A1 | 2/2009 |
| WO | WO-2009023851 A1 | 2/2009 |
| WO | WO-2009033057 A2 | 3/2009 |
| WO | WO-2009039506 A1 | 3/2009 |
| WO | WO-2009046394 A1 | 4/2009 |
| WO | WO-2009067649 A2 | 5/2009 |
| WO | WO-2009091497 A2 | 7/2009 |
| WO | WO-2009120944 A2 | 10/2009 |
| WO | WO-2009137761 A2 | 11/2009 |
| WO | WO-2009143092 A1 | 11/2009 |
| WO | WO-2009143331 A1 | 11/2009 |
| WO | WO-2009150650 A2 | 12/2009 |
| WO | WO-2009152307 A1 | 12/2009 |
| WO | WO-2010028332 A2 | 3/2010 |
| WO | WO-2010030434 A1 | 3/2010 |
| WO | WO-2010045425 A1 | 4/2010 |
| WO | WO-2010050771 A2 | 5/2010 |
| WO | WO-2010054404 A1 | 5/2010 |
| WO | WO-2010056714 A1 | 5/2010 |
| WO | WO-2010063795 A1 | 6/2010 |
| WO | WO-2010090940 A1 | 8/2010 |
| WO | WO-2010093333 A1 | 8/2010 |
| WO | WO-2010098871 A2 | 9/2010 |
| WO | WO-2011008672 A2 | 1/2011 |
| WO | WO-2011013103 A1 | 2/2011 |
| WO | WO-2011044343 A2 | 4/2011 |
| WO | WO-2011060311 A2 | 5/2011 |
| WO | WO-2012006306 A2 | 1/2012 |
| WO | WO-2012/013577 A1 | 2/2012 |
| WO | WO-2012021671 A2 | 2/2012 |
| WO | WO-2012040438 A1 | 3/2012 |
| WO | WO-2012044551 A1 | 4/2012 |
| WO | WO-2012044554 A1 | 4/2012 |
| WO | WO-2012044597 A1 | 4/2012 |
| WO | WO-2012044606 A2 | 4/2012 |
| WO | WO-2012044820 A1 | 4/2012 |
| WO | WO-2012044844 A2 | 4/2012 |
| WO | WO-2012044853 A1 | 4/2012 |
| WO | WO-2012058213 A2 | 5/2012 |
| WO | WO-2012068156 A2 | 5/2012 |
| WO | WO-2012127462 A1 | 9/2012 |
| WO | WO-2012135705 A1 | 10/2012 |
| WO | WO-2012143913 A2 | 10/2012 |
| WO | WO-2012148667 A2 | 11/2012 |
| WO | WO-2012148703 A2 | 11/2012 |
| WO | WO-2012160163 A1 | 11/2012 |
| WO | WO-2012166503 A1 | 12/2012 |
| WO | WO-2013009699 A2 | 1/2013 |
| WO | WO-2013016633 A1 | 1/2013 |
| WO | WO-2013036409 A1 | 3/2013 |
| WO | WO-2013043707 A2 | 3/2013 |
| WO | WO-2013043717 A1 | 3/2013 |
| WO | WO-2013043721 A2 | 3/2013 |
| WO | WO-2013062978 A2 | 5/2013 |
| WO | WO-2013148762 A2 | 10/2013 |
| WO | WO-2013167427 A1 | 11/2013 |
| WO | WO-2014004199 A1 | 1/2014 |
| WO | WO-2014004294 A2 | 1/2014 |
| WO | WO-2016/057225 A1 | 4/2016 |

OTHER PUBLICATIONS

"Indian Standard: Automotive Vehicles—Brakes and Braking Systems (IS 11852-1:2001)", Mar. 1, 2001.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Anonymous: "Stamping (metalworking)—Wikipedia," Jun. 6, 2016, Retrieved from the Internet: URL: https://en.wikipedia.org/w/index.

(56) References Cited

OTHER PUBLICATIONS php?title-Stamping_(metalworking)&oldid=723906245 [retrieved on May 15, 2018].
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Breedveld et al., "A New, Easily Miniaturized Sterrable Endoscope," IEEE Engineering in Medicine and Biology Magazine (Nov./Dec. 2005).
Byrne et al., "Molecular Imprinting Within Hydrogels," Advanced Drug Delivery Reviews, 54 (2002) pp. 149-161.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Chen et al., "Elastomeric Biomaterials for Tissue Engineering," Progress in Polymer Science 38 (2013), pp. 584-671.
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Curved Tip Reload with Tri-Staple™ Technology," (2012), 2 pages.
Covidien Brochure, "Endo GIA™ Reloads with Tri-Staple™ Technology and Endo GIA™ Ultra Universal Staplers," (2010), 2 pages.
Covidien Brochure, "Endo GIA™ Reloads with Tri-Staple™ Technology," (2010), 1 page.
Covidien Brochure, "Endo GIA™ Reloads with Tri-Staple™ Technology," (2010), 2 pages.
Covidien Brochure, "Endo GIA™ Black Reload with Tri-Staple™ Technology," (2012), 2 pages.
Covidien Brochure, "Endo GIA™ Ultra Universal Stapler," (2010), 2 pages.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Disclosed Anonymously, "Motor-Driven Surgical Stapler Improvements," Research Disclosure Database No. 526041, Published: Feb. 2008.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Erdmann et al., "Evaluation of the Soft Tissue Biocompatibility of MgCa0.8 and Surgical Steel 316L In Vivo: A Comparative Study in Rabbits," Biomed. Eng. OnLine 2010 9:63 (17 pages).
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
http://ninpgan.net/publications/51-100/89.pdf; 2004, Ning Pan, On Uniqueness of Fibrous Materials, Design & Nature II. Eds: Colins, M. and Brebbia, C. Wit Press, Boston, 493-504.
Jeong et al., "Thermosensitive Sol-Gel Reversible Hydrogels," Advanced Drug Delivery Reviews, 54 (2002) pp. 37-51.
Li et al. "Mg—Zr—Sr Alloys as Biodegradable Implant Materials," Acta Biomaterialia 8 (2012) 3177-3188 (12 pages).
Matsuda, "Thermodynamics of Formation of Porous Polymeric Membrane from Solutions," Polymer Journal, vol. 23, No. 5, pp. 435-444 (1991).
Miyata et al., "Biomolecule-Sensitive Hydrogels," Advanced Drug Delivery Reviews, 54 (2002) pp. 79-98.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Pitt et al., "Attachment of Hyaluronan to Metallic Surfaces," J. Biomed. Mater. Res. 68A: pp. 95-106, 2004.
Qiu et al., "Environment-Sensitive Hydrogels for Drug Delivery," Advanced Drug Delivery Reviews, 53 (2001) pp. 321-339.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Seils et al., Covidien Summary: Clinical Study "UCONN Biodynamics: Final Report on Results," (2 pages).
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Solorio et al., "Gelatin Microspheres Crosslinked with Genipin for Local Delivery of Growth Factors," J. Tissue Eng. Regen. Med. (2010), 4(7): pp. 514-523.
The Sodem Aseptic Battery Transfer Kit, Sodem Systems, 2000, 3 pages.
Van Meer et al., "A Disposable Plastic Compact Wrist for Smart Minimally Invasive Surgical Tools," LAAS/CNRS (Aug. 2005).
Yan et al, Comparison of the effects of Mg—6Zn and Ti—3Al-2.5V alloys on TGF-$\beta$/TNF-$\alpha$/VEGF/b-FGF in the healing of the intestinal track in vivo, Biomed. Mater. 9 (2014), 11 pages.
Yan et al., "Comparison of the effects of Mg—6Zn and titanium on intestinal tract in vivo," J Mater Sci: Mater Med (2013), 11 pages.
Young, "Microcellular foams via phase separation," Journal of Vacuum Science & Technology A 4(3), (May/Jun. 1986).

\* cited by examiner

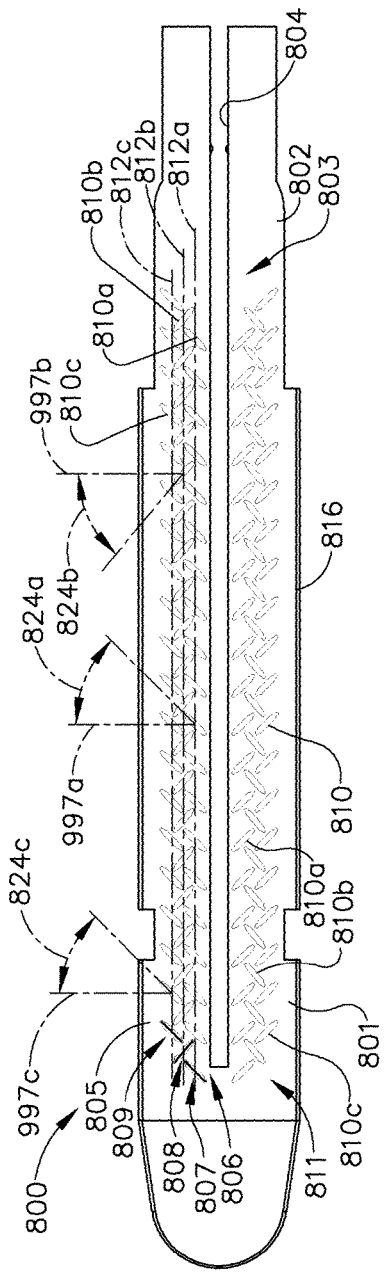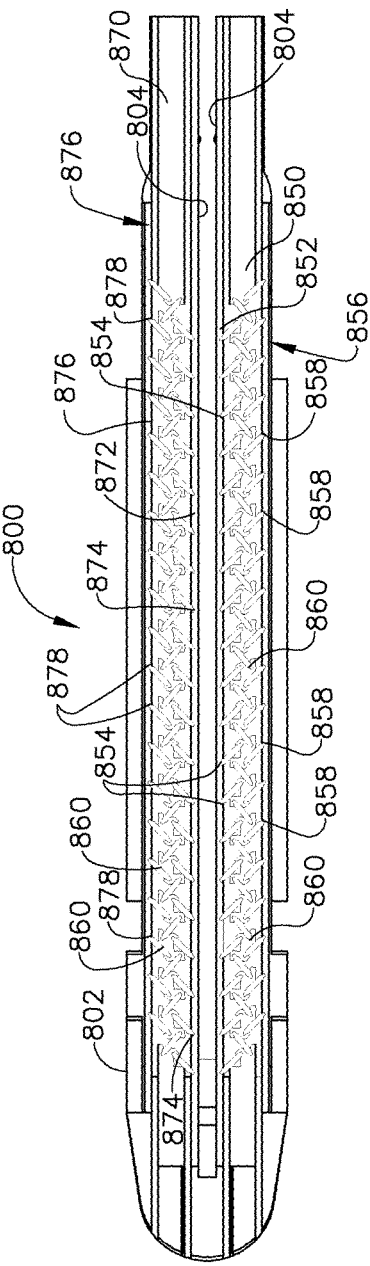

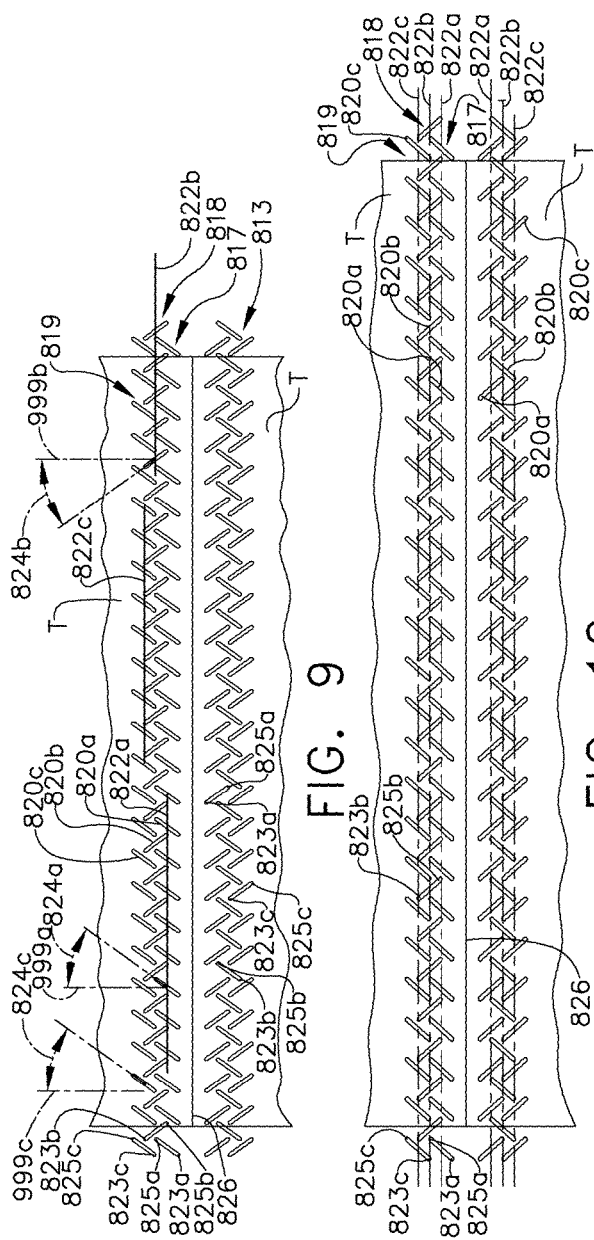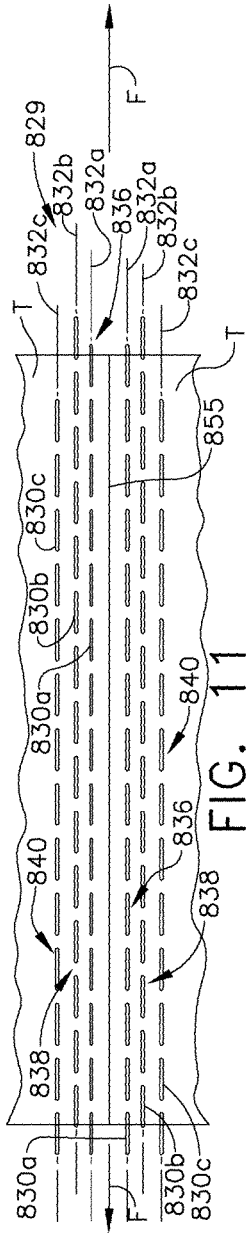

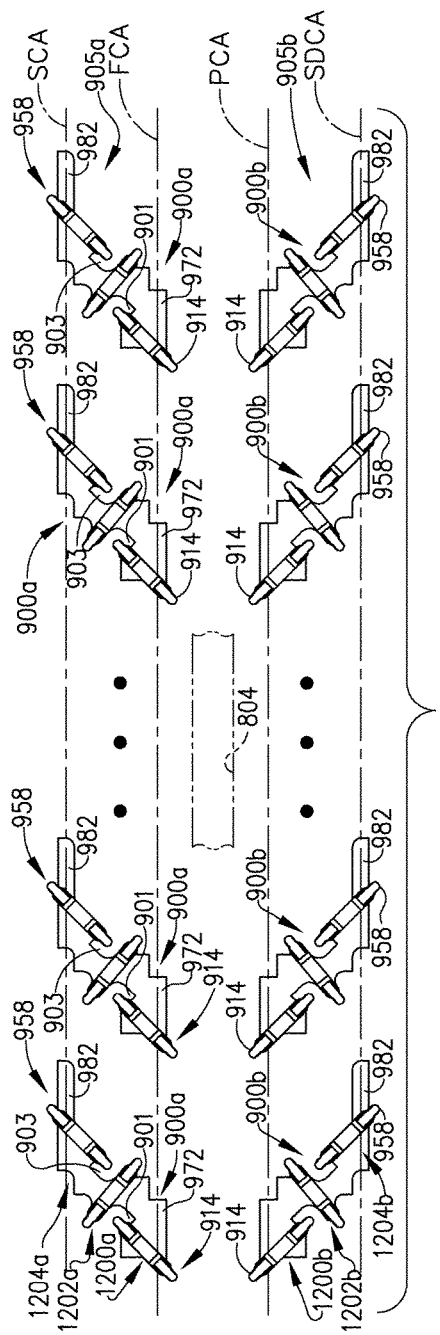
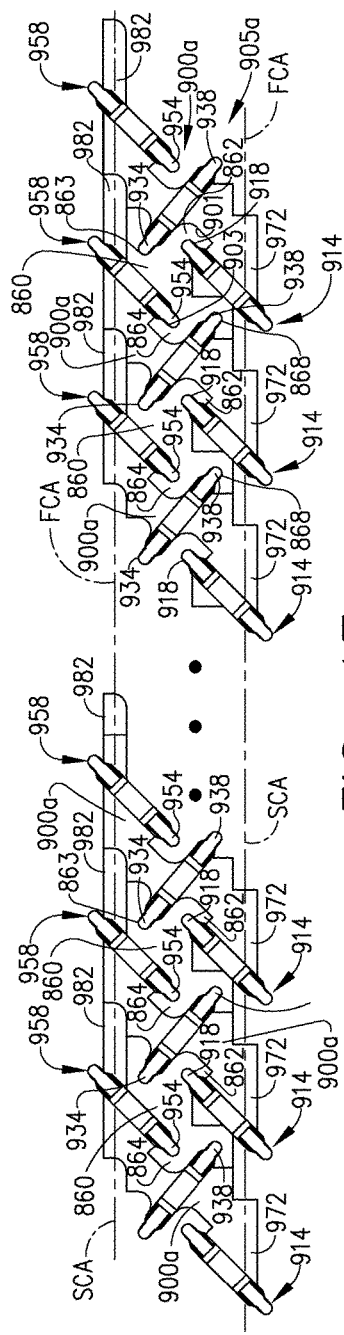
FIG. 16
FIG. 17

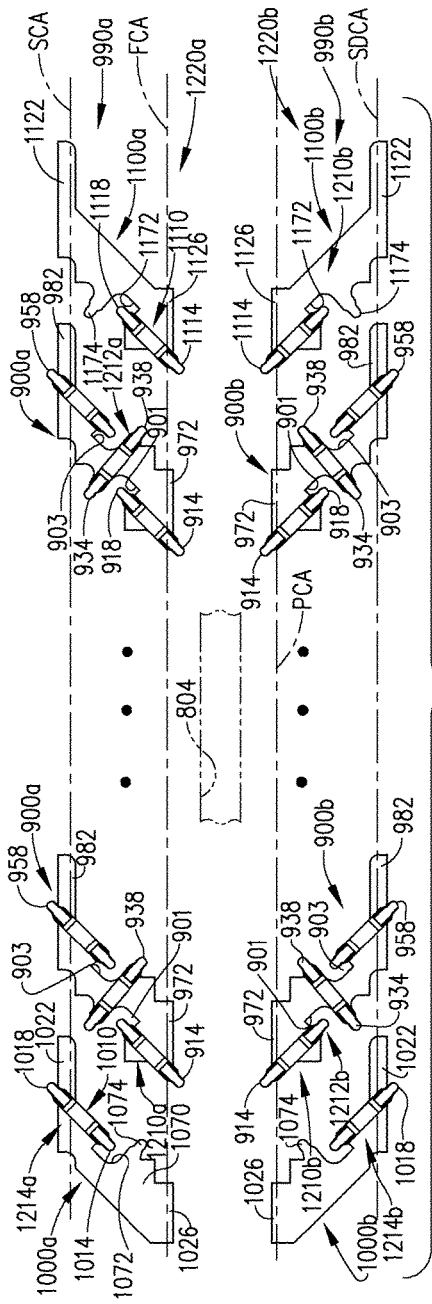
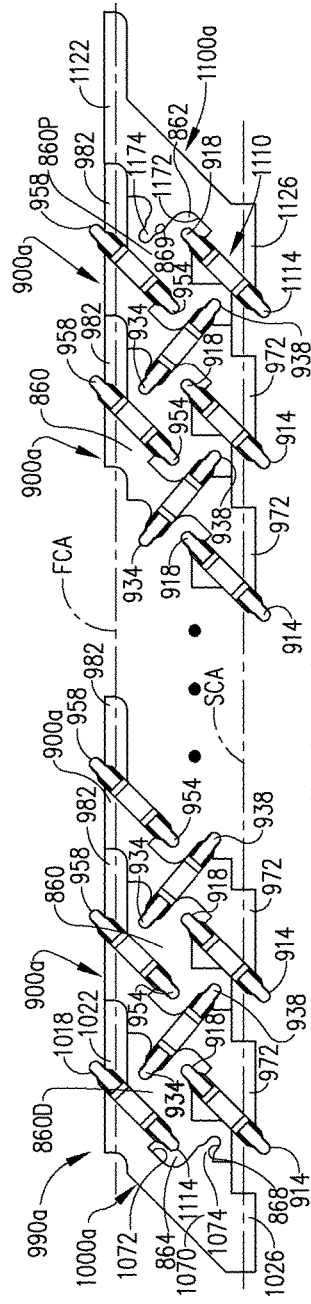
FIG. 20
FIG. 21

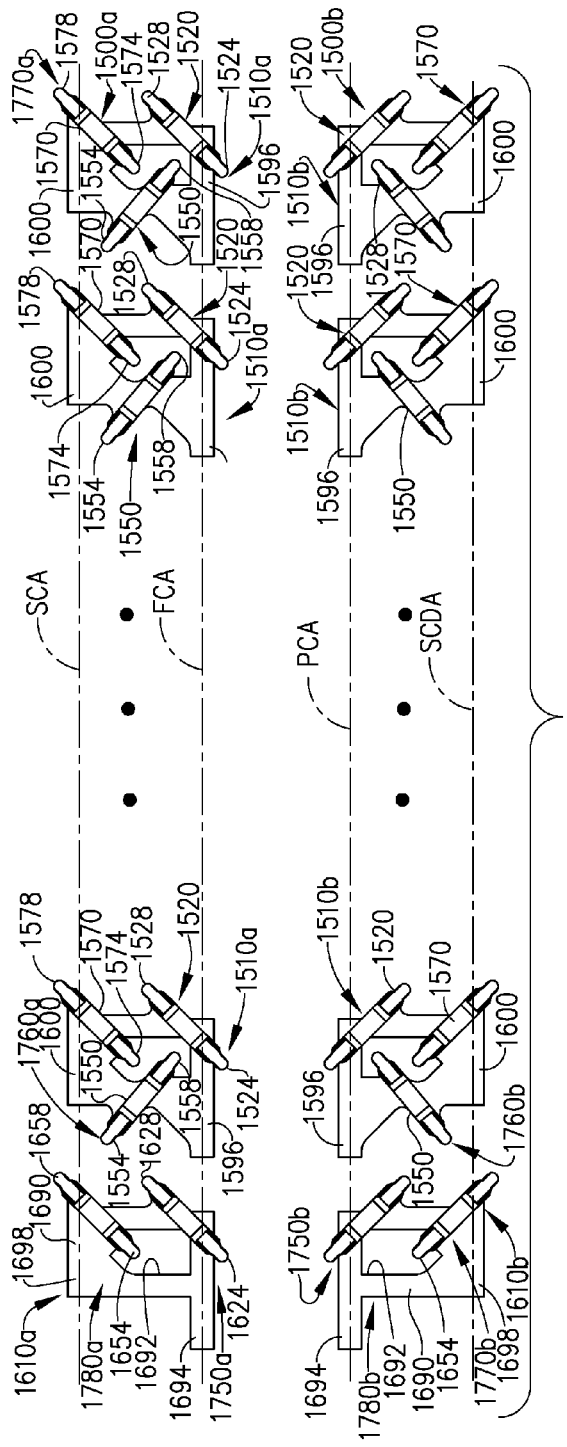
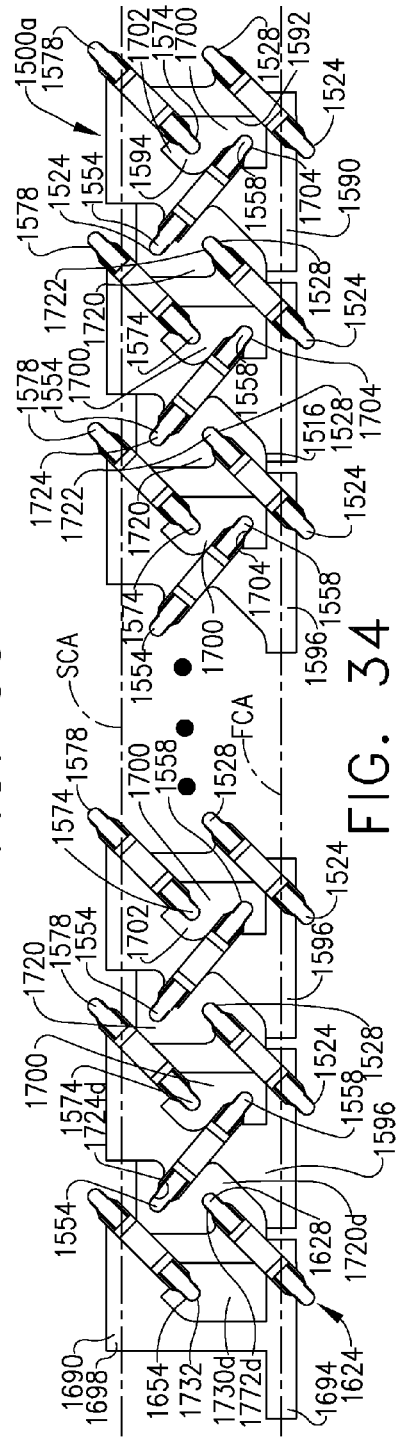
FIG. 33
FIG. 34

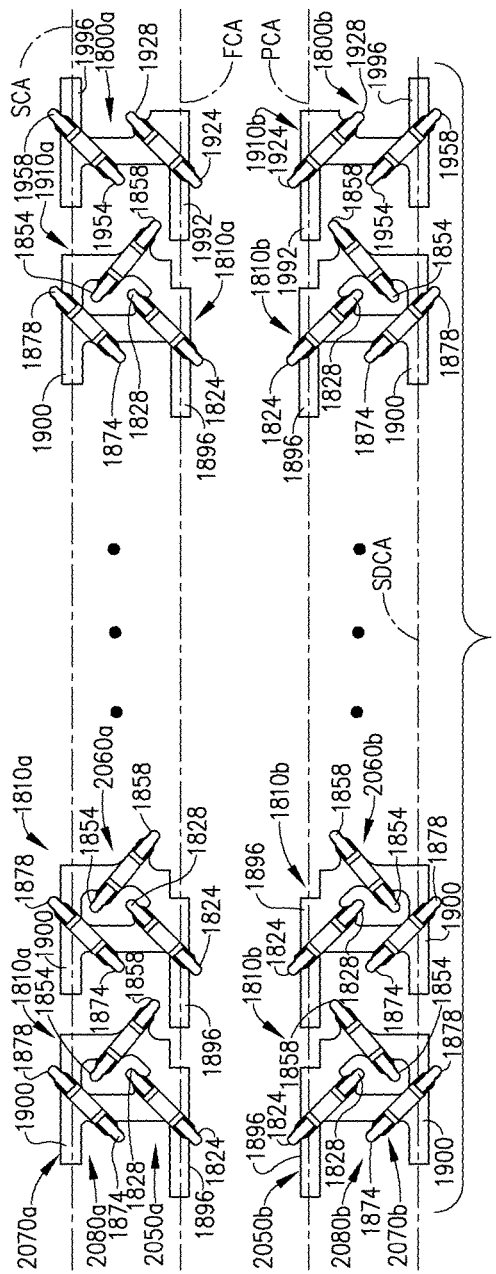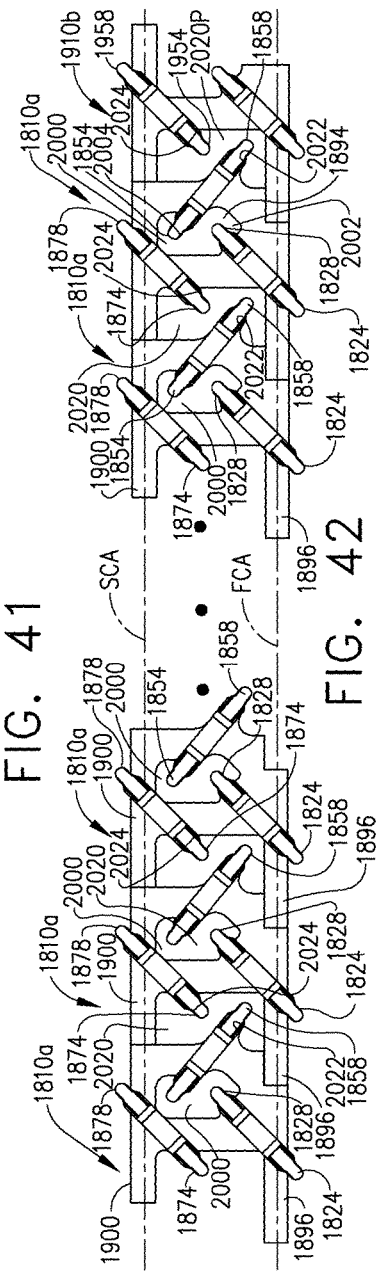
FIG. 41
FIG. 42

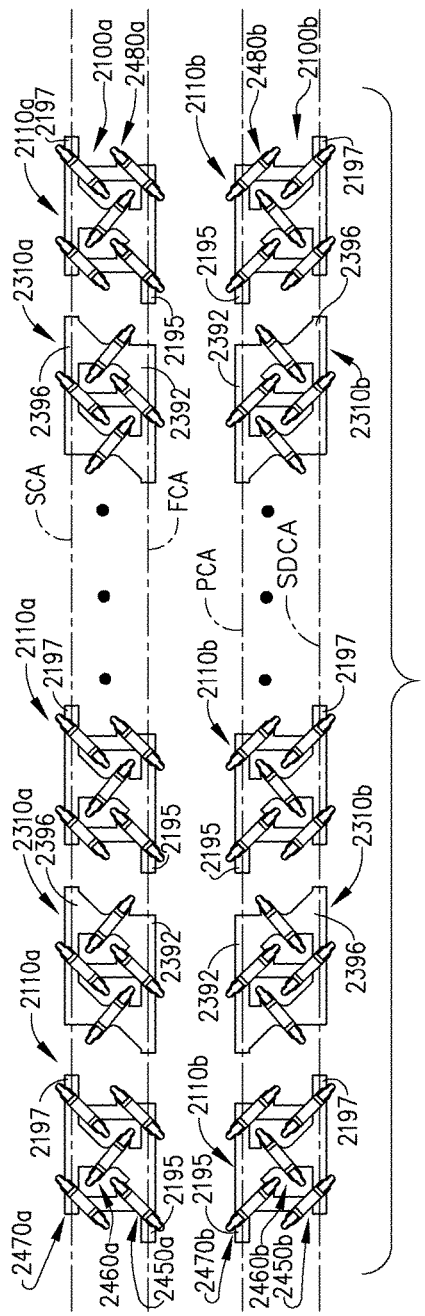
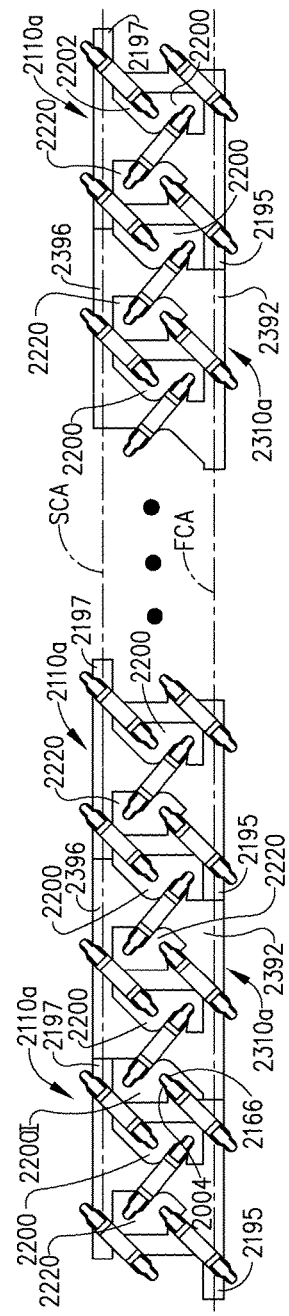
FIG. 49
FIG. 50

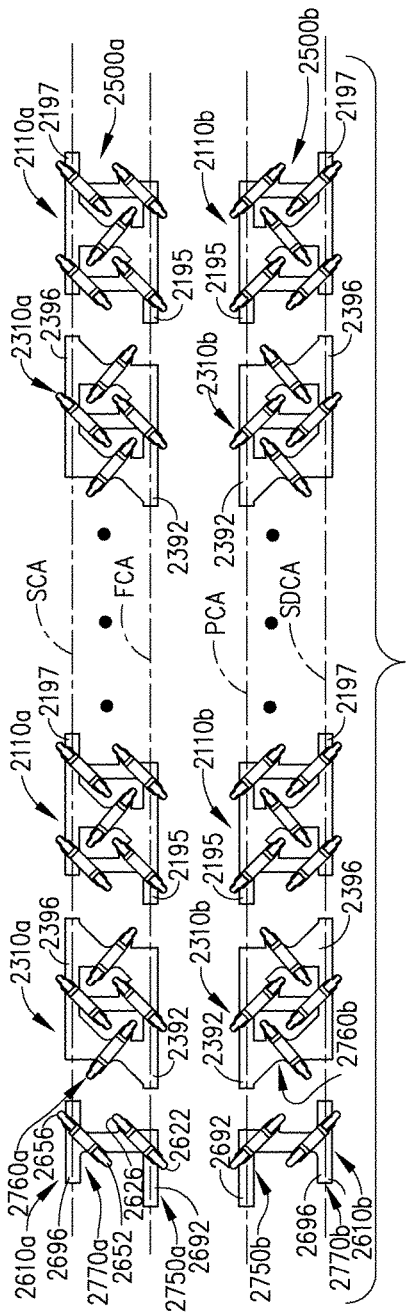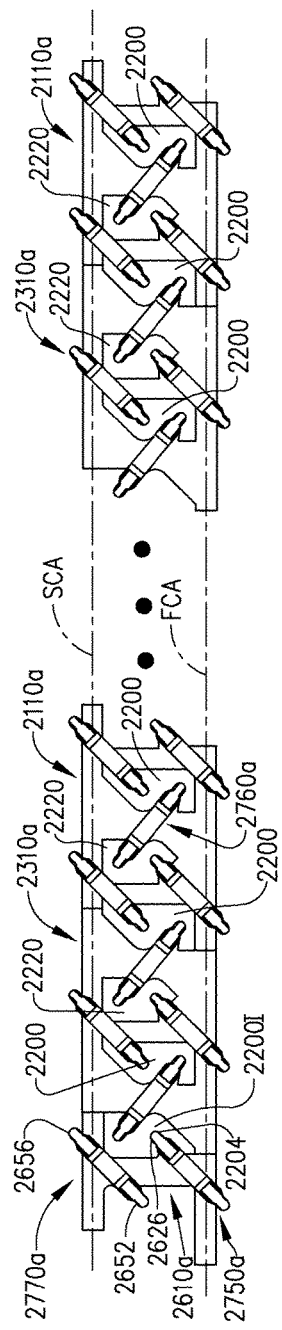

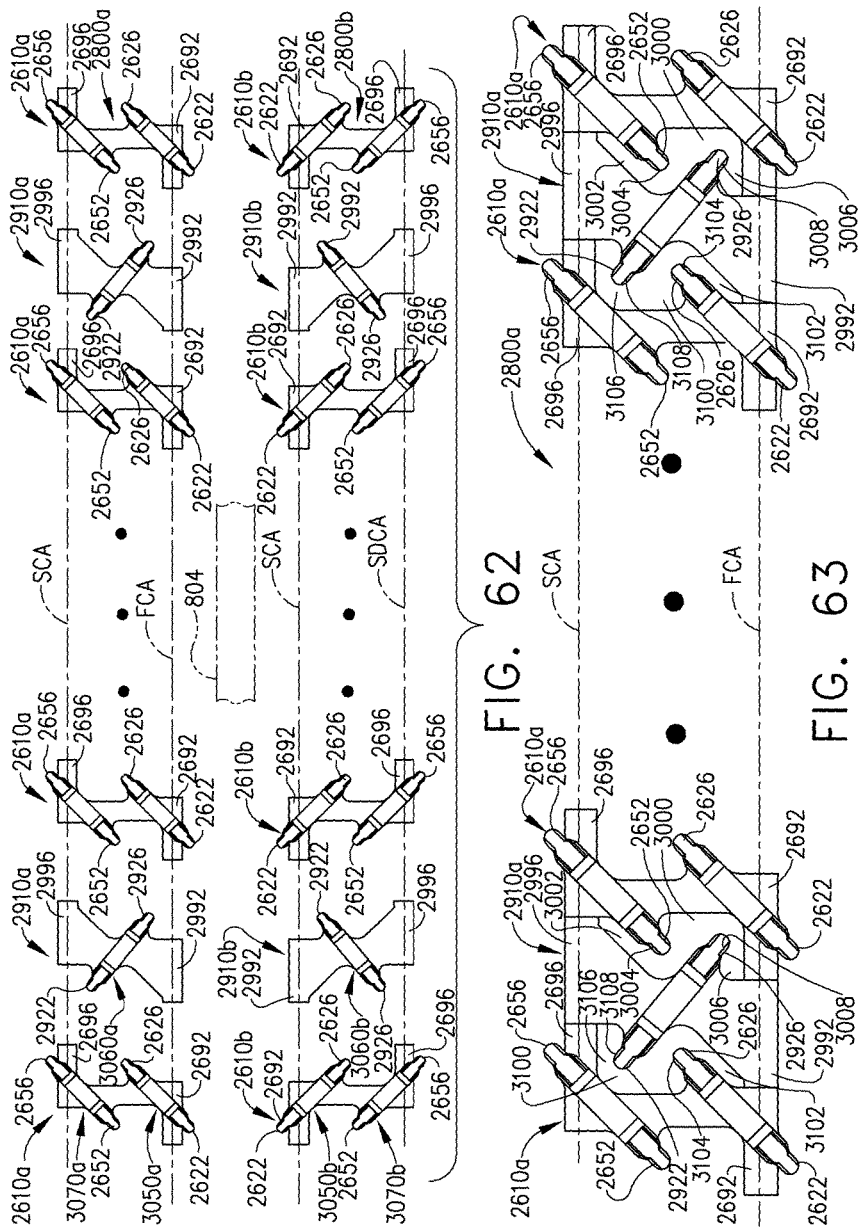

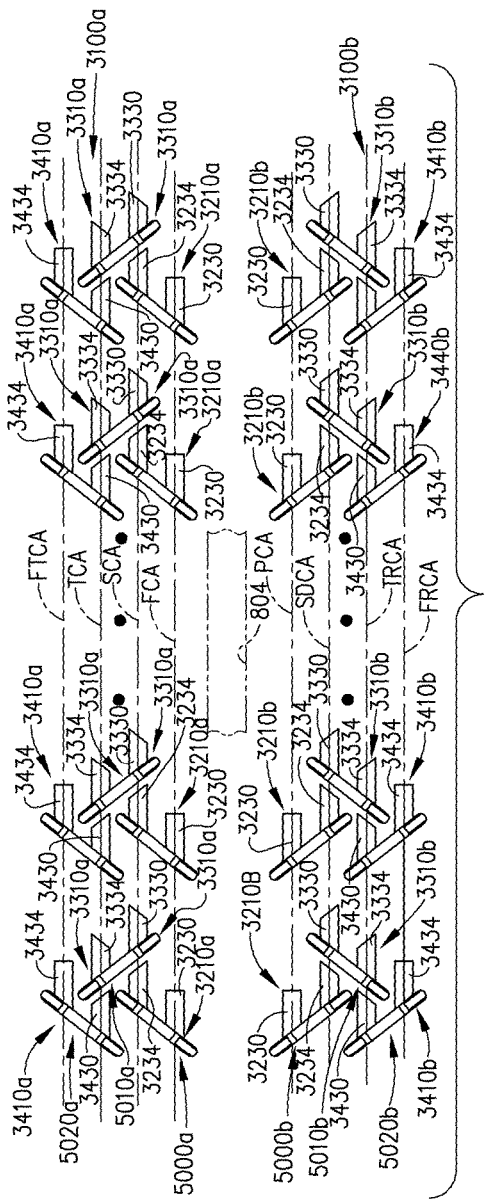
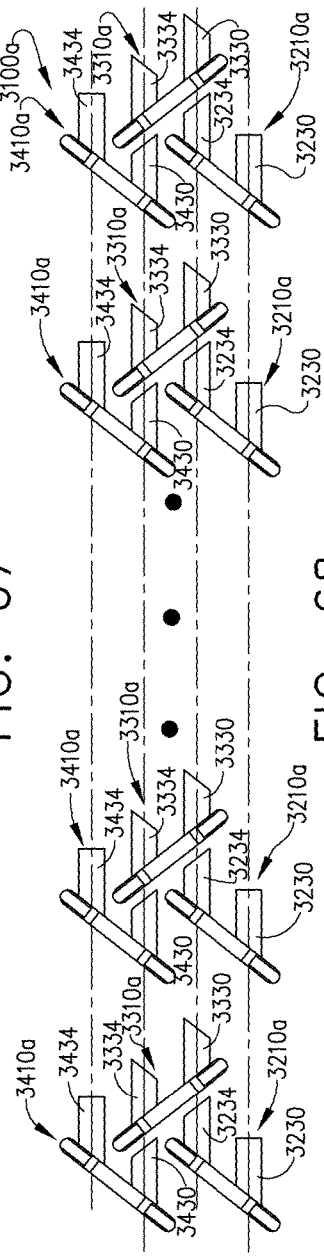
FIG. 67
FIG. 68 understand# SURGICAL STAPLE CARTRIDGE WITH IMPROVED STAPLE DRIVER CONFIGURATIONS

BACKGROUND

The present invention relates to surgical instruments and, in various embodiments, to surgical stapling and cutting instruments and staple cartridges for use therewith.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows.

The foregoing discussion is intended only to illustrate various aspects of the related art in the field of the invention at the time, and should not be taken as a disavowal of claim scope.

BRIEF DESCRIPTION OF THE DRAWINGS

Various features of the embodiments described herein, together with advantages thereof, may be understood in accordance with the following description taken in conjunction with the accompanying drawings as follows:

FIG. 7 is a top view of a surgical staple cartridge embodiment;

FIG. 8 is a bottom view of the surgical staple cartridge embodiment of FIG. 7;

FIG. 9 depicts the staple pattern deployed by the cartridge of FIGS. 7 and 8;

FIG. 10 depicts the staple pattern of FIG. 9 in a stretched condition;

FIG. 11 depicts a previous staple pattern implanted in tissue;

FIG. 16 is a top view of corresponding driver arrays employed in the surgical staple cartridge of FIG. 15;

FIG. 17 is another top view of one of the driver arrays of FIG. 16 supported in corresponding portions of a staple cartridge embodiment;

FIG. 20 is a top view of corresponding portions of other driver array embodiments;

FIG. 21 is another top view of one of the driver arrays of FIG. 20;

FIG. 33 is a top view of corresponding portions of other driver array embodiments;

FIG. 34 is a top view of one of the driver arrays of FIG. 33;

FIG. 41 is a top view of corresponding portions of other driver array embodiments;

FIG. 42 is a top view of one of the driver arrays of FIG. 41;

FIG. 49 is a top view of corresponding portions of other driver array embodiments;

FIG. 50 is a top view of one of the driver arrays of FIG. 49;

FIG. 57 is a top view of corresponding portions of other driver array embodiments;

FIG. 58 is a top view of one of the driver arrays of FIG. 57;

FIG. 62 is a top view of corresponding portions of other driver array embodiments;

FIG. 63 is a top view of one of the driver arrays of FIG. 62 in connection with a portion of a surgical staple cartridge;

FIG. 67 is a top view of corresponding portions of other driver array embodiments;

FIG. 68 is an enlarged top view of one of the driver arrays of FIG. 67;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
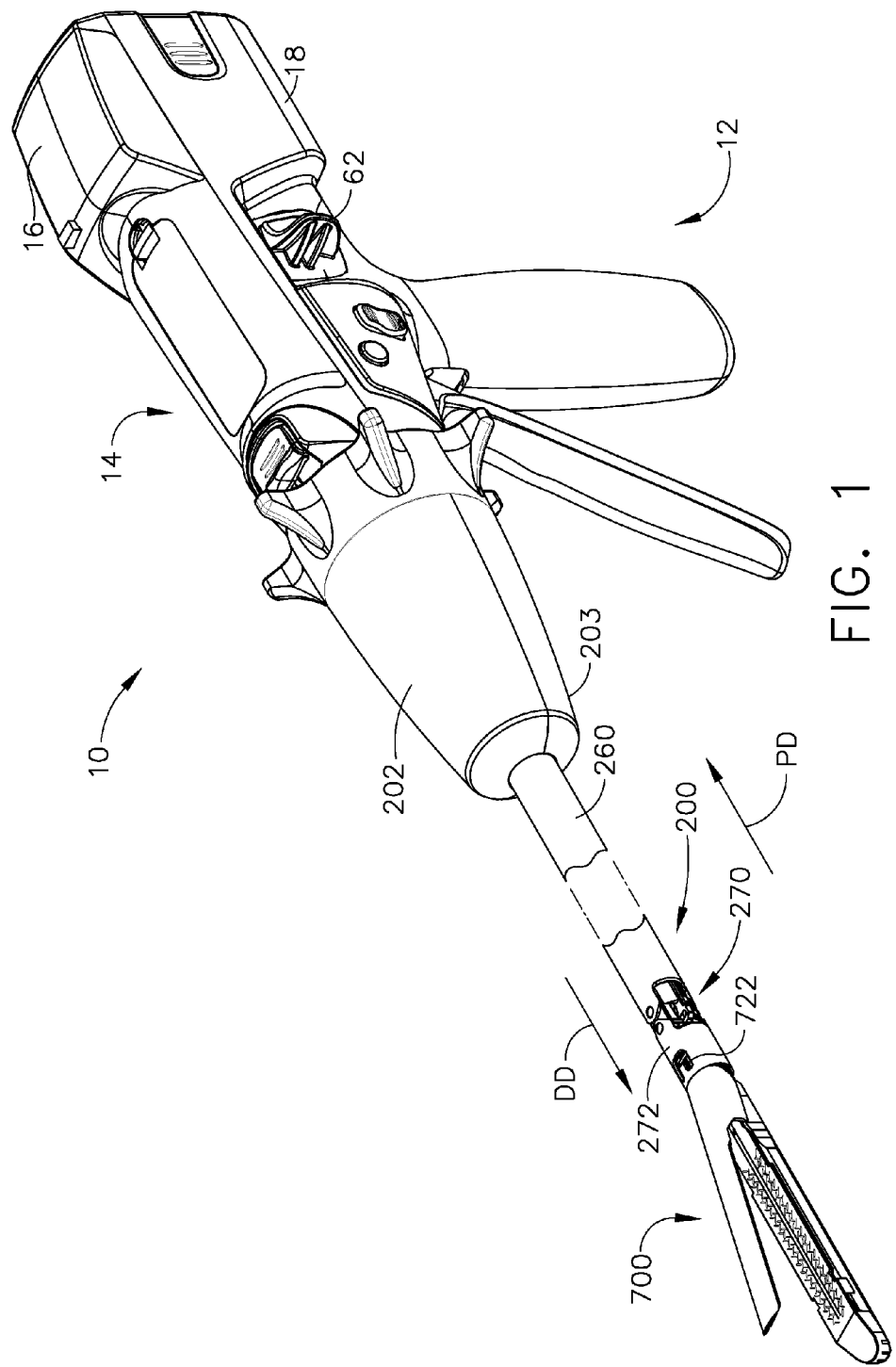
FIG. 1 is a perspective view of a surgical instrument and an elongate shaft assembly embodiment.

Applicant of the present application owns the following patent applications that were filed on Sep. 2, 2015 and which are each herein incorporated by reference in their respective entireties:

U.S. patent application Ser. No. 14/843,196, entitled SURGICAL STAPLE DRIVER ARRAYS, now U.S. Patent Application Publication No. 2017/0056012;

U.S. patent application Ser. No. 14/843,216, entitled SURGICAL STAPLE CARTRIDGE STAPLE DRIVERS WITH CENTRAL SUPPORT FEATURES, now U.S. Patent Application Publication No. 2017/0056013;

U.S. patent application Ser. No. 14/843,243, entitled SURGICAL STAPLE CONFIGURATIONS WITH CAMMING SURFACES LOCATED BETWEEN PORTIONS SUPPORTING SURGICAL STAPLES, now U.S. Patent Application Publication No. 2017/0056014; and U.S. patent application Ser. No. 14/843,267, entitled SURGICAL STAPLE CARTRIDGES WITH DRIVER ARRANGEMENTS FOR ESTABLISHING HERRINGBONE STAPLE PATTERNS, now U.S. Patent Application Publication No. 2017/0056015.

Applicant of the present application owns the following patent applications that were filed on Mar. 6, 2015 and which are each herein incorporated by reference in their respective entireties:

U.S. patent application Ser. No. 14/640,746, entitled POWERED SURGICAL INSTRUMENT;

U.S. patent application Ser. No. 14/640,795, entitled MULTIPLE LEVEL THRESHOLDS TO MODIFY OPERATION OF POWERED SURGICAL INSTRUMENTS;

U.S. patent application Ser. No. 14/640,832, entitled ADAPTIVE TISSUE COMPRESSION TECHNIQUES TO ADJUST CLOSURE RATES FOR MULTIPLE TISSUE TYPES;

U.S. patent application Ser. No. 14/640,935, entitled OVERLAID MULTI SENSOR RADIO FREQUENCY (RF) ELECTRODE SYSTEM TO MEASURE TISSUE COMPRESSION;

U.S. patent application Ser. No. 14/640,831, entitled MONITORING SPEED CONTROL AND PRECISION INCREMENTING OF MOTOR FOR POWERED SURGICAL INSTRUMENTS;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES;

U.S. patent application Ser. No. 14/640,817, entitled INTERACTIVE FEEDBACK SYSTEM FOR POWERED SURGICAL INSTRUMENTS;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE;

U.S. patent application Ser. No. 14/640,837, entitled SMART SENSORS WITH LOCAL SIGNAL PROCESSING;

U.S. patent application Ser. No. 14/640,765, entitled SYSTEM FOR DETECTING THE MIS-INSERTION OF A STAPLE CARTRIDGE INTO A SURGICAL STAPLER;

U.S. patent application Ser. No. 14/640,799, entitled SIGNAL AND POWER COMMUNICATION SYSTEM POSITIONED ON A ROTATABLE SHAFT; and U.S. patent application Ser. No. 14/640,780, entitled SURGICAL INSTRUMENT COMPRISING A LOCKABLE BATTERY HOUSING.

Applicant of the present application owns the following patent applications that were filed on Feb. 27, 2015, and which are each herein incorporated by reference in their respective entireties:

U.S. patent application Ser. No. 14/633,576, entitled SURGICAL INSTRUMENT SYSTEM COMPRISING AN INSPECTION STATION;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND;

U.S. patent application Ser. No. 14/633,560, entitled SURGICAL CHARGING SYSTEM THAT CHARGES AND/OR CONDITIONS ONE OR MORE BATTERIES;

U.S. patent application Ser. No. 14/633,566, entitled CHARGING SYSTEM THAT ENABLES EMERGENCY RESOLUTIONS FOR CHARGING A BATTERY;

U.S. patent application Ser. No. 14/633,555, entitled SYSTEM FOR MONITORING WHETHER A SURGICAL INSTRUMENT NEEDS TO BE SERVICED;

U.S. patent application Ser. No. 14/633,542, entitled REINFORCED BATTERY FOR A SURGICAL INSTRUMENT;

U.S. patent application Ser. No. 14/633,548, entitled POWER ADAPTER FOR A SURGICAL INSTRUMENT;

U.S. patent application Ser. No. 14/633,526, entitled ADAPTABLE SURGICAL INSTRUMENT HANDLE;

U.S. patent application Ser. No. 14/633,541, entitled MODULAR STAPLING ASSEMBLY; and U.S. patent application Ser. No. 14/633,562, entitled SURGICAL APPARATUS CONFIGURED TO TRACK AN END-OF-LIFE PARAMETER.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING;

U.S. patent application Ser. No. 14/574,483, entitled SURGICAL INSTRUMENT ASSEMBLY COMPRISING LOCKABLE SYSTEMS;

U.S. patent application Ser. No. 14/575,139, entitled DRIVE ARRANGEMENTS FOR ARTICULATABLE SURGICAL INSTRUMENTS;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE;

U.S. patent application Ser. No. 14/575,143, entitled SURGICAL INSTRUMENTS WITH IMPROVED CLOSURE ARRANGEMENTS;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS;

U.S. patent application Ser. No. 14/574,493, entitled SURGICAL INSTRUMENT ASSEMBLY COMPRISING A FLEXIBLE ARTICULATION SYSTEM; and U.S. patent application Ser. No. 14/574,500, entitled SURGICAL INSTRUMENT ASSEMBLY COMPRISING A LOCKABLE ARTICULATION SYSTEM.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Patent Application Publication No. 2014/0246474;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Patent Application Publication No. 2014/0246477;

U.S. patent application Ser. No. 13/782,481, entitled SENSOR STRAIGHTENED END EFFECTOR DURING REMOVAL THROUGH TROCAR, now U.S. Patent Application Publication No. 2014/0246479;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Patent Application Publication No. 2014/0246473; and U.S. patent application Ser. No. 13/782,536, entitled SURGICAL INSTRUMENT SOFT STOP, now U.S. Patent Application Publication No. 2014/0246476.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Patent Application Publication No. 2014/0263537;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Patent Application Publication No. 2014/0263553;

U.S. patent application Ser. No. 13/803,130, entitled DRIVE TRAIN CONTROL ARRANGEMENTS FOR MODULAR SURGICAL INSTRUMENTS, now U.S. Patent Application Publication No. 2014/0263543; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Patent Application Publication No. 2014/0263539.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS;

U.S. patent application Ser. No. 14/226,099, entitled STERILIZATION VERIFICATION CIRCUIT;

U.S. patent application Ser. No. 14/226,094, entitled VERIFICATION OF NUMBER OF BATTERY EXCHANGES/PROCEDURE COUNT;

U.S. patent application Ser. No. 14/226,117, entitled POWER MANAGEMENT THROUGH SLEEP OPTIONS OF SEGMENTED CIRCUIT AND WAKE UP CONTROL;

U.S. patent application Ser. No. 14/226,075, entitled MODULAR POWERED SURGICAL INSTRUMENT WITH DETACHABLE SHAFT ASSEMBLIES;

U.S. patent application Ser. No. 14/226,093, entitled FEEDBACK ALGORITHMS FOR MANUAL BAIL-OUT SYSTEMS FOR SURGICAL INSTRUMENTS;

U.S. patent application Ser. No. 14/226,116, entitled SURGICAL INSTRUMENT UTILIZING SENSOR ADAPTATION;

U.S. patent application Ser. No. 14/226,071, entitled SURGICAL INSTRUMENT CONTROL CIRCUIT HAVING A SAFETY PROCESSOR;

U.S. patent application Ser. No. 14/226,097, entitled SURGICAL INSTRUMENT COMPRISING INTERACTIVE SYSTEMS;

U.S. patent application Ser. No. 14/226,126, entitled INTERFACE SYSTEMS FOR USE WITH SURGICAL INSTRUMENTS;

U.S. patent application Ser. No. 14/226,133, entitled MODULAR SURGICAL INSTRUMENT SYSTEM;

U.S. patent application Ser. No. 14/226,081, entitled SYSTEMS AND METHODS FOR CONTROLLING A SEGMENTED CIRCUIT;

U.S. patent application Ser. No. 14/226,076, entitled POWER MANAGEMENT THROUGH SEGMENTED CIRCUIT AND VARIABLE VOLTAGE PROTECTION;

U.S. patent application Ser. No. 14/226,111, entitled SURGICAL STAPLING INSTRUMENT SYSTEM; and U.S. patent application Ser. No. 14/226,125, entitled SURGICAL INSTRUMENT COMPRISING A ROTATABLE SHAFT.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE;

U.S. patent application Ser. No. 14/479,119, entitled ADJUNCT WITH INTEGRATED SENSORS TO QUANTIFY TISSUE COMPRESSION;

U.S. patent application Ser. No. 14/478,908, entitled MONITORING DEVICE DEGRADATION BASED ON COMPONENT EVALUATION;

U.S. patent application Ser. No. 14/478,895, entitled MULTIPLE SENSORS WITH ONE SENSOR AFFECTING A SECOND SENSOR'S OUTPUT OR INTERPRETATION;

U.S. patent application Ser. No. 14/479,110, entitled USE OF POLARITY OF HALL MAGNET DETECTION TO DETECT MISLOADED CARTRIDGE;

U.S. patent application Ser. No. 14/479,098, entitled SMART CARTRIDGE WAKE UP OPERATION AND DATA RETENTION;

U.S. patent application Ser. No. 14/479,115, entitled MULTIPLE MOTOR CONTROL FOR POWERED MEDICAL DEVICE; and U.S. patent application Ser. No. 14/479,108, entitled LOCAL DISPLAY OF TISSUE PARAMETER STABILIZATION.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

A surgical fastening instrument 10 is depicted in FIG. 1. The surgical fastening instrument 100 is configured to deploy an "elastic" or "expandable" staple line. Various elastic staple lines are disclosed herein and the surgical fastening instrument 10 is capable of deploying any one of these elastic staple lines. Moreover, surgical instruments other than the surgical fastening instrument 100 are capable of deploying any one of the expandable staple lines disclosed herein.

As can be seen in FIGS. 1-4, the surgical fastening instrument 10 includes a housing 12 that comprises a handle 14 that is configured to be grasped, manipulated and actuated by the clinician. The housing 12 is configured for operable attachment to an elongate shaft assembly 200 that has a surgical end effector 700 operably coupled thereto that is configured to perform one or more surgical tasks or procedures. The elongate shaft assembly 200 may be interchangeable with other shaft assemblies in the various manners disclosed, for example, in U.S. patent application Ser. No. 14/226,075, entitled MODULAR POWERED SURGICAL INSTRUMENT WITH DETACHABLE SHAFT ASSEMBLIES, the entire disclosure of which is hereby incorporated by reference herein. In other arrangements, the elongate shaft assembly may not be interchangeable with other shaft assemblies and essentially comprise a dedicated non-removable portion of the instrument. It will be further understood that the various forms of shaft assemblies and end effectors disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the elongate shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the shaft assemblies and end effector arrangements disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, which is hereby incorporated by reference herein in its entirety.

FIG. 1 illustrates the housing 12 or handle 14 of the surgical instrument 10 with an interchangeable elongate shaft assembly 200 operably coupled thereto. As can be seen in FIG. 1, the handle 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle 14 operably supports a plurality of drive systems therein that are configured to generate and apply various control motions to corresponding portions of the interchangeable shaft assembly that is operably attached thereto.

Figure 2:
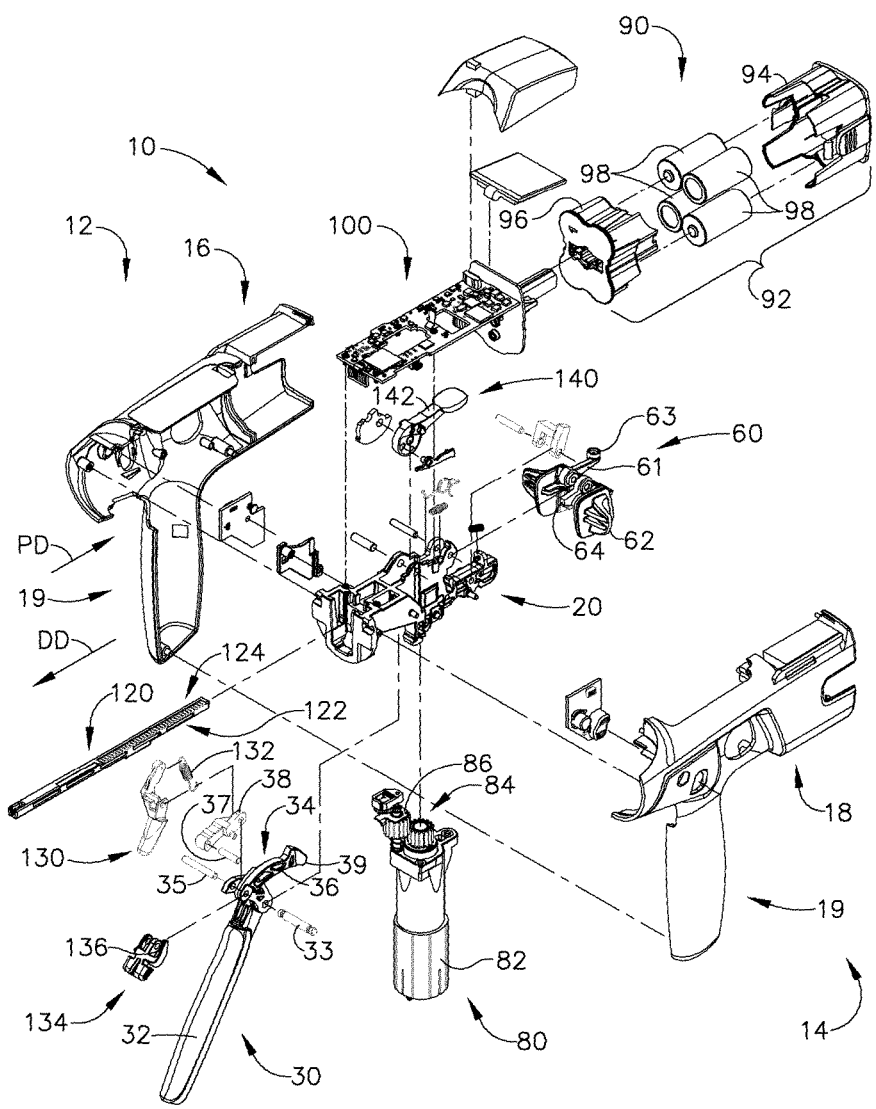
FIG. 2 is an exploded assembly view of the handle or housing portion of the surgical instrument of FIG. 1.

Referring now to FIG. 2, the handle 14 may further include a frame 20 that operably supports a plurality of drive systems. For example, the frame 20 can operably support a "first" or closure drive system, generally designated as 30, which may be employed to apply closing and opening motions to the elongate shaft assembly 200 that is operably attached or coupled thereto. In at least one form, the closure drive system 30 may include an actuator in the form of a closure trigger 32 that is pivotally supported by the frame 20. More specifically, as illustrated in FIG. 2, the closure trigger 32 is pivotally coupled to the housing 14 by a pin 33. Such arrangement enables the closure trigger 32 to be manipulated by a clinician such that when the clinician grips the pistol grip portion 19 of the handle 14, the closure trigger 32 may be easily pivoted from a starting or "unactuated" position to an "actuated" position and more particularly to a fully compressed or fully actuated position. The closure trigger 32 may be biased into the unactuated position by spring or other biasing arrangement (not shown). In various forms, the closure drive system 30 further includes a closure linkage assembly 34 that is pivotally coupled to the closure trigger 32. As can be seen in FIG. 2, the closure linkage assembly 34 may include a first closure link 36 and a second closure link 38 that are pivotally coupled to the closure trigger 32 by a pin 35. The second closure link 38 may also be referred to herein as an "attachment member" and include a transverse attachment pin 37.

Still referring to FIG. 2, it can be observed that the first closure link 36 may have a locking wall or end 39 thereon that is configured to cooperate with a closure release assembly 60 that is pivotally coupled to the frame 20. In at least one form, the closure release assembly 60 may comprise a release button assembly 62 that has a distally protruding locking pawl 64 formed thereon. The release button assembly 62 may be pivoted in a counterclockwise direction by a release spring (not shown). As the clinician depresses the closure trigger 32 from its unactuated position towards the pistol grip portion 19 of the handle 14, the first closure link 36 pivots upward to a point wherein the locking pawl 64 drops into retaining engagement with the locking wall 39 on the first closure link 36 thereby preventing the closure trigger 32 from returning to the unactuated position. Thus, the closure release assembly 60 serves to lock the closure trigger 32 in the fully actuated position. When the clinician desires to unlock the closure trigger 32 to permit it to be biased to the unactuated position, the clinician simply pivots the closure release button assembly 62 such that the locking pawl 64 is moved out of engagement with the locking wall 39 on the first closure link 36. When the locking pawl 64 has been moved out of engagement with the first closure link 36, the closure trigger 32 may pivot back to the unactuated position. Other closure trigger locking and release arrangements may also be employed.

When the closure trigger 32 is moved from its unactuated position to its actuated position, the closure release button 62 is pivoted between a first position and a second position. The rotation of the closure release button 62 can be referred to as being an upward rotation; however, at least a portion of the closure release button 62 is being rotated toward the circuit board 100. Still referring to FIG. 2, the closure release button 62 can include an arm 61 extending therefrom and a magnetic element 63, such as a permanent magnet, for example, mounted to the arm 61. When the closure release button 62 is rotated from its first position to its second position, the magnetic element 63 can move toward the circuit board 100. The circuit board 100 can include at least one sensor that is configured to detect the movement of the magnetic element 63. In at least one embodiment, a "Hall effect" sensor can be mounted to the bottom surface of the circuit board 100. The Hall effect sensor can be configured to detect changes in a magnetic field surrounding the Hall effect sensor that are caused by the movement of the magnetic element 63. The Hall effect sensor can be in signal communication with a microcontroller, for example, which can determine whether the closure release button 62 is in its first position, which is associated with the unactuated position of the closure trigger 32 and the open configuration of the end effector, its second position, which is associated with the actuated position of the closure trigger 32 and the closed configuration of the end effector, and/or any position between the first position and the second position.

Also in the illustrated arrangement, the handle 14 and the frame 20 operably support another drive system referred to herein as a firing drive system 80 that is configured to apply firing motions to corresponding portions of the interchangeable shaft assembly attached thereto. The firing drive system may 80 also be referred to herein as a "second drive system". The firing drive system 80 may employ an electric motor 82, located in the pistol grip portion 19 of the handle 14. In various forms, the motor 82 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 82 may be powered by a power source 90 that in one form may comprise a removable power pack 92. As can be seen in FIG. 2, for example, the power pack 92 may comprise a proximal housing portion 94 that is configured for attachment to a distal housing portion 96. The proximal housing portion 94 and the distal housing portion 96 are configured to operably support a plurality of batteries 98 therein. Batteries 98 may each comprise, for example, a Lithium Ion ("LI") or other suitable battery. The distal housing portion 96 is configured for removable operable attachment to a control circuit board assembly 100 which is also operably coupled to the motor 82. A number of batteries 98 may be connected in series may be used as the power source for the surgical instrument 10. In addition, the power source 90 may be replaceable and/or rechargeable.

As outlined above with respect to other various forms, the electric motor 82 includes a rotatable shaft (not shown) that operably interfaces with a gear reducer assembly 84 that is mounted in meshing engagement with a with a set, or rack, of drive teeth 122 on a longitudinally-movable drive member 120. In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the drive member 120 will be axially driven in the distal direction "DD". When the motor 82 is driven in the opposite rotary direction, the drive member 120 will be axially driven in a proximal direction "PD". The handle 14 can include a switch which can be configured to reverse the polarity applied to the electric motor 82 by the power source 90. As with the other forms described herein, the handle 14 can also include a sensor that is configured to detect the position of the drive member 120 and/or the direction in which the drive member 120 is being moved.

Actuation of the motor 82 is controlled by a firing trigger 130 that is pivotally supported on the handle 14. The firing trigger 130 may be pivoted between an unactuated position and an actuated position. The firing trigger 130 may be biased into the unactuated position by a spring 132 or other biasing arrangement such that when the clinician releases the firing trigger 130, it may be pivoted or otherwise returned to the unactuated position by the spring 132 or biasing arrangement. In at least one form, the firing trigger 130 can be positioned "outboard" of the closure trigger 32 as was discussed above. In at least one form, a firing trigger safety button 134 may be pivotally mounted to the closure trigger 32 by pin 35. The safety button 134 may be positioned between the firing trigger 130 and the closure trigger 32 and have a pivot arm 136 protruding therefrom. See FIG. 2. When the closure trigger 32 is in the unactuated position, the safety button 134 is contained in the handle 14 where the clinician cannot readily access it and move it between a safety position preventing actuation of the firing trigger 130 and a firing position wherein the firing trigger 130 may be fired. As the clinician depresses the closure trigger 32, the safety button 134 and the firing trigger 130 pivot down wherein they can then be manipulated by the clinician.

As discussed above, the handle 14 includes a closure trigger 32 and a firing trigger 130. The firing trigger 130 can be pivotably mounted to the closure trigger 32. When the closure trigger 32 is moved from its unactuated position to its actuated position, the firing trigger 130 can descend downwardly, as outlined above. After the safety button 134 has been moved to its firing position, the firing trigger 130 can be depressed to operate the motor of the surgical instrument firing system. In various instances, the handle 14 can include a tracking system configured to determine the position of the closure trigger 32 and/or the position of the firing trigger 130.

As indicated above, in at least one form, the longitudinally movable drive member 120 has a rack of drive teeth 122 formed thereon for meshing engagement with a corresponding drive gear 86 of the gear reducer assembly 84. At least one form also includes a manually-actuatable "bailout" assembly 140 that is configured to enable the clinician to manually retract the longitudinally movable drive member 120 should the motor 82 become disabled. The bailout assembly 140 may include a lever or bailout handle assembly 142 that is configured to be manually pivoted into ratcheting engagement with teeth 124 also provided in the drive member 120. Thus, the clinician can manually retract the drive member 120 by using the bailout handle assembly 142 to ratchet the drive member 120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein, is hereby incorporated by reference in its entirety.

Figure 3:
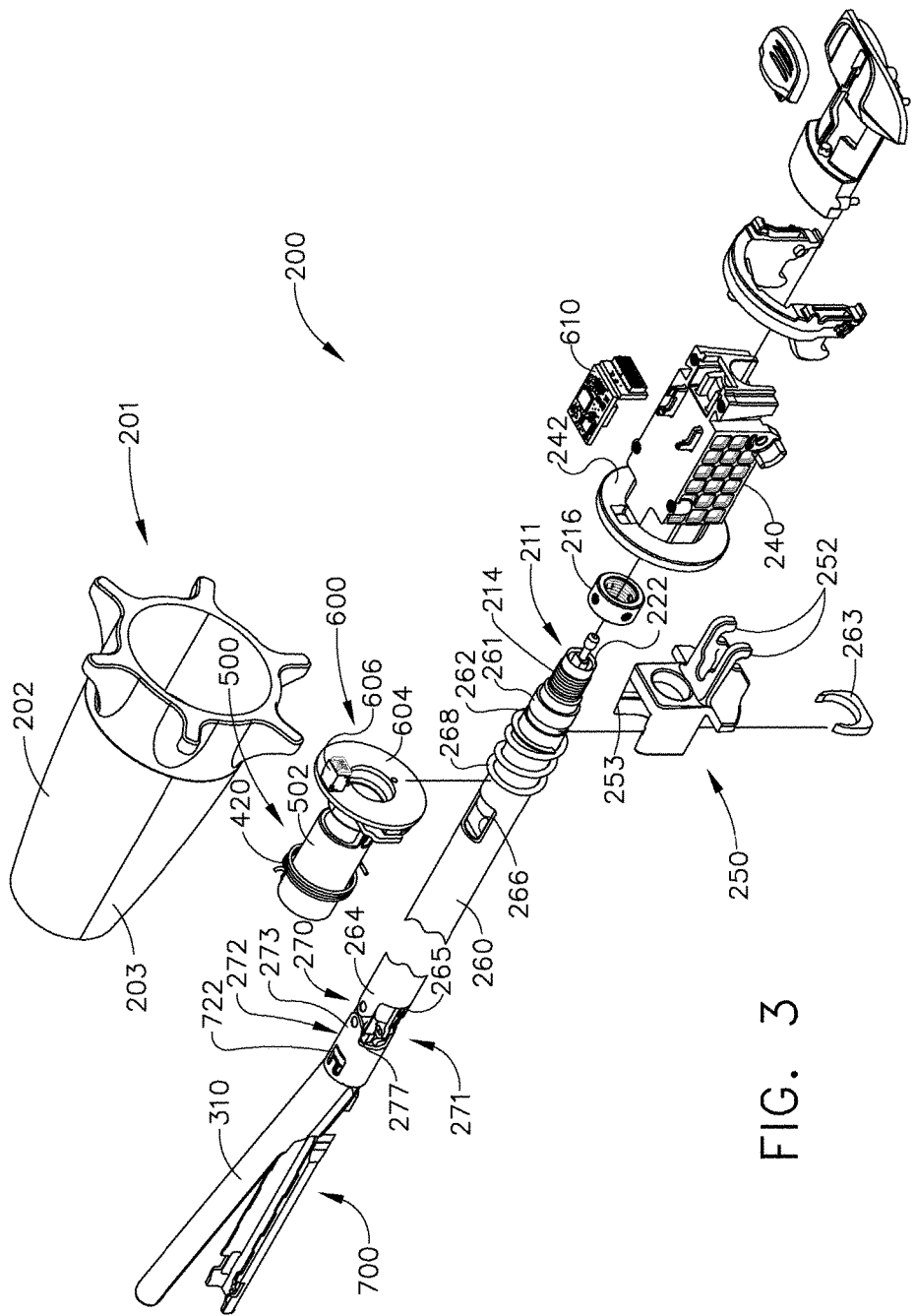
FIG. 3 is an exploded assembly view of a portion of an elongate shaft assembly.
Figure 4:
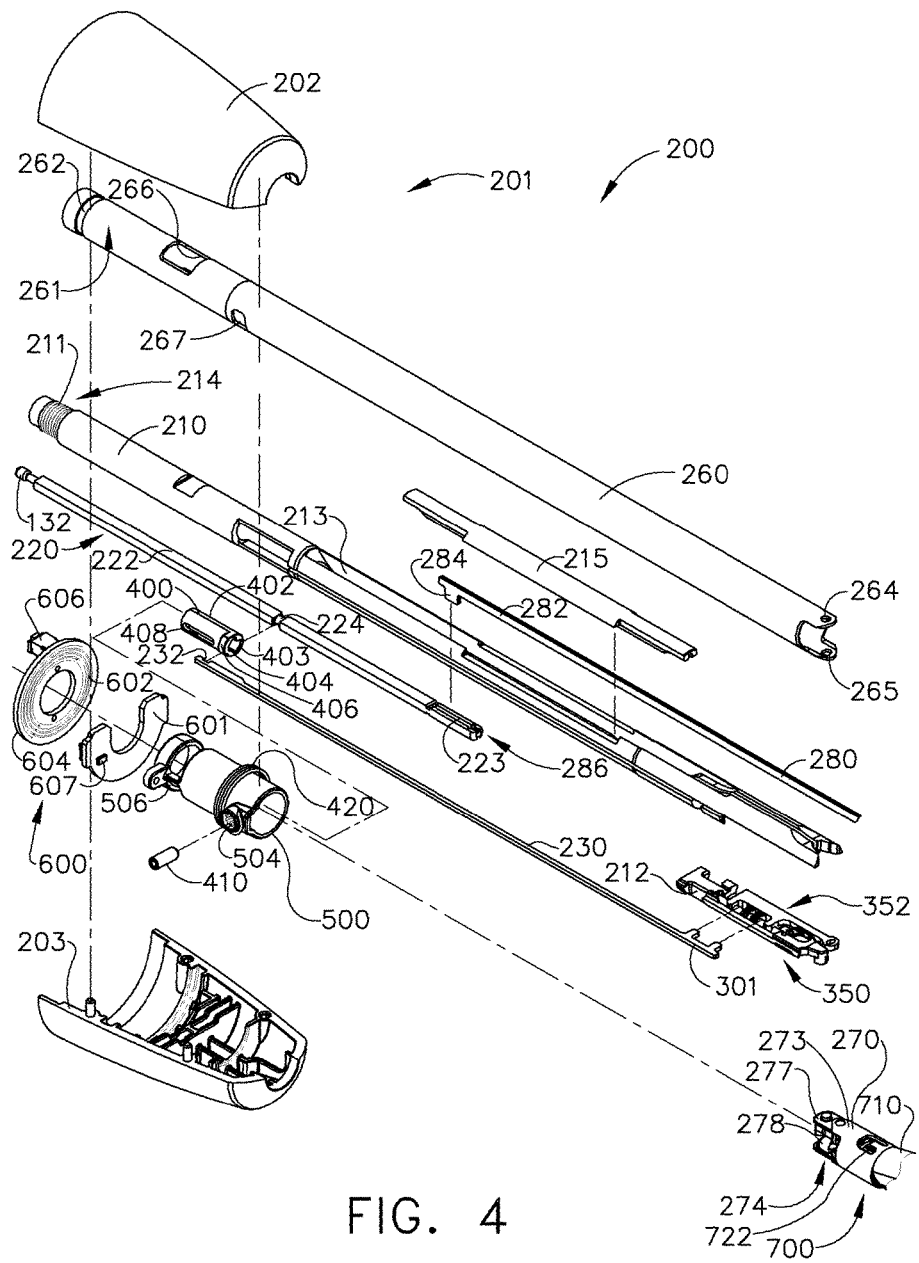
FIG. 4 is another exploded assembly view of another portion of the elongate shaft assembly of FIG. 3.

Turning now to FIGS. 1 and 3, the elongate shaft assembly 200 includes a surgical end effector 700 that comprises an elongate channel 702 that is configured to operably support a staple cartridge 800 therein. The end effector 700 may further include an anvil 710 that is pivotally supported relative to the elongate channel 702. As will be discussed in further detail below, the surgical end effector 700 may be articulated relative to the elongate shaft assembly about an articulation joint 270. Various embodiments are also envisioned wherein the end effector is not articulatable. As can be seen in FIGS. 3 and 4, the shaft assembly 200 can further include a proximal housing or nozzle 201 comprised of nozzle portions 202 and 203. The shaft assembly 200 further includes a closure tube 260 which can be utilized to close and/or open an anvil 310 of the end effector 700. As can be seen in FIG. 4, the shaft assembly 200 includes a spine 210 which can be configured to fixably support a shaft frame portion 212 of and articulation lock 350. Details regarding the construction and operation of the articulation lock 350 are set forth in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the disclosure of which is hereby incorporated by reference herein in its entirety. The spine 210 is configured to, one, slidably support a firing member 220 therein and, two, slidably support the closure tube 260 which extends around the spine 210. The spine 210 also slidably supports a proximal articulation driver 230. The proximal articulation driver 230 has a distal end 301 that is configured to operably engage the articulation lock 350. In one arrangement, the articulation lock 350 interfaces with an articulation frame 352 that is adapted to operably engage a drive pin (not shown) on the end effector frame (not shown).

In the illustrated arrangement, the spine 210 comprises a proximal end 211 which is rotatably supported in a chassis 240. In one arrangement, for example, the proximal end 211 of the spine 210 has a thread 214 formed thereon for threaded attachment to a spine bearing 216 configured to be supported within the chassis 240. See FIG. 3. Such arrangement facilitates rotatable attachment of the spine 210 to the chassis 240 such that the spine 210 may be selectively rotated about a shaft axis SA-SA relative to the chassis 240. The shaft assembly 200 also includes a closure shuttle 250 that is slidably supported within the chassis 240 such that it may be axially moved relative thereto. As can be seen in FIG. 3, the closure shuttle 250 includes a pair of proximally-protruding hooks 252 that are configured for attachment to the attachment pin 37 that is attached to the second closure link 38 as will be discussed in further detail below. See FIG. 2. A proximal end 261 of the closure tube 260 is coupled to the closure shuttle 250 for relative rotation thereto. For example, a U-shaped connector 263 is inserted into an annular slot 262 in the proximal end 261 of the closure tube 260 and is retained within vertical slots 253 in the closure shuttle 250. See FIG. 3. Such arrangement serves to attach the closure tube 260 to the closure shuttle 250 for axial travel therewith while enabling the closure tube 260 to rotate relative to the closure shuttle 250 about the shaft axis SA-SA. A closure spring 268 is journaled on the closure tube 260 and serves to bias the closure tube 260 in the proximal direction "PD" which can serve to pivot the closure trigger into the unactuated position when the shaft assembly 200 is operably coupled to the handle 14.

As was also indicated above, the elongate shaft assembly 200 further includes a firing member 220 that is supported for axial travel within the shaft spine 210. The firing member 220 includes an intermediate firing shaft portion 222 that is configured for attachment to a distal cutting portion or firing beam 280. The firing member 220 may also be referred to herein as a "second shaft" and/or a "second shaft assembly". As can be seen in FIG. 4, the intermediate firing shaft portion 222 may include a longitudinal slot 223 in the distal end thereof which can be configured to receive a tab 284 on the proximal end 282 of the distal firing beam 280. The longitudinal slot 223 and the proximal end 282 can be sized and configured to permit relative movement therebetween and can comprise a slip joint 286. The slip joint 286 can permit the intermediate firing shaft portion 222 of the firing drive 220 to be moved to articulate the surgical end effector 700 without moving, or at least substantially moving, the firing beam 280. Once the surgical end effector 700 has been suitably oriented, the intermediate firing shaft portion 222 can be advanced distally until a proximal sidewall of the longitudinal slot 223 comes into contact with the tab 284 in order to advance the firing beam 280 and fire a staple cartridge that may be supported in the end effector 700. As can be further seen in FIG. 4, the shaft spine 210 has an elongate opening or window 213 therein to facilitate assembly and insertion of the intermediate firing shaft portion 222 into the shaft frame 210. Once the intermediate firing shaft portion 222 has been inserted therein, a top frame segment 215 may be engaged with the shaft frame 212 to enclose the intermediate firing shaft portion 222 and firing beam 280 therein. Further description of the operation of the firing member 220 may be found in U.S. patent application Ser. No. 13/803,086, now U.S. Patent Application Publication No. 2014/0263541.

Further to the above, the illustrated shaft assembly 200 includes a clutch assembly 400 which can be configured to selectively and releasably couple the articulation driver 230 to the firing member 220. In one form, the clutch assembly 400 includes a lock collar, or sleeve 402, positioned around the firing member 220 wherein the lock sleeve 402 can be rotated between an engaged position in which the lock sleeve 402 couples the articulation driver 230 to the firing member 220 and a disengaged position in which the articulation driver 230 is not operably coupled to the firing member 200. When lock sleeve 402 is in its engaged position, distal movement of the firing member 220 can move the articulation driver 230 distally and, correspondingly, proximal movement of the firing member 220 can move the proximal articulation driver 230 proximally. When lock sleeve 402 is in its disengaged position, movement of the firing member 220 is not transmitted to the proximal articulation driver 230 and, as a result, the firing member 220 can move independently of the proximal articulation driver 230. In various circumstances, the proximal articulation driver 230 can be held in position by the articulation lock 350 when the proximal articulation driver 230 is not being moved in the proximal or distal directions by the firing member 220.

As can be further seen in FIG. 4, the lock sleeve 402 can comprise a cylindrical, or an at least substantially cylindrical, body including a longitudinal aperture 403 defined therein configured to receive the firing member 220. The lock sleeve 402 can comprise diametrically-opposed, inwardly-facing lock protrusions 404 and an outwardly-facing lock member 406. The lock protrusions 404 can be configured to be selectively engaged with the firing member 220. More particularly, when the lock sleeve 402 is in its engaged position, the lock protrusions 404 are positioned within a drive notch 224 defined in the firing member 220 such that a distal pushing force and/or a proximal pulling force can be transmitted from the firing member 220 to the lock sleeve 402. When the lock sleeve 402 is in its engaged position, a second lock member 406 is received within a drive notch 232 defined in the proximal articulation driver 230 such that the distal pushing force and/or the proximal pulling force applied to the lock sleeve 402 can be transmitted to the proximal articulation driver 230. In effect, the firing member 220, the lock sleeve 402, and the proximal articulation driver 230 will move together when the lock sleeve 402 is in its engaged position. On the other hand, when the lock sleeve 402 is in its disengaged position, the lock protrusions 404 may not be positioned within the drive notch 224 of the firing member 220 and, as a result, a distal pushing force and/or a proximal pulling force may not be transmitted from the firing member 220 to the lock sleeve 402. Correspondingly, the distal pushing force and/or the proximal pulling force may not be transmitted to the proximal articulation driver 230. In such circumstances, the firing member 220 can be slid proximally and/or distally relative to the lock sleeve 402 and the proximal articulation driver 230.

As can also be seen in FIG. 4, the elongate shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the proximal articulation driver 230. A rotary torsion spring 420 is configured to engage the shaft boss 504 on the switch drum 500 and a portion of the nozzle housing 203 to apply a biasing force to the switch drum 500. The switch drum 500 can further comprise at least partially circumferential openings 506 defined therein which, referring to FIGS. 5 and 6, can be configured to receive circumferential mounts extending from the nozzle portions 202, 203 and permit relative rotation, but not translation, between the switch drum 500 and the proximal nozzle 201. The mounts also extend through openings 266 in the closure tube 260 to be seated in recesses in the shaft spine 210. However, rotation of the nozzle 201 to a point where the mounts reach the end of their respective slots 506 in the switch drum 500 will result in rotation of the switch drum 500 about the shaft axis SA-SA. Rotation of the switch drum 500 will ultimately result in the rotation of the actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. patent application Ser. No. 13/803,086, now U.S. Patent Application Publication No. 2014/0263541.

As also illustrated in FIGS. 3 and 4, the elongate shaft assembly 200 can comprise a slip ring assembly 600 which can be configured to conduct electrical power to and/or from the end effector 700 and/or communicate signals to and/or from the surgical end effector 700, for example. The slip ring assembly 600 can comprise a proximal connector flange 604 mounted to a chassis flange 242 extending from the chassis 240 and a distal connector flange 601 positioned within a slot defined in the shaft housings 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the distal connector flange 601 and may have a plurality of contacts (not shown) wherein each contact corresponds to and is in electrical contact with one of the conductors 602. Such arrangement permits relative rotation between the proximal connector flange 604 and the distal connector flange 601 while maintaining electrical contact therebetween. The proximal connector flange 604 can include an electrical connector 606 which can place the conductors 602 in signal communication with a shaft circuit board 610 mounted to the shaft chassis 240, for example. In at least one instance, a wiring harness comprising a plurality of conductors can extend between the electrical connector 606 and the shaft circuit board 610. U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, is incorporated by reference herein in its entirety. U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551 is incorporated by reference herein in its entirety. Further details regarding slip ring assembly 600 may be found in U.S. patent application Ser. No. 13/803,086, now U.S. Patent Application Publication No. 2014/0263541.

As discussed above, the elongate shaft assembly 200 can include a proximal portion which is fixably mounted to the handle 14 and a distal portion which is rotatable about a longitudinal shaft axis SA-SA. The rotatable distal shaft portion can be rotated relative to the proximal portion about the slip ring assembly 600, as discussed above. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system (i.e., the proximal articulation driver 230) may be operably disengaged from the firing drive system and, thus, the operation of the firing drive system may not articulate the end effector 700 of the shaft assembly 200. When the switch drum 500 is in its second position, the articulation drive system (i.e., the proximal articulation driver 230) may be operably engaged with the firing drive system and, thus, the operation of the firing drive system may articulate the end effector 700 of the shaft assembly 200. When the switch drum 500 is moved between its first position and its second position, the switch drum 500 is moved relative to distal connector flange 601. In various instances, the shaft assembly 200 can comprise at least one sensor that is configured to detect the position of the switch drum 500.

Referring again to FIG. 4, the closure tube assembly 260 includes a double pivot closure sleeve assembly 271. According to various forms, the double pivot closure sleeve assembly 271 includes an end effector closure sleeve 272 that includes upper and lower distally projecting tangs 273, 274. An upper double pivot link 277 includes upwardly projecting distal and proximal pivot pins that engage respectively an upper distal pin hole in the upper proximally projecting tang 273 and an upper proximal pin hole in an upper distally projecting tang 264 on the closure tube 260. A lower double pivot link 278 includes upwardly projecting distal and proximal pivot pins that engage respectively a lower distal pin hole in the lower proximally projecting tang 274 and a lower proximal pin hole in the lower distally projecting tang 265.

Figure 5:
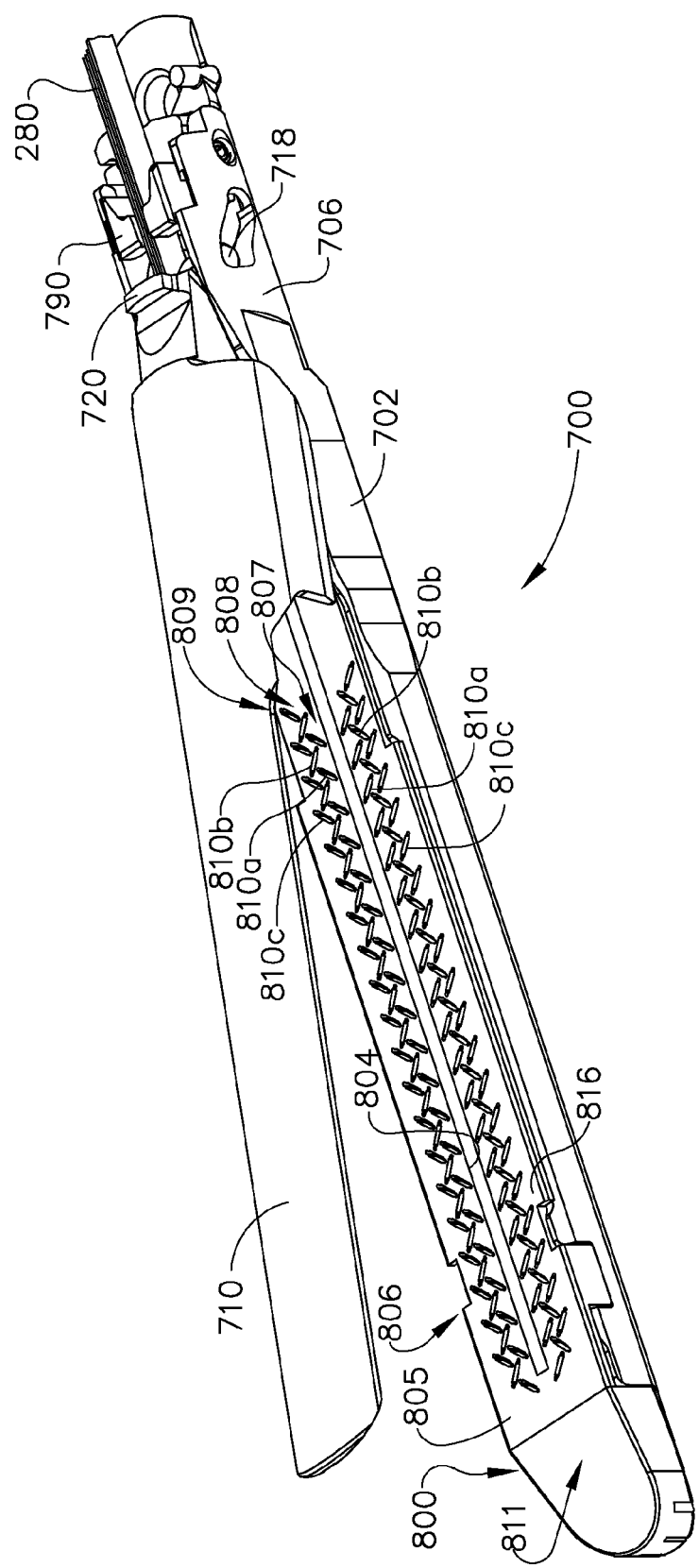
FIG. 5 is a perspective view of a portion of a surgical end effector embodiment.
Figure 6:
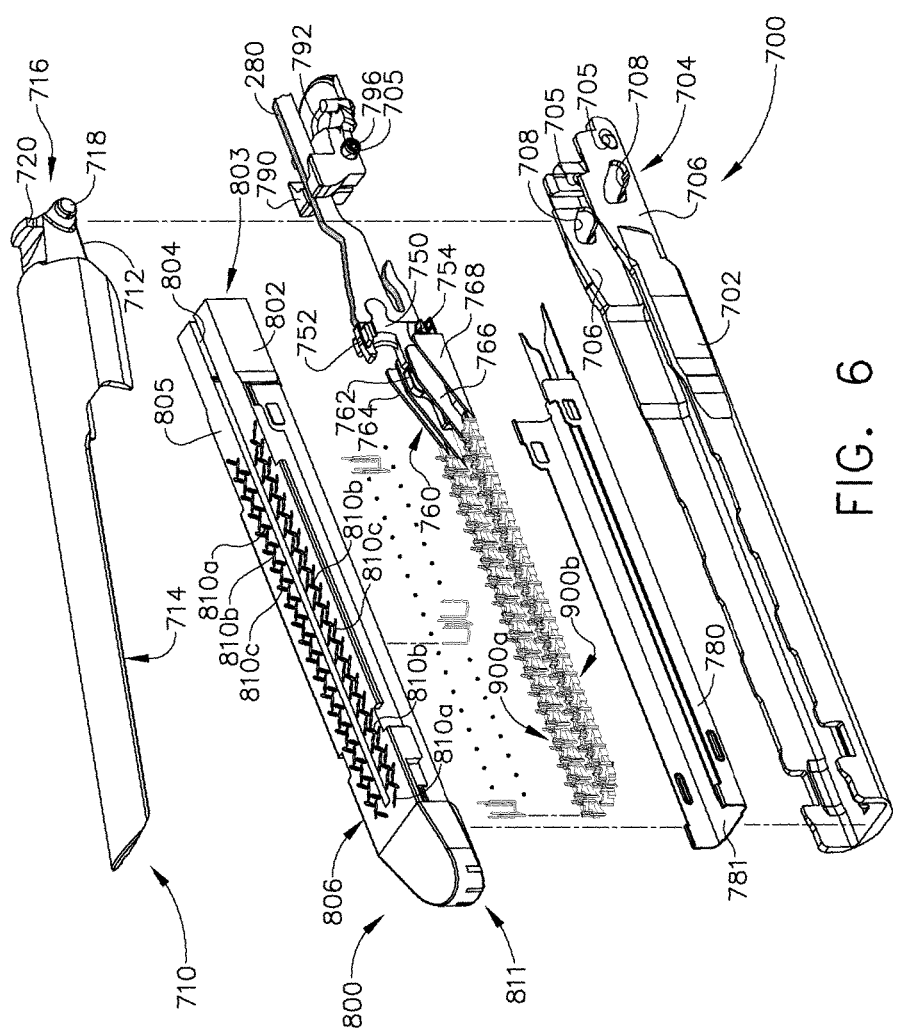
FIG. 6 is an exploded assembly view of the surgical end effector of FIG. 5.

As can be seen in FIGS. 5 and 6, the surgical end effector 700 includes an elongate channel 702 that is configured to operably support a surgical staple cartridge 800 therein. The elongate channel 702 has a proximal end portion 704 that includes two upstanding lateral walls 706. The surgical end effector 700 further includes an anvil 710 that has an anvil body 712 that has a staple-forming undersurface 714 formed thereon. The proximal end 716 of the anvil body 712 includes a laterally protruding anvil trunnion 718. A trunnion slot 708 is provided in each lateral wall 706 of the elongate channel 702 for receiving a corresponding one of the anvil trunnions 718 therein. Such arrangement serves to movably affix the anvil 710 to the elongate channel 702 for selective pivotable travel between open and closed or clamped positions. The anvil 710 includes a tab 720 that is engageable with a horseshoe-shaped slot 722 in the end effector closure sleeve 272. When the closure tube 260 and, more particularly, the end effector closure sleeve 272, is moved distally, a side wall of the slot 722 can engage the tab 720 to rotate the anvil 710 toward the elongate channel 702.

To open the anvil 710, the closure tube 260 and, more particularly, the end effector closure sleeve 272 is moved in the proximal direction. In doing so, a central tab portion defined by the horseshoe shaped slot 722 cooperates with the tab 720 on the anvil 710 to pivot the anvil 710 to an open position. Other anvil and closure arrangements are disclosed in U.S. patent application Ser. No. 14/742,914, entitled MOVABLE FIRING BEAM SUPPORT ARRANGEMENTS FOR ARTICULATABLE SURGICAL INSTRUMENTS, filed Jun. 18, 2015, the entire disclosure of which is hereby incorporated by reference herein.

Referring now to FIGS. 6-8, an exemplary staple cartridge 800 comprises a cartridge body 802 that may be molded for example, from a polymer material and be configured to be removably retained within the elongate channel 702. The staple cartridge body 802 includes a centrally disposed elongate slot 804 that is configured to receive a tissue cutting member 750 therein. A plurality of staple cavities 810a, 810b, 810c are arranged in the cartridge body 802 on each side of the elongate slot 804. In the embodiment depicted in FIGS. 6-8, the staple cavities 810a, 810b, 810c are generally oriented in a "herringbone-like" pattern. Each staple cavity 810a, 810b, 810c is configured to removably store a staple therein, although it is possible that some staple cavities 810a, 810b, 810c may not contain a staple stored therein. As will be discussed in further detail below, the staple cartridge 800 further comprises a plurality of staple drivers 900a, 900b that are movably positioned within the cartridge body 802 in conjunction with corresponding staple cavities. Each staple driver 900a, 900b is configured to support one or more staples thereon and/or lift the staples out of their respective staple cavities 810a, 810b, 810c at the same time, or concurrently when contacted by a sled or camming actuator 760.

Referring to FIG. 6, as indicated above, the end effector 700 can include a tissue cutting member 750 that is configured to incise tissue captured between the staple cartridge 800 and the anvil 710. In the illustrated example, the tissue cutting member 750 is coupled to or integrally formed on a distal end of the firing beam 280 and is oriented for movement within the elongate slot 804. Distal advancement of the firing beam 280 will therefore result in the distal advancement of the tissue cutting member 750 within the elongate slot 804 in the staple cartridge body 802. The anvil 710 also includes a longitudinal slot configured to at least partially receive a portion of the tissue cutting member 750; however, embodiments are envisioned in which only one of the cartridge 800 and the anvil 710 includes a slot configured to receive a tissue cutting member. In the illustrated embodiment, the tissue cutting member 750 comprises at least one first projection 752 extending therefrom which is configured to engage the anvil 710 and at least one second projection 754 that is configured to engage the elongate channel 702. The projections 752 and 754 can position the anvil 710 and the staple cartridge 800 relative to one another. As the tissue cutting member 750 is advanced distally, the projections 752 and 754 can position the anvil 710 and set the tissue gap between the staple forming undersurface 714 of the anvil 710 and the deck surface 816 of the staple cartridge 800 supported in the elongate channel 702.

As can be seen in FIG. 6, for example, the sled or camming actuator 760 is configured to be engaged by the tissue cutting member 750 as the tissue cutting member 750 is distally driven through the staple cartridge 800 by the firing beam 280. In other arrangements, however, the sled 760 and tissue cutting member 750 may be formed as a single component. In still other arrangements that do not employ a tissue cutting member, the firing beam may contact the sled or camming member or be integrally formed therewith. The sled 760 comprises one or more ramp or camming surfaces which are configured to drivingly contact or slide under the staple drivers 900a, 900b and lift the staple drivers 900a, 900b upwardly toward the deck surface 816 of the staple cartridge 800. In the illustrated embodiment, the sled 760 comprises four ramp or camming surfaces or camming members 762, 764, 766 and 768. As will be discussed in further detail below, the sled 760 is movable from a proximal end 803 of the staple cartridge 800 toward a distal end 811 of the cartridge 800 to sequentially lift the staple drivers 900a, 900b in their respective "driver arrays" on each side of the elongate slot 804. When the drivers 900a, 900b are driven toward the deck surface 816 by the sled 760, the staple drivers 900a, 900b lift the staples supported thereon toward the staple forming undersurface 714 of the anvil 710. As the sled 760 is progressed distally, the staples are driven against the staple-forming undersurface 714 of the anvil 710 and are ejected from the staple cavities 810a, 810b, 810c by the staple drivers 900a, 900b. The staple cartridge 800 can further comprise a support pan 780 attached thereto which extends around the bottom of the staple cartridge body 802 and retains the staple drivers 900a, 900b, the staples, and/or the sled 760 within the cartridge 800.

As indicated above, in the illustrated exemplary embodiment, the surgical instrument 10 includes an articulation drive system 500, which when actuated can articulate the end effector 700 about an articulation joint 270. When the proximal articulation driver 230 is pushed in a first direction, the end effector 700 can be rotated in a first direction and, when the proximal articulation driver 230 is pushed in a second direction, the end effector 700 can be rotated in a second, or opposite, direction. In other embodiments, the end effector is not capable of articulation. Referring now to FIG. 6, the illustrated end effector 700 includes an end effector mounting assembly 790 that is adapted to be pivotally mounted to, for example, a portion of the articulation lock 350 (FIG. 4) that is configured to be rotatably received within the mounting hole 792 in the end effector mounting assembly 790. In the illustrated embodiment, the end effector mounting assembly 790 is mounted to the elongate channel 702 via a spring pin 796 which extends through apertures 705 defined in the elongate channel 702 and the end effector mounting assembly 790. As described in further detail in U.S. Patent Application Publication No. 2014/0263541, which has been herein incorporated by reference in its entirety, the articulation lock 350 may be movable between a first, locked or engaged, position in which the lock is engaged with the end effector mounting assembly 790 and a second, or unlocked or disengaged, position. When the articulation lock 350 is in its engaged or locked position, the articulation lock 350 can hold the end effector 700 in position. When the articulation lock 350 is in its disengaged position, the end effector 700 can be rotated about the articulation joint 270. Other articulation arrangements are disclosed in U.S. patent application Ser. No. 14/314,788, entitled ROBOTICALLY-CONTROLLED SHAFT BASED ROTARY DRIVE SYSTEMS FOR SURGICAL INSTRUMENTS, which was filed on Jun. 25, 2014, now U.S. Patent Application Publication No. 2014/0305993, and which is herein incorporated by reference in its entirety. Still other articulation arrangements are disclosed in U.S. Patent Application Publication No. 2013/0168435, entitled SURGICAL STAPLING INSTRUMENT WITH AN ARTICULATABLE END EFFECTOR, which was filed on Feb. 26, 2013, which is hereby incorporated by reference herein in its entirety.

Turning now to FIGS. 7 and 8, the staple cavities 810a, 810b, 810c of the staple cartridge 800 open through the deck surface 816 and can be positioned and arranged such that the staples stored in the staple cavities 810a, 810b, 810c are deployed as part of an extensible or "flexible" or "elastic" staple line. The staple cavities 810a, 810b, 810c are arranged in a "staple cavity array" generally designated as 806. In at least one arrangement, the staple cavity array 806 comprises a first row 807 of staple cavities 810a which removably stores a first row of staples. The first row 807 of staple cavities 810a extends along a first longitudinal axis 812a adjacent the elongate slot 804. The staple cavity array 806 also comprises a second row 808 of staple cavities 810b which removably stores a second row of staples. The second row 808 of staple cavities 810b extends along a second longitudinal axis 812b adjacent the first row 807 of staple cavities 810a. The staple cavity array 806 further comprises a third row 809 of staple cavities 810c which removably store a third row of staples. The third row 809 of staple cavities 810c extends along a third longitudinal axis 812c adjacent the second row 808 of staple cavities 810b. The first longitudinal axis 812a is parallel, or at least substantially parallel, to the second longitudinal axis 812b; however, other arrangements are possible in which the first longitudinal axis 812a is not parallel to the second longitudinal axis 812b. The second longitudinal axis 812b is parallel, or at least substantially parallel, to the third longitudinal axis 812c; however, other arrangements are possible in which the second longitudinal axis 812b is not parallel to the third longitudinal axis 812c. The first longitudinal axis 812a is parallel, or at least substantially parallel, to the third longitudinal axis 812c; however, other arrangements are possible in which the first longitudinal axis 812a is not parallel to the third longitudinal axis 812c. Referring again to FIGS. 7 and 8, the staple cartridge 800 comprises a first portion of the staple cavity array 806 including a first row 807 of staple cavities 810a, a second row 808 of second staple cavities 810b, and a third row 809 of third staple cavities 810c on a first side 805 of the longitudinal slot 804 and a second portion of the cavity array 806 including a first row 810a, a second row 810b, and a third row 810c on a second side 801 of the longitudinal slot 804. The first cavity array portion is a mirror image of the second cavity array portion with respect to the longitudinal slot; however, other arrangements may be utilized.

Still referring to FIG. 7, each of the first staple cavities 810a is oriented at a first angle 824a with respect a first reference axis 997a that is perpendicular to the first longitudinal axis 812a. Also in the illustrated arrangement, each of the second staple cavities 810b is oriented at a second angle 824b with respect to a second reference axis 997b that is perpendicular to the second longitudinal axis 812b. In addition, each of the third staple cavities 810c is oriented at a third angle 824c with respect to a third reference axis 997c that is perpendicular to the third longitudinal axis 812c. The first angle 824a is different than the second angle 824b; however, in other embodiments, the first angle 824a and the second angle 824b can be the same. The third angle 824c is different than the second angle 824b; however, in other embodiments, the third angle 824c and the second angle 824b can be the same. The first angle 824a is the same as the third angle 824c; however, in other embodiments, the first angle 824a and the third angle 824c can be different. In at least one embodiment, angle 824a may be approximately forty-five (45) degrees (with a range of ±thirty (30) degrees for example); angle 824b may be approximately fifty (50) degrees (with a range of ±thirty (30) degrees, for example); and angle 824c may be approximately forty-five (45) degrees with a range of ±thirty (30) degrees, for example).

The staple cartridge 800 is configured to deploy the staple pattern 813 depicted in FIG. 9. The staple cartridge 800 is configured to deploy a first row 817 of staples 820a along a first longitudinal axis 822a, a second row 818 of staples 820b along a second longitudinal axis 822b, and a third row 819 of staples 820c along a third longitudinal axis 822c. In various instances, the staple cartridge 800 is configured to deploy a first row 817 of staples 820a, a second row 818 of staples 820b, and a third row 819 of staples 820c on a first side of a longitudinal incision 826 and a first row 817 of staples 820a, a second row 818 of staples 820b, and a third row 819 of staples 820c on a second side of the longitudinal incision 826. The first rows 817 of staples 820a can be positioned adjacent the longitudinal incision 826 and the third row 819 of staples 820c can be positioned furthest away from the longitudinal incision 826. Each second row 818 of staples 820b can be positioned intermediate a first row 817 of staples 820a and a third row 819 of staples 820c.

Further to the above, the first staples 820a are removably stored in the first staple cavities 810a, the second staples 820b are removably stored in the second staple cavities 810b, and the third staples 820c are removably stored in the third staple cavities 810c. The staple cavities 810a-810c are configured and arranged to deploy the staples 820a-820c in the arrangement depicted in FIGS. 9 and 10. For example, the first staples 820a are oriented at the first angle 824a with respect to a first reference axis 999a that is perpendicular to the first longitudinal axis 822a. The second staples 820b are oriented at the second angle 824b with respect to a second reference axis 999b that is perpendicular to the second longitudinal axis 822b. The third staples 820c are oriented at the third angle 824c with respect to a third reference axis 999c that is perpendicular to the third longitudinal axis 822c.

The first staples 820a, the second staples 820b, and the third staples 820c can be positioned and arranged such that they provide "laterally-overlapping" staple lines. More particularly, referring again to FIG. 9, the second longitudinal row 818 of second staples 820b is positioned laterally with respect to the first longitudinal row 817 of first staples 820a such that the second staples 820b are aligned with the gaps between the first staples 820a and, similarly, the third longitudinal row 819 of third staples 820c is positioned laterally with respect to the second longitudinal row 818 of second staples 820b such that the third staples 820c are aligned with the gaps between the second staples 820b. Such an arrangement can limit the flow of blood from the tissue T to the longitudinal incision 826.

Further to the above, the staple pattern disclosed in FIG. 9 comprises six longitudinal rows of staples. Other embodiments are envisioned which comprise less than six rows of staples, such as four rows of staples, for example, or more than six rows of staples, such as eight rows of staples, for example. The first staples 820a, the second staples 820b, and the third staples 820c can comprise any suitable configuration such as, for example, a V-shaped configuration or a U-shaped configuration. A staple comprising a V-shaped configuration can include a base or crown, a first leg extending from a first end of the base or crown, and a second leg extending from a second end of the base or crown, wherein the first leg and the second leg extend in directions which are non-parallel to one another. A staple comprising a U-shaped configuration can include a base or crown, a first leg extending from a first end of the base or crown, and a second leg extending from a second end of the base or crown, wherein the first leg and the second leg extend in directions which are parallel to one another.

With regard to the staple pattern disclosed in FIG. 9, for example, each first staple 820a comprises a first staple base or crown 827a (FIG. 12) that has a first proximal staple leg 825a and a first distal staple leg 823a protruding therefrom. A staple cartridge 800 configured to deploy the staple pattern 813 disclosed in FIG. 9 can include a proximal end 803 and a distal end 811. The first proximal staple leg 825a can be closer to the proximal end 803 of the staple cartridge 800 than the first distal staple leg 823a and, similarly, the first distal staple leg 823a can be closer to the distal end 811 of the staple cartridge 800 than the first proximal staple leg 825a. The first crown 827a of each first staple 820a can define a first base axis "FBA". Each of the first proximal staple leg 825a and the first distal staple leg 823a can extend from the first base axis FBA. The first staples 820a can be positioned and arranged such that the first base axes FBA's extend toward the longitudinal cut line 826 and toward the distal end of the staple cartridge 800. Stated another way, the first base axis FBA may be transverse to the elongate slot 804.

With regard to the staple pattern 813 disclosed in FIG. 9, for example, each second staple 820b comprises a second staple base or crown 827b (FIG. 12) that has a second proximal staple leg 825b and a second distal staple leg 823b protruding therefrom. The second proximal staple leg 825b can be closer to the proximal end 803 of the staple cartridge 800 than the second distal staple leg 823b and, similarly, the second distal staple leg 823b can be closer to the distal end 811 of the staple cartridge 800 than the second proximal staple leg 825b. The base second crown 827b of each second staple 820b can define a second base axis "SBA". The second proximal staple leg 825b and the second distal staple leg 823b can extend from the second base axis SBA. The second staples 820b can be positioned and arranged such that the second base axes SBA's extend toward the longitudinal incision 826 and toward the proximal end 803 of the staple cartridge 800. In the illustrated example, the second base axes SBA are transverse to the first base axes as well as to the elongate slot 804.

With regard to the staple pattern 813 disclosed in FIG. 9, for example, each third staple 820c comprises a third base or crown 827c (FIG. 12) that has a third proximal staple leg 825c and a third distal staple leg 823c protruding therefrom. The third proximal staple leg 825c can be closer to the proximal end 803 of the staple cartridge 800 than the third distal staple leg 823c and, similarly, the third distal staple leg 823c can be closer to the distal end 811 of the staple cartridge 800 than the third proximal staple leg 825c. The third crown 827c of each third staple 820c can define a third base axis "TBA". The third proximal staple leg 825c and the third distal staple leg 823c can extend from the third base axis TBA. The third staples 820c can be positioned and arranged such that the third base axes TBA's extend toward the longitudinal cut line 826 and toward the distal end of the staple cartridge. In the illustrated example, the third base axes TBA are parallel to the first base axes FBA and are transverse to the second base axes SBA as well as to the elongate slot 804. This is but one exemplary embodiment and any suitable arrangement could be utilized.

Further to the above, the first staples 820a straddle the first longitudinal axis 822a. See FIG. 9. The first distal legs 823a of the first staples 820a are positioned on one side of the first longitudinal axis 822a and the first proximal legs

825a are positioned on the other side of the first longitudinal axis 822a. Stated another way, the legs of the first staples 820a are offset with respect to the first longitudinal axis 822a. Alternative embodiments are envisioned in which the first staples 820a are aligned with or collinear with the first longitudinal axis 822a. The second staples 820b straddle the second longitudinal axis 822b. The second distal legs 823b of the second staples 820b are positioned on one side of the second longitudinal axis 822b and the second proximal legs 825b are positioned on the other side of the second longitudinal axis 822b. Stated another way, the legs of the second staples 820b are offset with respect to the second longitudinal axis 822b. Alternative embodiments are envisioned in which the second staples 820b are aligned with or collinear with the second longitudinal axis 822b.

In the illustrated example, the third staples 820c straddle the third longitudinal axis 820c. The third distal legs 823c of the third staples 820c are positioned on one side of the third longitudinal axis 820c and the third proximal legs 825c are positioned on the other side of the third longitudinal axis 822c. Stated another way, the legs of the third staples 820c are offset with respect to the third longitudinal axis 822c. Alternative embodiments are envisioned in which the third staples 820c are aligned with or collinear with the third longitudinal axis 822c. In certain embodiments, a first staple 820a can comprise a first proximal leg 825a which is aligned with the second distal leg 823b of an adjacent second staple 820b. Similarly, a third staple 820c can comprise a third proximal leg 825c which is aligned with the second distal leg 823b of an adjacent second staple 820b. In various embodiments, a first staple 820a can comprise a first proximal leg 825a which is positioned distally with respect to the second distal leg 823b of an adjacent second staple 820b. Similarly, a third staple 820c can comprise a third proximal leg 825c which is positioned distally with respect to the second distal leg 823b of an adjacent second staple 820b. The row of second staples 820b is bounded by the row of first staples 820a and the row of third staples 820c. A second staple 820b is bounded on one side by a first staple 820a and on the other side by a third staple 820c. More particularly, a first staple 820a is positioned laterally inwardly with respect to the second proximal leg 825b of a second staple 820b and, similarly, a third staple 820c is positioned laterally outwardly with respect to the second distal leg 823b of the second staple 820b. As a result, the first staples 820a can provide a boundary on one side of the second staples 820b and the third staples 820b can provide a boundary on the other side of the second staples 820b.

A traditional staple pattern 829 is illustrated in FIG. 11. This staple pattern 829 comprises a first row 836 of first staples 830a positioned along a first longitudinal axis 832a, a second row 838 of second staples 830b positioned along a second longitudinal axis 832b, and a third row 840 of third staples 830c positioned along a third longitudinal axis 832c positioned on a first side of a longitudinal incision 835 in the tissue T. The first staples 830a are aligned, or at least substantially aligned, with the first longitudinal axis 832a; the second staples 830b are aligned, or at least substantially aligned, with the second longitudinal axis 832b; and the third staples 830c are aligned, or at least substantially aligned, with the third longitudinal axis 832c. Stated another way, the first staples 830a are not oriented at an angle with respect to the first longitudinal axis 832a, the second staples 830b are not oriented at an angle with respect to the second longitudinal axis 832b, and the third staples 830c are not oriented at an angle with respect to the third longitudinal axis 832c. This traditional staple pattern also comprises a first row 836 of staples 830a positioned along a first longitudinal axis 832a, a second row 838 of staples 830b positioned along a second longitudinal axis 832b, and a third row 840 of staples 830c positioned along a third longitudinal axis 832c positioned on a second, or opposite, side of the longitudinal incision 835.

When a longitudinal tensile force is applied to the tissue T stapled by the staple pattern 829 illustrated in FIG. 11, the tissue T will stretch longitudinally. Moreover, in various instances, the staples 830a, 830b and 830c can translate longitudinally as the tissue T is stretched longitudinally. Such an arrangement can be suitable in many circumstances; however, the staples 830a, 830b and 830c can restrict the stretching and/or movement of the tissue T. In some instances, the tissue T that has been stapled by the staples 830a, 830b and 830c may be far less flexible than the adjacent tissue that has not been stapled. Stated another way, the staple pattern 829 comprising the staples 830a, 830b, and 830c can create a sudden change in the material properties of the tissue. In at least one instance, a large strain gradient can be created within the tissue T as a result of the staple pattern which, in turn, can create a large stress gradient within the tissue T.

When the staples 830a-830c are ejected from a staple cartridge, the legs of the staples can puncture the tissue T. As a result, the staple legs create holes in the tissue. Various types of tissues are resilient and can stretch around the staple legs as the staple legs pass through the tissue. In various instances, the resiliency of the tissue can permit the tissue to stretch and resiliently return toward the staple legs to reduce or eliminate gaps present between the tissue and the staple legs. Such resiliency or elasticity can also permit the tissue to stretch when a stretching force is applied to the tissue; however, such resiliency can be inhibited by certain staple patterns. In at least one instance, the staple pattern 829 depicted in FIG. 11 can inhibit the longitudinal stretching of the tissue. When a longitudinal stretching force is applied to the tissue stapled by the staple pattern of FIG. 11, the tissue may begin to pull away from the staple legs and create gaps therebetween. In some instances, especially in bariatric resection applications, such gaps can result in increased bleeding from the stomach tissue. In certain instances, especially in lung resection applications, air leaks can result in the lung tissue, for example.

The staple pattern 813 depicted FIGS. 9 and 10 is more flexible or elastic than "traditional" staple pattern 829 arrangements of the type depicted in FIG. 11. For example, when a longitudinal tensile force is applied to the tissue T, referring now to FIG. 10, the staples 820a, 820b, and 820c can, one, translate longitudinally as the tissue is stretched longitudinally and/or, two, rotate as the tissue is stretched longitudinally. Moreover, the compliant staple pattern 813 depicted in FIG. 9 can reduce or eliminate the gaps between the staple legs and the tissue T when a longitudinal stretching force is applied to the tissue and, as a result, reduce the bleeding and/or air leaks between the staple legs and the tissue. The staple pattern 813 depicted in FIG. 9 is depicted in an unstretched condition. When the tissue stapled by the staple pattern depicted in FIG. 9 is stretched longitudinally, the staples can move longitudinally with the tissue and/or rotate within the tissue, as illustrated in FIG. 10. U.S. patent application Ser. No. 14/498,121, entitled FASTENER CARTRIDGE FOR CREATING A FLEXIBLE STAPLE LINE, filed Sep. 26, 2014, the entire disclosure of which is hereby incorporated by reference herein discloses various advantages as well as other variations of the elastic or compliant staple lines described above.

As indicated above, the staples 820a, 820b, 820c are supported on corresponding drivers 900a, 900b that are movably supported in cavities formed in the cartridge body 802. To achieve staples with consistent "formed" shapes, it may be desirable for each of the staples to exit out of their respective cavity so that the staple legs thereof are generally perpendicular to the corresponding portion of the staple forming undersurface 714 of the anvil 710. As indicated above, the staple drivers on which the staples are supported are driven upwardly when they are drivingly contacted by the corresponding ramps or camming members of the distally-moving sled or camming member 760. Because the sled ramps are moving in directions that are essentially transverse to the direction in which the drivers are moving, the driving motion applied by the sled ramps to the drivers could, at times, skew a staple driver within its respective cavity as it is driven upward therein. Such skewing of the staple driver(s) may undesirably result in one, an increase in the force required to drive the firing beam and/or two result in the skewing of the staples as they are ejected from the cartridge body which could ultimately lead to inconsistently formed staples or even malformed staples. Thus, it may be desirable to employ staple driver arrangements and corresponding cartridge body arrangements that afford sufficient amounts of support to the staple drivers as they are drivingly contacted by the sled ramps.

Figure 12:
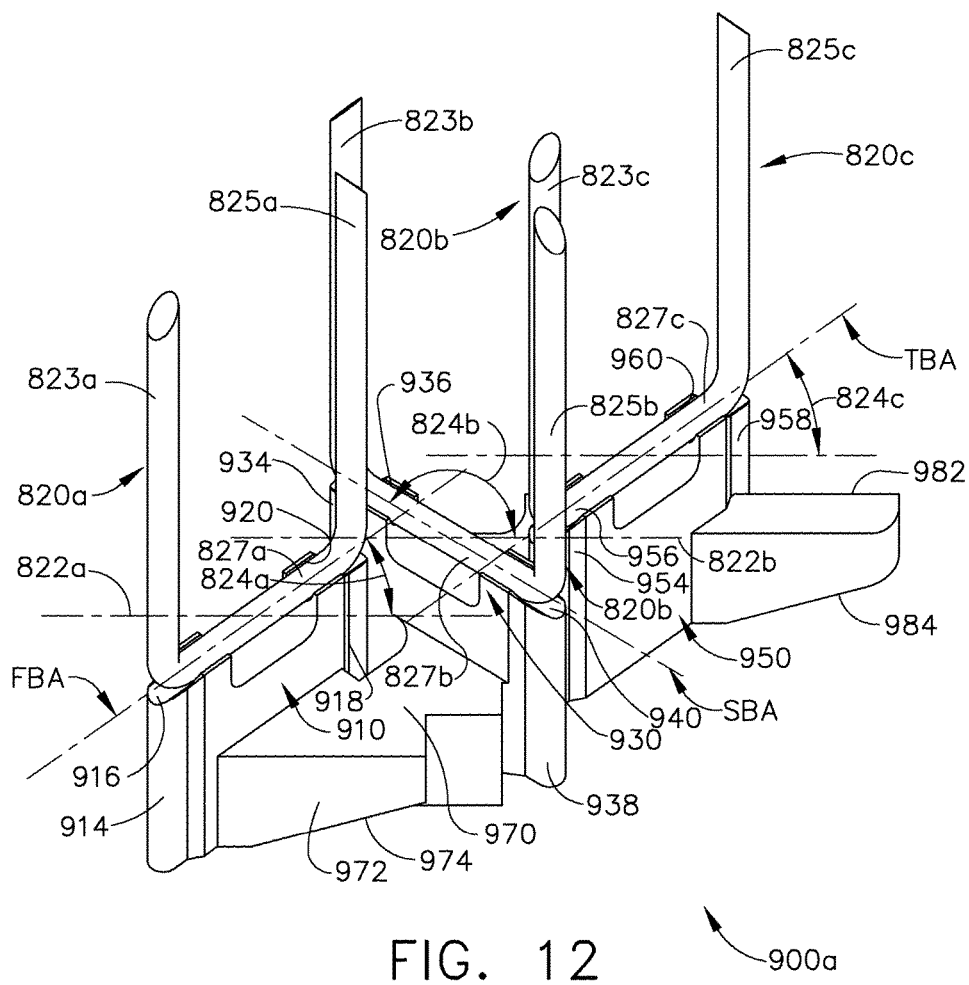
FIG. 12 is a perspective view of a staple driver embodiment.
Figure 13:
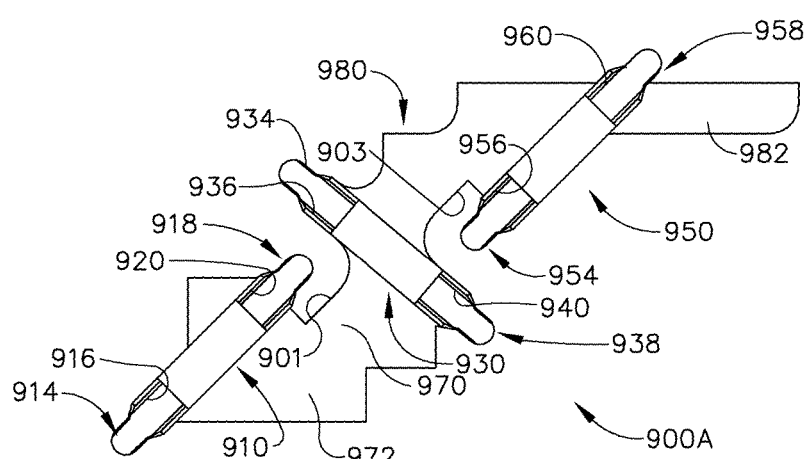
FIG. 13 is a top view of the staple driver embodiment of FIG. 12.
Figure 14:
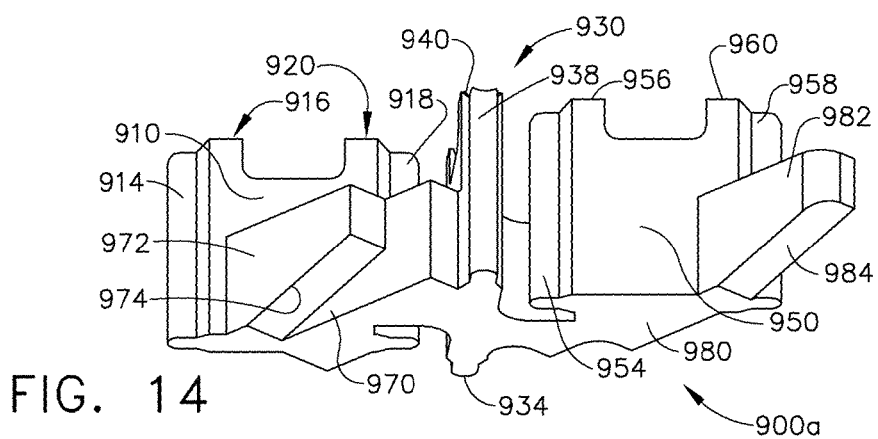
FIG. 14 is a bottom perspective view of the staple driver of FIGS. 12 and 13.

FIGS. 12-14 illustrate a staple driver 900a according to at least one embodiment of the present invention. In at least one arrangement, the staple drivers 900b may be mirror images of staple drivers 900a. As can be seen in FIG. 12, one staple driver 900a can support three staples 820a, 820b, 820c thereon. The staple driver 900a includes a first or innermost staple support portion 910 that is configured to support a first staple 820a thereon, a second or central staple support portion 930 that is configured to support a second staple 820b thereon and a third or outermost staple support portion 950 that is configured to support a third staple 820c thereon. As used in this context, the term "innermost" refers to the staple support portion that is closest to the elongate slot 804 in the cartridge body 802 and the term "outermost" refers to the staple support portion that is the farthest away from the elongate slot 804.

As can be seen in FIG. 12, the first staple support portion 910 comprises a first distal support column 914 and a first proximal support column 918. The first staple support portion 910 further includes a first distal support cradle 916 and a first proximal support cradle 920 for supporting portions of the first staple crown 827a. As can be further seen in FIG. 12, when the first staple crown 827a of the first staple 820a is supported on the support cradles 916 and 920, the first distal leg 823a is essentially axially aligned with the first distal support column 914 and the first proximal leg 825a is essentially axially aligned with the first proximal support column 918.

Still referring to FIG. 12, the driver 900a further comprises second staple support portion 930 that comprises a second distal support column 934 and a second proximal support column 938. The second staple support portion 930 further includes a second distal support cradle 936 and a second proximal support cradle 940 for supporting portions of the second staple crown 827b therein. As can also be seen in FIG. 12, when the second staple crown 827b of the second staple 820b is supported in the second cradles 936, 940, the second distal leg 823b is essentially axially aligned with the second distal support column 934 and the second proximal leg 825b is essentially axially aligned with the second proximal support column 938.

As can also be seen in FIG. 12, the driver 900a comprises a third staple support portion 950 that includes a third distal support column 954 and a third proximal support column 958. The third staple support portion 950 further includes a third distal support cradle 956 and a third proximal support cradle 960 that are configured to support portions of the third staple crown 827c of the third staple 820c therein. As can be seen in FIG. 12, when the third crown 827c of the third staple 820c is supported in the third cradles 956, 960, the third distal leg 823c is essentially axially aligned with the third distal support column 954 and the third proximal leg 825c is essentially axially aligned with the third proximal support column 958.

Still referring to FIGS. 12-14, in at least one arrangement the first staple support portion 910 is coupled to the second staple support portion 930 by a first or distal connection member 970. The first connection member 970 includes a first cam portion that has a first camming surface or ramp 974 formed on the underside thereof. The second staple support portion 930 is likewise connected to the third staple support portion 950 by a second or proximal connection member 980. A second cam member 982 protrudes from or is attached to the third staple support portion 950 and has a second camming surface or ramp 984 formed thereon. In the illustrated arrangement, the first and second camming surfaces 974, 984 are formed with the same angle and are essentially parallel to each other. In other arrangements, however, the first and second camming surfaces 974, 984 may differ from each other. The camming angle of the first and second camming surface 974, 984 may relate to the cam angles of the corresponding ramp or camming surfaces of the sled 760. In at least one embodiment, the staple driver 900a (and 900b) is integrally formed from or molded from, for example, Ultem®, with no fill. However, other materials such as, for example, Ultem® with a glass or mineral fill or Nylon or Nylon with a glass file could be used. In other arrangements, the various portions of the staple driver 900a (and 900b) may be separately fabricated from other materials and be attached together by adhesive, solder, etc.

Figure 15:
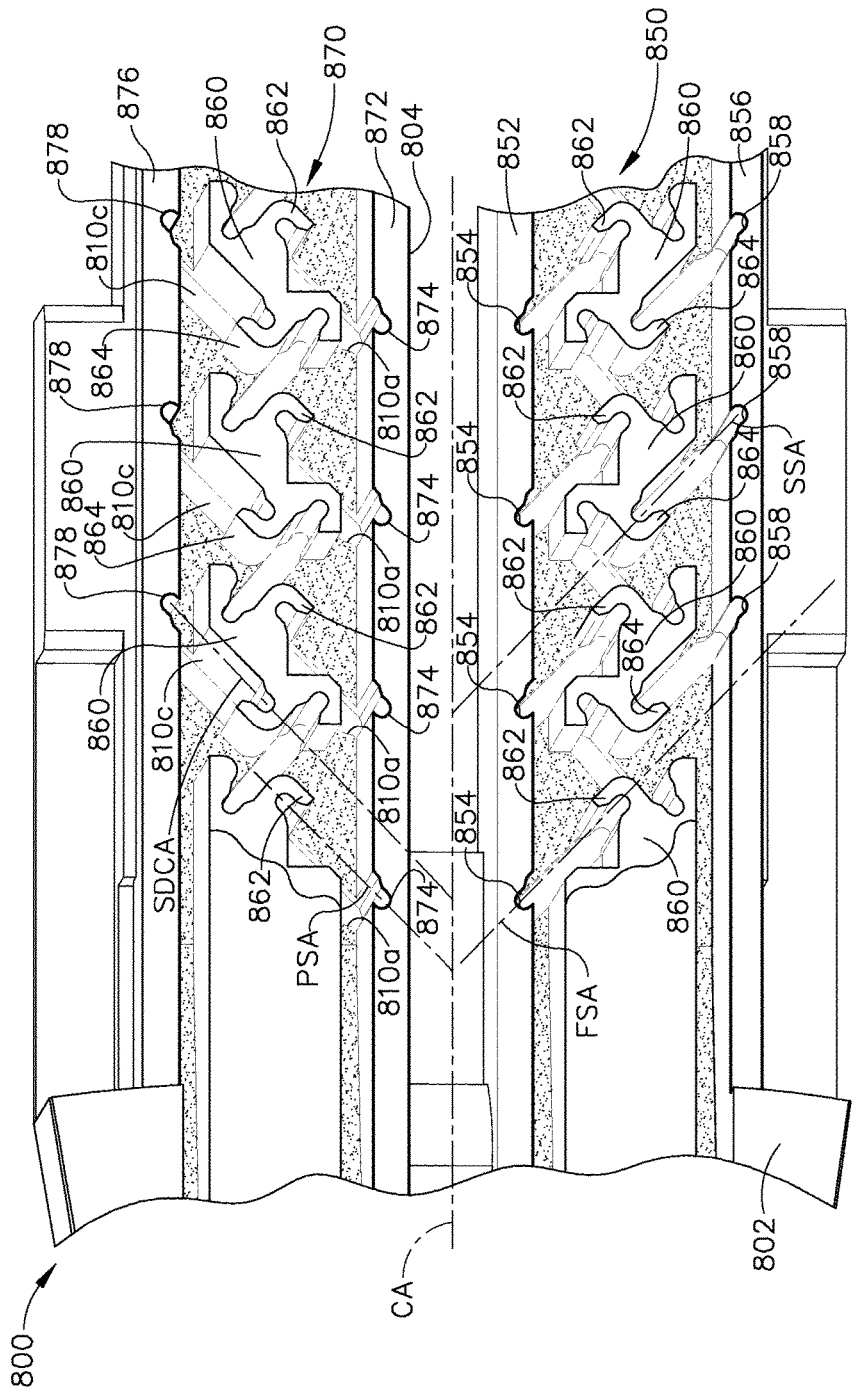
FIG. 15 is a bottom perspective view of a portion of a surgical staple cartridge embodiment.

FIG. 15 is a bottom perspective view of a portion of one form of the surgical staple cartridge body 802. As indicated above, in at least one embodiment, the cartridge body 802 includes an elongate slot 804 that may be centrally disposed in the body 802. In the embodiment depicted in FIG. 15, for example, the elongate slot 804 bifurcates the cartridge body 802 into two body portions 850, 870 and extends along the centrally-disposed cartridge axis "CA". As can be seen in that Figure, the first body portion 850 includes a first cartridge wall portion 852 that includes first support grooves or slots 854 that are each arranged on a corresponding first slot axis "FSA" that is transverse to the cartridge axis CA. The first body portion 850 further includes a second cartridge wall portion 856 that contains second support grooves or slots 858 therein that are each arranged on a corresponding second slot axis "SSA" that is transverse to the cartridge axis CA. Located between the first cartridge wall portion 852 and the second cartridge wall portion 856 are a plurality of spaced, staple driver guides 860. In at least one arrangement, the staple driver guides 860 are integrally formed with one or both of the cartridge wall portions 852, 856 in the cartridge body 802. In other arrangements, the staple driver guides 860 are attached to the wall portions of the cartridge body 802. Each staple driver guide 860 may be configured to slidably interlock with or, stated another way, slidably support two adjacent staple drivers 900a. See FIG. 17.

Referring now to FIGS. 16 and 17, in at least one arrangement, each of the staple drivers 900a includes opposed, hooked shaped slots 901, 903 that are configured to be "hookingly engaged" by corresponding opposed hook-shaped portions 862, 864, respectively of the staple driver guide 860. The hook-shaped portions 862 are configured to slidably support the first proximal support column 918 of a corresponding staple driver 900a and the hook-shaped portions 864 are configured to slidably support a third distal support column 954 of a corresponding staple driver 900a. In addition, the staple driver guide 860 further includes a proximal slot 863 that is configured to slidably support the second distal support column 934 of a corresponding staple driver 900a as well as a distal slot 868 that is configured to slidably support the second proximal support column 938 of the corresponding staple driver 900a. Thus, each staple driver 900a that is in sliding engagement with a corresponding staple driver guide 860 is slidably movable relative to the staple driver guide 860 when the staple driver 900a is drivingly contacted by the sled ramps or camming surfaces 762, 764.

Referring again to FIG. 15, the second body portion 870 includes a primary cartridge wall portion 872 that includes primary staple leg grooves or slots 874 therein that are each arranged on a corresponding primary slot axis "PSA" that is transverse to the cartridge axis CA. The second body portion further includes a secondary cartridge wall portion 876 that contains second support grooves or slots 878 therein that are each oriented on a corresponding secondary slot axis SDSA that is transverse to the cartridge axis CA. Located between the primary cartridge wall portion 872 and the secondary cartridge wall portion 876 are a plurality of other spaced driver guides 860 that are each configured to slidably interlock with two adjacent staple drivers 900b which may be mirror images of staple drivers 900a in the manner described above. Thus, each staple driver 900b that is in slidable engagement with a corresponding driver guide 860 is slidably movable relative to the driver guide 860 when the staple driver 900b is drivingly contacted by the sled ramps or camming members 766, 768. See FIG. 6.

In the illustrated embodiment, staple drivers 900a are arranged in first "staple driver array" generally designated as 905a as shown in FIGS. 16 and 17. When the staple drivers 900a are arranged as shown in FIGS. 16 and 17, each staple driver 900a may be in slidable engagement with two corresponding staple guides 860. See FIG. 17. In addition, the first distal support column 914 of each staple driver 900a may be slidably received within a corresponding first support groove or slots 854 in the first cartridge wall portion 852. See FIGS. 8 and 15. Likewise, the third proximal support column 958 of each staple driver 900a may be slidably received within a corresponding second support groove or slot 858 in the second cartridge wall portion 856. Thus, each of the support columns of the staple driver 900a are slidably supported by a corresponding staple driver guide 860 or they are supported by the corresponding cartridge wall portion. Such arrangement may serve to prevent any skewing of the support columns when the staple driver is driven upward within the cartridge body.

Referring again to FIG. 16, it can be seen that each of the first cam portions 972 of the staple drivers 900a are aligned along a first cam axis "FCA". Thus, in at least one embodiment, each of the first camming surfaces 974 is axially aligned on the first cam axis FCA. Also, each of the second cam members 982 of the staple drivers 900a is axially aligned along a second cam axis "SCA". Thus, each of the second camming surfaces 984 of the staple drivers 900a is axially aligned along the second cam axis SCA. In at least one arrangement, for example, the cam axes FCA and SCA are parallel to each other as well as to the elongate slot 804 (represented in segmented lines in FIG. 16) in the staple cartridge. Also in the illustrated staple driver array 905b, each of the first cam members 972 of the staple drivers 900b are aligned along a primary first cam axis "PCA". Thus, in at least one embodiment, each of the first camming surfaces 974 of the staple drivers 900b are axially aligned on the primary cam axis PCA. Also, each of the second cam members 982 of the staple drivers 900b are all axially aligned along a secondary cam axis "SDCA". Thus, each of the second camming surfaces 984 of the staple drivers 900b are axially aligned along the secondary cam axis SDCA.

Figure 18:
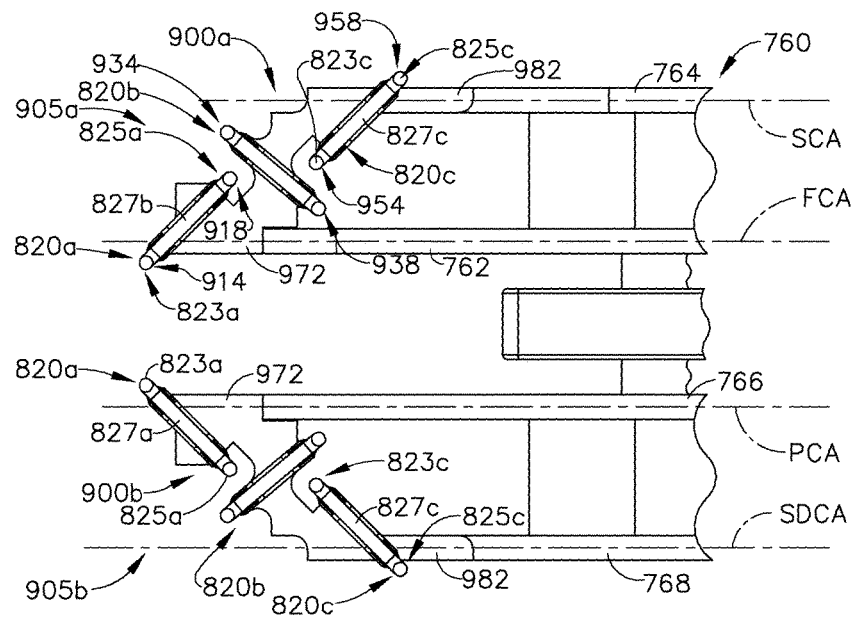
FIG. 18 is a top view of portions of the driver arrays of FIGS. 16 and 17 in connection with a sled or camming actuator of a surgical instrument.
Figure 19:
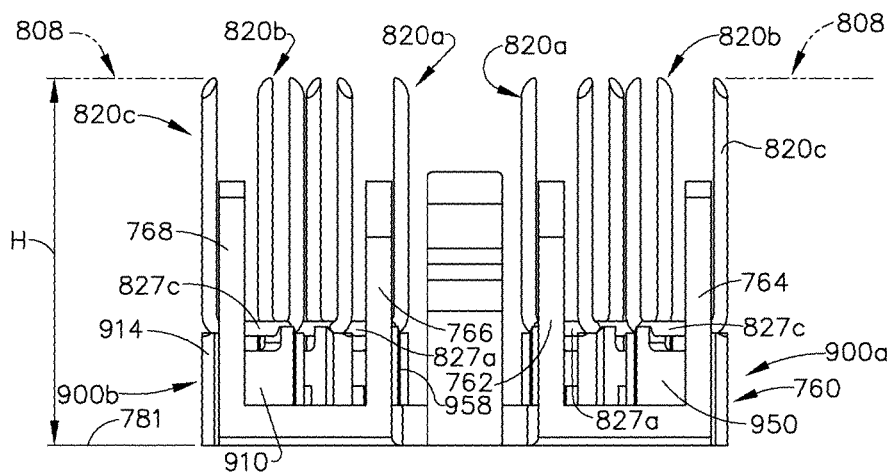
FIG. 19 is a front elevational view of the driver array and sled/cam actuator depicted in FIG. 18.

FIGS. 18 and 19 illustrate the position of the sled or camming actuator 760 relative to the staple drivers 900a, 900b. As can be seen in FIG. 18, in the array 905a of staple drivers 900a, the ramp or camming member 764 is aligned with the second cam axis SCA. The ramp surface or camming member 762 is aligned with the first cam axis FCA. The ramp or camming member 766 is aligned on the primary cam axis PCA and the ramp or camming member 768 is aligned with the secondary cam axis SDCA. Thus, the ramp or camming member 764 is situated to proceed under a portion of each of the crowns 827c of staples 820c that are supported on the drivers 900a. The ramp or camming surface 762 is situated to proceed under a portion of each of the crowns 827c of staples 820a that are supported on the drivers 900a. Likewise, in the array 905b of the staple drivers 900b, the ramp or camming member 766 is situated to proceed under a portion of the crowns 827a of each of the staples 820a supported on the drivers 900b. The ramp or camming member 768 is situated to proceed under a portion of the crown 827c of each of the staples 820c supported on the drivers 900b. Stated another way, none of the ramps or camming members 764, 762, 766, 768 are aligned with any of the staple legs of the staples 820a, 820b, 820c that are supported on the drivers 900a, 900b. Such arrangement therefore enables the third proximal support columns 958 of each of the staple drivers 900a to be slidably received within corresponding second support grooves or slots 858 in the second cartridge wall portion 856 of the cartridge body 802. In addition, the first distal support columns 914 of each of the staple drivers 900a are slidably received within corresponding first support grooves or slots 854 in the first cartridge wall portion 852 of the cartridge 800. Likewise, each of the support columns 918, 934, 938, 954 is also slidably supported in corresponding driver guides 860 that are formed in or attached to the cartridge body 802. Each of the driver guides 860 may have the same height or similar height as the heights of the wall portions 852, 856.

Referring to FIG. 19 for example, the first and second cartridge wall portions 852, 856 (not shown in FIG. 19) have a height represented by "H". The staple driver guides 860 may have the same or similar heights "H". This height may also essentially comprise the height of the cartridge body 802 in at least some embodiments. Other embodiments may employ a "stepped deck" which is a deck surface that has more than one planar portion that have different heights which may be measured from the bottom of the cartridge body for example. In FIG. 19, element 816 may represent the staple deck surface (or at least one staple deck surface in embodiments employing a stepped deck) and 781 may represent a surface upon which the staple drivers 900a, 900b sit when they are in an unactuated orientation within the cartridge body. For example, element number 781 may represent the upper surface of the support pan 780. See FIG. 6. In at least one arrangement, the driver guides 860 may also have a height that is equal to or nearly equal to height "H" of the cartridge wall portions 852, 856. Thus, the support columns of each driver 900a, 900b are essentially slidably supported throughout their entire path of travel (distance "H") when they are driven upward in the cartridge body when contacted by the ramps or camming members on the sled 760. In other embodiments, the support columns of each driver 900a, 900b are each supported for a distance or height that is at least (0.134 inch staple+at least 0.066 inch driver (0.2 inches total) for a staple cartridge that may be used to staple lung tissue for example). Stated another way, the driver can be advanced a distance that is at least as long as the height of the staple (e.g., height of 820). The staple crown is "ejected" from the staple pocket in the cartridge to prevent tissue from being stuck between the driver and the cartridge deck in its fully advanced state. Such feature may help to avoid the staple drivers 900a, 900b from skewing during actuation which may reduce the likelihood of the formation of malformed staples.

When the surgical instrument is "fired" or, stated another way, when the firing drive system 80 is actuated to drive the firing beam 280 distally, the tissue cutting member 750 contacts the sled or camming member 760 and drives the camming member 760 distally through the staple cartridge 800. As can be seen in FIG. 16, the camming members 982 of the staple driver 900a are located "inboard" (i.e., closer to the elongate slot 804) from the support columns 958 (and the staple legs 825c supported thereon). Likewise, the camming members 982 of the staple drivers 900b are located inboard of the support columns 958 of those staple drivers 900b and the staple legs 825c supported thereon. Such arrangements permit those support columns 958 to be completely slidably supported through their entire range of upward travel by the corresponding wall portions 856, 876 of the staple cartridge. In addition, the support columns 934, 938, 918, 954 are supported through their entire range of upward travel by the corresponding staple driver guides 860 formed in the cartridge body 802. Likewise the support column 914 of each of the staple drivers 900a, 900b are slidably supported in the corresponding wall portions 852, 872 of the cartridge body 802 through their entire range of upward travel.

Still referring to FIGS. 16 and 17, the driver array 905a comprises a plurality of staple drivers 900a that are each configured to support three staples 820a, 820b, 820c thereon. Of course during use, each driver 900a may actually support one, two or all three of such staples. On each staple driver 900a, staple 820a lies along axis FBA. Stated more precisely, the staple crown 827a of staple 820a lies along axis FBA. Staple 820c lies along axis TBA. Stated more precisely, the staple crown 827c of staple 820c lies along the third base axis TBA. In at least one arrangement axes FBA and TBA are parallel to each other. Staple 820b is centrally supported between staples 820a and 820c and lies along an axis SBA. Stated more precisely, the staple crown of 827b lies along the second base axis SBA. In the illustrated arrangement, SBA is transverse to axes FBA and TBA. Stated another way, the staple driver 900a is configured to support two surgical staples that are parallel to each other or extend in the same direction and one staple that is transverse to the other two staples or extends in another direction that differs from the directions in which the other two staples extend. In the illustrated arrangement, when the staple drivers 900a, 900b are all operably supported in the staple cartridge 800, all of the axes FBA, SBA, TBA are each transverse to the elongate slot 804.

As can be appreciated from reference to FIG. 16, when the staple drivers 900a are all operably supported in the staple cartridge in the staple driver array 905a, the staple drivers 900a form a first longitudinal row 1200a of staples 820a that is adjacent to elongate slot 804 in the cartridge body 802. Each of the staples 820a in the first longitudinal row 1200a extend in a first direction as was described above. Likewise, the staple drivers 900a form a second longitudinal row 1202a of staples 820b that are adjacent the first longitudinal row 1200a. The staples 820b in the second longitudinal row 1202a extend in a second direction that is different from the first direction of the staples 820a in the first longitudinal row 1200a. In addition, the staple drivers 900a form a third longitudinal row 1204a of staples 820c that are oriented in a third direction which may or may not be in the same direction as staples 820a. For example, in the illustrated embodiment, the first and third directions are the same. The third longitudinal row 1204a is adjacent to the second longitudinal row 1202a.

Still referring to FIG. 16, when the staple drivers 900b are all operably supported in the staple cartridge in the staple driver array 905b, the staple drivers 900b form a first longitudinal row 1200b of staples 820a that is adjacent to elongate slot 804 in the cartridge body 802. Each of the staples 820a in the first longitudinal row 1200b extend in a first direction as was described above. Likewise, the staple drivers 900b form a second longitudinal row 1202b of staples 820b that are adjacent the first longitudinal row 1200b. The staples 820b in the second longitudinal row 1202a extend in a second direction that is different from the first direction of the staples 820a in the first longitudinal row 1200a. In addition, the staple drivers 900b form a third longitudinal row 1204b of staples 820c that are oriented in a third direction which may or may not be in the same direction as staples 820a. For example, in the illustrated embodiment, the first and third directions are the same. The third longitudinal row 1204b is adjacent to the second longitudinal row 1202b.

Figure 22:
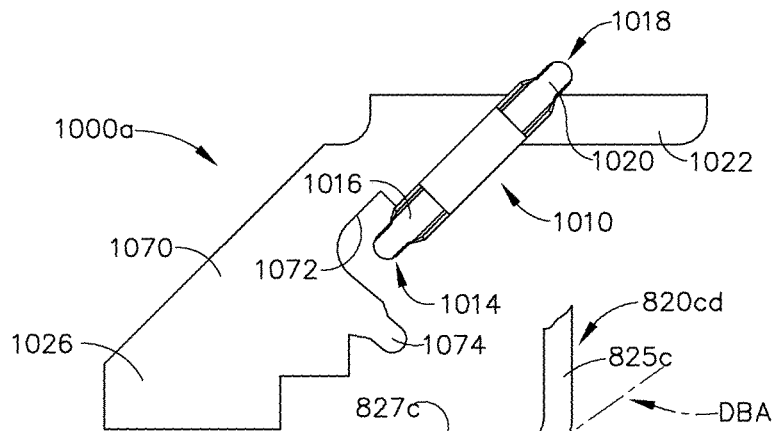
FIG. 22 is a top view of a distal driver of the driver array illustrated in FIG. 20.
Figure 23:
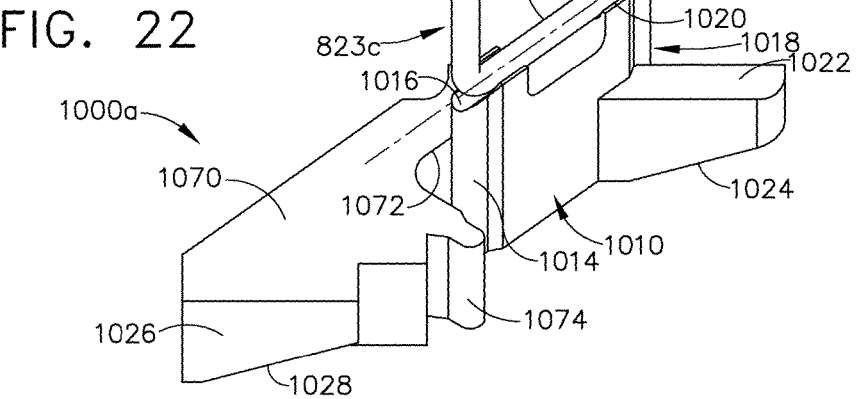
FIG. 23 is a perspective view of the distal driver of FIG. 22 supporting a staple thereon.
Figure 24:
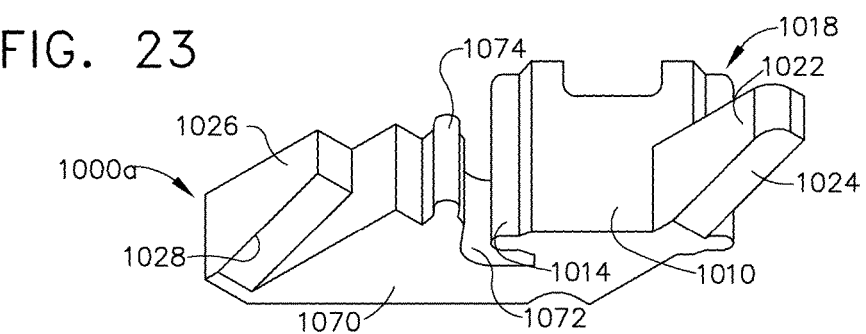
FIG. 24 is a bottom perspective view of the distal driver of FIGS. 22 and 23.

Other staple driver arrays 990a, 990b are illustrated in FIGS. 20 and 21. As can be seen in those Figures, the staple driver array 990a employs a distal staple driver 1000a and a proximal staple driver 1100a in addition to a plurality of the staple drivers 900a. Likewise, the staple driver array 990b includes a distal staple driver 1000b and a proximal staple driver 1100b. Distal staple driver 1000b may essentially be a mirror image of distal staple driver 1000a and proximal staple driver 1100b may essentially be a mirror image of proximal staple driver 1100a. FIGS. 22-24 illustrate one exemplary form of a distal staple driver 1000a with it being understood that, in at least one arrangement, the distal staple driver 1000b essentially contains the same features as a distal staple driver 1000a, but is a mirror image thereof. Each distal staple driver 1000a, 1000b includes a distal staple support portion 1010 that is configured to support a corresponding distal most staple 820cd thereon. As can be seen in FIGS. 22-24, the distal staple support portion 1010 comprises a distal support column 1014 and a proximal support column 1018. The distal staple support portion 1010 further includes a distal support cradle 1016 and a proximal support cradle 1020 for supporting portions of the staple crown 827c of the corresponding distal staple 820cd. When the staple crown 827c of the distal staple 820cd is supported on the support cradles 1016 and 1020, the first distal leg 823c of the staple 820cd is essentially axially aligned with the first distal support column 1016 and the first proximal leg 825c is essentially axially aligned with the first proximal support column 1018. In at least one arrangement, the distal staple drivers 1000a, 1000b include a distal connection member 1070. The distal connection member 1070 is configured to slidably engage the corresponding distal-most driver guide (designated as 860D in FIG. 21).

In at least one arrangement, the distal connection member 1070 includes a hook-shaped distal slot 1072 that is configured to be "hookingly engaged" by the hook-shaped portion 864 on the corresponding distal-most driver guide 860D. In addition, the distal connection member 1070 may include a projection 1074 that is configured to be slidably received within a corresponding slot 868 in the distal most driver guide 860D. See FIG. 21. Thus, each distal staple driver 1000*a*, 1000*b* is slidably engaged with a corresponding driver guide 860. In addition, in the array 990*a* of staple drivers 900*a*, 1000*a*, the proximal support column 1018 of the distal staple driver 1000*a* may be slidably received within a corresponding second support groove or slot 858 in the second cartridge wall portion 856. Likewise, the proximal support column 1018 of the distal staple driver 1100*b* may be slidably received within a corresponding second support groove or slot 878 in the secondary cartridge wall portion 876. As can also be seen in FIGS. 23 and 24, a first cam member 1022 protrudes from or is attached to the distal staple support portion 1010 and has a first camming surface or ramp 1024 formed thereon. The distal connection member 1070 further includes a second distal cam portion 1026 that has a second or distal camming surface or ramp 1028 formed thereon as shown in FIGS. 23 and 24. In at least one arrangement, the camming surfaces 1024 have the same slope or angle as the slope/angle of camming surfaces 984. Likewise, the camming surfaces 1028 have the same slope/angle as the slope/angle of camming surfaces 974. In at least one embodiment, each distal staple driver 1000*a*, 1000*b* is integrally formed from or molded from, for example, Ultem®, with no fill. However, other materials such as, for example, Ultem® with a glass or mineral fill or Nylon or Nylon with a glass file could be used. In other arrangements, the various portions of the distal staple drivers 1000*a*, 1000*b* may be separately fabricated from other materials and be attached together by adhesive, solder, etc.

Figure 25:
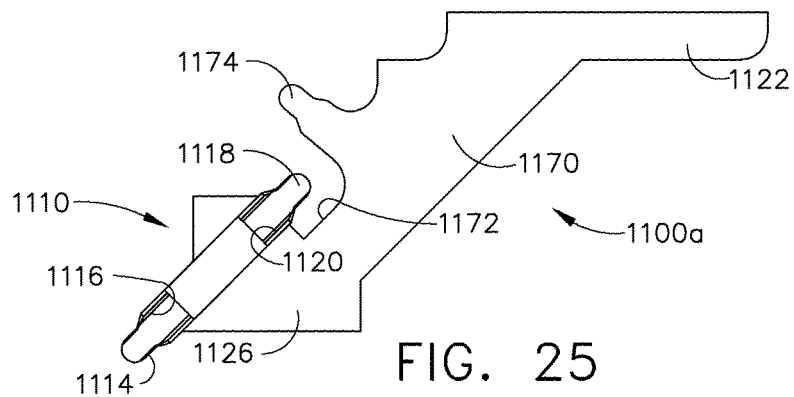
FIG. 25 is a top view of a proximal driver of the driver array depicted in FIG. 20.
Figure 26:
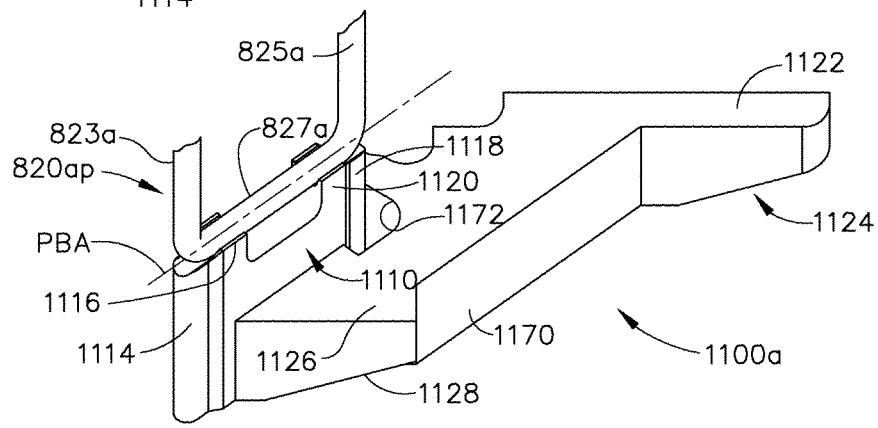
FIG. 26 is a perspective view of the proximal driver of FIG. 25 supporting a staple thereon.
Figure 27:
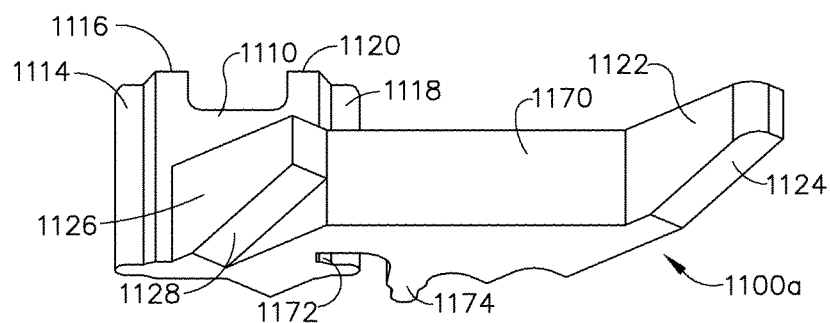
FIG. 27 is a bottom perspective view of the proximal driver of FIGS. 25 and 26.

FIGS. 25-27 illustrate an exemplary proximal staple driver 1100*a*. Proximal staple driver 1100*b* may essentially be a mirror image of proximal staple driver 1100*a*. Each proximal staple driver 1100*a*, 1100*b* includes a proximal staple support portion 1110 that is configured to support a corresponding proximal most staple 820*ap* thereon. As can be seen in FIGS. 25-27, the proximal staple support portion 1110 comprises a distal support column 1114 and a proximal support column 1118. The proximal staple support portion 1110 further includes a distal support cradle 1116 and a proximal support cradle 1120 for supporting portions of the staple crown 827*a* of the corresponding proximal staple 820*ap*. When the staple crown 827*a* of the proximal staple 820*ap* is supported on the support cradles 1116 and 1120, the distal leg 823*a* of the staple 820*ap* is essentially axially aligned with the distal support column 1116 and the proximal leg 825*a* is essentially axially aligned with the proximal support column 1118. In at least one arrangement, the proximal staple drivers 1100*a*, 1100*b* include a body member 1170. The body member 1170 is configured to slidably engage the corresponding proximal-most driver guide (designated as 860P in FIG. 21).

In at least one arrangement, the body member 1170 includes a hook-shaped distal slot 1172 that is configured to be "hookingly engaged" by the hook-shaped portion 862 of the proximal-most driver guide 860P. In addition, the body member 1170 may include a projection 1174 that is configured to be slidably received within a corresponding slot 869 in the proximal most staple driver guide 860P. Thus, each proximal staple driver 1100*a*, 1100*b* is slidably engaged with a corresponding driver guide 860P. In addition, in the array 990*a* of staple drivers 900*a*, 1000*a*, 1100*a*, the distal support column 1114 of the proximal staple driver 1100*a* may be slidably received within a corresponding first staple leg groove 854 in the first cartridge wall portion 852. Likewise, the distal support column 1114 of the proximal staple driver 1110*b* may be slidably received within a corresponding primary staple leg groove 874 in the primary cartridge wall portion 872. As can also be seen in FIGS. 26 and 27, a first proximal cam portion 1122 protrudes from or is attached to the body member 1170 and has a first proximal camming surface or ramp 1124 formed thereon. The body member 1170 also includes a second distal cam portion or ramp 1126 that has a second distal camming surface 1128 formed thereon. In at least one arrangement, the camming surfaces 1124 have the same slope or angle as the slopes/angles of the camming surfaces or ramps 984, 1024. Likewise, the camming surfaces 1128 may have the same slope/angle as the slope/angle of camming surface 974 and 1028. In at least one embodiment, each proximal staple driver 1100*a*, 1100*b* is integrally formed from or molded from, for example, Ultem®, with no fill. However, other materials such as, for example, Ultem® with a glass or mineral fill or Nylon or Nylon with a glass file could be used. In other arrangements, the various portions of the proximal staple drivers 1100*a*, 1100*b* may be separately fabricated from other materials and be attached together by adhesive, solder, etc.

Referring again to FIG. 20, it can be seen that in the staple driver array 990*a* in the illustrated arrangement, the distal cam portion 1126 of the proximal staple driver 1100*a* as well as each of the first cam members 972 of the staple drivers 900*a*, as well as the distal cam portion 1026 of the distal staple driver 1000*a* are all aligned along a first cam axis FCA. Thus, in at least one embodiment, each of the first distal camming surfaces 1028, 1128 as well as each of the first camming surfaces 974 is axially aligned on the first cam axis FCA. Also, the second proximal cam portion 1122 of the proximal staple driver 1100*a* and the proximal cam portion 1022 of the distal staple driver 1000*a*, as well as each of the second cam members 982 of the staple drivers 900*a* is all axially aligned along a second cam axis SCA. Thus, the proximal camming surfaces 1024, 1124 and the second camming surfaces 984 of the staple drivers 900*a* are axially aligned along the second cam axis SCA. Also in the illustrated staple driver array 990*b*, the distal cam portion 1126 of the proximal staple driver 1100*b* as well as the distal cam portion 1026 of the distal staple driver 1000*b* as well as each of the cam members 972 of the staple drivers 900*b* are all aligned along a primary cam axis PCA. Thus, in at least one embodiment, the distal camming surfaces 1128, 1028, as well as each of the first camming surfaces 974 in the staple driver array 990*b* are axially aligned on the primary cam axis PCA.

Still referring to FIG. 20, the staple driver array 990*b* in the illustrated arrangement, the first distal cam portion 1126 of the proximal staple driver 1100*b* as well as each of the first cam members 972 of the staple drivers 900*b* as well as the first distal cam portion 1026 of the distal staple driver 1000*b* are all aligned along a primary cam axis PCA. Thus, in at least one embodiment, each of the first distal camming surfaces 1028, 1128 as well as each of the first camming surfaces 974 in the staple driver array 990*b* is axially aligned on the primary cam axis PCA. Also, the second proximal cam portion 1122 of the proximal staple driver 1100*b* and second proximal cam portion 1022 of the distal staple driver

1000*b*, as well as each of the second cam members 982 of the staple drivers 900*b* are all axially aligned along a secondary cam axis SDCA. Thus each of the proximal camming surfaces 1024, 1124 and the second camming surfaces 984 of the staple drivers 900*b* are axially aligned along the second cam axis SDCA.

As was discussed above, in the array 990*a*, the ramp or camming surface 764 of the sled or camming member 760 is aligned with the second cam axis SCA. Likewise, the ramp or camming surface 762 is aligned with the first cam axis FCA. The ramp or camming surface 766 is aligned on the primary cam axis PCA and the ramp or camming surface 768 is aligned with the secondary cam axis SDCA. Thus, the ramp surface 764 is aligned with a portion of each of the crowns 827*c* of staples 820*c*. The ramp surface 762 is aligned with a portion of each of the crowns 827*c* of staples 820*a* as well as the crowns 827*c* of the staples 820*cd*. Likewise, in the array 990*b* of the staple drivers 1000*b*, 900*b*, 1100*b*, the ramp surface 766 is aligned with a portion of the crowns 827*a* of each of the staples 820*a* as well as a portion of the crown 827*a* of the proximal most staple 820*ap*. The ramp surface 768 is aligned with a portion of the crown 827*c* of each of the staples 820*c* as well as a portion of the crown 827*c* of the distal most staple 820*cd*. Stated another way, none of the ramps 764, 762, 766, 768 are aligned with any of the staple legs of the staples 820*a*, 820*b*, 820*c*, 820*cd* and 820*ap*. Such arrangement therefore enables the third proximal support columns 958 of each of the staple drivers 900*a* to be slidably received within corresponding second support grooves or slots 858 in the second cartridge wall portion 856 of the cartridge body 802. As well as the proximal support column 1018 of the distal staple driver 1000*a* to be slidably received within a corresponding support groove or slot 858 in the cartridge wall portion 856. In addition, the first distal support columns 914 of each of the staple drivers 900*a* are slidably received within corresponding first support grooves or slots 854 in the first cartridge wall portion 852 of the cartridge 800. In addition, the distal support column 1114 of the proximal staple driver 1100*a* is slidably received within a support groove or slot 854. In the staple driver array 990*a*, each of the support columns 1014, 918, 934, 938, 954, 1118 are also slidably supported in corresponding driver guides 860D, 860, 860P that are formed in the cartridge body 802 and may have the same heights or similar heights as the heights of the wall portions 852, 856.

When the surgical instrument is "fired" or stated another way, when the firing drive system 80 is actuated to drive the firing beam 280 distally, the tissue cutting member 750 contacts the sled or camming member 760 and drives the camming member 760 distally through the staple cartridge 800. As can be seen in FIG. 20, the camming members 982 of the staple driver 900*a* are located "inboard" from the support columns 958 (and the staple legs 825*c* supported thereon). Likewise, the camming member 1022 of the distal staple driver 1000*a* is located inboard of the proximal support column 1018 (and the staple leg 825*c* of the distal most staple 820*cd* supported thereon). In addition, the camming members 972 are all located inboard of the proximal support columns 914 (and the staple legs 823*a* of the staples 820*a* supported thereon). Also, the camming member 1126 of the proximal staple driver 1100*a* is located inboard of the support column 1114 (and the staple leg 823*a* of the proximal most staple 820*ap* supported thereon). The drivers 1000*b*, 900*b*, 1100*b* in driver array 990*b* are similarly configured. Such arrangements permit the support columns to either be slidably supported in corresponding slots in the cartridge wall portions or in slots in corresponding driver guides formed within the cartridge body through their entire range of upward travel.

As can be appreciated from reference to FIG. 20, when the staple drivers 900*a*, 1000*a* and 1100*a* are all operably supported in the staple cartridge in the staple driver array 990*a*, the staple drivers 900*a*, 1000*a*, 1100*a* form a first longitudinal row 1210*a* of staples 820*a* that is adjacent to elongate slot 804 in the cartridge body 802. Each of the staples 820*a* in the first longitudinal row 1210*a* extend in a first direction as was described above. Likewise, the staple drivers 900*a* form a second longitudinal row 1212*a* of staples 820*b* that are adjacent the first longitudinal row 1210*a*. The staples 820*b* in the second longitudinal row 1212*a* extend in a second direction that is different from the first direction of the staples 820*a* in the first longitudinal row 1210*a*. In addition, the staple drivers 900*a* form a third longitudinal row 1214*a* of staples 820*c* that are oriented in a third direction which may or may not be in the same direction as staples 820*a*. For example, in the illustrated embodiment, the first and third directions are the same. The third longitudinal row 1214*a* is adjacent to the second longitudinal row 1212*a*.

Still referring to FIG. 20, when the staple drivers 900*b* are all operably supported in the staple cartridge in the staple driver array 990*b*, the staple drivers 900*b* form a first longitudinal row 1210*b* of staples 820*a* that is adjacent to elongate slot 804 in the cartridge body 802. Each of the staples 820*a* in the first longitudinal row 1201*b* extend in a first direction as was described above. Likewise, the staple drivers 900*b* form a second longitudinal row 1212*b* of staples 820*b* that are adjacent the first longitudinal row 1210*b*. The staples 820*b* in the second longitudinal row 1210*b* extend in a second direction that is different from the first direction of the staples 820*a* in the first longitudinal row 1210*b*. In addition, the staple drivers 900*b* form a third longitudinal row 1214*b* of staples 820*c* that are oriented in a third direction which may or may not be in the same direction as staples 820*a*. For example, in the illustrated embodiment, the first and third directions are the same. Stated another way, the staple crown of the staples 820*a* may lie along an axis and the staples 820*c* may lie along another axis that is parallel to the axis along which the staple crowns of the staples 820*a* lie as will be discussed in further detail below. The third longitudinal row 1214*b* is adjacent to the second longitudinal row 1212*b*.

Thus, when employing the staple driver arrays 990*a*, 990*b*, there are two staples extending side by side in the same direction or along parallel axes along both ends of each of the staple lines. In particular, the distal driver 1000*a* supports a distal most staple 820*cd* in the longitudinal row of staples 1214*a* that is extending in the same direction and essentially beside the distal most staple 820*a* in the longitudinal row 1210*a*. Similarly, the proximal driver 1100*a* supports a proximal most staple 820*ap* in the longitudinal row 1210*a* of staples that extends in the same direction and is essentially beside the proximal most staple 820*c* in the longitudinal row 1214*a*. Likewise, distal driver 1000*b* supports a distal most staple 820*cd* in the longitudinal row of staples 1214*b* that is extending in the same direction and essentially beside the distal most staple 820*a* in the longitudinal row 1210*b*. Similarly, the proximal driver 1100*b* supports a proximal most staple 820*ap* in the longitudinal row 1210*b* of staples that extends in the same direction and is essentially beside the proximal most staple 820*c* in the longitudinal row 1214*b*. Such staple pattern may provide a redundant seal arrangement at both ends of each line of staples. As used in this context, the term "line of staples" collectively refers to the longitudinal rows of staples on one side of the elongate slot 804 in the staple cartridge body 802. For example, line of staples, generally designated as 1220a, collectively refers to the longitudinal rows 1200a, 1202a, 1204a. Line of staples 1220b collectively refers to the longitudinal rows 1200b, 1202b, 1204b.

Figure 28:
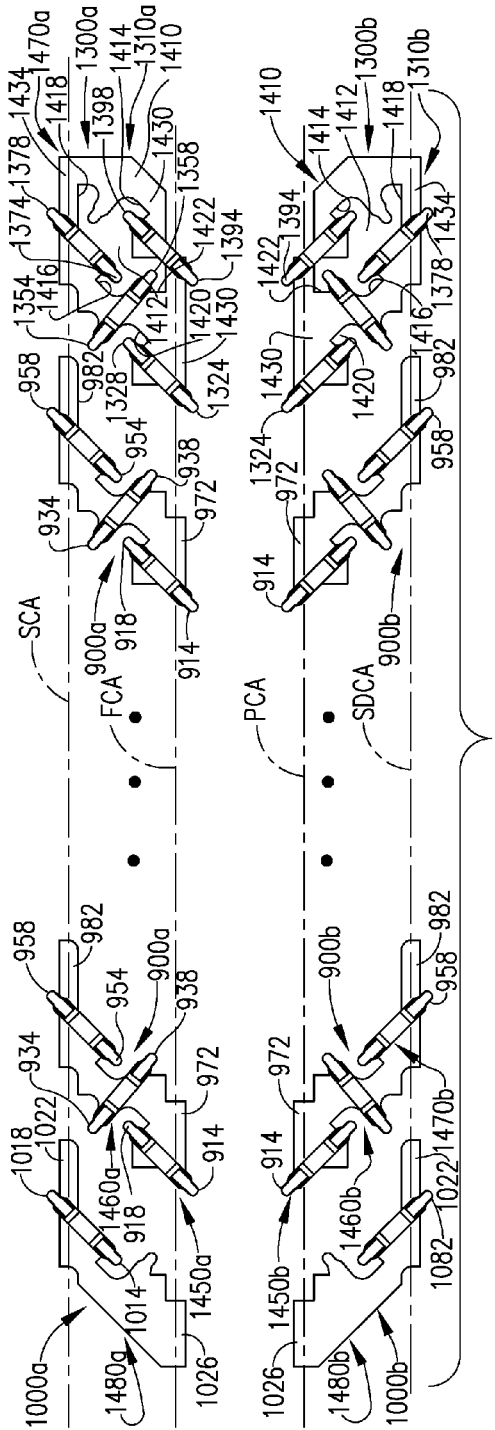
FIG. 28 is a top view of corresponding portions of other driver array embodiments.
Figure 29:
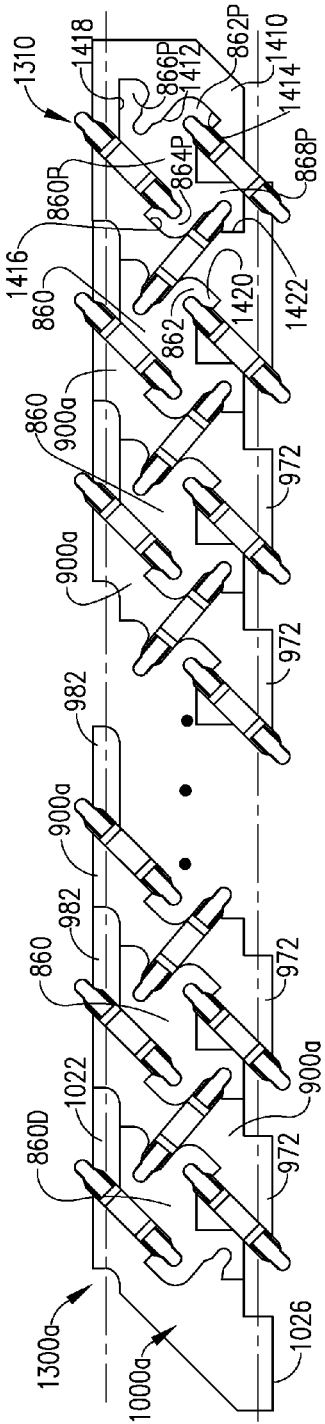
FIG. 29 is a top view of one of the driver arrays of FIG. 28.
Figure 30:
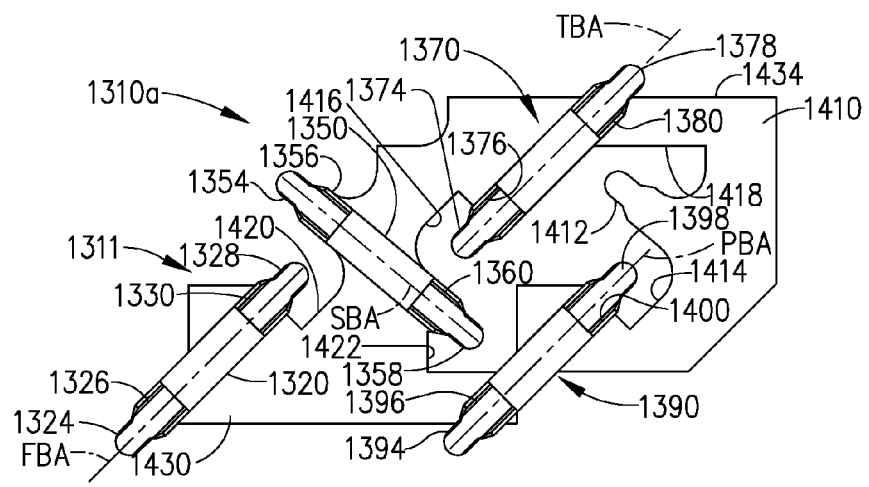
FIG. 30 is a top view of one of the drivers of the driver array of FIG. 29.
Figure 32:
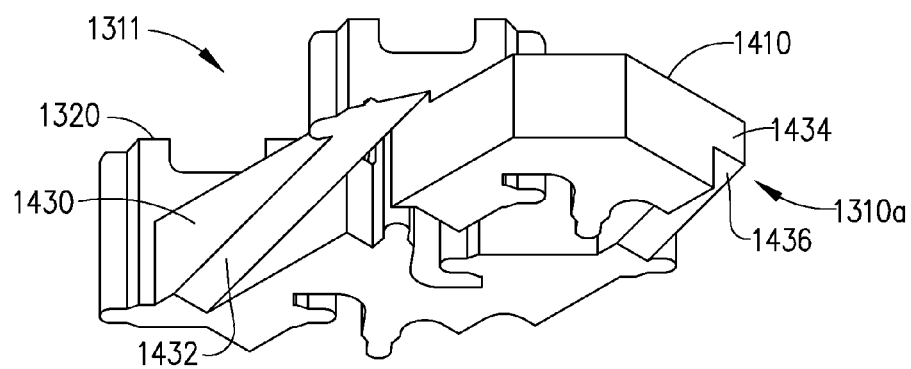
FIG. 32 is a bottom perspective view of the driver of FIGS. 30 and 31.
Figure 31:
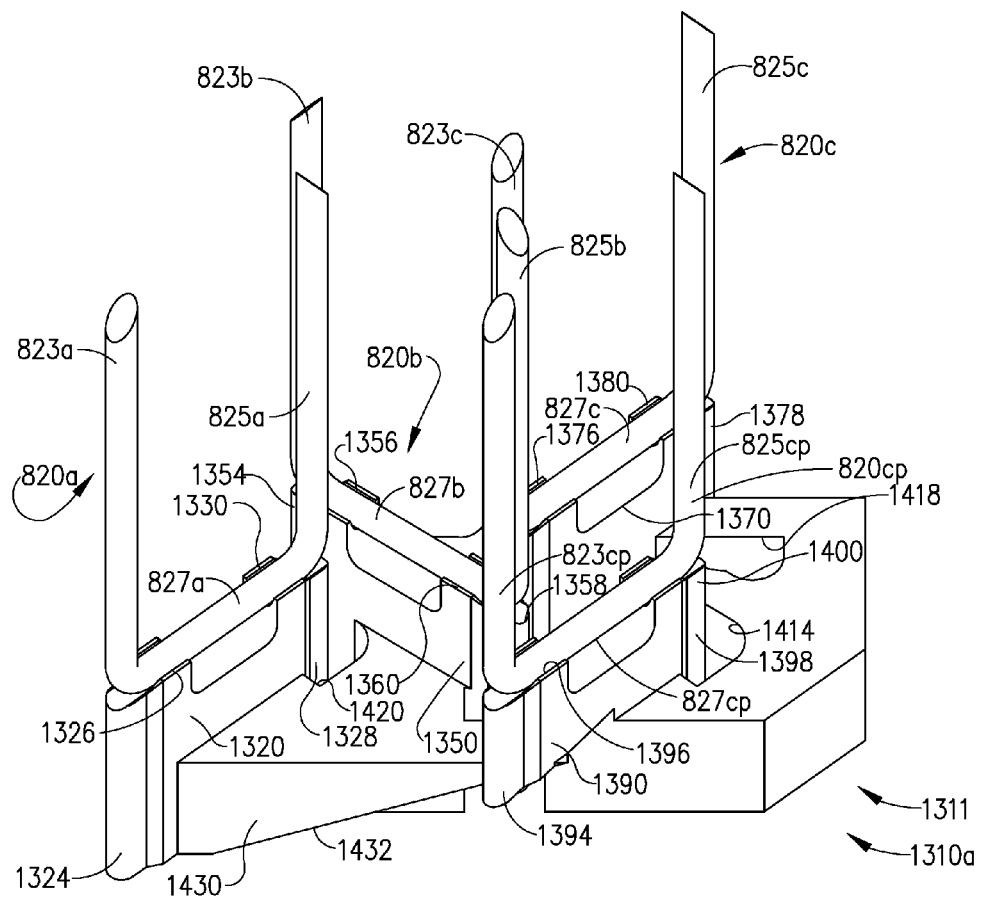
FIG. 31 is a perspective view of the driver of FIG. 30 supporting four staples thereon.

Other staple driver arrays 1300a, 1300b are illustrated in FIGS. 28 and 29. As can be seen in those Figures, the staple driver array 1300a employs a distal staple driver 1000a and a plurality of staple drivers 900a in the manners described above. This array also employs a proximal staple driver 1310a that operably supports a total of four staples. FIGS. 30-32 illustrate one exemplary form of a proximal staple driver 1310a with it being understood that, in at least one arrangement, the proximal staple driver 1310b essentially contains the same features as a proximal staple driver 1310a and may be a mirror image thereof. Each proximal staple driver 1310a, 1310b comprises a driver body 1311. In at least one form, the driver body 1311 includes a first or innermost staple support portion 1320 that is configured to support a staple 820a thereon, a second or central staple support portion 1350 that is configured to support a staple 820b thereon, third support portion 1370 that is configured to support a staple 820c thereon and a fourth or proximal most staple support portion 1390 that is configured to support a proximal most staple 820cp thereon.

As can be seen in FIGS. 30 and 31, the first staple support portion 1320 comprises a first distal support column 1324 and a first proximal support column 1328. The first staple support portion 1320 further includes a first distal support cradle 1326 and a first proximal support cradle 1330 for supporting portions of the first staple crown 827a. As can be seen in FIG. 31, when the first staple crown 827a of the first staple 820a is supported on the support cradles 1326 and 1330, the first distal leg 823a is essentially axially aligned with the first distal support column 1324 and the first proximal leg 825a is essentially axially aligned with the first proximal support column 1328. In addition, the staple crown 827a is supported or oriented along a first base axis FBA.

Still referring to FIGS. 30 and 31, the proximal staple driver 1310a further comprises second staple support portion 1350 that comprises a second distal support column 1354 and a second proximal support column 1358. The second staple support portion 1350 further includes a second distal support cradle 1356 and a second proximal support cradle 1360 for supporting portions of the second staple crown 827b therein. As can be seen in FIG. 31, when the second staple crown 827b of the second staple 820b is supported in the cradles 1356, 1360, the second distal leg 823b is essentially axially aligned with the second distal support column 1354 and the second proximal leg 825b is essentially axially aligned with the second proximal support column 1358. In addition, the staple crown 827b is supported or oriented along a second base axis SBA that, in at least one arrangement, is transverse to the first base axis FBA.

As can also be seen in FIGS. 30 and 31, the proximal staple driver 1310a comprises a third staple support portion 1370 that includes a third distal support column 1374 and a third proximal support column 1378. The third staple support portion 1370 further includes a third distal support cradle 1376 and a third proximal support cradle 1380 configured to support portions of the third staple crown 827c of the third staple 820c therein. As can be seen in FIG. 31, when the third crown 827c of the third staple 820c is supported in the cradles 1376, 1380, the third distal leg 823c is essentially axially aligned with the third distal support column 1374 and the third proximal leg 825c is essentially axially aligned with the third proximal support column 1378. In addition, the staple crown 827c is supported or oriented along a third base axis TBA that is, in at least one arrangement, parallel with the first base axis FBA and transverse to the second base axis SBA.

Still referring to FIGS. 30 and 31, the proximal staple driver 1310a comprises a fourth staple support portion 1390 that includes a fourth distal support column 1394 and a fourth proximal support column 1398. The fourth staple support portion 1390 further includes a fourth distal support cradle 1396 and a third proximal support cradle 1400 configured to support portions of the fourth staple crown 827cp of the proximal most or fourth staple 820cp therein. As can be seen in FIG. 31, when the fourth crown 827cp of the fourth staple 820cp is supported in the cradles 1396, 1400, the fourth distal leg 823cp is essentially axially aligned with the fourth distal support column 1394 and the fourth proximal leg 825cp is essentially axially aligned with the fourth proximal support column 1398. In addition, the staple crown 827cp is supported or oriented along a proximal base axis PBA that is, in at least one arrangement, parallel with the first base axis and the third base axis TBA and transverse to the second base axis SBA.

In at least one arrangement, the first staple support portion 1320, the second staple support portion 1350, the third staple support portion 1370 and the fourth staple support portion 1390 are all coupled together by a connector portion 1410. In at least one arrangement, the connector portion 1410 is formed with a centrally disposed opening or aperture 1412 that is configured to slidably receive the proximal most driver guide 860P therein. See FIG. 29. The connector portion 1410 is formed with a first hook-shaped slot 1414 that is adapted to be hookingly engaged by a hooked shaped portion 862P and a second hook shaped slot 1416 that is adapted to be hookingly engaged by a hook shaped portion 864P on the proximal most driver guide 860P that is formed in the cartridge body. In addition, a third slot 1418 is formed in the connector portion 1410 for slidably engaging a correspondingly shaped portion 866P of the driver guide 860P. A fourth slot 1420 is formed in the connector portion 1410 for slidably engaging a hook shaped portion 862 of the adjacent driver guide 860. See FIG. 29. Also in the illustrated embodiment, the connector portion 1410 includes a fifth slot 1422 for slidably receiving a correspondingly shaped portion 868P of the proximal most driver guide 860P. In addition, in the array 1300a of staple drivers 900a, 1000a, 1310a, the support columns 1324, 1394 of the proximal staple driver 1310a may be slidably received within a corresponding first support groove or slot 854 in the first cartridge wall portion 852 in the manner described above. In addition, the support column 1378 may be slidably supported in a corresponding support groove or slot 858 in the second cartridge wall portion 856. Likewise, the support columns 1324, 1394 of the proximal staple driver 1310b may be slidably received within a corresponding primary support groove or slot 874 in the primary cartridge wall portion 872 in the manner described above. In addition, the support column 1378 of the proximal staple driver 1310b may be slidably supported in a corresponding support groove or slot 878 in the secondary cartridge wall portion 876.

As can also be seen in FIGS. 31 and 32, the connector portion 1410 includes a first cam portion 1430 that has a first camming surface or ramp 1432 formed thereon. The connector portion 1410 also includes a second cam portion 1434 that has a second a second camming surface 1436 formed thereon. In at least one arrangement, the camming surfaces 1432, 1436 have the same slope or angle which may be the same or different from the slope(s) and/or angles(s) of the camming surfaces or ramps 974, 984. In at least one embodiment, each proximal staple driver 1310a, 1310b is integrally formed from or molded from, for example, Ultem®, with no fill. However, other materials such as, for example, Ultem® with a glass or mineral fill or Nylon or Nylon with a glass file could be used. In other arrangements, the various portions of the proximal staple drivers 1310a, 1310b may be separately fabricated from other materials and be attached together by adhesive, solder, etc.

Referring again to FIG. 28, it can be seen that in the staple driver array 1300a in the illustrated arrangement, the first cam portion 1430 of the proximal staple driver 1310a and the distal cam portion 1026 of the distal staple driver 1000a, as well as each of the first cam members 972 of the staple drivers 900a are all axially aligned along a first cam axis FCA. Thus the proximal camming surface 1028, the second camming surfaces 974 of the staple drivers 900a and the camming surface 1432 are all axially aligned along the first cam axis FCA. The second cam portion 1434 of the proximal staple driver 1310a, as well as each of the second cam members 982 of the staple drivers 900a, as well as the cam member 1022 of the distal staple driver 1000a are all aligned along a second cam axis SCA. Thus, in at least one embodiment, the camming surface 1436, as well as each of the camming surfaces 984 and camming surface 1024 are all axially aligned on the second cam axis SCA. Also in the illustrated staple driver array 1300b, the cam portion 1430 of the proximal staple driver 1310b, as well as each of the cam members 972 of the staple drivers 900b, as well as the cam portion 1026 of the distal staple driver 1000b are all aligned along a primary cam axis PCA. Thus, the second camming surface 1432 of the proximal staple driver 1310b, the second camming surfaces 974 of the staple drivers 900b and the camming surface 1028 of the distal staple driver 1000b are all axially aligned along the second primary cam axis PCA. Still referring to FIG. 28, in the staple driver array 1300b of the illustrated arrangement, the second cam portion 1434 of the proximal staple driver 1310b, as well as each of the cam members 982 of the staple drivers 900b as well as the first proximal cam portion 1022 of the distal staple driver 1000b are all aligned along a secondary cam axis SDCA. Thus, in at least one embodiment, each of the camming surfaces 1436 as well as each of the camming surfaces 984 and camming surface 1024 are axially aligned on the secondary cam axis SDCA.

As can be appreciated from reference to FIG. 28, when the staple drivers 900a, 1000a and 1310a are all operably supported in the staple cartridge in the staple driver array 1300a, the staple drivers 900a, 1000a, 1310a form a first longitudinal row 1450a of staples 820a that is adjacent to elongate slot 804 in the cartridge body 802. Each of the staples 820a in the first longitudinal row 1450a extend in a first direction as was described above. Likewise, the staple drivers 900a and the proximal staple driver 1310a form a second longitudinal row 1460a of staples 820b that are adjacent the first longitudinal row 1450a. The staples 820b in the second longitudinal row 1460a extend in a second direction that is different from the first direction of the staples 820a in the first longitudinal row 1450a. In addition, the staple drivers 1000a, 900a and 1310a form a third longitudinal row 1470a of staples 820c that are oriented in a third direction which may or may not be in the same direction as staples 820a. For example, in the illustrated embodiment, the first and third directions are the same. The third longitudinal row 1470a is adjacent to the second longitudinal row 1460a.

Still referring to FIG. 28, when the staple drivers 1000b, 900b and 1310b are all operably supported in the staple cartridge in the staple driver array 1300b, the staple drivers 1000b, 900b and 1310b form a primary longitudinal row 1450b of staples 820a that is adjacent to elongate slot 804 in the cartridge body 802. Each of the staples 820a in the primary longitudinal row 1450b extend in a first direction as was described above. Likewise, the staple drivers 900b and 1310b form a secondary longitudinal row 1460b of staples 820b that are adjacent the primary longitudinal row 1450b. The staples 820b in the secondary longitudinal row 1460b extend in a second direction that is different from the first direction of the staples 820a in the primary longitudinal row 1450b. In addition, the staple drivers 1000b, 900b and 1310b form a tertiary longitudinal row 1470b of staples 820c that are oriented in a third direction which may or may not be in the same direction as staples 820a. For example, in the illustrated embodiment, the first and third directions are the same. The tertiary longitudinal row 1470b is adjacent to the secondary longitudinal row 1460b.

Thus, when employing the staple driver arrays 1300a, 1300b, there are two staples extending side by side in the same direction or along parallel axes along both ends of each of the staple lines. In particular, the distal driver 1000a supports a distal most staple 820cd in the longitudinal row of staples 1470a that is extending in the same direction and essentially beside the distal most staple in the longitudinal row 1450a. Similarly, the proximal driver 1310a supports two proximal most staples 820c and 820cp in the longitudinal rows 1450a and 1470a, respectively, of staples that extend in the same direction as the proximal most staple in the longitudinal row 1470a. Likewise, distal driver 1000b supports a distal most staple 820cd in the longitudinal row of staples 1470b that is extending in the same direction and essentially beside the distal most staple in the longitudinal row 1450b. Similarly, the proximal driver 1310b supports a proximal most staple in the longitudinal row 1450b of staples that extends in the same direction and is essentially beside the proximal most staple in the longitudinal row 1470b. Such staple pattern may provide a redundant seal arrangement at both ends of each line of staples. As used in this context, the term "line of staples" collectively refers to the longitudinal rows of staples on one side of the elongate slot 804 in the staple cartridge body 802. For example, line of staples, generally designated as 1480a, collectively refers to the longitudinal rows 1450a, 1460a, 1470a of staples. Line of staples 1480b collectively refers to the longitudinal rows 1450b, 1460b, 1470b of staples.

As was discussed above, in the array 1300a, the ramp or camming member 764 of the sled or camming actuator 760 is aligned with the second cam axis SCA. Likewise, the ramp or camming member 762 is aligned with the first cam axis FCA. The ramp or camming member 766 is aligned on the primary cam axis PCA and the ramp or camming member 768 is aligned with the secondary cam axis SDCA. Thus, the ramp or camming member 764 is aligned with a portion of each of the crowns 827c of staples 820c and 820cd. The ramp or camming member 762 is aligned with a portion of each of the crowns 827a of staples 820a as well as the crown 827c of the proximal most staple 820cp. Likewise, in the array 1300b of the staple drivers 1000b, 900b, 1310b, the ramp or camming member 766 is aligned with a portion of the crowns 827a of each of the staples 820a as well as a portion of the crown 827c of the proximal most staple 820*cp*. The ramp or camming member 768 is aligned with a portion of the crown 827*c* of each of the staples 820*c* as well as a portion of the crown 827*c* of the distal most staple 820*cd*. Stated another way, none of the ramps or camming members 764, 762, 766, 768 are aligned with any of the staple legs of the staples 820*a*, 820*b*, 820*c*, 820*cd* and 820*cp*. Such arrangement therefore enables the third proximal support columns 958 of each of the staple drivers 900*a*, as well as the proximal support column 1018 of the distal staple driver 1000*a*, as well as the support column 1378 of the proximal staple driver 1310 a to be slidably received within corresponding second support grooves or slots 858 in the second cartridge wall portion 856 of the cartridge body 802. Likewise, the first distal support columns 914 of each of the staple drivers 900*a*, as well as the support columns 1324, 1394 of the proximal staple driver 1310*a* are all slidably received within corresponding first support grooves or slots 854 in the first cartridge wall portion 852 of the cartridge 800. In the staple driver array 1300*a*, each of the support columns 1014, 918, 934, 938, 954, 1328, 1354, 1358, 1374, 1398 are also slidably supported in corresponding driver guides 860D, 860, 860P that are formed in the cartridge body 802 and may have the same heights or similar heights as the heights of the wall portions 852, 856.

Other staple driver arrays 1500*a*, 1500*b* are illustrated in FIGS. 33 and 34. As can be seen in those Figures, the staple driver array 1500*a* employs a plurality of staple drivers 1510*a* that operably supports three staples. The staple driver array 1500*a* also includes a distal staple driver 1610*a* that operably supports two staples. Likewise, staple driver array 1500*b* includes a plurality of staple drivers 1510*b* and a distal staple driver 1610*b*. Staple drivers 1510*b* may be mirror images of staple drivers 1510*a* and include the same features. Distal staple drivers 1610*b* may be mirror images of staple drivers 1610*a* and include the same features.

Figure 35:
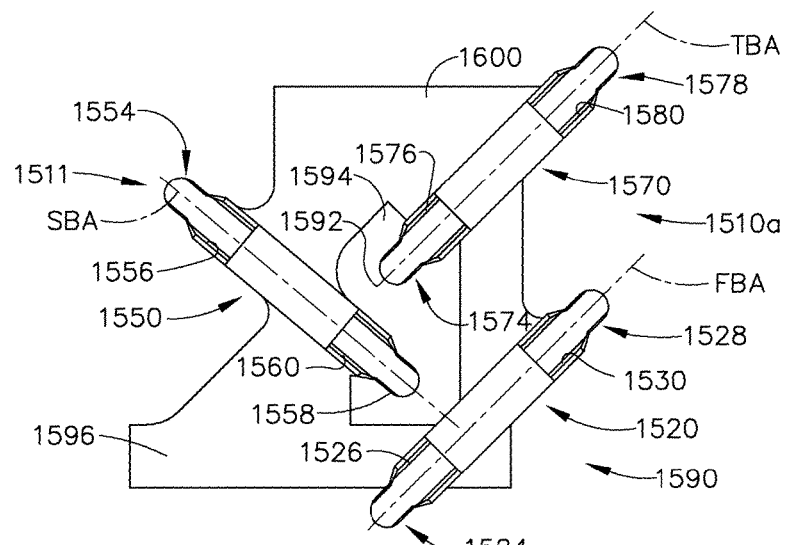
FIG. 35 is a top view of a proximal driver of the driver array of FIG. 34.
Figure 37:
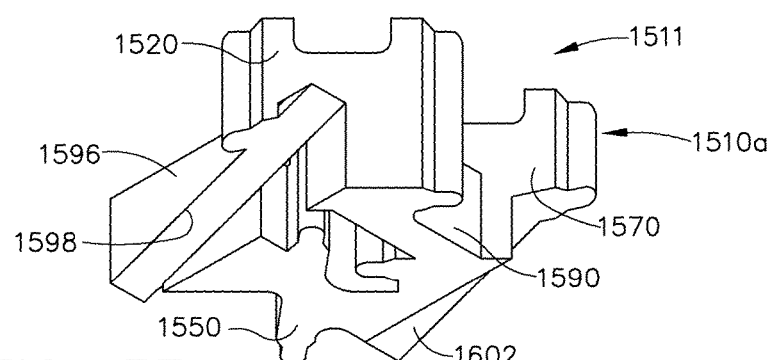
FIG. 37 is a bottom perspective view of driver of FIGS. 35 and 36.
Figure 36:
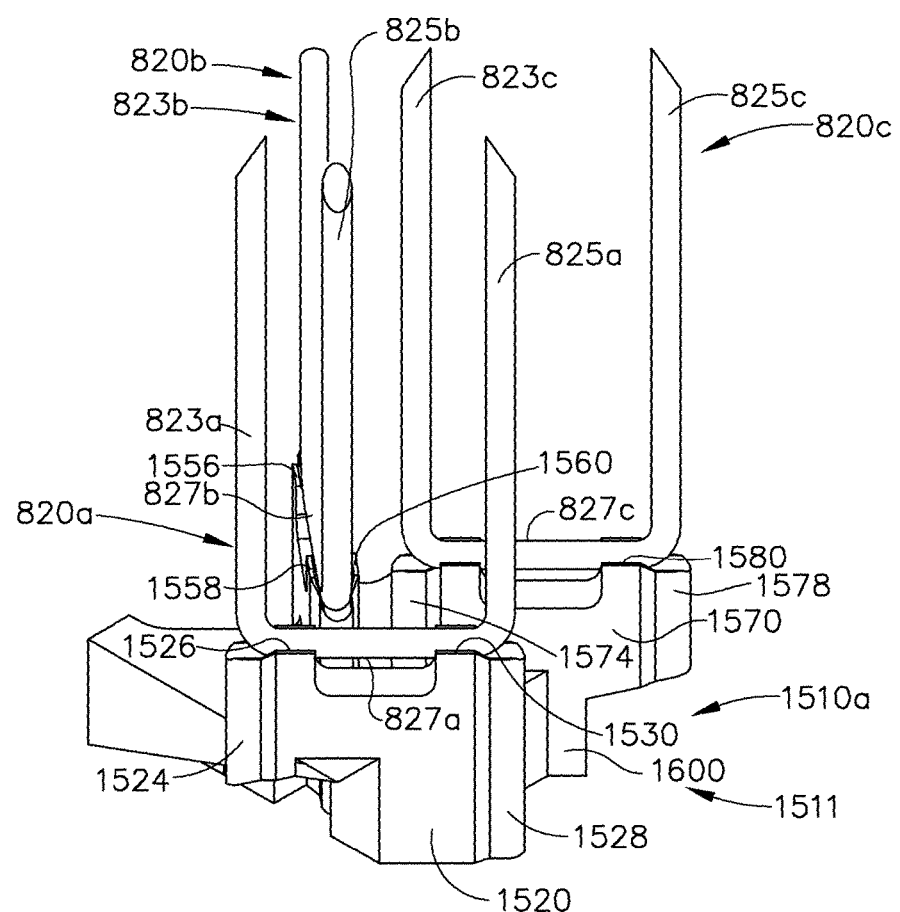
FIG. 36 is a perspective view of the driver of FIG. 35 supporting three staples thereon.

FIGS. 35-37 illustrate one exemplary form of a staple driver 1510*a* with it being understood that, in at least one arrangement, a staple driver 1510*b* essentially contains the same features as a staple driver 1510*a* and may be a mirror image thereof. Each staple driver 1510*a*, 1510*b* comprises a staple driver body 1511. In the illustrated arrangement, the driver body 1511 includes a first or innermost staple support portion 1520 that is configured to support a staple 820*a* thereon, a second or central staple support portion 1550 that is configured to support a staple 820*b* thereon and a third support portion 1570 that is configured to support a staple 820*c* thereon. As can be seen in FIG. 35, the first staple support portion 1520 comprises a first distal support column 1524 and a first proximal support column 1528. The first staple support portion 1520 further includes a first distal support cradle 1526 and a first proximal support cradle 1530 for supporting portions of the staple crown 827*a* of a staple 820*a*. As can be seen in FIG. 31, when the staple crown 827*a* of the staple 820*a* is supported on the support cradles 1526 and 1530, the distal leg 823*a* is essentially axially aligned with the first distal support column 1524 and the first proximal leg 825*a* is essentially axially aligned with the first proximal support column 1528. When the staple 820*a* is supported on the first staple support portion 1520, the staple crown 827*a* is aligned on a first base axis FBA.

Still referring to FIGS. 35 and 36, the proximal staple driver 1510*a* further comprises second staple support portion 1550 that comprises a second distal support column 1554 and a second proximal support column 1558. The second staple support portion 1550 further includes a second distal support cradle 1556 and a second proximal support cradle 1560 for supporting portions of a staple crown 827*b* of a staple 820*b* therein. As can be seen in FIG. 36, when the staple crown 827*b* of the staple 820*b* is supported in the cradles 1556, 1560, the distal leg 823*b* is essentially axially aligned with the second distal support column 1554 and the proximal leg 825*b* is essentially axially aligned with the second proximal support column 1558. When the staple 820*b* is supported on the second staple support portion 1550, the staple crown 827*b* is aligned on a second base axis SBA. In the illustrated arrangement, the second base axis SBA is transverse to the first base axis FBA.

As can also be seen in FIGS. 35 and 36, the proximal staple driver 1510*a* comprises a third staple support portion 1570 that includes a third distal support column 1574 and a third proximal support column 1578. The third staple support portion 1570 further includes a third distal support cradle 1576 and a third proximal support cradle 1580 configured to support portions of a staple crown 827*c* of a third staple 820*c* therein. As can be seen in FIG. 31, when the crown 827*c* of the staple 820*c* is supported in the cradles 1576, 1580, the distal leg 823*c* is essentially axially aligned with the distal support column 1574 and the proximal leg 825*c* is essentially axially aligned with the third proximal support column 1578. When the staple 820*c* is supported on the third staple support portion 1570, the staple crown 827*c* is aligned on a third base axis TBA. In the illustrated arrangement, the third base axis TBA is parallel to the first base axis FBA and transverse to the second base axis SBA.

Still referring to FIGS. 35-37, in at least one arrangement, the first staple support portion 1520, the second staple support portion 1550 and the third staple support portion 1570 are all coupled together by a connector portion 1590. In at least one arrangement, the connector portion 1590 is formed with a centrally disposed opening or aperture 1592 that is configured to slidably receive a corresponding first driver guide 1700 therein. See FIG. 34. The connector portion 1590 is formed with a first hook-shaped slot 1594 that is adapted to be hookingly engage by a hooked shaped portion 1702 on the first driver guide 1700. The hook shaped portion 1702 is adapted to slidably support the support column 1574 therein. In addition, as can be further seen in FIG. 34, each first driver guide 1700 includes a slot 1704 that is configured to slidably receive the second proximal support column 1558 of the corresponding staple driver 1510*a* therein. Each staple driver 1510*a* is also configured to slidably engage a second driver guide 1720 as shown in FIG. 34. Each second driver guide 1720 includes a first slot 1722 that is configured to slidably receive therein a first proximal support column 1528 of a corresponding staple driver 1510*a*. In addition, each second driver guide 1720 further has a second slot 1724 that is configured to slidably receive therein a second distal support column 1554 of the corresponding staple driver 1510*a* therein.

As can also be seen in FIGS. 35 and 36, the connector portion 1590 includes a first cam portion 1596 that has a first camming surface or ramp 1598 formed thereon. The connector portion 1590 also includes a second cam portion 1600 that has a second a second camming surface 1602 formed thereon. In at least one arrangement, the camming surfaces 1598, 1602 have the same slope or angle or they may have different slopes/angles. In at least one embodiment, each staple driver 1510*a*, 1510*b* is integrally formed from or molded from, for example, Ultem®, with no fill. However, other materials such as, for example, Ultem® with a glass or mineral fill or Nylon or Nylon with a glass file could be used. In other arrangements, the various portions of the proximal staple drivers 1510a, 1510b may be separately fabricated from other materials and be attached together by adhesive, solder, etc.

Figure 38:
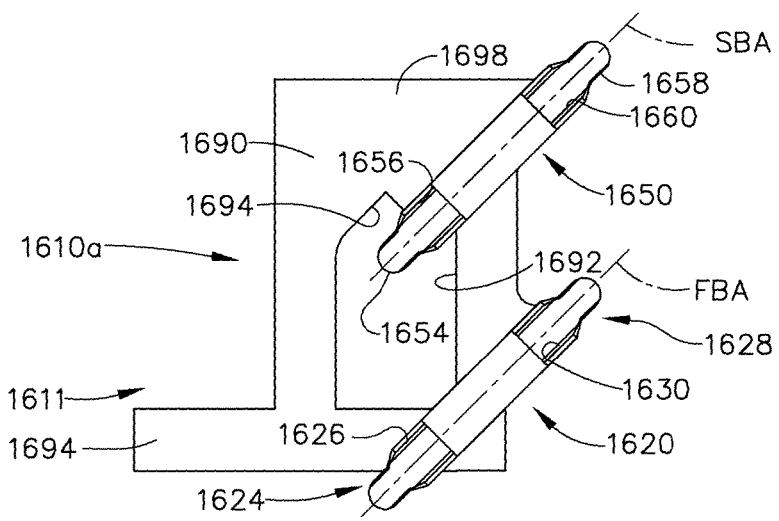
FIG. 38 is a top view of a distal driver of the driver array of FIG. 34.
Figure 40:
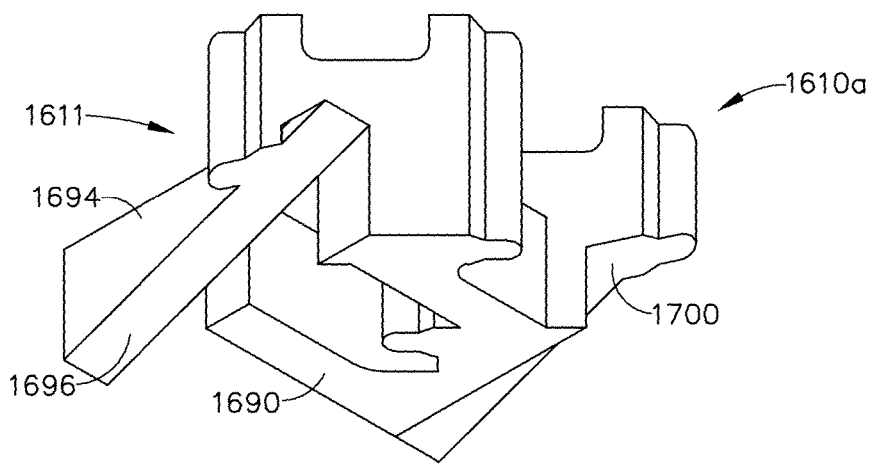
FIG. 40 is a bottom perspective view of the driver of FIGS. 38 and 39.
Figure 39:
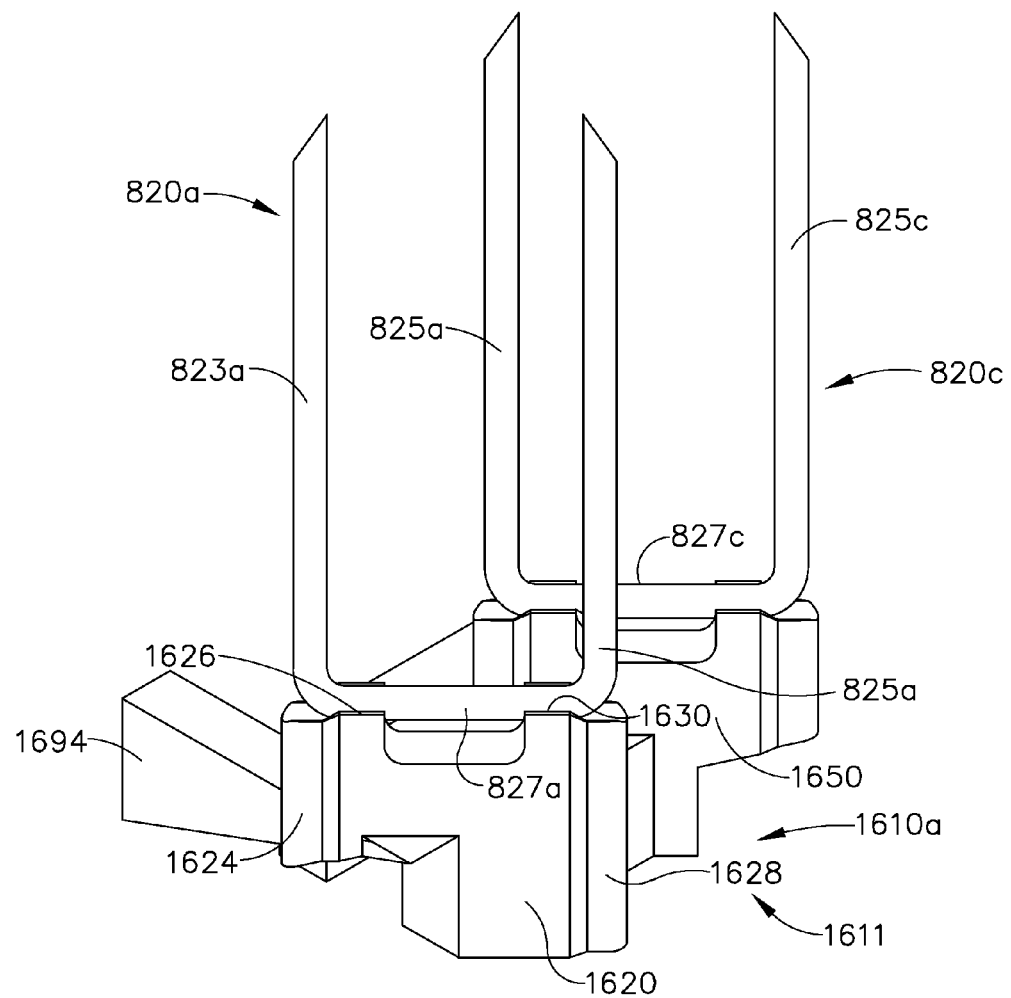
FIG. 39 is a perspective view of the driver of FIG. 38 supporting two staples thereon.

The staple driver array 1500a in the illustrated embodiment also comprises a distal staple driver 1610a that is configured to operably support two staples. FIGS. 38-40 illustrate one exemplary form of a distal staple driver 1610a with it being understood that, in at least one arrangement, a staple driver 1610b essentially contains the same features as a staple driver 1610a and may be a mirror image thereof. Each staple driver 1610a, 1610b includes a driver body 1611. In the illustrated arrangement, each driver body 1611 includes a first staple support portion 1620 that is configured to support a staple 820a thereon and a second staple support portion 1650 that is configured to support a staple 820c thereon. As can be seen in FIG. 30, the first staple support portion 1620 comprises a first distal support column 1624 and a first proximal support column 1628. The first staple support portion 1620 further includes a first distal support cradle 1626 and a first proximal support cradle 1630 for supporting portions of the first staple crown 827a. As can be seen in FIG. 39, when the staple crown 827a of the staple 820a is supported on the support cradles 1626 and 1630, the distal leg 823a is essentially axially aligned with the first distal support column 1624 and the proximal leg 825a is essentially axially aligned with the first proximal support column 1628. When the staple 820a is supported on the first staple support portion 1620, the staple crown 827a is aligned on a first base axis FBA.

Still referring to FIGS. 38 and 39, the distal staple driver 1610a further comprises second staple support portion 1650 that comprises a second distal support column 1654 and a second proximal support column 1658. The second staple support portion 1650 further includes a second distal support cradle 1656 and a second proximal support cradle 1660 for supporting portions of the staple crown 827c of a staple 820c therein. As can be seen in FIG. 39, when the staple crown 827c of the staple 820c is supported in the cradles 1656, 1660, the distal leg 823c is essentially axially aligned with the second distal support column 1654 and the proximal leg 825c is essentially axially aligned with the second proximal support column 1658. When the staple 820c is supported on the second staple support portion 1650, the staple crown 827c is aligned on a second base axis SBA. In the illustrated arrangement, the second base axis SBA is parallel to the first base axis FBA.

In at least one arrangement, the first staple support portion 1620 and the second staple support portion 1650 of the distal staple driver 1610a are coupled together by a connector portion 1690. In at least one arrangement, the driver body portion 1690 is formed with a centrally disposed opening or aperture 1692 that is configured to slidably receive a corresponding distal driver guide 1730d therein. See FIG. 34. The distal driver guide 1730d includes a slot 1732 that is configured to slidably receive the first distal support column 1624 of the distal staple driver 1610a therein. The distal staple driver 1610a is also configured to slidably engage the distal most second driver guide 1720d as shown in FIG. 34. The distal most second staple driver guide 1720d includes a first slot 1722d that is configured to slidably receive therein the first proximal support column 1628 of the distal staple driver 1610a. In addition, the distal most second staple driver guide 1720d further has a second slot 1724d that is configured to slidably receive therein a second distal support column 1554 of the corresponding staple driver 1510a therein.

As can also be seen in FIGS. 39 and 40, the connector portion 1690 includes a first cam portion 1694 that has a first camming surface or ramp 1696 formed thereon. The connector portion 1690 also includes a second cam portion 1698 that has a second camming surface 1700 formed thereon. In at least one arrangement, the camming surfaces 1696, 1700 have the same slope or angle or they may have different slopes/angles. In at least one embodiment, each distal driver 1610a, 1610b is integrally formed from or molded from, for example, Ultem®, with no fill. However, other materials such as, for example, Ultem® with a glass or mineral fill or Nylon or Nylon with a glass file could be used. In other arrangements, the various portions of the distal drivers 1610a, 1610b may be separately fabricated from other materials and be attached together by adhesive, solder, etc.

Referring again to FIG. 33, it can be seen that in the staple driver array 1500a in the illustrated arrangement, the first cam portion 1596 of each of the staple drivers 1510a and the cam portion 1694 of the distal staple driver 1610a are all axially aligned along a first cam axis FCA. Thus the camming surface 1598 of each of the drivers 1510a and the camming surface 1696 of the distal driver 1610a are axially aligned along the first cam axis FCA. The second cam portion 1600 of each of the drivers 1510a and the cam portion 1698 of the distal staple driver 1610a are all aligned along a second cam axis SCA. Thus, in at least one embodiment, the camming surface 1602 of each of the drivers 1510a and the camming surface 1700 of the distal driver 1610a are axially aligned on the second cam axis SCA. Also in the illustrated staple driver array 1500b, the cam portion 1596 of each of the drivers 1510b and the cam portion 1694 of the distal driver 1610b are all aligned along a primary cam axis PCA. Thus, the camming surface 1598 of each of the drivers 1510b and the camming surface 1696 of the distal driver 1610b are axially aligned along the primary cam axis PCA. Still referring to FIG. 33, in the staple driver array 1500b of the illustrated arrangement, the cam portion 1600 of each of the drivers 1510b and the cam portion 1698 of the distal driver 1610b are all aligned along a secondary cam axis SDCA. Thus, in at least one embodiment, the camming surface 1602 of each of the drivers 1510b and the camming surface 1700 of the distal driver 1610b are axially aligned on the secondary cam axis SDCA.

As can be appreciated from reference to FIG. 33, when the drivers 1510a and 1610a are all operably supported in the staple cartridge in the staple driver array 1500a, the staple drivers 1510a, 1610a form a first longitudinal row 1750a of staples 820a that is adjacent to elongate slot 804 in the cartridge body 802. Each of the staples 820a in the first longitudinal row 1750a extend in a first direction as was described above. Likewise, the drivers 1510a form a second longitudinal row 1760a of staples 820b that are adjacent the first longitudinal row 1750a. The staples 820b in the second longitudinal row 1760a extend in a second direction that is different from the first direction of the staples 820a in the first longitudinal row 1750a. In addition, the drivers 1510a and 1610a form a third longitudinal row 1770a of staples 820c that are oriented in a third direction which may or may not be in the same direction as staples 820a. For example, in the illustrated embodiment, the first and third directions are the same. The third longitudinal row 1770a is adjacent to the second longitudinal row 1760a.

Still referring to FIG. 33, when the staple drivers 1510b and 1610b are all operably supported in the staple cartridge in the staple driver array 1500b, the staple drivers 1510b and 1610b form a primary longitudinal row 1750b of staples 820a that is adjacent to elongate slot 804 in the cartridge body 802. Each of the staples 820a in the primary longitudinal row 1750b extend in a first direction as was described above. Likewise, the staple drivers 1510b form a secondary longitudinal row 1760b of staples 820b that are adjacent the primary longitudinal row 1750b. The staples 820b in the secondary longitudinal row 1760b extend in a second direction that is different from the first direction of the staples 820a in the primary longitudinal row 1750b. In addition, the staple drivers 1510b and 1610b form a tertiary longitudinal row 1770b of staples 820c that are oriented in a third direction which may or may not be in the same direction as staples 820a. For example, in the illustrated embodiment, the first and third directions are the same. The tertiary longitudinal row 1770b is adjacent to the secondary longitudinal row 1760b.

Thus, when employing the staple driver arrays 1500a, 1500b, there are two staples extending side by side in the same direction or along parallel axes along both ends of each of the staple lines. In particular, the distal driver 1610a supports two distal most staples in the longitudinal rows 1750a, 1770a that each extend in the same direction. Similarly, the proximal most driver 1510a supports two proximal most staples in the longitudinal rows 1550a and 1570a of staples that extend in the same direction. Likewise, distal driver 1610b supports two distal most staples in the longitudinal rows 1750b, 1770b of staples that extend in the same direction. Such staple pattern may provide a redundant seal arrangement at both ends of each line of staples. As used in this context, the term "line of staples" collectively refers to the longitudinal rows of staples on one side of the elongate slot 804 in the staple cartridge body 802. For example, line of staples, generally designated as 1780a, collectively refers to the longitudinal rows 1750a, 1760a, 1770a of staples. Line of staples 1780b collectively refers to the longitudinal rows 1750b, 1760b, 1770b of staples.

As was discussed above, in the array 1500a, the ramp or camming surface 764 of the sled or camming actuator 760 is aligned with the second cam axis SCA. Likewise, the ramp or camming member 762 is aligned with the first cam axis FCA. The ramp or camming member 766 is aligned on the primary cam axis PCA and the ramp or camming member 768 is aligned with the secondary cam axis SDCA. Thus, the ramp or camming member 764 is aligned with a portion of each of the crowns 827c of staples 820c. The ramp or camming member 762 is aligned with a portion of each of the crowns 827a of staples 820a. Likewise, in the array 1500b of the staple drivers 1510b, 1610b, the ramp or camming member 766 is aligned with a portion of the crowns 827a of each of the staples 820a. The ramp or camming member 768 is aligned with a portion of the crown 827c of each of the staples 820c. Stated another way, none of the ramps or camming members 764, 762, 766, 768 are aligned with any of the staple legs of the staples 820a, 820c. Such arrangement therefore enables the third proximal support columns 1578 of each of the staple drivers 1510a, as well as the proximal support column 1658 of the distal staple driver 1610a to be slidably received within corresponding second support grooves or slots 858 in the second cartridge wall portion 856 of the cartridge body 802. Likewise, the first distal support columns 1524 of each of the staple drivers 1510a, as well as the support column 1624 of the distal staple driver 1610a are all slidably received within corresponding first support grooves or slots 854 in the first cartridge wall portion 852 of the cartridge body 800. In the staple driver array 1500a, each of the support columns 1654, 1628, 1554, 1558, 1574, 1528 are also slidably supported in corresponding driver guides 1700, 1720, 1730d that are formed in the cartridge body 802 and may have the same heights or similar heights as the heights of the cartridge wall portions 852, 856.

Other staple driver arrays 1800a, 1800b are illustrated in FIGS. 41 and 42. As can be seen in those Figures, the staple driver array 1800a employs a plurality of staple drivers 1810a that operably supports three staples. The staple driver array 1800a also includes a proximal staple driver 1910a that operably supports two staples. Likewise, staple driver array 1800b includes a plurality of staple drivers 1810b and a proximal staple driver 1910b. Staple drivers 1810b may be mirror images of staple drivers 1810a and include the same features. Proximal staple drivers 1910b may be mirror images of staple drivers 1910a and include the same features.

Figure 43:
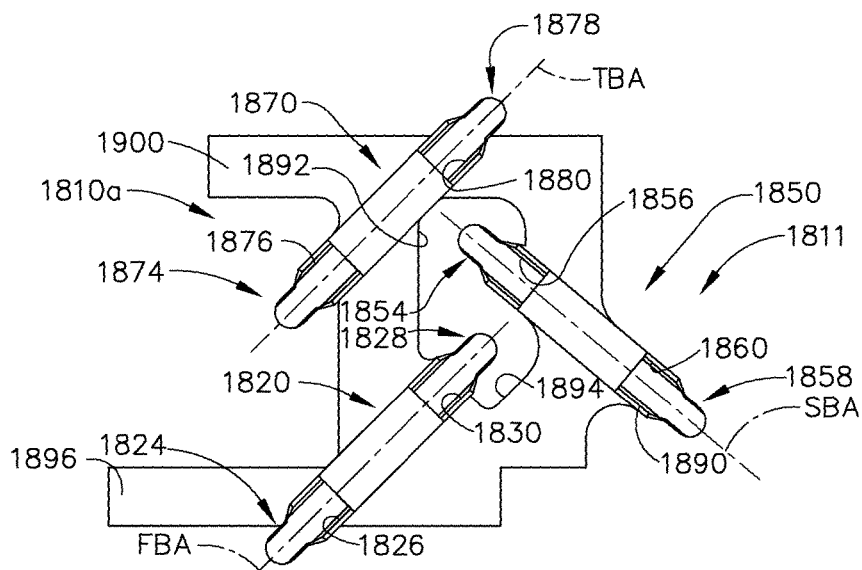
FIG. 43 is a top view of a distal driver of the driver array of FIG. 42.
Figure 45:
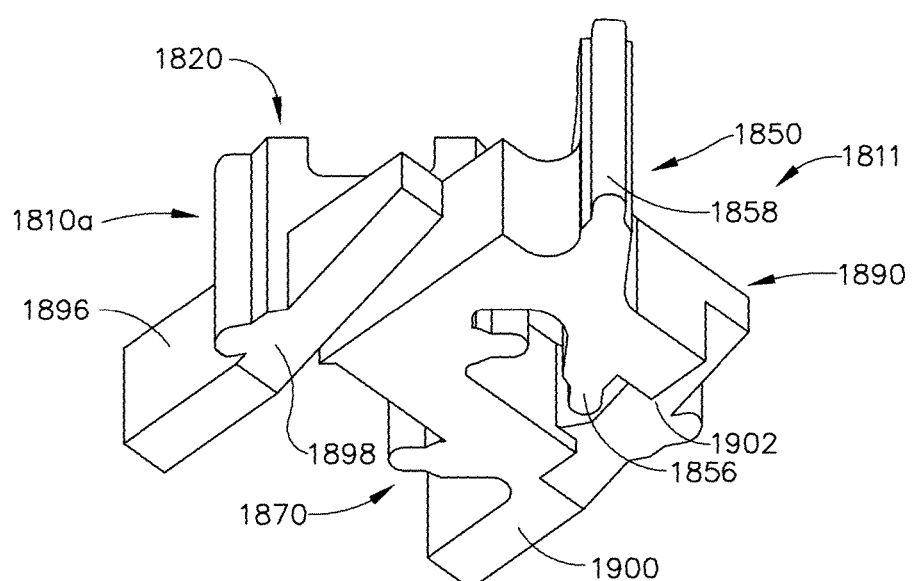
FIG. 45 is a bottom perspective view of the driver of FIGS. 43 and 44.
Figure 44:
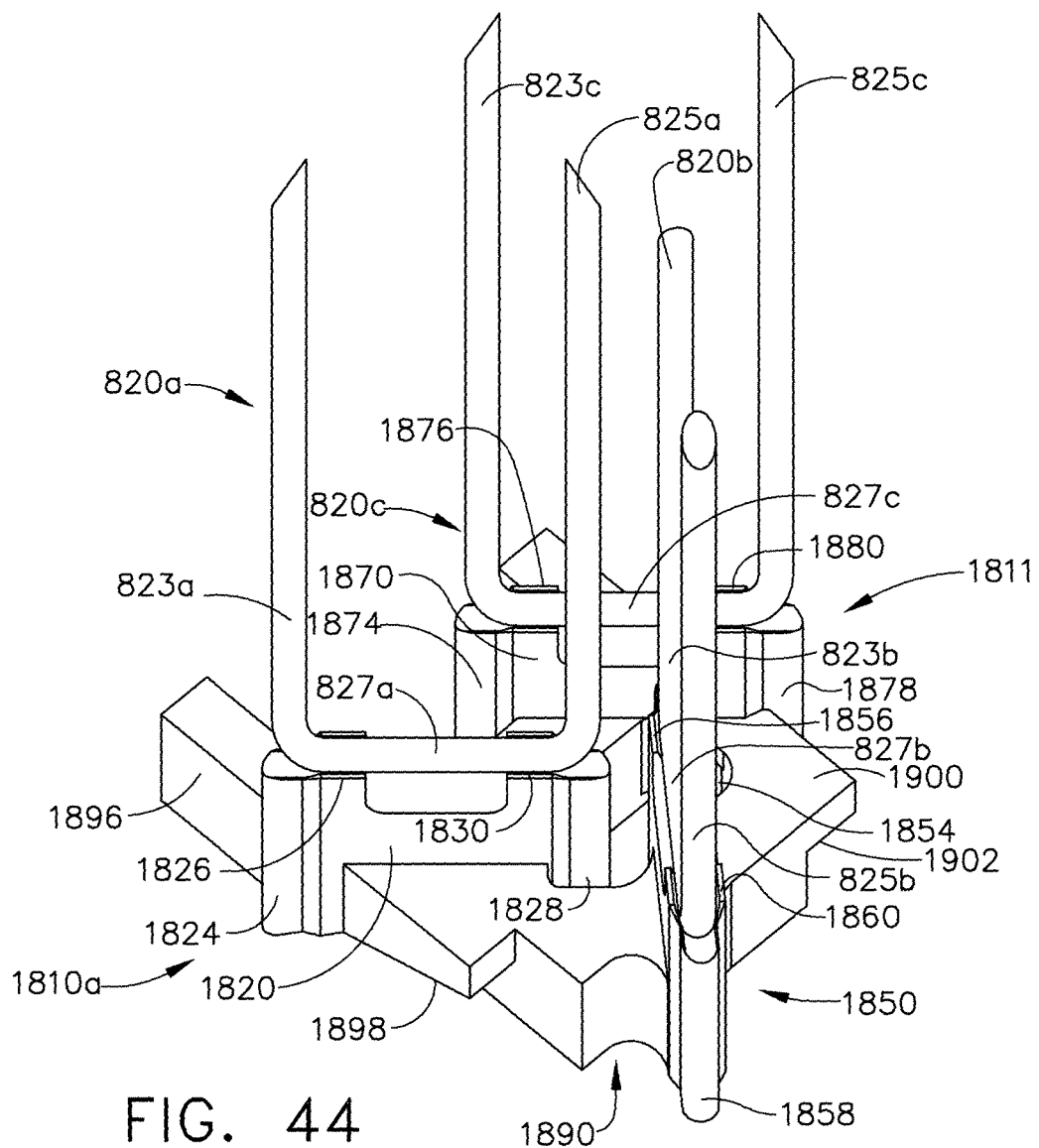
FIG. 44 is a perspective view of the driver of FIG. 43 supporting three staples thereon.

FIGS. 43-45 illustrate one exemplary form of a staple driver 1810a with it being understood that, in at least one arrangement, a staple driver 1810b essentially contains the same features as a staple driver 1810a and may be a mirror image thereof. Each staple driver 1810a, 1810b comprises a staple driver body 1811. In the illustrated arrangement, the driver body 1811 includes a first or innermost staple support portion 1820 that is configured to support a staple 820a thereon, a second or central staple support portion 1850 that is configured to support a staple 820b thereon and a third support portion 1870 that is configured to support a staple 820c thereon. As can be seen in FIG. 43, the first staple support portion 1820 comprises a first distal support column 1824 and a first proximal support column 1828. The first staple support portion 1820 further includes a first distal support cradle 1826 and a first proximal support cradle 1830 for supporting portions of the staple crown 827a of a staple 820a. As can be seen in FIG. 44, when the staple crown 827a of the staple 820a is supported on the support cradles 1826 and 1830, the distal leg 823a is essentially axially aligned with the first distal support column 1824 and the first proximal leg 825a is essentially axially aligned with the first proximal support column 1828. When the staple 820a is supported on the first staple support portion 1820, the staple crown 827a is aligned on a first base axis FBA.

Still referring to FIGS. 43 and 44, the staple driver 1810a further comprises second staple support portion 1850 that comprises a second distal support column 1854 and a second proximal support column 1858. The second staple support portion 1850 further includes a second distal support cradle 1856 and a second proximal support cradle 1860 for supporting portions of a staple crown 827b of a staple 820b therein. As can be seen in FIG. 44, when the staple crown 827b of the staple 820b is supported in the cradles 1856, 1860, the distal leg 823b is essentially axially aligned with the second distal support column 1854 and the proximal leg 825b is essentially axially aligned with the second proximal support column 1858. When the staple 820b is supported on the second staple support portion 1850, the staple crown 827b is aligned on a second base axis SBA. In the illustrated arrangement, the second base axis SBA is transverse to the first base axis FBA. See FIG. 43.

As can also be seen in FIGS. 43 and 44, the staple driver 1810a comprises a third staple support portion 1870 that includes a third distal support column 1874 and a third proximal support column 1878. The third staple support portion 1870 further includes a third distal support cradle 1876 and a third proximal support cradle 1880 configured to support portions of a staple crown 827c of a third staple 820c therein. As can be seen in FIG. 44, when the crown 827c of the staple 820c is supported in the cradles 1876, 1880, the distal leg 823c is essentially axially aligned with the distal support column 1874 and the proximal leg 825c is essentially axially aligned with the third proximal support column 1878. When the staple 820c is supported on the third staple support portion 1870, the staple crown 827c is aligned on a third base axis TBA. In the illustrated arrangement, the third base axis TBA is parallel to the first base axis FBA and transverse to the second base axis SBA. See FIG. 43.

Still referring to FIGS. 43-45, in at least one arrangement, the first staple support portion 1820, the second staple support portion 1850 and the third staple support portion 1870 are all coupled together by a connector portion 1890. In at least one arrangement, the connector portion 1890 is formed with a centrally disposed opening or aperture 1892 that is configured to slidably receive a corresponding first driver guide 2000 therein. See FIG. 42. The connector portion 1890 is formed with a first hook-shaped slot 1894 that is adapted to be hookingly engaged by a hooked shaped portion 2002 on the first driver guide 2000. The hook shaped portion 2002 is adapted to slidably support the support column 1828 therein. In addition, as can be further seen in FIG. 42, each first driver guide 2000 includes a slot 2004 that is configured to slidably receive the support column 1878 of the corresponding staple driver 1810a therein. Each staple driver 1810a is also configured to slidably engage a second driver guide 2020 as shown in FIG. 42. Each second driver guide 2020 includes a first slot 2022 that is configured to slidably receive therein a support column 1858 of a corresponding staple driver 1810a. In addition, each second driver guide 2020 further has a second slot 2024 that is configured to slidably receive therein a support column 1874 of the corresponding staple driver 1810a therein.

As can also be seen in FIGS. 44 and 45, the connector portion 1890 includes a first cam portion 1896 that has a first camming surface or ramp 1898 formed thereon. The connector portion 1890 also includes a second cam portion 1900 that has a second a second camming surface 1902 formed thereon. In at least one arrangement, the camming surfaces 1898, 1902 have the same slope or angle or they may have different slopes/angles. In at least one embodiment, each staple driver 1810a, 1810b is integrally formed from or molded from, for example, Ultem®, with no fill. However, other materials such as, for example, Ultem® with a glass or mineral fill or Nylon or Nylon with a glass file could be used. In other arrangements, the various portions of the proximal staple drivers 1810a, 1810b may be separately fabricated from other materials and be attached together by adhesive, solder, etc.

Figure 46:
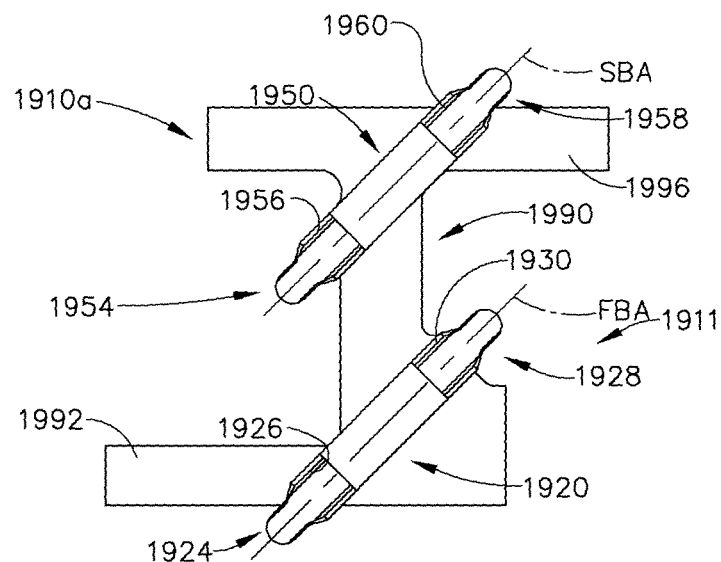
FIG. 46 is a top view of a proximal staple driver of the driver array of FIG. 42.
Figure 48:
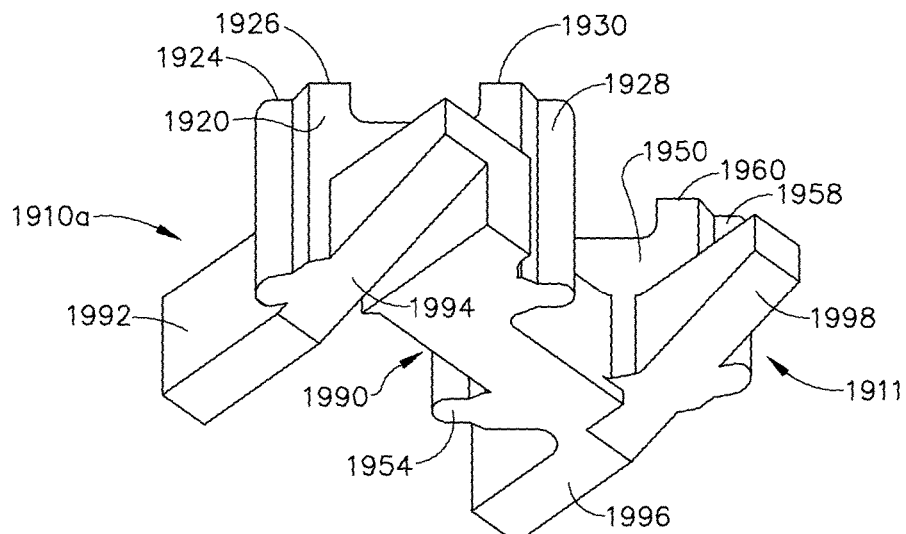
FIG. 48 is a bottom perspective view of the driver of FIGS. 46 and 47.
Figure 47:
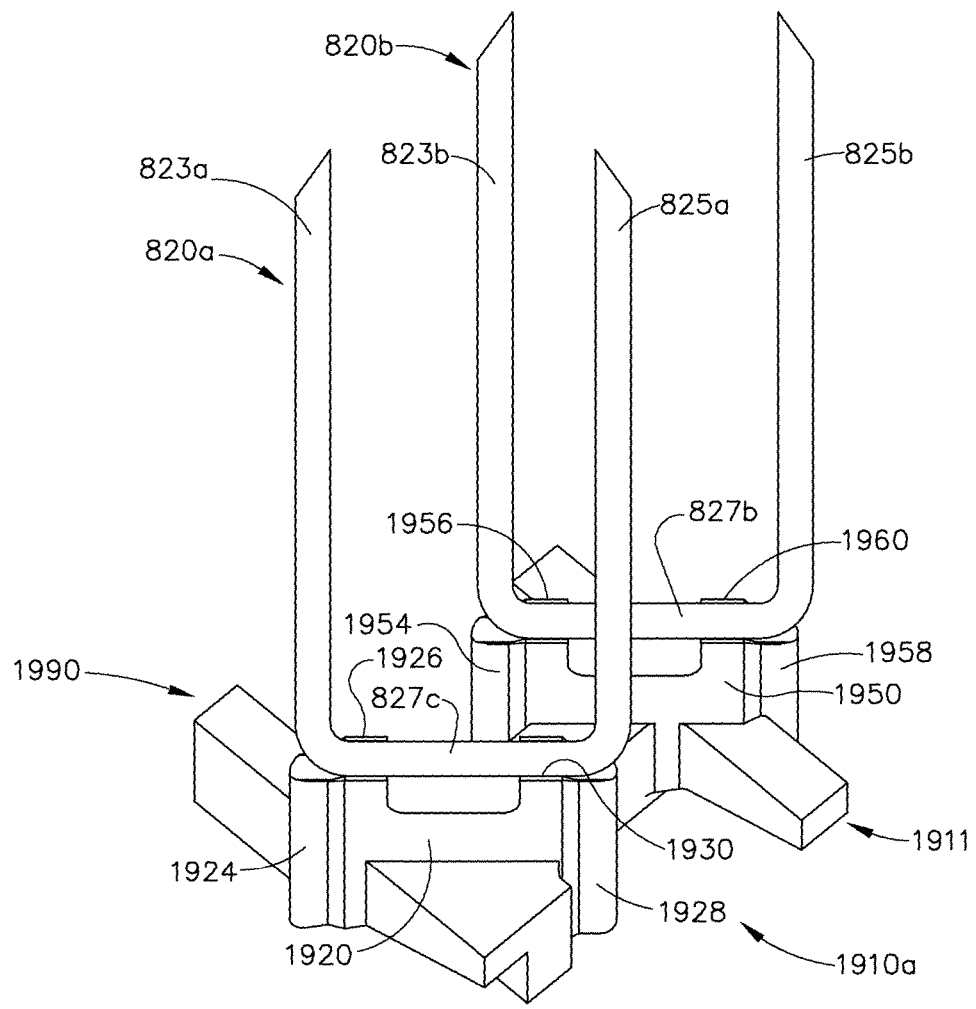
FIG. 47 is a perspective view the driver of FIG. 46 supporting two staples thereon.

The staple driver array 1800a in the illustrated embodiment also comprises a proximal staple driver 1910a that is configured to operably support two staples. FIGS. 46-48 illustrate one exemplary form of a distal staple driver 1910a with it being understood that, in at least one arrangement, a staple driver 1910b essentially contains the same features as a staple driver 1910a and may be a mirror image thereof. Each staple driver 1910a, 1910b includes a driver body 1911. In the illustrated arrangement, each driver body 1911 includes a first staple support portion 1920 that is configured to support a staple 820a thereon and a second staple support portion 1950 that is configured to support a staple 820c thereon. As can be seen in FIG. 46, the first staple support portion 1920 comprises a first distal support column 1924 and a first proximal support column 1928. The first staple support portion 1920 further includes a first distal support cradle 1926 and a first proximal support cradle 1930 for supporting portions of the first staple crown 827a. As can be seen in FIG. 47, when the staple crown 827a of the staple 820a is supported on the support cradles 1926 and 1930, the distal leg 823a is essentially axially aligned with the first distal support column 1924 and the proximal leg 825a is essentially axially aligned with the first proximal support column 1928. When the staple 820a is supported on the first staple support portion 1920, the staple crown 827a is aligned on a first base axis FBA. See FIG. 47.

Still referring to FIGS. 46 and 47, the distal staple driver 1910a further comprises second staple support portion 1950 that comprises a second distal support column 1954 and a second proximal support column 1958. The second staple support portion 1950 further includes a second distal support cradle 1956 and a second proximal support cradle 1960 for supporting portions of the staple crown 827c of a staple 820c therein. As can be seen in FIG. 47, when the staple crown 827c of the staple 820c is supported in the cradles 1956, 1960, the distal leg 823c is essentially axially aligned with the second distal support column 1954 and the proximal leg 825c is essentially axially aligned with the second proximal support column 1958. When the staple 820c is supported on the second staple support portion 1950, the staple crown 827c is aligned on a second base axis SBA. In the illustrated arrangement, the second base axis SBA is parallel to the first base axis FBA.

Still referring to FIGS. 46-48, in at least one arrangement, the first staple support portion 1920 and the second staple support portion 1950 of the proximal staple driver 1910a are coupled together by a connector portion 1990. In at least one arrangement, the connector portion 1990 is formed to slidably mate with a proximal most second driver guide 2020P. See FIG. 42. The support column 1954 of the proximal driver 1910a is configured to be slidably supported in the slot 2024 in the proximal most second driver guide 2020P.

As can also be seen in FIGS. 47 and 48, the connector portion 1990 includes a first cam portion 1992 that has a first camming surface or ramp 1994 formed thereon. The connector portion 1990 also includes a second cam portion 1996 that has a second camming surface 1998 formed thereon. In at least one arrangement, the camming surfaces 1994, 1998 have the same slope or angle or they may have different slopes/angles. In at least one embodiment, each proximal driver 1910a, 1910b is integrally formed from or molded from, for example, Ultem®, with no fill. However, other materials such as, for example, Ultem® with a glass or mineral fill or Nylon or Nylon with a glass file could be used. In other arrangements, the various portions of the distal drivers 1910a, 1910b may be separately fabricated from other materials and be attached together by adhesive, solder, etc.

Referring again to FIG. 41, it can be seen that in the staple driver array 1800a in the illustrated arrangement, the cam portion 1896 of each of the staple drivers 1810a and the cam portion 1992 of the proximal staple driver 1910a are all axially aligned along a first cam axis FCA. Thus the camming surface 1994 of each of the drivers 1910a and the camming surface 1994 of the proximal driver 1910a are axially aligned along the first cam axis FCA. The second cam portion 1900 of each of the drivers 1910a and the cam portion 1996 of the proximal staple driver 1910a are all aligned along a second cam axis SCA. Thus, in at least one embodiment, the camming surface 1902 of each of the drivers 1910a and the camming surface 1998 of the proximal driver 1910a are axially aligned on the second cam axis SCA. Also in the illustrated staple driver array 1900b, the cam portion 1896 of each of the staple drivers 1810b and the cam portion 1992 of the proximal driver 1910b are all aligned along a primary cam axis PCA. Thus, the camming surface 1898 of each of the drivers 1810b and the camming surface 1994 of the proximal driver 1910b are axially aligned along the primary cam axis PCA. Still referring to FIG. 41, in the staple driver array 1800b of the illustrated arrangement, the cam portion 1900 of each of the drivers 1810b and the cam portion 1996 of the proximal driver 1910b are all aligned along a secondary cam axis SDCA. Thus, in at least one embodiment, the camming surface 1902 of each of the drivers 1810b and the camming surface 1998 of the proximal driver 1910b are axially aligned on the secondary cam axis SDCA.

As can be appreciated from reference to FIG. 41, when the drivers 1810a and 1910a are all operably supported in the staple cartridge in the staple driver array 1800a, the staple drivers 1810a, 1910a form a first longitudinal row 2050a of staples 820a that is adjacent to elongate slot 804 in the cartridge body 802. Each of the staples 820a in the first longitudinal row 2050a extend in a first direction as was described above. Likewise, the drivers 1810a form a second longitudinal row 2060a of staples 820b that are adjacent the first longitudinal row 2050a. The staples 820b in the second longitudinal row 2060a extend in a second direction that is different from the first direction of the staples 820a in the first longitudinal row 2050a. In addition, the drivers 1810a and 1910a form a third longitudinal row 2070a of staples 820c that are oriented in a third direction which may or may not be in the same direction as staples 820a. For example, in the illustrated embodiment, the first and third directions are the same. The third longitudinal row 2070a is adjacent to the second longitudinal row 2070a.

Still referring to FIG. 41, when the staple drivers 1810b and 1910b are all operably supported in the staple cartridge in the staple driver array 1800b, the staple drivers 1810b and 1910b form a primary longitudinal row 2050b of staples 820a that is adjacent to elongate slot 804 in the cartridge body 802. Each of the staples 820a in the primary longitudinal row 2050b extend in a first direction as was described above. Likewise, the staple drivers 1810b form a secondary longitudinal row 2060b of staples 820b that are adjacent the primary longitudinal row 2050b. The staples 820b in the secondary longitudinal row 2060b extend in a second direction that is different from the first direction of the staples 820a in the primary longitudinal row 2050b. In addition, the staple drivers 1810b and 1910b form a tertiary longitudinal row 2070b of staples 820c that are oriented in a third direction which may or may not be in the same direction as staples 820a. For example, in the illustrated embodiment, the first and third directions are the same. The tertiary longitudinal row 2070b is adjacent to the secondary longitudinal row 2060b.

Thus, when employing the staple driver arrays 1800a, 1800b, there are two staples extending side by side in the same direction or along parallel axes along both ends of each of the staple lines. In particular, the proximal driver 1910a supports two distal most staples in the longitudinal rows 2050a, 2070a that each extend in the same direction. Similarly, the distal most driver 1810a supports two proximal most staples in the longitudinal rows 2050a and 2070a of staples that extend in the same direction. Such staple pattern may provide a redundant seal arrangement at both ends of each line of staples. As used in this context, the term "line of staples" collectively refers to the longitudinal rows of staples on one side of the elongate slot 804 in the staple cartridge body 802. For example, line of staples, generally designated as 2080a, collectively refers to the longitudinal rows 2050a, 2060a, 2070a of staples. Line of staples 2080b collectively refers to the longitudinal rows 2050b, 2060b, 2070b of staples.

As was discussed above, in the array 1800a, the ramp or camming member 764 of the sled or camming actuator 760 is aligned with the second cam axis SCA. Likewise, the ramp or camming member 762 is aligned with the first cam axis FCA. The ramp or camming member 766 is aligned on the primary cam axis PCA and the ramp or camming member 768 is aligned with the secondary cam axis SDCA. Thus, the ramp or camming member 764 is aligned with a portion of each of the crowns 827c of staples 820c. The ramp or camming member 762 is aligned with a portion of each of the crowns 827a of staples 820a. Likewise, in the array 1800b of the staple drivers 1810b, 1910b, the ramp or camming member 766 is aligned with a portion of the crowns 827a of each of the staples 820a. The ramp or camming member 768 is aligned with a portion of the crown 827c of each of the staples 820c. Stated another way, none of the ramps or camming members 764, 762, 766, 768 are aligned with any of the staple legs of the staples 820a, 820c. Such arrangement therefore enables the third proximal support columns 1878 of each of the staple drivers 1810a, as well as the proximal support column 1958 of the proximal staple driver 1910a to be slidably received within corresponding second support grooves or slots 858 in the second cartridge wall portion 856 of the cartridge body 802. Likewise, the first distal support columns 1824 of each of the staple drivers 1810a, as well as the support column 1924 of the proximal staple driver 1910a are all slidably received within corresponding first support grooves or slots 854 in the first cartridge wall portion 852 of the cartridge 800. In the staple driver array 1800a, each of the support columns 1874, 1828, 1854, 1858, 1954, 1928 are also slidably supported in corresponding driver guides 2000, 2020, 2020P that are formed in the cartridge body 802.

Figure 50A:
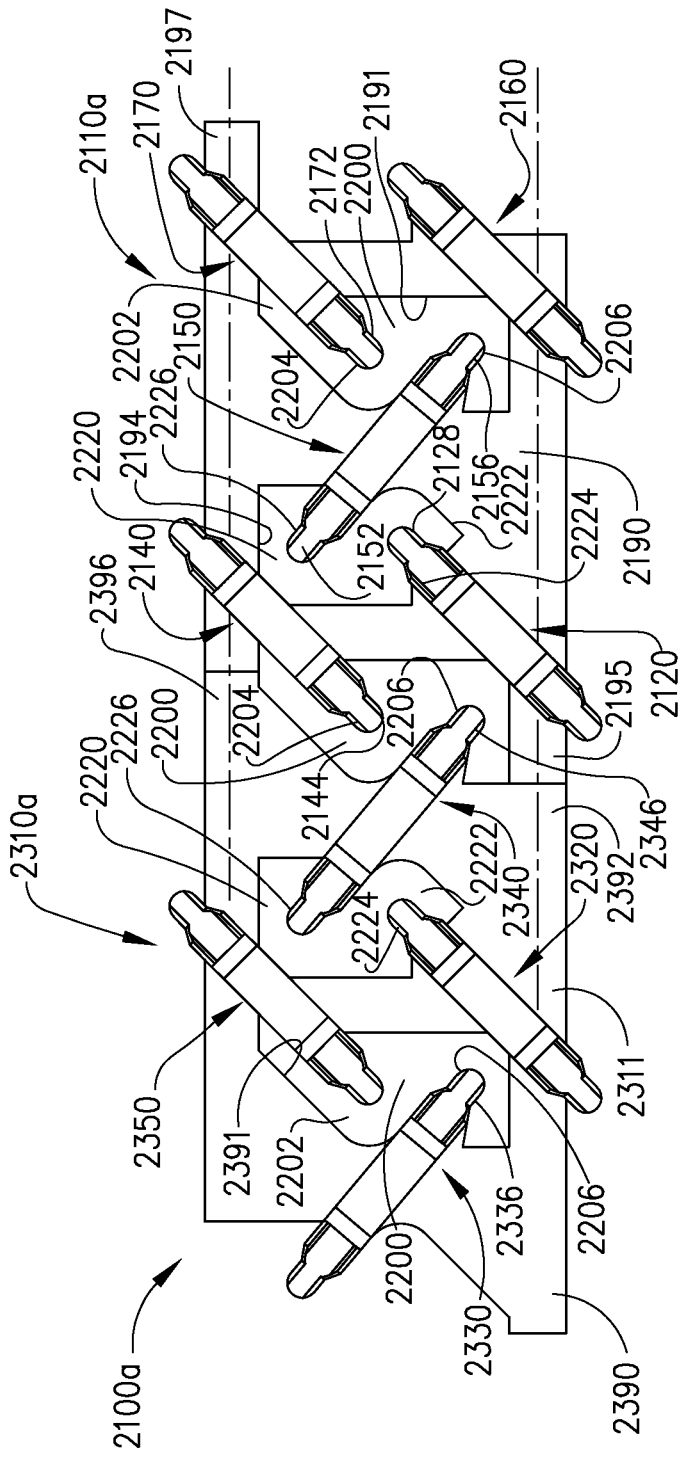
FIG. 50A is an enlarged view of a portion of the driver array of FIG. 50.
Figure 50B:
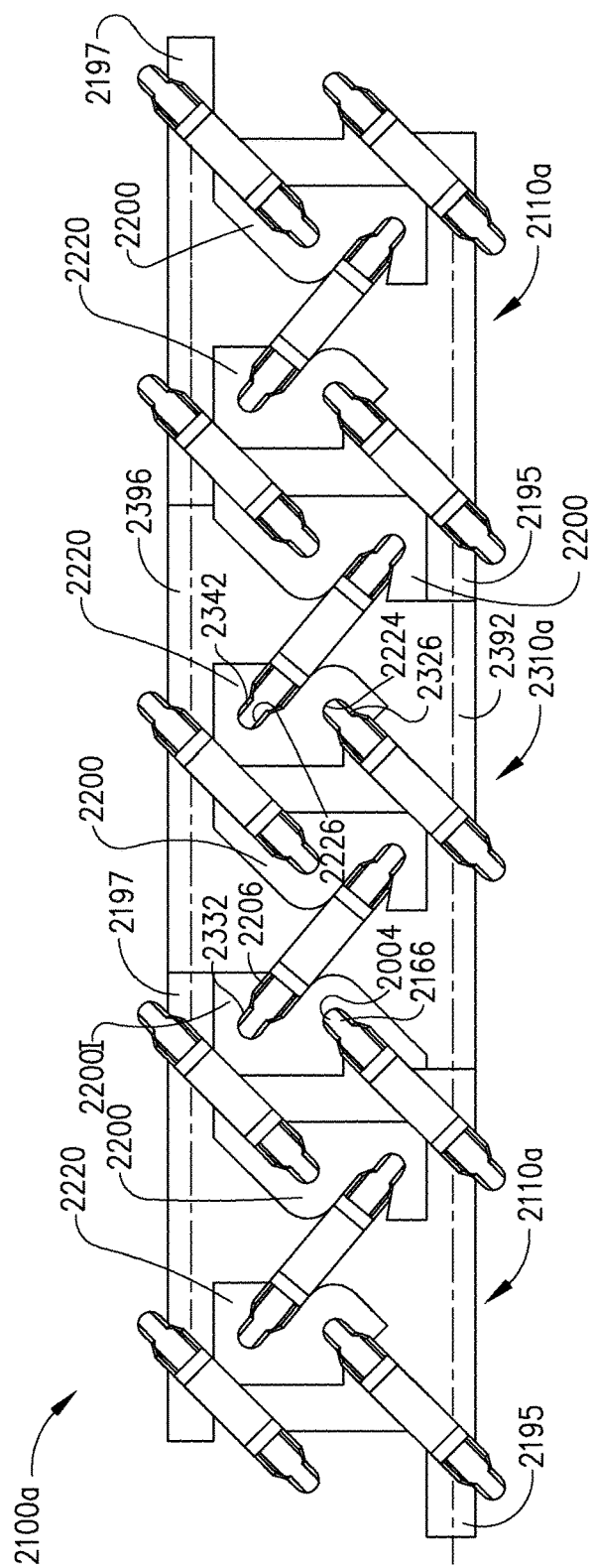
FIG. 50B is an enlarged view of another portion of the driver array of FIG. 50.

Other staple driver arrays 2100a, 2100b are illustrated in FIGS. 49 and 50. As can be seen in those Figures, the staple driver array 2100a employs a plurality of staple drivers 2110a that operably support five staples and a plurality of drivers 2310a that operably support four staples. Likewise, staple driver array 2100b includes a plurality of staple drivers 2310b and a distal staple driver 2310b. Staple drivers 2110b may be mirror images of staple drivers 2110a and include the same features. Staple drivers 2310b may be mirror images of staple drivers 2310a and include the same features.

Figure 51:
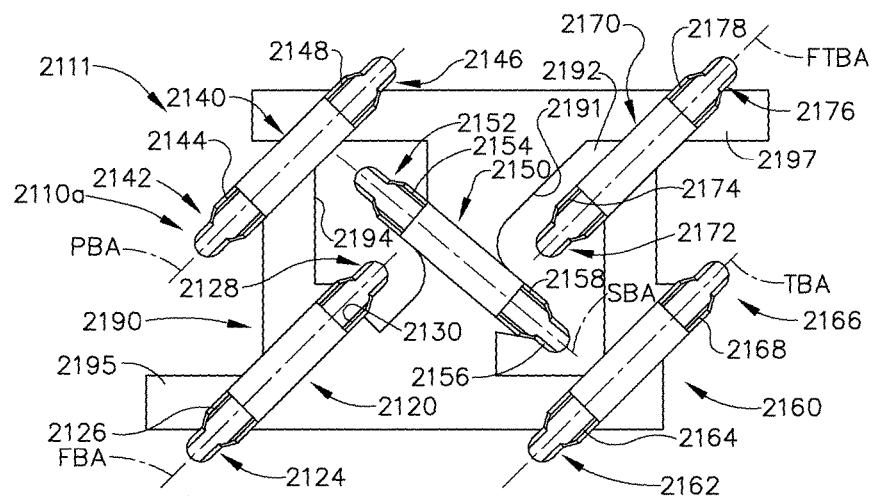
FIG. 51 is a top view of one of the drivers of the driver array depicted in FIG. 50.
Figure 53:
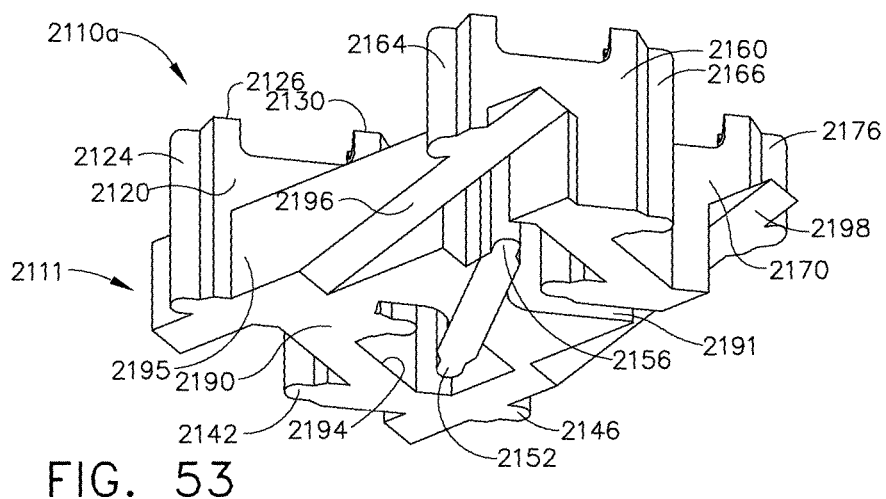
FIG. 53 is a bottom perspective view of the driver of FIGS. 51 and 52.
Figure 52:
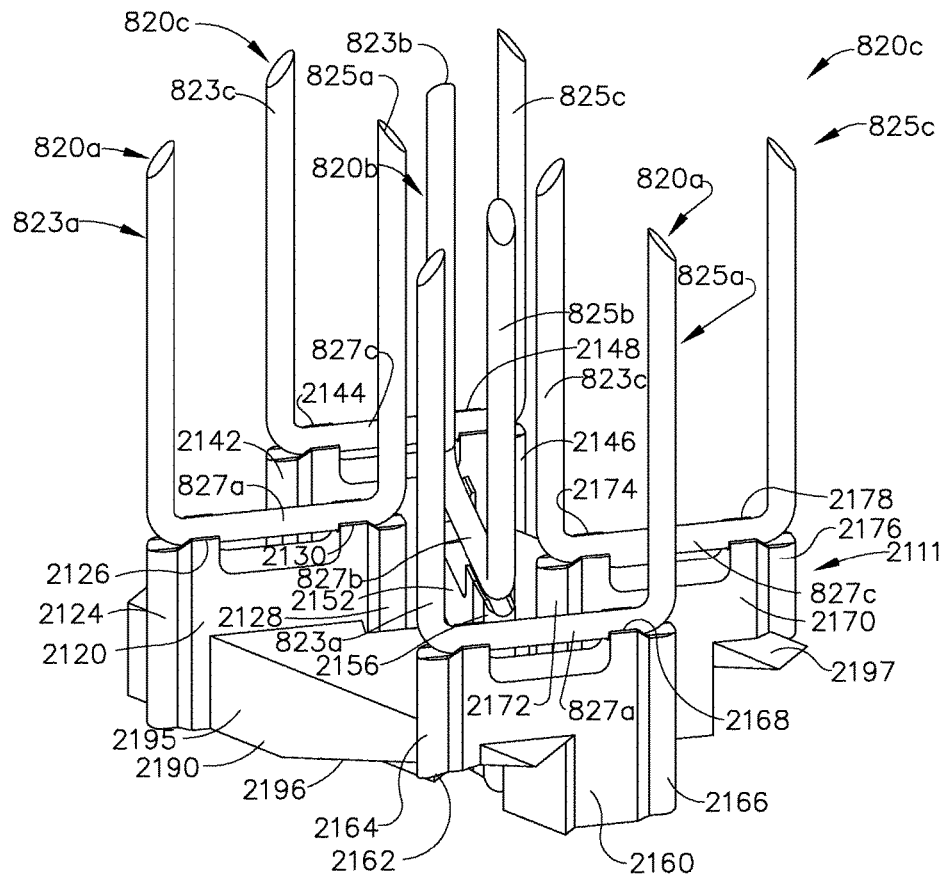
FIG. 52 is a perspective view of the driver of FIG. 51 supporting a total of five staples thereon.

FIGS. 51-53 illustrate one exemplary form of a staple driver 2110a with it being understood that, in at least one arrangement, a staple driver 2110b essentially contains the same features as a staple driver 2110a and may be a mirror image thereof. Each staple driver 2110a, 2110b comprises a staple driver body 2111. In the illustrated arrangement, the driver body 2111 includes a first staple support portion 2120 that is configured to support a staple 820a thereon. As can be seen in FIG. 51, the first staple support portion 2120 comprises a first distal support column 2124 and a first proximal support column 2128. The first staple support portion 2120 further includes a first distal support cradle 2126 and a first proximal support cradle 2130 for supporting portions of the staple crown 827a of a corresponding staple 820a thereon. As can be seen in FIG. 52, when the staple crown 827a of the staple 820a is supported on the support cradles 2126 and 2130, the distal leg 823a is essentially axially aligned with the first distal support column 2124 and the first proximal leg 825a is essentially axially aligned with the first proximal support column 2128. When the staple 820a is supported on the first staple support portion 2120, the staple crown 827a is aligned on a first base axis FBA.

Still referring to FIGS. 51 and 52, the staple driver 2110a further comprises a primary staple support portion 2140 that comprises a second distal support column 2142 and a second proximal support column 2146. The second staple support portion 2140 further includes a second distal support cradle 2144 and a second proximal support cradle 2148 for supporting portions of a staple crown 827c of a staple 820c therein. As can be seen in FIG. 52, when the staple crown 827c of the staple 820c is supported in the cradles 2144, 2148, the distal leg 823c is essentially axially aligned with the second distal support column 2142 and the proximal leg 825c is essentially axially aligned with the second proximal support column 2146. When the staple 820c is supported on the primary staple support portion 2140, the staple crown 827c is aligned on a primary base axis PBA. In the illustrated arrangement, the primary base axis PBA is parallel to the first base axis FBA. See FIG. 51.

The staple driver 2110a further comprises second staple support portion 2150 that comprises a second distal support column 2154 and a second proximal support column 2158. The second staple support portion 2150 further includes a second distal support cradle 2156 and a second proximal support cradle 2160 for supporting portions of a staple crown 827b of a staple 820b therein. As can be seen in FIG. 52, when the staple crown 827b of the staple 820b is supported in the cradles 2156, 2160, the distal leg 823b is essentially axially aligned with the second distal support column 2154 and the proximal leg 825b is essentially axially aligned with the second proximal support column 2158. When the staple 820b is supported on the second staple support portion 2150, the staple crown 827b is aligned on a second base axis SBA. In the illustrated arrangement, the second base axis SBA is transverse to the first base axis FBA and the primary base axis PBA. See FIG. 51.

As can also be seen in FIGS. 51 and 52, the staple driver 2110a comprises a third staple support portion 2160 that includes a third distal support column 2162 and a third proximal support column 2166. The third staple support portion 2160 further includes a third distal support cradle 2164 and a third proximal support cradle 2168 configured to support portions of a staple crown 827a of a staple 820a therein. As can be seen in FIG. 52, when the crown 827a of the staple 820a is supported in the cradles 2164, 2168, the distal leg 823a is essentially axially aligned with the distal support column 2162 and the proximal leg 825a is essentially axially aligned with the third proximal support column 2166. When the staple 820a is supported on the third staple support portion 2160, the staple crown 827a is aligned on a third base axis TBA. In the illustrated arrangement, the third base axis TBA is parallel to the first base axis FBA and the primary base axis PBA and transverse to the second base axis SBA. See FIG. 51.

As can be further seen in FIGS. 51 and 52, the staple driver 2110a comprises a fourth staple support portion 2170 that includes a fourth distal support column 2172 and a fourth proximal support column 2176. The fourth staple support portion 2170 further includes a fourth distal support cradle 2174 and a fourth proximal support cradle 2178 configured to support portions of a staple crown 827c of a staple 820c therein. As can be seen in FIG. 52, when the crown 827c of the staple 820c is supported in the cradles 2174, 2178, the distal leg 823c is essentially axially aligned with the distal support column 2172 and the proximal leg 825c is essentially axially aligned with the fourth proximal support column 2176. When the staple 820c is supported on the fourth staple support portion 2160, the staple crown 827a is aligned on a fourth base axis FTBA. In the illustrated arrangement, the fourth base axis FTBA is parallel to the first base axis FBA, the primary base axis PBA and the third base axis TBA and is transverse to the second base axis SBA. See FIG. 51.

Still referring to FIGS. 51-53, in at least one arrangement, the first staple support portion 2120, the primary staple support portion 2140, the second staple support portion 2150, the third staple support portion 2160 and the fourth staple support portion 2170 are all coupled together by a connector portion 2190. In at least one arrangement, the connector portion 2190 is formed with a first opening or aperture 2191 that is configured to slidably receive a corresponding first driver guide 2200 therein as will be further discussed below. See FIGS. 50 and 50A. The connector portion 2190 is formed with a first hook-shaped slot 2192 that is adapted to hookingly engage a hooked shaped portion 2202 on the first driver guide 2200. In one instance, the hook shaped portion 2202 has a slot 2204 that is adapted to slidably support a corresponding support column 2172 therein. See FIG. 50A. In another instance, the slot 2204 is configured to receive a corresponding support portion 2144 therein as shown in FIG. 50A. In addition, as can be further seen in FIG. 50A, each first driver guide 2200 includes a slot 2206 that is configured to slidably receive the support column 2156 of the corresponding staple driver 2110a therein. As can be seen in FIGS. 50A and 51, the connector portion 2190 further has a second opening 2194 therethrough that is configured to slidably engage a second driver guide 2220. Each second driver guide 2220 includes a first hook shaped portion 2222 that has a slot 2224 therein. In one instance, the slot 2224 is configured to slidably receive therein a support column 2128 of a corresponding staple driver 2110a. In addition, each second driver guide 2220 further has a second slot 2226 that is configured, in one instance, to slidably receive therein a support column 2152 of the corresponding staple driver 2110a therein.

As can also be seen in FIGS. 52 and 53, the connector portion 2190 includes a first cam portion 2195 that has a first camming surface or ramp 2196 formed thereon. The connector portion 2190 also includes a second cam portion 2197 that has a second a second camming surface 2198 formed thereon. In at least one arrangement, the camming surfaces 2196, 2198 have the same slope or angle or they may have different slopes/angles. In at least one embodiment, each staple driver 2110a, 2110b is integrally formed from or molded from, for example, Ultem®, with no fill. However, other materials such as, for example, Ultem® with a glass or mineral fill or Nylon or Nylon with a glass file could be used. In other arrangements, the various portions of the proximal staple drivers 2110a, 2110b may be separately fabricated from other materials and be attached together by adhesive, solder, etc.

Figure 54:
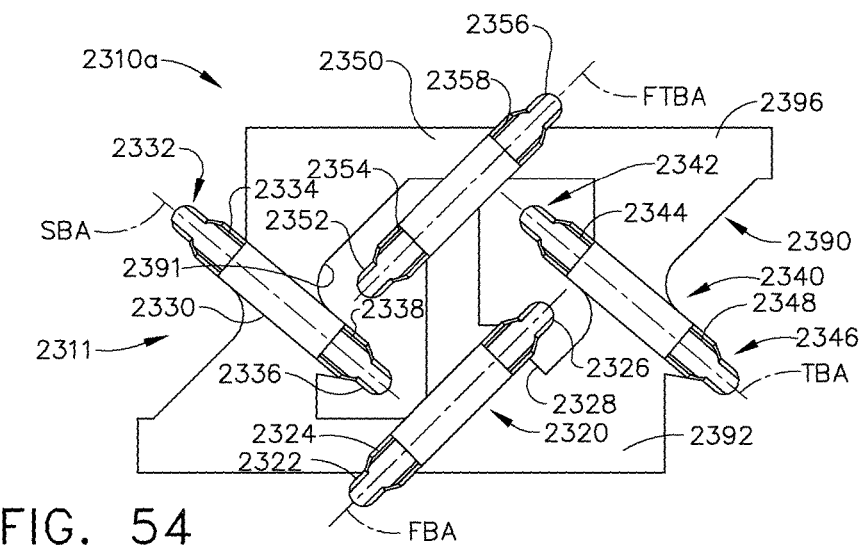
FIG. 54 is a top view of another driver of the driver array of FIG. 50.
Figure 56:
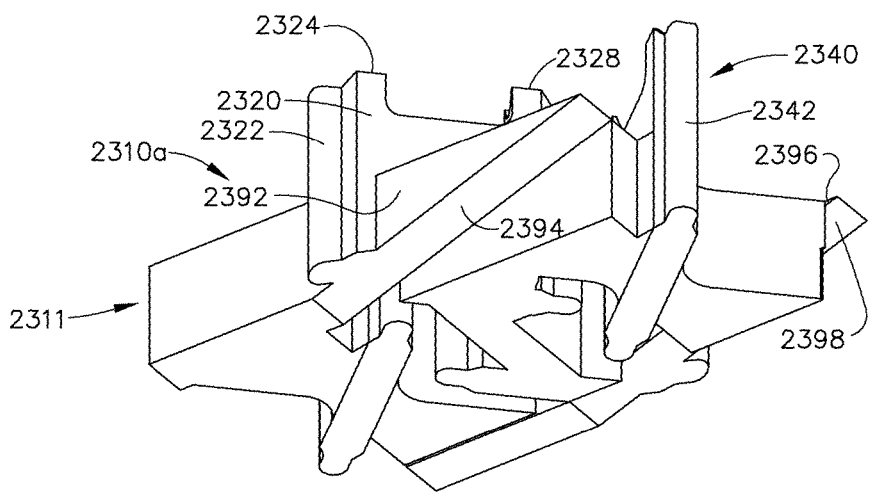
FIG. 56 is a bottom perspective view of the driver of FIG. 55.
Figure 55:
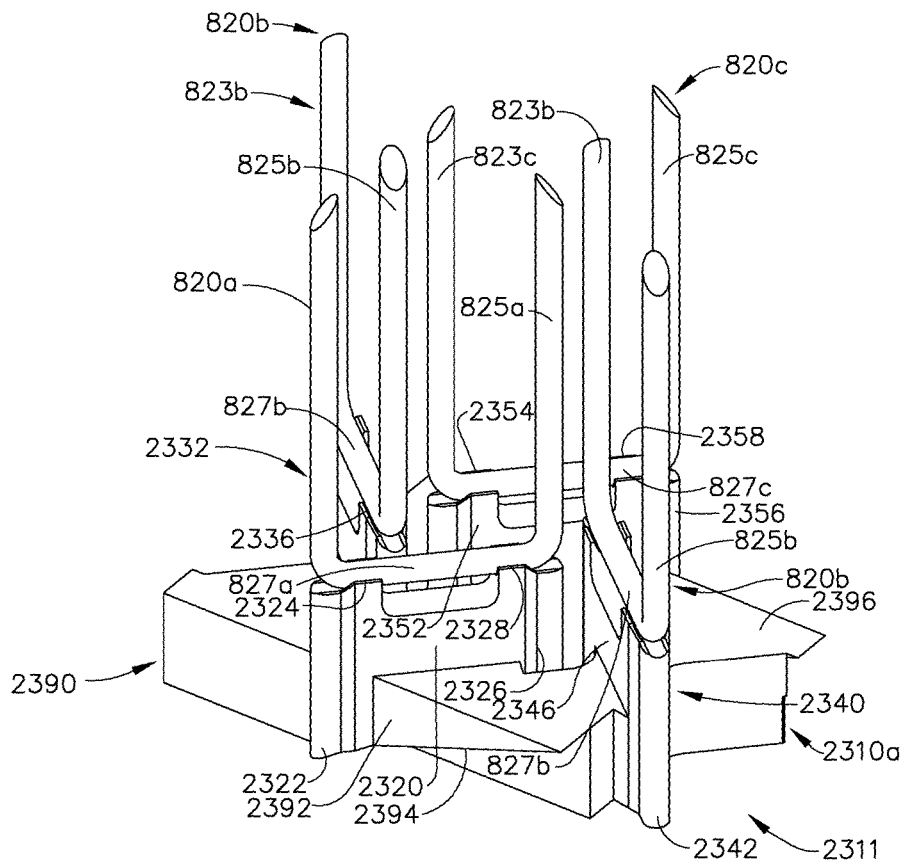
FIG. 55 is a perspective view of the driver of FIG. 54 supporting four staples thereon.

The staple driver array 2100a in the illustrated embodiment also comprises a second staple driver 2310a that is configured to operably support four staples. FIGS. 54-56 illustrate one exemplary form of a distal staple driver 2310a with it being understood that, in at least one arrangement, a staple driver 2310b essentially contains the same features as a staple driver 2310a and may be a mirror image thereof. Each staple driver 2310a, 2310b includes a driver body 2311. In the illustrated arrangement, each driver body 2311 includes a first staple support portion 2320 that is configured to support a staple 820a thereon, a second staple support portion 2330 that is configured to support a staple 820b thereon, a third staple support portion 2340 that is configured to operably support another staple 820b thereon and a fourth staple support portion 2350 that is configured to operably support a staple 820c thereon. As can be seen in FIG. 54, the first staple support portion 2320 comprises a first distal support column 2322 and a first proximal support column 2326. The first staple support portion 2320 further includes a first distal support cradle 2324 and a first proximal support cradle 2328 for supporting portions of the first staple crown 827a. As can be seen in FIG. 55, when the staple crown 827a of the staple 820a is supported on the support cradles 2324 and 2328, the distal leg 823a is essentially axially aligned with the first distal support column 2322 and the proximal leg 825a is essentially axially aligned with the first proximal support column 2326. When the staple 820a is supported on the first staple support portion 1620, the staple crown 827a is aligned on a first base axis FBA. See FIG. 54.

Still referring to FIGS. 54 and 55, the second staple driver 2310a further comprises second staple support portion 2330 that comprises a second distal support column 2332 and a second proximal support column 2326. The second staple support portion 2330 further includes a second distal support cradle 2334 and a second proximal support cradle 2338 for supporting portions of the staple crown 827b of a staple 820b therein. As can be seen in FIG. 55, when the staple crown 827b of the staple 820b is supported in the cradles 2334, 2338, the distal leg 823b is essentially axially aligned with the second distal support column 2332 and the proximal leg 825b is essentially axially aligned with the second proximal support column 2336. When the staple 820b is supported on the second staple support portion 2330, the staple crown 827b is aligned on a second base axis SBA. In the illustrated arrangement, the second base axis SBA is transverse to the first base axis FBA.

Also in the illustrated embodiment, the second staple driver 2310a further comprises a third staple support portion 2340 that comprises a third distal support column 2342 and a third proximal support column 2346. The third staple support portion 2340 further includes a third distal support cradle 2344 and a third proximal support cradle 2348 for supporting portions of the staple crown 827b of another staple 820b therein. As can be seen in FIG. 55, when the staple crown 827b of the other staple 820b is supported in the cradles 2344, 2348, the distal leg 823b is essentially axially aligned with the third distal support column 2342 and the proximal leg 825b is essentially axially aligned with the third proximal support column 2346. When the other staple 820b is supported on the third staple support portion 2340, the staple crown 827b is aligned on a third base axis TBA. In the illustrated arrangement, the third base axis TBA is parallel with the second base axis SBA and transverse to the first base axis FBA.

Still referring to FIGS. 54 and 55, the second staple driver 2310a further comprises fourth staple support portion 2350 that comprises a fourth distal support column 2352 and a second proximal support column 2356. The fourth staple support portion 2350 further includes a fourth distal support cradle 2354 and a fourth proximal support cradle 2358 for supporting portions of the staple crown 827c of a staple 820c therein. As can be seen in FIG. 55, when the staple crown 827c of the staple 820c is supported in the cradles 2354, 2358, the distal leg 823c is essentially axially aligned with the fourth distal support column 2352 and the proximal leg 825c is essentially axially aligned with the fourth proximal support column 2356. When the staple 820c is supported on the fourth staple support portion 2350, the staple crown 827c is aligned on a fourth base axis FTBA. In the illustrated arrangement, the fourth base axis FTBA is parallel to the first base axis FBA and transverse to the second base axis SBA and the third base axis TBA.

In at least one arrangement, the first staple support portion 2320, the second staple support portion 2330, the third staple support portion 2340 and the fourth staple support portion 2350 of the second staple driver 2310a are coupled together by a connector portion 2390. In the illustrated example, the connector portion 2390 is formed to slidably mate with a corresponding first staple guide 2200 and a second staple guide 2220. In particular, the connector portion 2390 has a first opening 2391 therein that is configured to slidably receive therein a corresponding first staple guide 2200 therein. When the staple driver 2310a slidably interfaces with the corresponding first staple guides 2200, the support column 2346 is slidably received in the slot 2206 in the corresponding first driver guide 2200. Likewise, the column 2336 is slidably received in the slot 2206 of another first driver guide 2200. In addition, an inverted first driver guide 2200l interfaces between the first and second drivers 2110a and 2310a. As can be seen in FIG. 50, the support column 2166 of the first driver guide 2110a is slidably received within the slot 2004 in the inverted first driver guide 2200l and the support column 2332 of the corresponding second driver guide 2310a is slidably received within the slot 2206 of the inverted first driver guide 2200l. In addition, the support column 2342 of the second driver guide 2310a is slidably received within a slot 2226 in a corresponding second driver guide 2220 and the support column 2326 is slidably received within the slot 2224 in the corresponding second driver guide 2220.

As can also be seen in FIGS. 55 and 56, the connector portion 2390 includes a first cam portion 2392 that has a first camming surface or ramp 2394 formed thereon. The connector portion 2390 also includes a second cam portion 2396 that has a second camming surface 2398 formed thereon. In at least one arrangement, the camming surfaces 2394, 2398 have the same slope or angle or they may have different slopes/angles. In at least one embodiment, each second driver 2310a, 2310b is integrally formed from or molded from, for example, Ultem®, with no fill. However, other materials such as, for example, Ultem® with a glass or mineral fill or Nylon or Nylon with a glass file could be used. In other arrangements, the various portions of the second drivers 2310a, 2310b may be separately fabricated from other materials and be attached together by adhesive, solder, etc.

Referring again to FIG. 49, it can be seen that in the staple driver array 2100a in the illustrated arrangement, the cam portion 2195 of each of the first staple drivers 2110a and the cam portion 2392 of each of the second staple drivers 2310a are all axially aligned along a first cam axis FCA. Thus, the camming surface 2196 of each of the first drivers 2110a and the camming surface 2394 of each of the second drivers 2310a are axially aligned along the first cam axis FCA. As can also be seen in FIG. 49, the second cam portion 2197 of each of the first drivers 2110a and the cam portion 2396 of each of the second staple drivers 2310a are all aligned along a second cam axis SCA. Thus, in at least one embodiment, the camming surface 2198 of each of the first drivers 2110a and the camming surface 2398 of each of the second drivers 2310a are axially aligned on the second cam axis SCA. Also in the illustrated staple driver array 2100b, the cam portion 2195 of each of the first drivers 2110b and the cam portion 2392 of each of the second drivers 2310b are all aligned along a primary cam axis PCA. Thus, the camming surface 2196 of each of the first drivers 2110b and the camming surface 2394 of the each of the second drivers 2310b are axially aligned along the primary cam axis PCA. Still referring to FIG. 49, in the staple driver array 2100b of the illustrated arrangement, the cam portion 2197 of each of the first drivers 2110b and the cam portion 2396 of each of the second drivers 2310b are all aligned along a secondary cam axis SDCA. Thus, in at least one embodiment, the camming surface 2198 of each of the first drivers 2110b and the camming surface 2398 of each of the second drivers 2310b are axially aligned on the secondary cam axis SDCA.

As can be appreciated from reference to FIG. 49, when the first drivers 2110a and the second drivers 2310a are all operably supported in the staple cartridge in the staple driver array 2100a, the staple drivers 2110a, 2310a form a first longitudinal row 2450a of staples that is adjacent to elongate slot 804 in the cartridge body 802. Each of the staples in the first longitudinal row 2450a extends in a first direction as was described above. Likewise, the drivers 2110a and 2310a form a second longitudinal row 2460a of staples that are adjacent the first longitudinal row 2450a. The staples in the second longitudinal row 2460a extend in a second direction that is different from the first direction of the staples in the first longitudinal row 2450a. In addition, the drivers 2110a and 2310a form a third longitudinal row 2470a of staples that are oriented in a third direction which may or may not be in the same direction as staples in the first longitudinal row 2450a. For example, in the illustrated embodiment, the first and third directions are the same. The third longitudinal row 2470a is adjacent to the second longitudinal row 2060a.

Still referring to FIG. 49, when the staple drivers 2110b and 2310b are all operably supported in the staple cartridge in the staple driver array 2100b, the staple drivers 2110b and 2310b form a primary longitudinal row 2450b of staples that is adjacent to elongate slot 804 in the cartridge body 802. Each of the staples in the primary longitudinal row 2050b extend in a first direction as was described above. Likewise, the staple drivers 2110b and 2310b form a secondary longitudinal row 2460b of staples that are adjacent the primary longitudinal row 2450b. The staples in the secondary longitudinal row 2460b extend in a second direction that is different from the first direction of the staples in the primary longitudinal row 2450b. In addition, the staple drivers 2110b and 2310b form a tertiary longitudinal row 2470b of staples that are oriented in a third direction which may or may not be in the same direction as staples in the primary longitudinal row 2450b. For example, in the illustrated embodiment, the first and third directions are the same. The tertiary longitudinal row 2470b is adjacent to the secondary longitudinal row 2460b.

Thus, when employing the staple driver arrays 2100a, 2100b, there are two staples extending side by side in the same direction or along parallel axes along both ends of each of the staple lines. In particular, the proximal most first driver 2110a supports two proximal most staples in the longitudinal rows 2450a, 2470a that each extending in the same direction. Similarly, the distal most first driver 2110a supports two proximal most staples in the longitudinal rows 2450a and 2470a of staples that extend in the same direction. The same staple patterns are also established in the staple driver array 2100b. Such staple patterns may provide a redundant seal arrangement at both ends of each line of staples. As used in this context, the term "line of staples" collectively refers to the longitudinal rows of staples on one side of the elongate slot 804 in the staple cartridge body 802. For example, line of staples, generally designated as 2480a, collectively refers to the longitudinal rows 2450a, 2460a, 2470a of staples. Line of staples 2480b collectively refers to the longitudinal rows 2450b, 2460b, 2470b of staples.

As was discussed above, in the array 2100a, the ramp or camming member 764 of the sled or camming actuator 760 is aligned with the second cam axis SCA. Likewise, the ramp or camming member 762 is aligned with the first cam axis FCA. The ramp or camming member 766 is aligned on the primary cam axis PCA and the ramp or camming member 768 is aligned with the secondary cam axis SDCA. Thus, the ramp or camming member 764 is aligned with a portion of each of the crowns of staples in the longitudinal row 2470a of staples. The ramp or camming member 762 is aligned with a portion of each of the crowns of the staples in longitudinal row 2450a. Likewise, in the array 2100b of the staple drivers 2110b, 2310b, the ramp or camming member 766 is aligned with a portion of the crowns of each of the staples in the longitudinal row 2450b of staples. The ramp or camming member 768 is aligned with a portion of the crown of each of the staples in longitudinal row 2470b of staples. Stated another way, none of the ramps or camming members 764, 762, 766, 768 are aligned with any of the staple legs of the staples in longitudinal rows 2470a, 2450a, 2450b, 2470b. Such arrangement therefore enables the support columns 2176 and 2146 of each of the first drivers 2110a as well as the support column 2356 of each of the second drivers 2310a to be slidably received within corresponding second support grooves or slots 858 in the second cartridge wall portion 856 of the cartridge body 802. Likewise, the columns 2162 and 2124 of each of the first drivers 2110a as well as the support column 2322 of each of the second drivers 2310a are all slidably received within corresponding first support grooves or slots 854 in the first cartridge wall portion 852 of the cartridge 800. The remaining support columns of each of the first and second drivers 2110a, 2310a are all slidably received within corresponding driver guides 2200, 2220, 2200l. The same arrangement is achieved in the staple driver array 2100b.

Other staple driver arrays 2500a, 2500b are illustrated in FIGS. 57 and 58. As can be seen in those Figures, the staple driver array 2500a is similar to the staple driver array 2100a described above, except that the distal most driver in the array is a distal staple driver 2610a that is adjacent to a second staple driver 2310a. Whereas, in the staple driver array 2100a, the first staple driver 2110a is the distal most driver. The distal staple driver 2610a operably supports two staples. Likewise, staple driver array 2500b includes a plurality of first staple drivers 2110b and a plurality of second staple driver 2310b as well as a distal staple driver 2610b. Staple driver 2610b may be mirror images of staple driver 2610a and include the same features.

Figure 59:
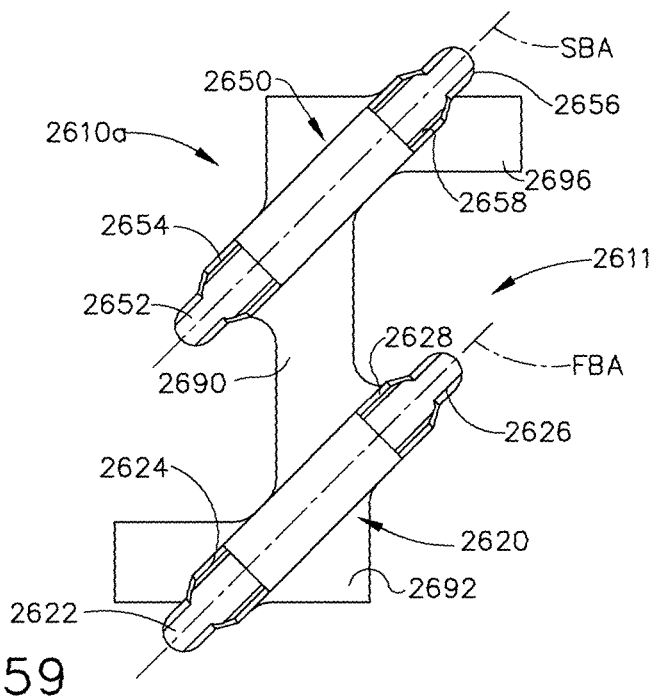
FIG. 59 is a top view of a distal driver of the driver array depicted in FIG. 58.
Figure 61:
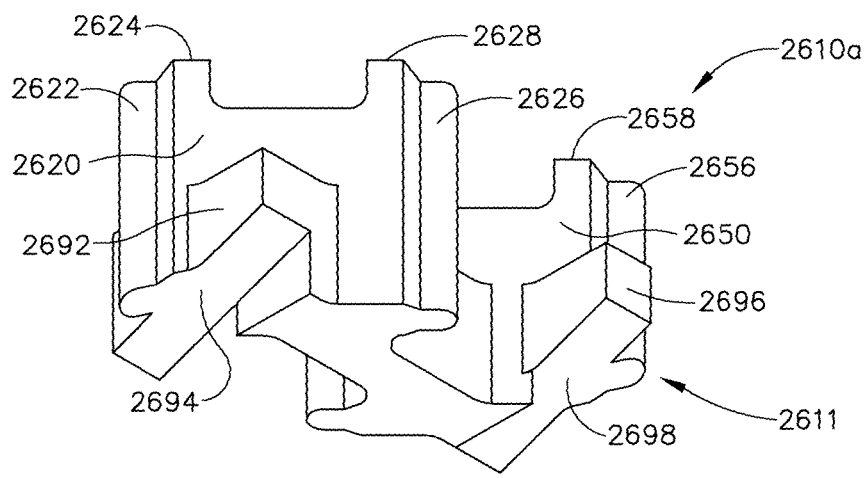
FIG. 61 is a bottom perspective view of the driver of FIGS. 59 and 60.
Figure 60:
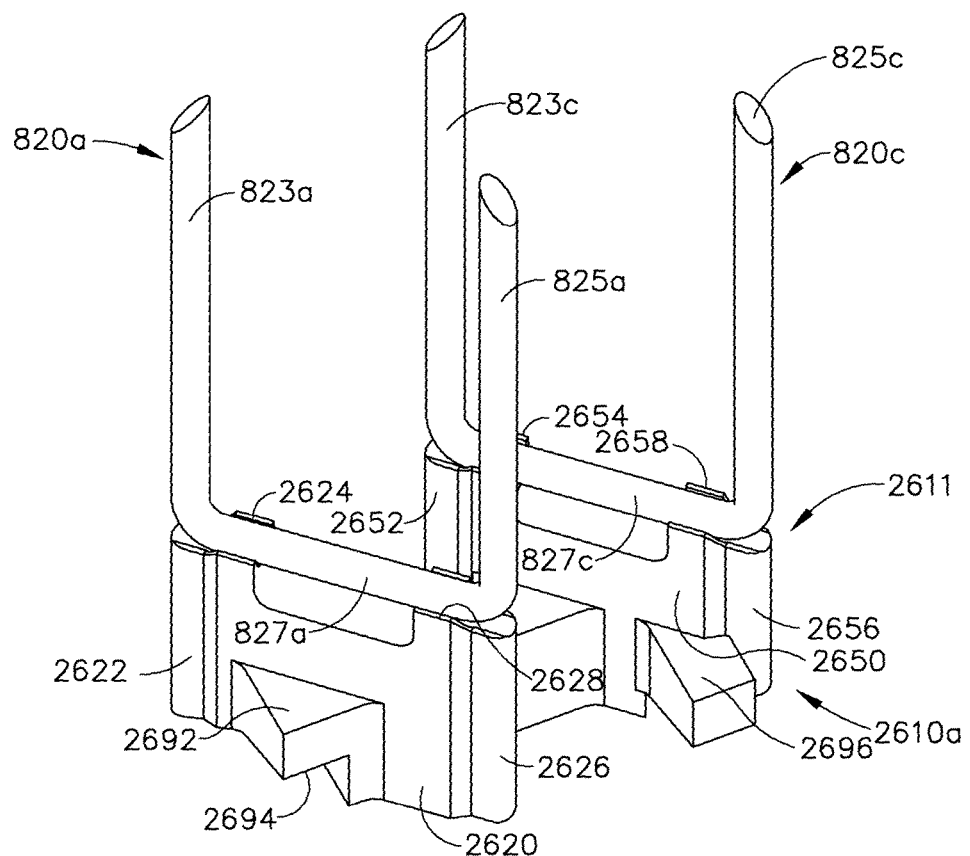
FIG. 60 is a perspective view of the distal driver of FIG. 59 supporting two staples thereon.

FIGS. 59-61 illustrate one exemplary form of a distal staple driver 2610a with it being understood that, in at least one arrangement, a distal staple driver 2610b essentially contains the same features as a distal staple driver 2610a and may be a mirror image thereof. Each staple driver 2610a, 2610b comprises a staple driver body 2611. In the illustrated arrangement, the driver body 2611 includes a first or innermost staple support portion 2620 that is configured to support a staple 820a thereon and a second or central staple support portion 2650 that is configured to support a staple 820c thereon. As can be seen in FIG. 59, the first staple support portion 2620 comprises a first distal support column 2622 and a first proximal support column 2626. The first staple support portion 2620 further includes a first distal support cradle 2624 and a first proximal support cradle 2628 for supporting portions of the staple crown 827a of a staple 820a. As can be seen in FIG. 60, when the staple crown 827a of the staple 820a is supported on the support cradles 2624 and 2628, the distal leg 823a is essentially axially aligned with the first distal support column 2622 and the first proximal leg 825a is essentially axially aligned with the first proximal support column 2626. When the staple 820a is supported on the first staple support portion 2620, the staple crown 827a is aligned on a first base axis FBA.

Still referring to FIGS. 59 and 60, the distal staple driver 2610a further comprises second staple support portion 2650 that comprises a second distal support column 2652 and a second proximal support column 2656. The second staple support portion 2650 further includes a second distal support cradle 2654 and a second proximal support cradle 2658 for supporting portions of a staple crown 827c of a staple 820c therein. As can be seen in FIG. 60, when the staple crown 827c of the staple 820c is supported in the cradles 2654, 2658, the distal leg 823c is essentially axially aligned with the second distal support column 2652 and the proximal leg 825c is essentially axially aligned with the second proximal support column 2656. When the staple 820c is supported on the second staple support portion 2650, the staple crown 827c is aligned on a second base axis SBA. In the illustrated arrangement, the second base axis SBA is parallel with the first base axis FBA.

In at least one arrangement, the first staple support portion 2620 and the second staple support portion 2650 are coupled together by a connector portion 2690 that is configured to slidably interface with the inverted driver guide 2200l. As can be seen in FIG. 58, for example, the support column 2626 of the distal driver 2610a is slidably received within the slot 2204 in the inverted driver guide 2200l. As can also be seen in FIGS. 59-61, the connector portion 2690 includes a first cam portion 2692 that has a first camming surface or ramp 2694 formed thereon. The connector portion 2690 also includes a second cam portion 2696 that has a second a second camming surface 2698 formed thereon. In at least one arrangement, the camming surfaces 2694, 2698 have the same slope or angle or as the corresponding camming surfaces on the first and second drivers 2310a, 2310a. In at least one embodiment, each staple driver 2610a, 2610b is integrally formed from or molded from, for example, Ultem®, with no fill. However, other materials such as, for example, Ultem® with a glass or mineral fill or Nylon or Nylon with a glass file could be used. In other arrangements, the various portions of the distal staple drivers 2610a, 2610b may be separately fabricated from other materials and be attached together by adhesive, solder, etc.

Referring again to FIG. 57, it can be seen that in the staple driver array 2500a in the illustrated arrangement, the cam portion 2195 of each of the first staple drivers 2110a and the cam portion 2392 of each of the second drivers 2310a, as well as the cam portion 2692 of the distal driver 2610a are all axially aligned along a first cam axis FCA. Thus the camming surface 2196 of each of the first drivers 2110a and the camming surface 2394 of each of the second drivers 2310a, as well as the camming surface 2694 of the distal driver 2610a are axially aligned along the first cam axis FCA. The cam portion 2197 of each of the first drivers 2110a and the cam portion 2396 of each of the second drivers 2310a, as well as the cam portion 2696 of the distal driver 2610a are all aligned along a second cam axis SCA. Thus, in at least one embodiment, the camming surface 2198 of each of the first drivers 2110a and the camming surface 2398 of each of the second drivers 2310a, as well as the camming surface of the distal driver 2610a are axially aligned on the second cam axis SCA. Also in the illustrated staple driver array 2500b, the cam portion 2195 of each of the first drivers 2110b and the cam portion 2392 of each of the second drivers 2310b, as well as the cam portion 2692 of the distal driver 2610b are all aligned along a primary cam axis PCA. Thus, the camming surface 2196 of each of the first drivers 2110b and the camming surface 2394 of each of the second drivers 2310b, as well as the camming surface 2694 of the distal driver 2610b are axially aligned along the primary cam axis PCA. Still referring to FIG. 57, in the staple driver array 2500b of the illustrated arrangement, the cam portion 2197 of each of the first drivers 2110b and the cam portion 2396 of each of the second drivers 2310b as well as the cam portion 2696 of the distal driver 2610b are all aligned along a secondary cam axis SDCA. Thus, in at least one embodiment, the camming surface 2198 of each of the first drivers 2110b and the camming surface 2398 of each of the second drivers 2310b as well as the camming surface 2698 of the distal driver 2610b are axially aligned on the secondary cam axis SDCA.

As can be appreciated from reference to FIG. 57, when the drivers 2110a, 2310a and 2610a are all operably supported in the staple cartridge in the staple driver array 2500a, the staple drivers 2110a, 2310a, 2610a form a first longitudinal row 2750a of staples 820a that is adjacent to elongate slot 804 in the cartridge body 802. Each of the staples 820a in the first longitudinal row 2750a extend in a first direction as was described above. Likewise, the drivers 2110a and 2310a form a second longitudinal row 2760a of staples 820b that are adjacent the first longitudinal row 2750a. The staples 820b in the second longitudinal row 2760a extend in a second direction that is different from the first direction of the staples 820a in the first longitudinal row 2750a. In addition, the drivers 2110a, 2310a, 2610a form a third longitudinal row 2770a of staples 820c that are oriented in a third direction which may or may not be in the same direction as staples 820a. For example, in the illustrated embodiment, the first and third directions are the same. The third longitudinal row 2770a is adjacent to the second longitudinal row 2760a.

Still referring to FIG. 57, when the staple drivers 2110b, 2310b, 2610b are all operably supported in the staple cartridge in the staple driver array 2500b, the staple drivers 2110b and 2310b and 2610b form a primary longitudinal row 2750b of staples 820a that is adjacent to elongate slot 804 in the cartridge body 802. Each of the staples 820a in the primary longitudinal row 2750b extend in a first direction as was described above. Likewise, the staple drivers 2110b and 2310b form a secondary longitudinal row 2760b of staples 820b that are adjacent the primary longitudinal row 2750b. The staples 820b in the secondary longitudinal row 2760b extend in a second direction that is different from the first direction of the staples 820a in the primary longitudinal row 1750b. In addition, the staple drivers 2110b, 2310b and 2610b form a tertiary longitudinal row 2770b of staples 820c that are oriented in a third direction which may or may not be in the same direction as staples 820a. For example, in the illustrated embodiment, the first and third directions are the same. The tertiary longitudinal row 2770b is adjacent to the secondary longitudinal row 2760b.

Thus, when employing the staple driver arrays 2500a, 2500b, there are two staples extending side by side in the same direction or along parallel axes along both ends of each of the staple lines. In particular, the distal driver 2610a supports two distal most staples in the longitudinal rows 2750a, 2770a that each extending in the same direction. Similarly, the proximal most first driver 2110a supports two proximal most staples in the longitudinal rows 2750a and 2770a of staples that extend in the same direction. Such staple pattern may provide a redundant seal arrangement at both ends of each line of staples.

Other staple driver arrays 2800a, 2800b are illustrated in FIGS. 62 and 63. As can be seen in those Figures, the staple driver array 2800*a* employs a plurality of staple drivers 2610*a* that were described above. A staple driver 2610*a* comprises a proximal most driver and another staple driver 2610*a* forms a distal most driver in the driver array 2800*a*. Additional staple drivers 2610*a* alternate with staple drivers 2910*a* that are each configured to operably support a single staple 820*b* thereon.

Figure 64:
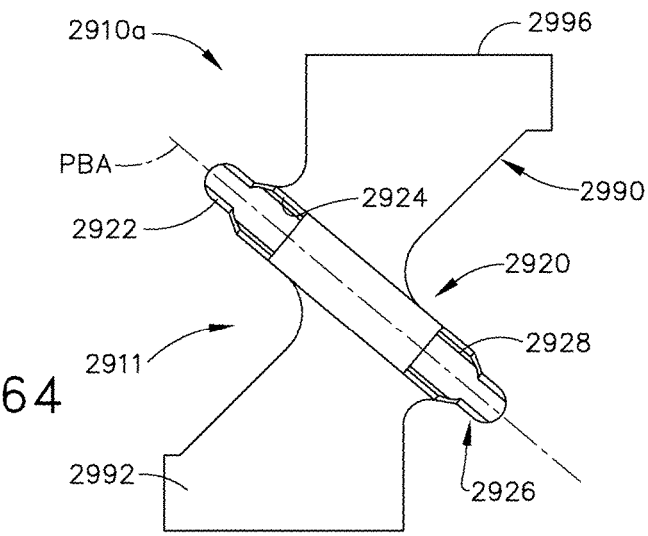
FIG. 64 is a top view of one of the drivers of the driver arrays of FIGS. 62 and 63.
Figure 66:
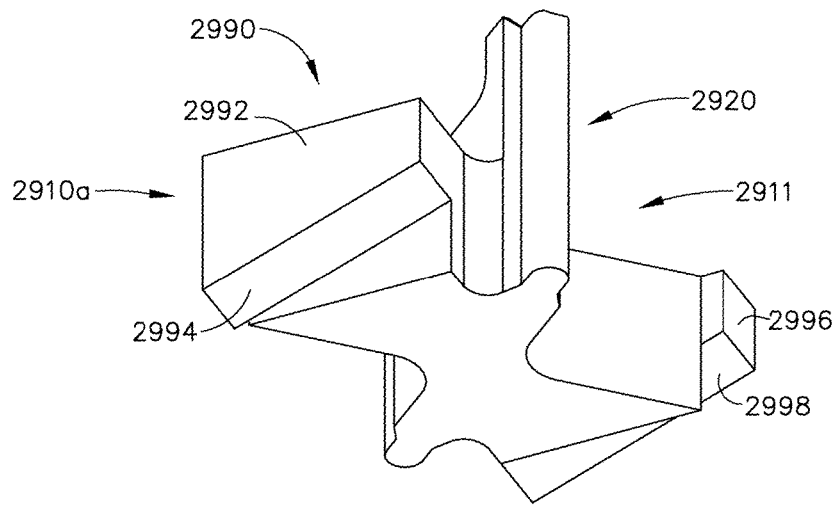
FIG. 66 is a bottom perspective view of the driver of FIGS. 64 and 65.
Figure 65:
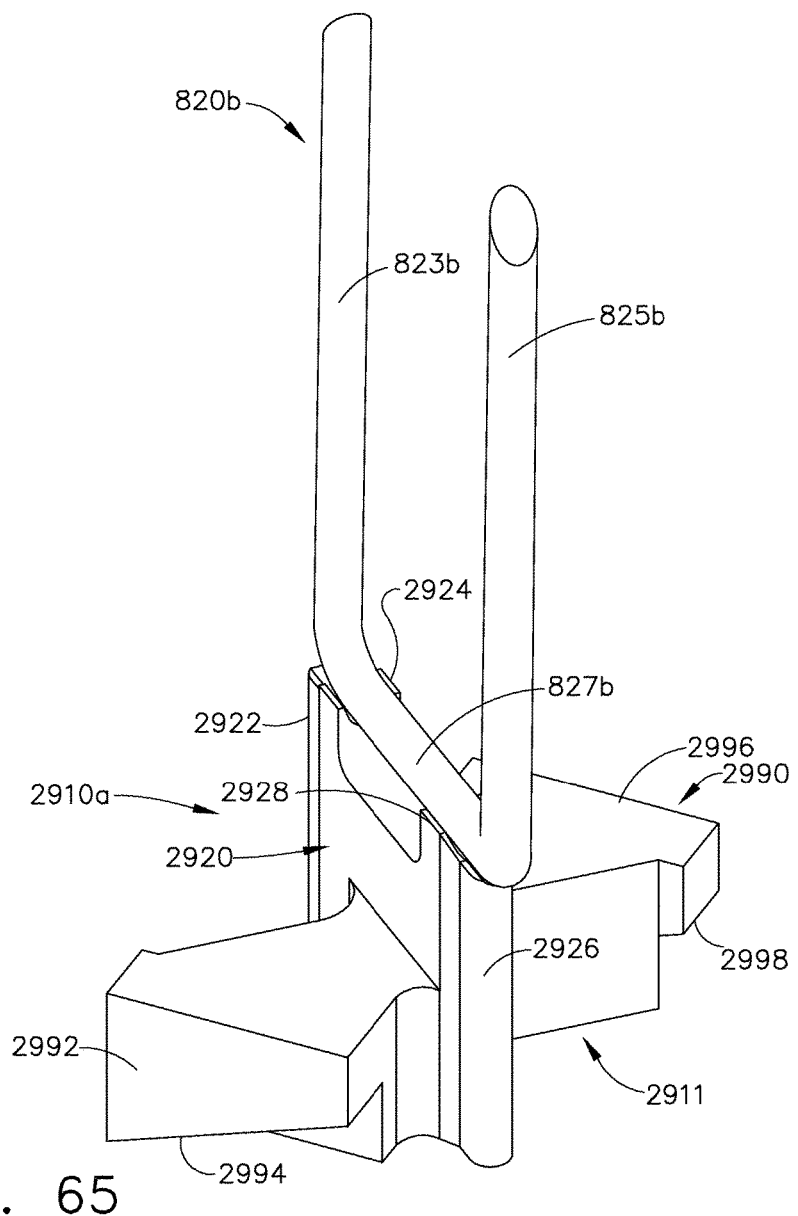
FIG. 65 is a perspective view of the driver of FIG. 64 supporting a staple thereon.

FIGS. 64-66 illustrate one exemplary form of a staple driver 2910*a* with it being understood that, in at least one arrangement, a distal staple driver 2910*b* essentially contains the same features as a distal staple driver 2910*a* and may be a mirror image thereof. Each staple driver 2910*a*, 2910*b* comprises a staple driver body 2911. In the illustrated arrangement, the driver body 2911 includes a first staple support portion 2920 that is configured to support a staple 820*b* thereon. As can be seen in FIG. 64, the first staple support portion 2920 comprises a first distal support column 2922 and a first proximal support column 2926. The first staple support portion 2920 further includes a first distal support cradle 2924 and a first proximal support cradle 2928 for supporting portions of the staple crown 827*b* of a staple 820*b*. As can be seen in FIG. 65, when the staple crown 827*b* of the staple 820*b* is supported on the support cradles 2924 and 2928, the distal leg 823*b* is essentially axially aligned with the first distal support column 2922 and the first proximal leg 825*b* is essentially axially aligned with the first proximal support column 2926. When the staple 820*b* is supported on the first staple support portion 2920, the staple crown 827*b* is aligned on a primary base axis PBA that is transverse to the first and second base axes of the drivers 2610*a*.

In the illustrated embodiment, the staple driver 2910*a* further comprises a connector portion 2990 that is configured to slidably interface with first and second driver guides 3000, 3100 that are formed in the staple cartridge. Referring to FIG. 63, a first driver guide 3000 includes a first hook-shaped portion 3002 that has a slot 3004 therein that is configured to slidably engage a support column 2652 of a corresponding staple driver 2610*a*. In addition, the first driver guide 3000 includes a second hook shaped portion 3006 that has a slot 3008 that is configured to slidably engage a support column 2926 of a corresponding staple driver 2910*a*. The second driver guide 3100 essentially comprises an inverted driver guide 3000. As can be seen in FIG. 63, the second driver guide 3100 includes a first hook shaped portion 3102 that has a slot 3104 that is configured to slidably engage a support column 2926 of a corresponding driver 2910*a*. The second driver guide 3100 further has a second hook shaped portion 3106 that has a slot 3108 that is configured to slidably engage the support column 2922 of the corresponding driver 2910*a*. As can also be seen in FIGS. 64-66, the connector portion 2990 includes a first cam portion 2992 that has a first camming surface or ramp 2994 formed thereon. The connector portion 2990 also includes a second cam portion 2996 that has a second a second camming surface 2998 formed thereon. In at least one arrangement, the camming surfaces 2994, 2998 have the same slope or angle as the corresponding camming surfaces on the drivers 2610*a*. In at least one embodiment, each staple driver 2910*a*, is integrally formed from or molded from, for example, Ultem®, with no fill. However, other materials such as, for example, Ultem® with a glass or mineral fill or Nylon or Nylon with a glass file could be used. In other arrangements, the various portions of the staple drivers 2910*a*, 2910*b* may be separately fabricated from other materials and be attached together by adhesive, solder, etc.

Referring again to FIG. 62, it can be seen that in the staple driver array 2800*a* in the illustrated arrangement, the cam portion 2692 of each of the staple drivers 2610*a* and the cam portion 2992 of each of the drivers 2910*a* are all axially aligned along a first cam axis FCA. Thus the camming surface 2694 of each of the drivers 2610*a* and the camming surface 2994 of each of the drivers 2910*a* are axially aligned along the first cam axis FCA. The cam portion 2696 of each of the drivers 2610*a* and the cam portion 2996 of each of the drivers 2910*a* are all aligned along a second cam axis SCA. Thus, in at least one embodiment, the camming surface 2698 of each of the drivers 2610*a* and the camming surface 2998 of each of the drivers 2910*a* are axially aligned on the second cam axis SCA. Also in the illustrated staple driver array 2800*b*, the cam portion 2692 of each of the drivers 2610*b* and the cam portion 2992 of each of the drivers 2910*b* are aligned along a primary cam axis PCA. Thus, the camming surface 2694 of each of the drivers 2610*b* and the camming surface 2994 of each of the drivers 2910*b* are axially aligned along the primary cam axis PCA. Still referring to FIG. 62, in the staple driver array 2800*b* of the illustrated arrangement, the cam portion 2696 of each of the drivers 2610*b* and the cam portion 2996 of each of the drivers 2910*b* are all aligned along a secondary cam axis SDCA. Thus, in at least one embodiment, the camming surface 2698 of each of the drivers 2610*b* and the camming surface 2998 of each of the drivers 2910*b* are axially aligned on the secondary cam axis SDCA.

As can be appreciated from reference to FIG. 62, when the drivers 2610*a* and 2910*a* are all operably supported in the staple cartridge in the staple driver array 2800*a*, the staple drivers 2610*a* form a first longitudinal row 3050*a* of staples 820*a* that is adjacent to elongate slot 804 in the cartridge body 802. Each of the staples 820*a* in the first longitudinal row 3050*a* extend in a first direction as was described above. Likewise, the drivers 2910*a* form a second longitudinal row 3060*a* of staples 820*b* that are adjacent the first longitudinal row 3050*a*. The staples 820*b* in the second longitudinal row 3060*a* extend in a second direction that is different from the first direction of the staples 820*a* in the first longitudinal row 3050*a*. In addition, the drivers 2610*a* form a third longitudinal row 3070*a* of staples 820*c* that are oriented in a third direction which may or may not be in the same direction as staples 820*a*. For example, in the illustrated embodiment, the first and third directions are the same. The third longitudinal row 3070*a* is adjacent to the second longitudinal row 3060*a*.

Still referring to FIG. 62, when the staple drivers 2610*b* and 2910*b* are all operably supported in the staple cartridge in the staple driver array 2800*b*, the staple drivers 2610*b* form a primary longitudinal row 3050*b* of staples 820*a* that is adjacent to elongate slot 804 in the cartridge body 802. Each of the staples 820*a* in the primary longitudinal row 3050*b* extend in a first direction as was described above. Likewise, the staple drivers 2910*b* form a secondary longitudinal row 3060*b* of staples 820*b* that are adjacent the primary longitudinal row 3050*b*. The staples 820*b* in the secondary longitudinal row 3060*b* extend in a second direction that is different from the first direction of the staples 820*a* in the primary longitudinal row 3050*b*. In addition, the staple drivers 2610*b* form a tertiary longitudinal row 3070*b* of staples 820*c* that are oriented in a third direction which may or may not be in the same direction as staples 820*a*. For example, in the illustrated embodiment, the first and third directions are the same. The tertiary longitudinal row 3070*b* is adjacent to the secondary longitudinal row 3060*b*.

Thus, when employing the staple driver arrays 2800a, 2800b, there are two staples extending side by side in the same direction or along parallel axes along both ends of each of the staple lines. In particular, the distal driver 2610a supports two distal most staples in the longitudinal rows 3050a, 3070a that each extend in the same direction. Similarly, the proximal most driver 2610a supports two proximal most staples in the longitudinal rows 3050a and 3070a of staples that extend in the same direction. Such staple pattern may provide a redundant seal arrangement at both ends of each line of staples.

Other staple driver arrays 3100a, 3100b are illustrated in FIGS. 67 and 68. As can be seen in those Figures, the staple driver array 3100a employs a plurality of staple drivers 3210a, 3310a, 3410a that each support a single staple thereon. Likewise, staple driver array 3100b includes a plurality of staple drivers 3210b, 3310b, 3410b. Staple drivers 3210a may be mirror images of staple drivers 3210b and include the same features. Staple drivers 3310a may be mirror images of staple drivers 3310b and include the same features. Staple drivers 3410a may be mirror images of staple drivers 3410b and include the same features.

Figure 69:
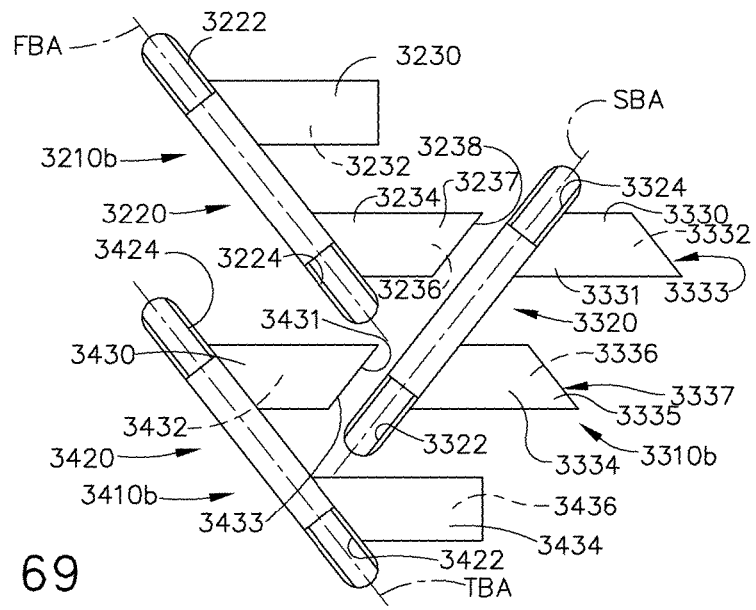
FIG. 69 is a top view of first, second and third staple driver embodiments of the staple driver arrays of FIGS. 67 and 68.

As can be seen in FIG. 69, a first driver 3210b includes a first staple supporting portion 3220 that has a distal cradle 3222 and a proximal cradle 3224 formed therein. The first staple supporting portion 3220 is configured to operably support a first staple (not shown) therein. When the first staple is supported in the first staple supporting portion 3220, the staple crown of the first staple is supported along a first base axis FBA. Also in the illustrated arrangement, a second driver 3310b includes a second staple supporting portion 3320 that has a distal cradle 3322 and a proximal cradle 3324 formed therein. The second staple supporting portion 3320 is configured to operably support a second staple (not shown) thereon. When the second staple is supported in the second staple supporting portion 3320, the staple crown of the second staple is supported along a second base axis SBA that is transverse to the first base axis FBA. The illustrated staple driver array 3100b also includes a third staple driver 3410b that has a third staple supporting portion 3420. The third staple supporting portion 3420 includes a proximal cradle 3422 and a distal cradle 3424 formed therein and is configured to operably support a third staple (not shown) thereon. When the third staple is supported on the third staple supporting portion 3420, the crown of the third staple is supported along a third base axis TBA that is parallel to the first base axis FBA and transverse to the second base axis SBA.

Figure 70:
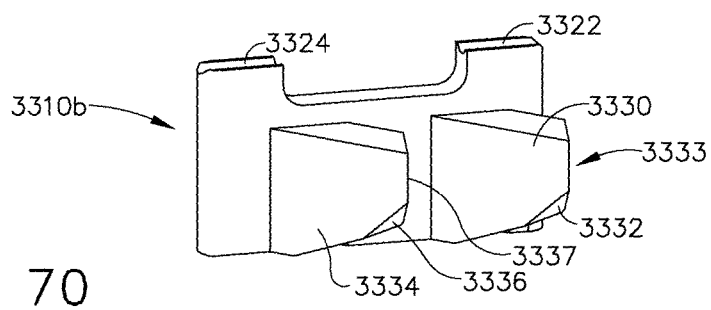
FIG. 70 is a perspective view of one of the staple drivers of FIG. 69.
Figure 71:
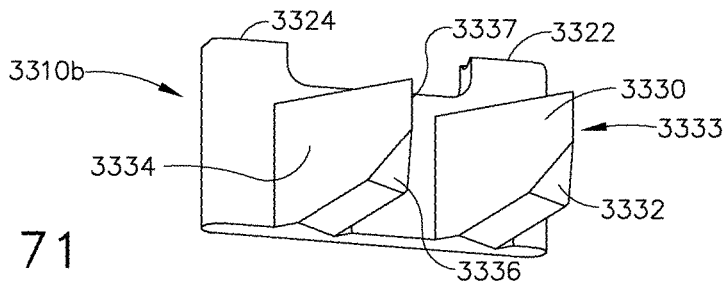
FIG. 71 is a bottom perspective view of the driver of FIG. 70.

Still referring to FIG. 69, each of the drivers 3210b, 3310b, 3410b has a pair of cam portions protruding therefrom that each have a cam or ramp surface formed thereon. For example, a first driver 3210b includes a first cam portion 3230 that has a ramp or camming surface 3232 formed thereon and a second cam portion 3234 that has a ramp or camming surface 3236 formed thereon. To provide clearance for the adjacent proximal second driver 3310b, the proximal end 3237 of the second cam portion 3234 has an angle 3238 formed thereon as shown in FIG. 69. A second driver 3310b includes a first cam portion 3330 that has a ramp or camming surface 3332 formed thereon and a second cam portion 3334 that has a ramp or camming surface 3336 formed thereon. To provide clearance for the adjacent proximal first driver 3210b and adjacent proximal third driver 3410b, the proximal end of 3331 of the first cam portion 3330 has a first angle 3333 formed thereon and the proximal end 3335 of the second cam portion 3334 has an angle 3337 formed thereon as shown in FIG. 69. A third driver 3410b includes a first cam portion 3430 that has a ramp or camming surface 3432 formed thereon and a second cam portion 3434 that has a ramp or camming surface 3436 formed thereon. To provide clearance for the adjacent proximal second driver 3310b, the proximal end 3431 of the first cam portion 3430 has an angle 3433 formed thereon. FIGS. 70 and 71 illustrate a second driver 3310b to show the ramps or camming surfaces 3332, 3336 with it being understood that the first and third drivers 3210a, 3410a are similarly constructed.

In the illustrated embodiment, each of the drivers 3210b, 3310b, 3410b has two cam portions with ramps or camming surfaces that are parallel to each other. Thus, each of the drivers 3210b, 3310b, 3410b is actuated by two ramps or camming members on the sled or cam actuator. In this embodiment, however, the sled or cam actuator is formed with a total of eight ramps (four on each side of the elongate slot 804). The camming surfaces on each of the drivers 3210b, 3310b, 3410b are configured at an angle that cooperates with the angle of the corresponding sled ramp or camming member to drive the respective driver upward within the staple cartridge as the sled or cam actuator is driven distally through the staple cartridge.

Figure 72:
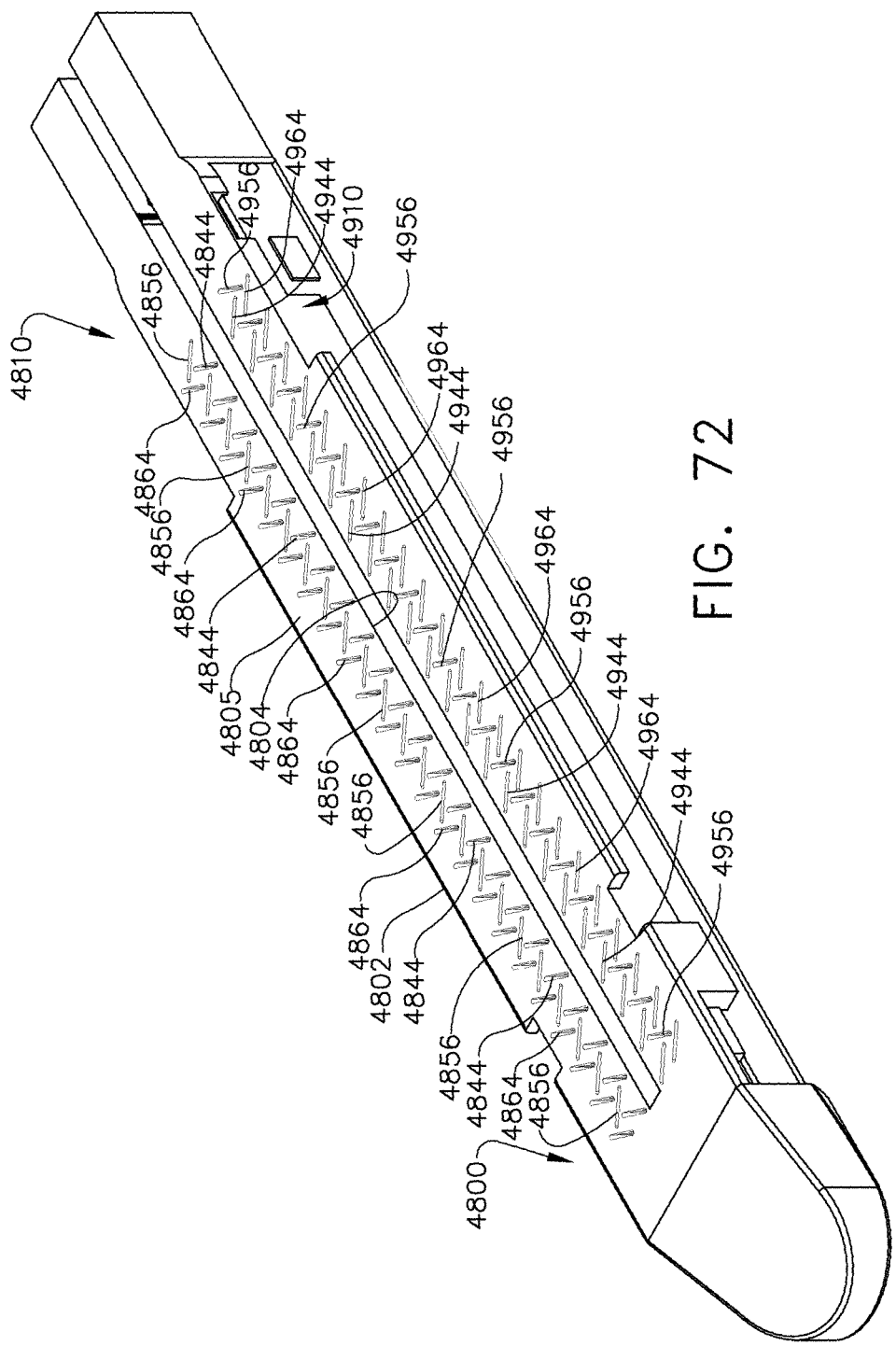
FIG. 72 is a perspective view of a surgical staple cartridge that employs the staple driver arrays of FIGS. 67 and 68.
Figure 73:
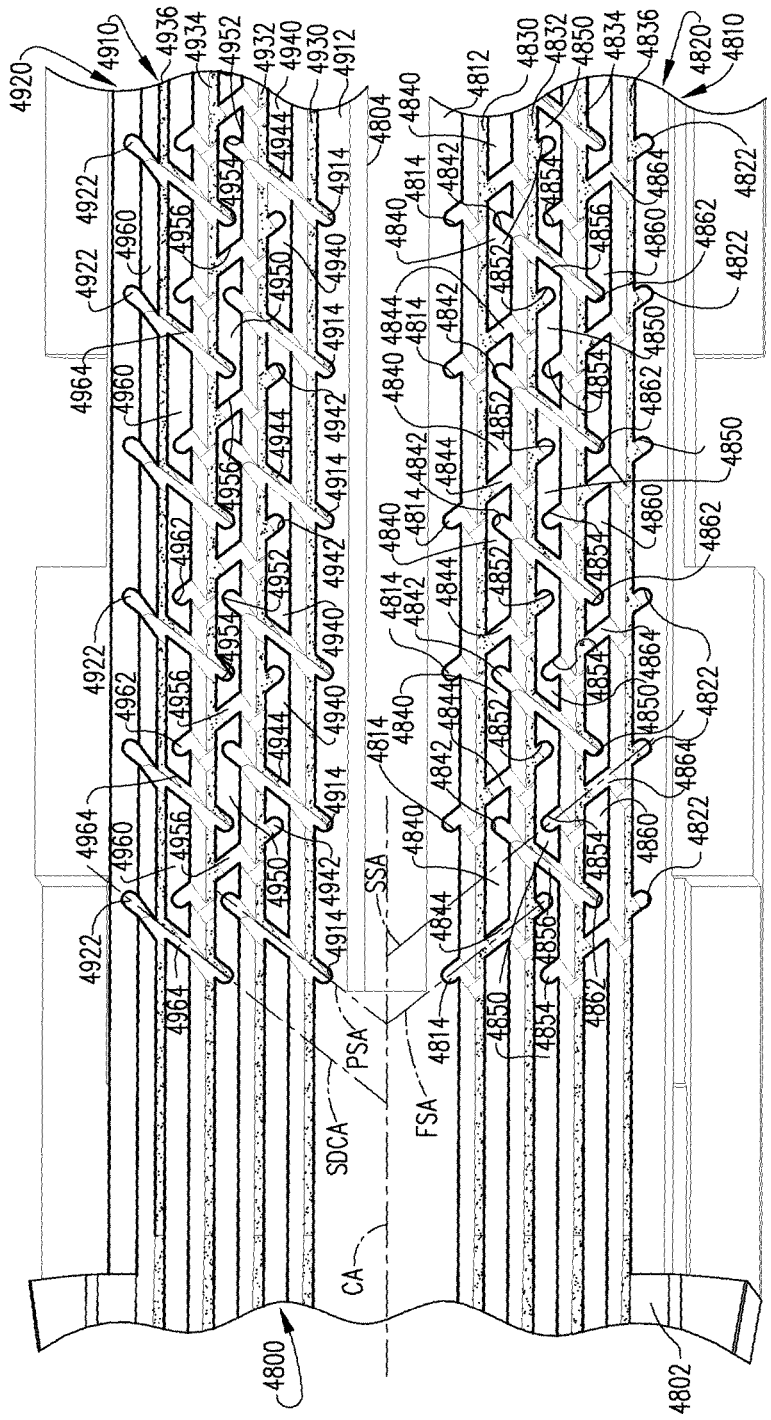
FIG. 73 is a partial bottom perspective view of the surgical staple cartridge of FIG. 72.

FIG. 72 illustrates an exemplary staple cartridge 4800 that has a cartridge body 4802 that includes an elongate slot 4804 for accommodating the tissue cutting member in the manner described herein. The elongate slot 4804 is centrally disposed along the cartridge axis CA and s bifurcates the cartridge body 4802 into two body portions 4810 and 4910. FIG. 73 illustrates a bottom perspective view of a portion of one form of the surgical staple cartridge body 802'. As can be seen in that Figure, the first body portion 4810 includes a first cartridge wall portion 4812 that includes first support grooves or slots 4814 therein that are each oriented on a corresponding first slot axis FSA that is transverse to the cartridge axis CA. The second body portion 4810 further includes a second cartridge wall portion 4820 that contains second support grooves or slots 4822 therein that are each oriented on a corresponding second slot axis SSA that is transverse to the cartridge axis CA. Located between the first cartridge wall portion 4812 and the second cartridge wall portion 4820 are four spaced slots 4830, 4832, 4834, 4836 for receiving corresponding ramps or camming members of the sled or cam actuator. Slots 4830 and 4832 define a plurality of segmented guide rails 4840 that each has a slot 4842 therein. Likewise, slots 4832 and 4834 define another plurality of segmented guide rails 4850 that each has two slots 4852 and 4854 therein. In addition, slots 4834 and 4836 define another plurality of segment guide rails 4860 that each has a slot 4862 therein.

Still referring to FIG. 73, the segmented guide rails 4840 are segmented by slots 4844 that are oriented to accommodate a staple supporting portion 3220 of a corresponding first staple driver 3210a. In addition, the ends of the staple supporting portion 3220 are received in corresponding slots 4814 and 4852 so that each of the first drivers 3210a is completely slidably supported in the cartridge body 4802 through its range of upward travel therein. Similarly, the segmented guide rails 4850 are segmented by second slots 4856 that are oriented to accommodate a staple supporting portion 3320 of a corresponding second staple driver 3310a. In addition, the ends of the staple supporting portion 3320 are received in corresponding slots 4842 and 4862 so that each of the second staple drivers 3310a is completely slidably supported in the cartridge body 4802 through its range of upward travel therein. Further, the segmented guide rails 4860 are segmented by third slots 4864 that are oriented to accommodate a staple supporting portion 3420 of a corresponding second staple driver 3410a. In addition, the ends of the staple supporting portion 3420 are received in corresponding slots 4822 and 4854 so that each of the third staple drivers 3410a is completely slidably supported in the cartridge body 4802 through its range of upward travel therein. It will be appreciated that the slots 4844, 4856 and 4864 extend through a deck surface 4805 of the cartridge body 4802 to enable the staples to exit the cartridge body 4802. The slots 4844, 4856, 4864 may also be referred to as "staple cavities". See FIG. 72.

Likewise, the second body portion 4910 includes a first cartridge wall portion 4912 that includes first support grooves or slots 4914 therein that each lie along a corresponding primary slot axis PSA that is transverse to the cartridge axis CA. The second body portion 4910 further includes a second cartridge wall portion 4920 that contains second support grooves or slots 4922 therein that each lie along a corresponding secondary slot axis SDSA that is transverse to the cartridge axis CA. Located between the first cartridge wall portion 4912 and the second cartridge wall portion 4920 are four spaced slots 4930, 4932, 4934, 4936 for receiving corresponding ramps or camming members of the sled or cam actuator. Slots 4930 and 4932 define a plurality of segmented guide rails 4940 that each has a slot 4942 therein. Likewise, slots 4932 and 4934 define another plurality of segmented guide rails 4950 that each has two slots 4952 and 4954 therein. In addition, slots 4934 and 4936 define another plurality of segment guide rails 4960 that each has a slot 4962 therein.

Still referring to FIG. 73, the segmented guide rails 4940 are segmented by slots 4944 that are oriented to accommodate a staple supporting portion 3220 of a corresponding first staple driver 3210b. In addition, the ends of the staple supporting portion 3220 are received in corresponding slots 4914 and 4952 so that each of the first drivers 3210b is completely slidably supported in the cartridge body 4802 through its range of upward travel therein. Similarly, the segmented guide rails 4950 are segmented by second slots 4956 that are oriented to accommodate a staple supporting portion 3320 of a corresponding second staple driver 3310b. In addition, the ends of the staple supporting portion 3320 are received in corresponding slots 4942 and 4962 so that each of the second staple drivers 3310b is completely slidably supported in the cartridge body 4802 through its range of upward travel therein. Further, the segmented guide rails 4960 are segmented by third slots 4964 that are oriented to accommodate a staple supporting portion 3420 of a corresponding second staple driver 3410b. In addition, the ends of the staple supporting portion 3420 are received in corresponding slots 4922 and 4954 so that each of the third staple drivers 3410b is completely slidably supported in the cartridge body 4802 through its range of upward travel therein. It will be appreciated that the slots 4944, 4956 and 4964 extend through the deck surface 4805 of the cartridge body 4802 to enable the staples to exit the cartridge body 4802. The slots 4944, 4956, 4964 may also be referred to as "staple cavities". See FIG. 72.

In the illustrated arrangement, when the drivers 3210a, 3310a, 3410a are installed in the cartridge body 4802 to form the staple driver array 3100a, the cam portion 3230 of each of the first drivers 3210a are axially aligned on a first cam axis FCA defined by the first slot 4830. Thus, the camming surfaces 3232 are also axially aligned on the first cam axis FCA for camming contact with a corresponding camming member or ramp on the sled or camming actuator. Likewise, the camming portion 3234 of each first driver 3210a as well as each of the camming portions 3330 of the second drivers 3310a are axially aligned on a second cam axis SCA defined by the slot 4832. Thus, the camming surfaces 3236 and 3332 are also axially aligned on the second cam axis SCA for camming contact with a corresponding camming member or ramp on the sled or camming actuator. In addition, the camming portion 3430 of each third driver 3410a as well as each of the camming portions 3334 of each of the second drivers 3310a are axially aligned on a third cam axis TCA defined by the slot 4834. Thus, the camming surfaces 3432 and 3336 are also axially aligned on the third cam axis TCA for camming contact with a corresponding camming member or ramp on the sled or camming actuator. Also, the camming portion 3434 of each third driver 3410a is axially aligned on a fourth axis FTCA defined by the slot 4836. Thus, the camming surfaces 3436 are also axially aligned on the fourth cam axis FTCA for camming contact with a corresponding camming member or ramp on the sled or camming actuator.

Also in the illustrated staple driver array 3100b, the cam portion 3230 of each of the first drivers 3210b are axially aligned on a primary cam axis PCA defined by the first slot 4930. Thus, the camming surfaces 3232 are also axially aligned on the first cam axis PCA for camming contact with a corresponding camming member or ramp on the sled or camming actuator. Likewise, the camming portion 3234 of each first driver 3210b as well as each of the camming portions 3330 of the second drivers 3310b are axially aligned on a secondary cam axis SDCA defined by the slot 4932. Thus, the camming surfaces 3236 and 3332 are also axially aligned on the secondary cam axis SDCA for camming contact with a corresponding camming member or ramp on the sled or camming actuator. In addition, the camming portion 3430 of each third driver 3410b as well as each of the camming portions 3334 of each of the second drivers 3310b are axially aligned on a tertiary cam axis TRCA defined by the slot 4934. Thus, the camming surfaces 3432 and 3336 are also axially aligned on the tertiary cam axis TRCA for camming contact with a corresponding camming member or ramp on the sled or camming actuator. Also, the camming portion 3434 of each third driver 3410a is axially aligned on another fourth axis FRCA defined by the slot 4936. Thus, the camming surfaces 3436 are also axially aligned on the another fourth cam axis FRCA for camming contact with a corresponding camming member or ramp on the sled or camming actuator.

In at least one arrangement, the camming surfaces 3232, 3236, 3332, 3336, 3432, 3436 may be formed with identical slopes or angles or they may have different slopes. However, in the illustrated arrangement, for example, the camming surfaces 3232 are oriented or otherwise configured to operably match the angle/orientation of the camming member or ramp of the sled or camming actuator. Also in the illustrated arrangement, the camming surfaces 3236 and 3332 are formed with the same slope or angle and/or are otherwise configured to operably match the angle/orientation of the corresponding camming member or ramp of the sled or camming actuator. However, it is conceivable that the angle or slope of the camming surfaces 3236, 3332 are not the same as the angle or slope of the camming surfaces 3232. Likewise, the camming surfaces 3432 and 3336 are formed with the same slope or angle and/or are otherwise configured to operably match the angle/orientation of the corresponding camming member or ramp of the sled or camming actuator. However, it is conceivable that the angle or slope of the camming surfaces 3432, 3336 are not the same as the angle or slope of the camming surfaces 3232, 3234, 3332. Also in the illustrated arrangement, the camming surfaces 3436 are formed with the same slope or angle and/or are otherwise configured to operably match the angle/orientation of the corresponding camming member or ramp of the sled or camming actuator. However, it is conceivable that the angle or slope of the camming surfaces 3436 is not the same as the angle or slope of the camming surfaces 3232, 3234, 3332, 3432, 3336.

Still referring to FIG. 67, when the staple drivers 3210a, 3310a, 3410a are all operably supported in the staple cartridge in the staple driver array 3100a, the staple drivers 3210a form a first longitudinal row 5000a of staples that is adjacent to elongate slot 804 in the cartridge body 4802. Each of the staples in the first longitudinal row 5000a extend in a first direction as was described above. Likewise, the staple drivers 3310a form a second longitudinal row 5010a of staples that are adjacent the first longitudinal row 5000a. The staples in the second longitudinal row 5010a extend in a second direction that is different from the first direction of the staples in the first longitudinal row 5000a. In addition, the staple drivers 3410a form a third longitudinal row 5020a of staples that are oriented in a third direction which may or may not be in the same direction as the staples in the second longitudinal row 5010a. For example, in the illustrated embodiment, the first and third directions are the same. The third longitudinal row 5020a is adjacent to the second longitudinal row 5010a.

In the illustrated arrangement, when the staple drivers 3210b, 3310b, 3410b are all operably supported in the staple cartridge in the staple driver array 3100b, the staple drivers 3210b form a primary longitudinal row 5000b of staples that is adjacent to elongate slot 804 in the cartridge body 4802. Each of the staples in the primary longitudinal row 5000b extend in a first direction as was described above. Likewise, the staple drivers 3310b form a secondary longitudinal row 5010b of staples that are adjacent the primary longitudinal row 5000b. The staples in the secondary longitudinal row 5010b extend in a second direction that is different from the first direction of the staples in the primary longitudinal row 5000b. In addition, the staple drivers 3410b form a tertiary longitudinal row 5020b of staples that are oriented in a third direction which may or may not be in the same direction as staples in the secondary longitudinal row 5010b. For example, in the illustrated embodiment, the first and third directions are the same. The tertiary longitudinal row 5020b is adjacent to the secondary longitudinal row 5010b.

Figure 74:
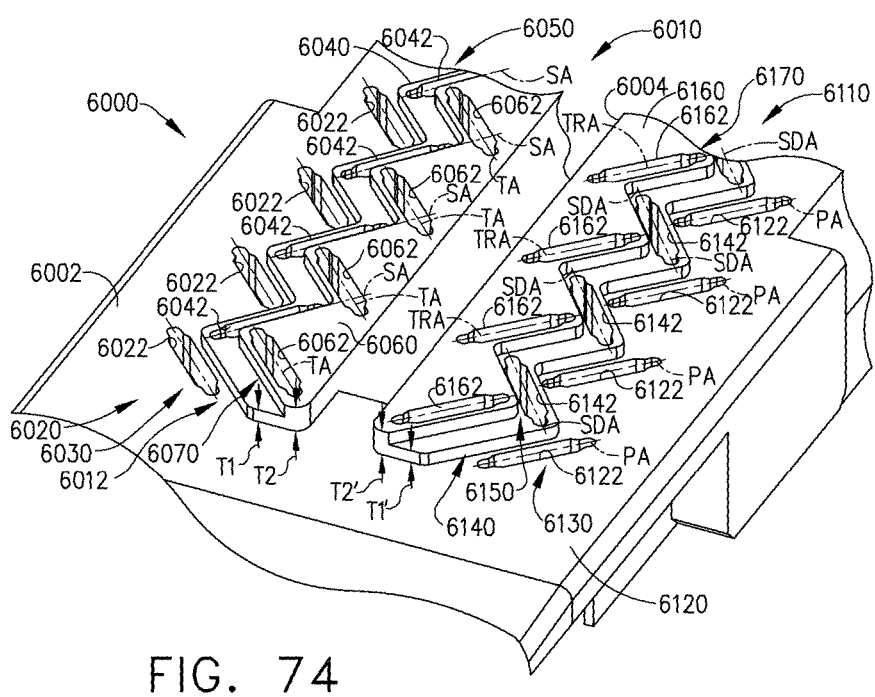
FIG. 74 is a perspective view of a portion of another surgical staple cartridge embodiment.

FIG. 74 illustrates a portion of another surgical staple cartridge 6000 that is configured to achieve lines of staples that each have different formed heights and that may employ various staple driver array arrangements disclosed herein. The surgical staple cartridge 6000 includes a cartridge body 6002 that has an elongate slot 6004 that divides the cartridge body into a first cartridge portion 6010 and a second cartridge portion 6110. The first cartridge portion 6010 includes a "stepped deck" 6012. In the illustrated example, the lowest deck surface or "first" deck portion is designated as 6020. A series of slots or first staple pockets 6022 that are configured to support a first longitudinal line 6030 of first surgical staples 7000 are provided in the first deck portion 6020. In the illustrated embodiment, the first staple pockets 6022 in the line 6030 are parallel to each other and are each oriented on a corresponding first axis FA.

As can be further seen in FIG. 74, the stepped deck 6012 further includes a second deck portion 6040 that has a height or thickness "T1". Stated another way, the second deck portion 6040 extends above the first deck portion 6020 the thickness T1. In one example, T1 may be approximately 0.01 inches. However, other thicknesses or height differences may be employed. For example, T1 may range from 0.005 inches-0.025 inches. A second series of slots or second staple pockets 6042 are oriented in the second deck portion 6040 to support a second line 6050 of second staples 7020 therein. The second staple pockets 6042 are parallel to each other and are each aligned on a second axis SA. The second axes may be transverse to the first axes FA.

Still referring to FIG. 74, the first stepped deck 6012 further includes a third deck portion 6060 that has a height or thickness "T2". Stated another way, the third deck portion 6060 extends above the first deck portion 6020 the thickness T2. In one example, T2 may be approximately 0.02 inches. However, other thicknesses or height differences may be employed. For example, T1 may range from 0.005 inches-0.030 inches. A third series of slots or second staple pockets 6062 are oriented in the third deck portion 6060 to support a third line 6070 of third staples 7020 therein. The third staple pockets 6062 are parallel to each other and are each aligned on a third axis TA. The third axes may be parallel to the first axes FA and transverse to the second axes SA, for example.

Figure 75:
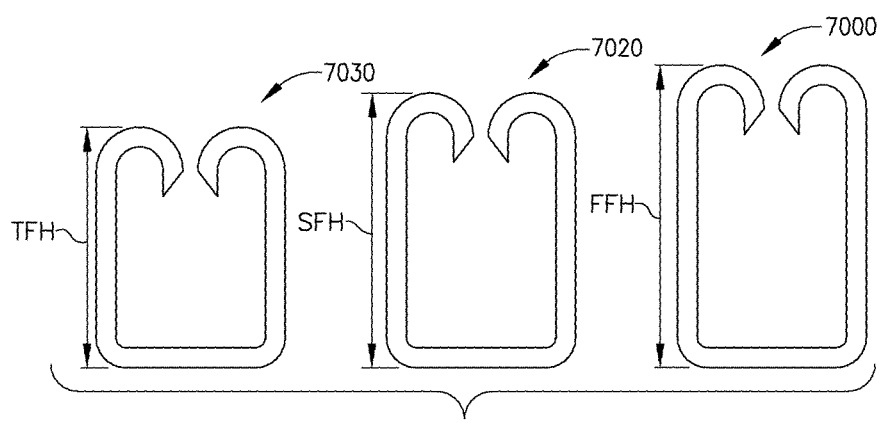
FIG. 75 is a view of three formed surgical staples that were formed using the surgical staple cartridge of FIG. 74.

In use, when the anvil of the surgical instrument is locked in a closed position wherein the staple forming undersurface of the anvil is positioned in confronting relationship with the deck of the staple cartridge 6000, the third deck portion 6070 will be closer to the undersurface of the anvil than the second deck portion 6040 and the first deck portion 6020. Likewise, the second deck portion 6040 is closer to the staple forming undersurface of the anvil than the first deck portion 6020. Thus, as illustrated in FIG. 75, the third staples 7030 supported in the third staple pockets 6062 will have a third forming height "TFH" that is less than the second forming height "SFH" of the second staples 7020 supported in the second staple pockets 6042 and second forming height SFH of the second staples 7020 is less than the first forming height "FFH" of the staples supported in the first staple pockets 6022. As shown in FIG. 74, the line 6070 of third staples 7030 may be adjacent to the elongate slot 6004. Thus, the staples 7030 that are the closest to the cut line in the tissue will have the shortest formed height.

The second cartridge portion 6110 includes a primary deck portion 6120 that is the lowest deck surface. A series of slots or primary staple pockets 6122 that are configured to support a primary longitudinal line 6130 of first surgical staples 7000 are provided in the primary deck portion 6120. In the illustrated embodiment, the primary staple pockets 6122 in the primary line 6130 are parallel to each other and are each oriented on a corresponding primary axis PA. As can be further seen in FIG. 74, the stepped deck 6012 further includes a secondary deck portion 6140 that has a height or thickness "T1'". Stated another way, the secondary deck portion 6140 extends above the primary deck portion 6120 the thickness T1'. In the illustrated arrangement T1' is equal to T1. However, other arrangements are contemplated wherein T1' does not equal T1. A second series of slots or second staple pockets 6142 are oriented in the secondary deck portion 6140 to support a secondary line 6150 of second staples 7020 therein. The secondary staple pockets 6142 are parallel to each other and are each aligned on a secondary axis SDA. The secondary axes SDA may be transverse to the primary axes PA.

Still referring to FIG. 74, the stepped deck 6012 further includes a tertiary deck portion 6160 that has a height or thickness "T2'". Stated another way, the tertiary deck portion 6160 extends above the primary deck portion 6120 the thickness T2'. In the illustrated arrangement, T2' is equal to T2. However, other arrangements are contemplated wherein T2' does not equal T2. A tertiary series of slots or tertiary staple pockets 6162 are oriented in the tertiary deck portion 6160 to support a tertiary line 6170 of third staples 7030 therein. The tertiary staple pockets 6162 are parallel to each other and are each aligned on a tertiary axis TRA. The tertiary axes TRA may be parallel to the primary axes PA and transverse to the secondary axes SDA, for example.

In use, when the anvil of the surgical instrument is locked in a closed position wherein the staple forming undersurface of the anvil is positioned in confronting relationship with the deck of the staple cartridge 6000, the tertiary deck portion 6160 will be closer to the undersurface than the second deck portion 6040 and the first deck portion 6020. Likewise, the secondary deck portion 6140 is closer to the staple forming undersurface of the anvil than the primary deck portion 6120. Thus, as illustrated in FIG. 75, the third staples 7030 supported in the third staple pockets 6062 will have a third forming height "TFH" that is less than the second forming height "SFH" of the second staples 7020 supported in the secondary staple pockets 6142 and second forming height SFH of the second staples 7020 is less than the first forming height "FFH" of the staples supported in the primary staple pockets 6122. As shown in FIG. 74, the line 6170 of third staples 7030 may be adjacent to the elongate slot 6004. Thus, the staples 7030 that are the closest to the cut line in the tissue will have the shortest formed height.

Various staple driver arrangements disclosed herein may be effectively employed with the above-described stepped deck arrangement to achieve staples having different formed heights. All of the various driver combinations and stepped deck configurations are contemplated herein. The various staples employed may start with different unformed heights. For example, all of the staples in one line of staples may have the same height, but have a different height than all of the staples in another line or other lines of staples in the cartridge. The staples may be U-shaped or be V-shaped. The staples may have different wire diameters. Further details regarding staple configurations, cartridge and driver arrangements for forming staples with different formed heights are disclosed in U.S. Pat. No. 7,669,746, entitled STAPLE CARTRIDGES FOR FORMING STAPLES HAVING DIFFERENT FORMED HEIGHTS; U.S. Pat. No. 7,500,979, entitled SURGICAL STAPLING DEVICE WITH MULTIPLE STACKED ACTUATOR WEDGE CAMS FOR DRIVING STAPLE DRIVERS; U.S. Pat. No. 7,673,781, entitled SURGICAL STAPLING DEVICE WITH STAPLE DRIVER THAT SUPPORTS MULTIPLE WIRE DIAMETER STAPLES; U.S. Pat. No. 8,636,187, entitled SURGICAL STAPLING SYSTEMS THAT PRODUCE FORMED STAPLES HAVING DIFFERENT LENGTHS; U.S. Pat. No. 7,934,630, entitled STAPLE CARTRIDGES FOR FORMING STAPLES HAVING DIFFERENT FORMED HEIGHTS; U.S. Pat. No. 8,567,656, entitled STAPLE CARTRIDGES FOR FORMING STAPLES HAVING DIFFERENT FORMED HEIGHTS; U.S. Pat. No. 8,464,923, entitled STAPLE CARTRIDGES FOR FORMING STAPLES HAVING DIFFERENT FORMED HEIGHTS, the entire disclosures of each being hereby incorporated by reference herein.

As the present Detailed Description proceeds, it will be understood that the various forms of surgical staple cartridges disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the elongate shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, which is hereby incorporated by reference herein in its entirety.

The surgical instrument systems described herein are motivated by an electric motor; however, the surgical instrument systems described herein can be motivated in any suitable manner. In various instances, the surgical instrument systems described herein can be motivated by a manually-operated trigger, for example. The motor or motor(s) may comprise a portion or portions of a robotically controlled system.

The surgical instrument systems described herein are motivated by one or more electric motors; however, the surgical instrument systems described herein can be motivated in any suitable manner. In various instances, the surgical instrument systems described herein can be motivated by a manually-operated trigger, for example.

EXAMPLES

Example 1

A surgical staple driver array for operable use with a surgical staple cartridge. In at least one configuration, the surgical staple driver array comprises a distal staple driver that is slidably supportable in the surgical staple cartridge and is configured to operably support a single distal surgical staple thereon that is oriented in a distal direction. A plurality of intermediate staple drivers is configured to be slidably supported in the surgical staple cartridge in series, wherein a distal most one of the intermediate staple drivers is adjacent to the distal staple driver. Each of the intermediate staple drivers is configured to operably support a first surgical staple that is oriented in a first direction as well as a second surgical staple that is oriented in a second direction and a third surgical staple that is oriented in a third direction. A proximal staple driver is slidably supported adjacent a proximal most one of the intermediate staple drivers. The proximal staple driver is configured to operably support a proximal surgical staple that is oriented in a proximal direction.

Example 2

The surgical staple driver array of Example 1, wherein the distal direction is parallel to at least one of the first, second and third directions.

Example 3

The surgical staple driver array of Examples 1 or 2, wherein the proximal direction is parallel to at least one of the first, second and third directions.

Example 4

The surgical staple driver array of Examples 1, 2 or 3, wherein the distal direction, the first direction, the third direction and the proximal direction are parallel to each other.

Example 5

The surgical staple driver array of Examples 1, 2, 3 or 4, wherein a distal crown of the distal surgical staple is supported along a distal base axis and a first crown of the first surgical staple is supported along a first base axis that is parallel to the distal base axis.

Example 6

The surgical staple driver array of Example 5, wherein a second staple crown of the second surgical staple is supported along a second base axis that is transverse to the first base axis.

Example 7

The surgical staple driver array of Examples 5 or 6, wherein a third staple crown of the third surgical staple is supported along a third base axis that is parallel to the first base axis.

Example 8

The surgical staple driver array of Example 7, wherein a proximal staple crown of the proximal surgical staple is supported along a proximal base axis that is parallel to the third base axis of the third surgical staple supported in the proximal most one of the intermediate staple drivers.

Example 9

A surgical staple cartridge that comprises a cartridge body that comprises a proximal end and a distal end. A distal staple driver is movably supported in the cartridge body and is configured to support a single, distal most surgical staple thereon that is oriented in a distal direction. A plurality of intermediate staple drivers is movably supported in the cartridge body in series, wherein a distal most one of the intermediate staple drivers is adjacent to the distal staple driver. Each intermediate staple driver supports a first surgical staple in a first direction, a second surgical staple in a second direction and a third surgical staple in a third direction. A proximal staple driver is slidably supported adjacent a proximal most one of the intermediate staple drivers. The proximal staple driver is configured to operably support a proximal surgical staple that is oriented in a proximal direction.

Example 10

The surgical staple cartridge of Example 9, wherein a distal crown of the distal surgical staple is supported along a distal base axis and a first crown of the first surgical staple is supported along a first base axis that is parallel to the distal base axis. A second staple crown of the second surgical staple is supported along a second base axis that is transverse to the first base axis. A third staple crown of the third surgical staple is supported along a third base axis that is parallel to the first base axis. A proximal staple crown of the proximal surgical staple is supported along a proximal base axis that is parallel to the third base axis of the third surgical staple that is supported in the proximal most intermediate staple driver.

Example 11

The surgical staple cartridge of Examples 9 or 10, wherein the distal staple driver comprises a distal staple support member that comprises a distal support column that is configured to support a distal leg of the distal surgical staple thereon. The distal staple support member further comprises a proximal support column that is configured to support a proximal leg of the distal surgical staple thereon. One of the distal and proximal support columns is slidably supported in one of a first wall portion and a second wall portion of the cartridge body.

Example 12

The surgical staple cartridge of Example 11, wherein the distal staple driver further comprises a distal camming surface that is aligned on a first cam axis that extends transversely between the distal and proximal support columns.

Example 13

The surgical staple cartridge of Examples 9, 10, 11 or 12, wherein at least one of the intermediate staple drivers comprises a first staple support member that comprises a first distal support column that is configured to support a first distal leg of a corresponding first surgical staple thereon. The first staple support member further comprises a first proximal support column that is configured to support a first proximal leg of the corresponding first surgical staple thereon. The intermediate staple driver further comprises a second staple support member that comprises a second distal support column that is configured to support a second distal leg of a corresponding second surgical staple thereon. The second staple support member further comprises a second proximal support column that is configured to support a second proximal leg of the corresponding second surgical staple thereon. The intermediate staple driver further comprises a third staple support member that comprises a third distal support column that is configured to support a third distal leg of a corresponding third surgical staple thereon. The third staple support member further comprises a third proximal support column that is configured to support a third proximal leg of the corresponding third surgical staple thereon. One of the third distal support column and the third proximal support column is slidably supported in one of first and second wall portions of the cartridge body.

Example 14

The surgical staple cartridge of Examples 9, 10, 11, 12 or 13, wherein the proximal staple driver comprises a proximal staple support member that comprises another distal support column that is configured to support another distal leg of the proximal surgical staple thereon. The proximal staple support member further comprises another proximal support column that is configured to support another proximal leg of the proximal surgical staple thereon. One of the another distal and the another proximal support columns is slidably supported in one of a first wall portion and a second wall portion of the cartridge body.

Example 15

The surgical staple cartridge of Example 14, further comprising at least one distal camming surface on the distal staple support member and at least one first camming surface on at least one of the first, second and third staple support members. At least one proximal camming surface is on the proximal staple support member.

Example 16

The surgical staple cartridge of Example 15, wherein the at least one distal camming surface, the at least one first camming surface and the at least one proximal camming surface are aligned on a common camming axis.

Example 17

The surgical staple cartridge of Examples 15 or 16, wherein the at least one distal camming surface comprises a first distal camming surface and a second distal camming surface that is spaced from the first distal camming surface. The first camming surface comprises a first camming surface and a second camming surface that is spaced from the first camming surface. At least one proximal camming surface comprises a first proximal camming surface and a second proximal camming surface.

Example 18

The surgical staple cartridge of Example 17, wherein the first distal camming surface, the first camming surface and the first proximal camming surface are aligned on a first camming axis and wherein the second distal camming surface, the second camming surface and the second proximal camming surface are aligned on a second camming axis.

Example 19

The surgical staple cartridge of Example 18, wherein the first camming surface is on the first staple support member and the second camming surface is on the third staple support member.

Example 20

A surgical instrument, comprising an axially movable sled that comprises first and second camming members. The surgical instrument further comprises a surgical staple cartridge and at least one distal staple driver that is movably supported in the surgical staple cartridge. Each distal staple driver is configured to operably support a corresponding distal staple thereon and comprises a first distal camming surface that is aligned for camming contact with the first camming member and a second distal camming surface that is aligned for camming contact with the second camming member. A plurality of intermediate staple drivers is movably supported in the surgical staple cartridge in series. A distal most one of the intermediate staple drivers is adjacent to one of the at least one distal staple drivers. Each of the intermediate staple drivers supports a corresponding first surgical staple, a corresponding second surgical staple and a corresponding third surgical staple thereon. Each intermediate staple driver comprises a first camming surface that is aligned for camming contact with the first camming member and a second camming surface that is aligned for camming contact with the second camming member. A proximal staple driver is slidably supported adjacent a proximal most one of the intermediate staple drivers. The proximal staple driver is configured to operably support a corresponding proximal surgical staple thereon and comprises a first proximal camming surface that is aligned for camming contact with the first camming member and a second proximal camming surface that is aligned for camming contact with the second camming member.

Example 21

A surgical staple driver array for operable use with a surgical staple cartridge. In at least one form, the surgical staple driver array comprises a distal staple driver that is configured to be slidably supported in the surgical staple cartridge. The surgical staple driver array is also configured to operably support at least two distal surgical staples thereon that are each oriented in a distal direction. At least one first intermediate staple driver is configured to be slidably supported in the surgical staple cartridge. The intermediate staple driver operably supports at least two first surgical staples that are each oriented in a first direction and at least two second surgical staples that are each oriented in a second direction that differs from the first direction. At least one second intermediate staple driver is configured to be slidably supported adjacent at least one of the distal staple drivers and a corresponding one of the at least one first intermediate staple drivers. Each of the at least one second intermediate staple drivers is configured to operably support five, second surgical staples thereon wherein at least two of the second surgical staples are each oriented in a primary direction and at least one other of the second surgical staples is oriented in a secondary direction that differs from the primary direction.

Example 22

The surgical staple driver array of Example 21, wherein at least one of the first and second directions is parallel to the distal direction.

Example 23

The surgical staple driver array of Examples 21 or 22, wherein the first and second directions are transverse to each other.

Example 24

The surgical staple driver array of Examples 21, 22 or 23, wherein at least one of the primary and secondary directions is parallel to the distal direction.

Example 25

The surgical staple driver array of Examples 21, 22, 23 or 24, wherein four of the second surgical staples are oriented in the primary direction and one other of the second staples is oriented in the secondary direction.

Example 26

The surgical staple driver array of Examples 21, 22, 23, 24 or 25, wherein one of the distal surgical staples comprises a distal crown that is aligned on a first distal base axis and another of the distal surgical staples comprises another distal crown that is aligned on a second distal base axis that is parallel to the first distal base axis. One of the first surgical staples comprises a first staple crown that is aligned on a first base axis and another one of the first surgical staples comprises another first staple crown that is aligned on another first base axis that is parallel to the first base axis. One of the second surgical staples comprises a second staple crown that is aligned on a second base axis and another of the second surgical staples comprises another second staple crown that is aligned on another second base axis that is parallel to the second base axis.

Example 27

The surgical staple driver array of Example 26, wherein the first and second distal base axes are parallel with the first base axis and the another first base axis and wherein the second base axis and the another second base axis are transverse to the first base axis and the another first base axis.

Example 28

The surgical staple driver array of Examples 21, 22, 23, 24, 25, 26 or 27, wherein the distal staple driver comprises at least one distal camming surface and wherein at least one of the at least one first intermediate staple drivers comprises at least one first camming surface and wherein at least one of the at least one second intermediate staple drivers comprises at least one primary camming surface and wherein the at least one distal camming surface and the at least one first camming surface and the at least one primary camming surface are axially aligned along a first camming axis.

Example 29

The surgical staple driver array of Example 28, wherein the distal staple driver comprises a first distal camming surface and a second distal camming surface that is spaced from the first distal camming surface. Each of the at least one first intermediate staple drivers comprises a first camming surface and a second camming surface that is spaced from the first camming surface. Each of the at least one second intermediate staple drivers comprises a primary camming surface and a secondary camming surface that is spaced from the primary camming surface. The first distal camming surface, each of the first camming surfaces and each of the primary camming surfaces are axially aligned on the first camming axis. The second distal camming surface, each of the second camming surfaces and each of the secondary camming surfaces are axially aligned on a second camming axis.

Example 30

A surgical staple cartridge, comprising a cartridge body that comprises a proximal end and a distal end. A distal staple driver is movably supported in the cartridge body and is configured to support at least two distal surgical staples thereon. Each of the distal surgical staples extends in a distal direction. At least one first intermediate staple driver is movably supported in the cartridge body. Each of the first intermediate staple drivers is configured to support at least two first surgical staples that each extends in a first direction and at least two other first surgical staples that each extend in a second direction. The surgical staple cartridge further comprises at least one second intermediate staple driver that is configured to be slidably supported adjacent to at least one of the distal staple drivers and a corresponding one of the first intermediate staple drivers. Each second intermediate staple driver is configured to operably support five other surgical staples thereon wherein at least two of the other surgical staples are each oriented in a primary direction and at least a third one of the other surgical staples is oriented in a secondary direction that differs from the primary direction.

Example 31

The surgical staple cartridge of Example 30, wherein a first one of the distal surgical staples comprises a first distal crown that is aligned on a first distal base axis and wherein a second one of the distal surgical staples comprises a second distal crown that is aligned on a second distal base axis that is parallel to the first distal base axis. At least one of the first surgical staples comprises a first staple crown that is aligned on a first base axis and wherein at least one other of the first surgical staples comprises another first staple crown that is aligned on another first base axis that is parallel to the first base axis. At least one of the second surgical staples comprises a second staple crown that is aligned on a second base axis and at least one other of the second surgical staples comprises another second staple crown that is aligned on another second base axis that is parallel to the second base axis.

Example 32

The surgical staple cartridge of Examples 30 or 31, wherein the distal staple driver comprises a distal staple support member that comprises a distal support column that is configured to support a distal leg of a distal surgical staple thereon. The distal staple driver further comprises a proximal support column that is configured to support a proximal leg of the distal surgical staple thereon. The distal staple driver also comprises another distal staple support member that comprises another distal support column that is configured to support another distal leg of another distal surgical staple thereon. The another distal staple support member further comprises another proximal support column that is configured to support another proximal leg of the another distal surgical staple thereon.

Example 33

The surgical staple cartridge of Example 32, wherein one of the distal support column and another distal support column is slidably supported in one of first and second cartridge wall portions in the cartridge body and wherein one of the proximal support column and another proximal support column is slidably supported in the other one of the first and second cartridge wall portions.

Example 34

The surgical staple cartridge of Examples 32 or 33, wherein the distal staple driver further comprises a first distal camming surface on the first distal staple support member and a second distal camming surface on the second distal staple support member.

Example 35

The surgical staple cartridge of Examples 30, 31, 32, 33 or 34, wherein at least one of the first intermediate staple drivers comprises a first staple support member that comprises a first distal support column that is configured to support a first distal leg of a corresponding first surgical staple thereon. The first staple support member further comprises a first proximal support column that is configured to support a first proximal leg of the corresponding first surgical staple thereon. The at least one of the first intermediate staple drivers further comprises a second staple support member that comprises a second distal support column that is configured to support a second distal leg of a corresponding second surgical staple thereon. The second staple support member further comprises a second proximal support column that is configured to support a second proximal leg of the corresponding second surgical staple thereon. The at least one of the first intermediate staple drivers also comprises a third staple support member that comprises a third distal support column that is configured to support a third distal leg of a corresponding third surgical staple thereon. The third staple support member further comprises a third proximal support column that is configured to support a third proximal leg of the corresponding third surgical staple thereon. The at least one of the first intermediate staple drivers further comprises a fourth staple support member that comprises a fourth distal support column that is configured to support a fourth distal leg of a corresponding fourth surgical staple thereon. The fourth staple support member further comprises a fourth proximal support column that is configured to support a fourth proximal leg of the corresponding fourth surgical staple thereon. A first crown of the corresponding first surgical staple and a second crown of the corresponding second surgical staple are parallel to each other. A third crown of the corresponding third surgical staple and a fourth crown of the fourth corresponding surgical staple are parallel to each other and transverse to the first and second crowns.

Example 36

The surgical staple cartridge of Example 35, wherein one of the first distal support column and the third proximal support column is slidably supported in one of first and second cartridge wall portions in the cartridge body and wherein the other one of the first distal support column and the third proximal support column is slidably supported in the other one of the first and second cartridge wall portions.

Example 37

The surgical staple cartridge of Examples 30, 31, 32, 33, 34, 35 or 36, wherein at least one of the second intermediate staple drivers comprises another first staple support member that comprises another first distal support column that is configured to support another first distal leg of a corresponding first other surgical staple thereon. The another first staple support member further comprises another first proximal support column that is configured to support another first proximal leg of the corresponding first other surgical staple thereon. The second intermediate staple driver further comprises another second staple support member that comprises another second distal support column that is configured to support another second distal leg of a corresponding second other surgical staple thereon. The another second staple support member further comprises another second proximal support column that is configured to support another second proximal leg of the corresponding second other surgical staple thereon. The second intermediate staple driver further comprises another third staple support member that comprises another third distal support column that is configured to support another third distal leg of a corresponding third other surgical staple thereon. The another third staple support member further comprises another third proximal support column that is configured to support another third proximal leg of the corresponding third other surgical staple thereon. The second intermediate staple driver further comprises another fourth staple support member that comprises another fourth distal support column that is configured to support another fourth distal leg of a corresponding fourth other surgical staple thereon. The another fourth staple support member further comprises another fourth proximal support column that is configured to support another fourth proximal leg of the corresponding fourth other surgical staple thereon. Another first crown of the first corresponding other surgical staple and another second crown of the second corresponding other surgical staple and another third crown of the third corresponding other surgical staple and another fourth crown of the fourth corresponding other surgical staple are parallel to each other. The second intermediate staple driver further comprises a fifth staple support member that comprises a fifth distal support column that is configured to support a fifth distal leg of a corresponding fifth other surgical staple thereon. The fifth staple support member further comprises a fifth proximal support column that is configured to support a fifth proximal leg of the corresponding fifth other surgical staple thereon. A fifth crown of the fifth corresponding other surgical staple is transverse to the another first crown, the another second crown, the another third crown and the another fourth crown.

Example 38

The surgical staple cartridge of Example 37, wherein the another first proximal support column and the another third proximal support column are each slidably supported in one of first and second cartridge wall portions of the cartridge body and wherein the another second proximal support column and the another fourth proximal support column are each slidably supported in the other one of the first and second cartridge wall portions.

Example 39

The surgical staple cartridge of Examples 37 or 38, further comprising a primary camming surface that is located adjacent to the another first proximal support column and the another third proximal support column and is located inboard relative thereto. A secondary camming surface is located adjacent to the another second proximal support column and the another fourth proximal support column and is located inboard relative thereto.

Example 40

A surgical instrument, comprising an axially movable sled that comprises first and second camming members. The surgical instrument further comprises a surgical staple cartridge and at least one distal staple driver that is movably supported in the surgical staple cartridge. Each distal staple driver is configured to operably support two distal surgical staples thereon and comprises a first distal camming surface that is aligned for camming contact with the first camming member. Each distal staple driver further comprises a second distal camming surface that is aligned for camming contact with the second camming member. At least one first intermediate staple driver is movably supported in the surgical staple cartridge and supports four surgical staples thereon. Each first intermediate staple driver comprises a first camming surface that is aligned for camming contact with the first camming member and a second camming surface that is aligned for camming contact with the second camming member. The surgical instrument further comprises at least one second intermediate staple driver that is slidably supported in the surgical staple cartridge adjacent at least one of the distal staple driver and a corresponding one of the first intermediate staple drivers. Each second intermediate staple driver is configured to operably support at least five other surgical staples thereon and comprises a first proximal camming surface that is aligned for camming contact with the first camming member. Each of the second intermediate staple drivers further comprises a second proximal camming surface that is aligned for camming contact with the second camming member.

Example 41

A surgical staple driver comprising a driver body that is configured to be slidably supported in a surgical staple cartridge. In at least one form, the driver body comprises at least two staple support members wherein each staple support member is configured to operably support a corresponding surgical staple thereon. The driver body further comprises a first camming surface and a second camming surface that is spaced from the first camming surface. The driver body further comprises at least one aperture that is configured to slidably receive therein a corresponding driver guide formed in the surgical staple cartridge.

Example 42

The surgical staple driver of Example 41, wherein each of the at least one apertures is located between the first and second camming surfaces.

Example 43

The surgical staple driver of Examples 41 or 42, wherein the driver body comprises a distal end and a proximal end and wherein at least one of the proximal end and the distal end is configured to slidably engage another one of the corresponding driver guides.

Example 44

The surgical staple driver of Examples 41, 42, or 43, wherein one of the at least two staple support members supports a corresponding surgical staple along a base axis and wherein another one of the staple support members supports another surgical staple along another base axis that is parallel with the base axis.

Example 45

The surgical staple driver of Example 44, wherein the another base axis is transverse to the base axis.

Example 46

The surgical staple driver of Examples 41, 42, 43, 44, or 45, wherein one of the staple support members comprises a proximal support column that is configured to support a proximal leg of a corresponding surgical staple thereon. The staple support member further comprises a distal support column that is configured to support a distal leg of the corresponding surgical staple thereon. Another one of the staple support members comprises another proximal support column that is configured to support another proximal leg of another corresponding surgical staple thereon. The another staple support member further comprises another distal support column that is configured to support another distal leg of the another corresponding surgical staple thereon. One of the proximal support column and the distal support column is slidably supported in a corresponding slot in a wall portion of the surgical staple cartridge. One of the another proximal support column and the another distal support column is slidably supported in another corresponding slot in another cartridge wall portion of the surgical staple cartridge.

Example 47

The surgical staple driver of Example 46, wherein the surgical staple cartridge defines a cartridge axis and wherein the corresponding slot and the another corresponding slot are each transverse to the cartridge axis.

Example 48

The surgical staple driver of Example 47, wherein the corresponding driver guide is centrally disposed between the cartridge wall portion and the another cartridge wall portion.

Example 49

A surgical staple cartridge, comprising a cartridge body that defines a cartridge axis and comprises a first cartridge wall and a second cartridge wall spaced from the first cartridge wall. The cartridge body further comprises at least two upstanding driver guides that are located between the first cartridge wall and the second cartridge wall. The surgical staple cartridge further comprises at least one surgical staple driver that comprises a driver body that comprises a proximal end that is configured to slidably engage one of the driver guides and a distal end that is configured to slidably engage another one of the driver guides. The driver body further comprises at least one staple support member that is configured to operably support a surgical staple thereon.

Example 50

The surgical staple cartridge of Example 49, wherein the at least one staple support member comprises a first staple support member that is configured to support a first surgical staple thereon and a second staple support member that is configured to support a second surgical staple thereon. A portion of the first staple support member is slidably supported in a corresponding slot in the first cartridge wall and another portion of the second staple support member is slidably supported in another corresponding slot in the second cartridge wall.

Example 51

The surgical staple cartridge of Example 50, wherein the corresponding slot and the another corresponding slot are each transverse to the cartridge axis.

Example 52

The surgical staple cartridge of Examples 49, 50 or 51, wherein the first surgical staple comprises a first crown supported on a first base axis and wherein the second surgical staple comprises a second crown on a second base axis that is parallel with the first base axis.

Example 53

The surgical staple cartridge of Example 52, wherein the second base axis is transverse to the first base axis.

Example 54

The surgical staple cartridge of Examples 49, 50, 51 or 52 wherein each surgical staple driver further comprises at least one aperture therein that is configured to slidably receive a corresponding additional driver guide therein.

Example 55

A surgical instrument, comprising an axially movable sled that comprises a first camming member that is configured to move along a first cam axis and a second camming member that configured to move along a second cam axis. The surgical instrument further comprises a surgical staple cartridge that comprises a cartridge body that comprises a first cartridge wall and a second cartridge wall that is spaced from the first cartridge wall. The cartridge body further comprises at least two upstanding staple guides that are located between the first cartridge wall and the second cartridge wall. The surgical instrument further comprises at least one surgical staple driver that comprises a driver body that comprises a proximal end that is configured to slidably engage one of the driver guides and a distal end that is configured to slidably engage another one of the driver guides. The surgical staple driver further comprises at least one staple support members that is configured to operably support a surgical staple thereon.

Example 56

The surgical instrument of Examples 55, wherein the driver body further comprises a first camming surface that is oriented on one side of each of the driver guides and is in axial alignment with the first cam axis and a second camming surface that is oriented on another side of each of the driver guides and is in axial alignment with the second cam axis.

Example 57

The surgical instrument of Example 55, wherein the driver body further comprises at least one aperture therein that is located between the first and second camming surfaces and is configured to slidably receive a corresponding additional driver guide therein.

Example 58

The surgical instrument of Examples 55, 56 or 57, wherein the at least one staple support member comprises a first staple support member that is configured to support a first surgical staple thereon and a second staple support member that is configured to support a second surgical staple thereon. A portion of the first staple support member is slidably supported in the first cartridge wall and another portion of the second staple support member is slidably supported in the second cartridge wall.

Example 59

The surgical instrument of Examples 55, 56, 57 or 58, wherein the surgical staple cartridge defines a cartridge axis and wherein the corresponding slot and the another corresponding slot are each transverse to the cartridge axis.

Example 60

The surgical instrument of Example 54, 55, 56, 57, 58 or 59, wherein the at least one staple support member comprises a first staple support member that is configured to support a first surgical staple thereon and a second staple support member that is configured to support a second surgical staple thereon. A portion of the first staple support member is slidably supported in the first cartridge wall and another portion of the second staple support member is slidably supported in the second cartridge wall.

Example 61

A surgical staple driver that is configured for use with a surgical staple cartridge that operably interfaces with a surgical instrument camming member that is axially movable along a first cam axis. In at least one form, the surgical staple driver comprises a driver body that is slidably supportable within the surgical staple cartridge. A camming surface is provided on the driver body and is oriented for camming engagement with the camming member of the surgical instrument along the first cam axis when the driver body is slidably supported in the surgical staple cartridge. A staple support portion is configured to operably support at least one surgical staple thereon relative to the camming surface such that when the camming member engages the camming surface, the camming member passes transversely under a portion of a staple crown of at least one of the at least one surgical staples that is supported on the staple support portion.

Example 62

The surgical staple driver of Example 61, wherein each of the at least one surgical staples that is supported on the staple supporting portion comprises a proximal leg that protrudes from the staple crown and a distal leg that protrudes from the staple crown. The staple support portion also supports the at least one surgical staple thereon relative to the camming surface such that when the camming member engages the camming surface, the camming member is not in axial alignment with the proximal and distal legs of any of the surgical staples supported on the staple support portion.

Example 63

The surgical staple driver of Examples 61 or 62, wherein the staple support portion comprises a first staple support portion that is configured to operably support a first surgical staple thereon. The first surgical staple comprises a first staple crown. A first distal leg protrudes from an end of the first staple crown and a first proximal leg protrudes from another end of the first staple crown. The first staple support portion operably supports the first staple crown along a first base axis that is transverse to the first cam axis and comprises a first proximal support column that is configured to support the first proximal leg of the first surgical staple thereon. The first staple support portion further comprises a first distal support column that is configured to support the first distal leg of the first surgical staple thereon. The camming surface is oriented relative to the first proximal support column and the first distal support column such that when the camming member engages the camming surface, the camming member passes between the first proximal support column and the first distal support column.

Example 64

The surgical staple driver of Example 63, wherein the staple support portion further comprises a second staple support portion that is configured to operably support a second surgical staple thereon. The second surgical staple comprises a second staple crown. A second distal leg protrudes from an end of the second staple crown and a second proximal leg protrudes from another end of the second staple crown. The second staple support portion comprises a second proximal support column that is configured to support the second proximal leg thereon. The second staple support portion further comprises a second distal support column that is configured to support the second distal leg thereon.

Example 65

The surgical staple driver of Example 64, wherein the second staple support portion operably supports the second staple crown along a second base axis that is transverse to the first base axis.

Example 66

The surgical staple driver of Example 64, wherein the staple support portion operably supports the second staple crown along a second base axis that is parallel to the first base axis.

Example 67

The surgical staple driver of Examples 60, 61, 62, 63, 64, 65 or 66, wherein the surgical instrument comprises a second axially movable camming member and wherein said staple support portion further comprises a second camming surface oriented for camming engagement with the second axially moving camming member.

Example 68

The surgical staple driver of Examples 60, 61, 62, 63, 64, 65 or 66, wherein the surgical instrument comprises a second axially movable camming member and wherein the staple support portion further comprises a second camming surface that is oriented for camming engagement with the second axially moving camming member.

Example 69

The surgical staple driver of Example 68, wherein the second camming surface is oriented relative to the second staple support portion such that when the second camming member engages the second camming surface, the second camming member passes between the second proximal support column and the second distal support column.

Example 70

The surgical staple driver of Examples 63, 64, 65, 66, 67, 68 or 69, wherein the driver body is slidably supported between a first cartridge wall portion and a second cartridge wall portion and wherein one of the first proximal support column and the first distal support column is slidably received in a corresponding wall slot in one of the first and second cartridge wall portions.

Example 71

The surgical staple driver of Example 70, wherein the surgical staple cartridge further comprises at least one driver guide and wherein one of the first proximal support column and the first distal support column is slidably supported in the corresponding wall slot and the other of the first proximal support column and the first distal support column is slidably supported in a corresponding guide slot in the at least one driver guide.

Example 72

The surgical staple driver of Example 71, wherein the surgical staple cartridge has a cartridge height and wherein the wall slot extends for the cartridge height and wherein the at least one driver guide has a guide height and wherein the corresponding guide slot has a slot length that equals the guide height.

Example 73

The surgical staple driver of Example 72, wherein the cartridge height and the guide height are equal.

Example 74

The surgical staple driver of Examples 64, 65, 66, 67, 68, 69, 70, 71, 72 or 73, wherein the staple support portion further comprises a third staple support portion that is configured to operably support a third surgical staple thereon. The third surgical staple comprises a third staple crown. A third proximal leg protrudes from an end of the third staple crown. A third proximal leg protrudes from another end of the third staple crown. The third staple support portion comprises a third proximal support column that is configured to support a third proximal leg thereon. The third staple support portion further comprises a third distal support column that is configured to support the third distal leg thereon.

Example 75

The surgical staple driver of Example 74, wherein the third staple support portion further comprises a second camming surface that is oriented relative to the third proximal support column and the third distal support column such that when a corresponding portion of the camming member engages the second camming surface, the corresponding portion of the camming member passes between the third proximal support column and the third distal support column.

Example 76

The surgical staple driver of Examples 74 or 75, wherein the third staple support portion operably supports the third staple crown along a third base axis that is parallel with the first base axis.

Example 77

The surgical staple driver of Examples 74, 75 or 76, wherein the staple support portion further comprises a fourth staple support portion that is configured to operably support a fourth surgical staple thereon. The fourth surgical staple comprises a fourth staple crown. A fourth distal leg protrudes from an end of the fourth staple crown. A fourth proximal leg protrudes from another end of the fourth staple crown. The fourth staple support portion comprises a fourth proximal support column that is configured to support the fourth proximal leg thereon. The fourth staple support portion further comprises a fourth distal support column that is configured to support the fourth distal leg thereon.

Example 78

The surgical staple driver of Example 77, wherein the fourth staple support portion further comprises a second camming surface that is oriented relative to the fourth proximal support column and the fourth distal support column such that when a corresponding portion of the camming member engages the second camming surface, the corresponding portion of the camming member passes between the fourth proximal support column and the fourth distal support column.

Example 79

The surgical staple driver of Examples 77 or 78, wherein the staple support portion further comprises a fifth staple support portion that is configured to operably support a fifth surgical staple thereon. The fifth surgical staple comprises a fifth staple crown. A fifth distal leg protrudes from an end of the fifth staple crown. A fifth proximal leg protrudes from another end of the fifth staple crown. The fifth staple support portion comprises a fifth proximal support column that is configured to support the fifth proximal leg thereon. The fifth staple support portion further comprises a fifth distal support column that is configured to support the fifth distal leg thereon.

Example 80

The surgical staple driver of Example 79, wherein the fifth staple support portion further comprises a second camming surface that is oriented relative to the fifth proximal support column and the fifth distal support column such that when a corresponding portion of the camming member engages the second camming surface, the corresponding portion of the camming member passes between the fifth proximal support column and the fifth distal support column.

Example 81

A surgical staple driver comprising a driver body that is configured to be slidably supported in a surgical staple cartridge. A staple support portion is configured to operably support a surgical staple thereon. The surgical staple comprises a staple crown. A proximal leg protrudes from an end of the staple crown and a distal leg protrudes from another end of the staple crown. The staple support portion comprises a proximal support column that is configured to support the proximal leg thereon. The staple support portion further comprises a distal support column that is configured to support the distal leg thereon. The driver body further comprises at least one camming surface that extends along a cam axis that extends transversely between the proximal and distal support columns.

Example 82

A surgical staple cartridge, comprising a cartridge body that comprises a first cartridge wall portion and a second cartridge wall portion. The surgical staple cartridge further comprises at least one staple driver that is slidably supported between the first cartridge wall portion and the second cartridge wall portion. The at least one staple driver comprises a driver body that is configured to operably support at least one surgical staple thereon. The surgical staple comprises a staple crown. A proximal leg protrudes from one end of the staple crown. A distal leg protrudes from another end of the staple crown. The driver body comprises a proximal support column that is configured to support the proximal leg thereon. The driver body further comprises a distal support column that is configured to support the distal leg thereon. At least one of the proximal and distal support columns is slidably supported in one of the first and second cartridge wall portions. The driver body further comprises at least one camming surface that extends along a cam axis that extends transversely between the proximal and distal support columns.

Example 83

A surgical staple driver array for operable use in a surgical staple cartridge. In at least one form, the surgical staple driver array comprises a plurality of first staple drivers that are each configured to be slidably supported in the surgical staple cartridge. Each first staple driver is further configured to operably support at least two first surgical staples thereon that are parallel to each other. The surgical staple driver array further comprises at least one second staple driver that is configured to be slidably supported in the surgical staple cartridge. Each second staple driver support is configured to support a single, second surgical staple thereon. The second surgical staple extends in a second direction that is transverse to each of the first surgical staples supported on the at least one adjacent corresponding first staple driver. The first and second staple drivers are oriented in a line in the surgical staple cartridge such that one of the first staple drivers is located on each axial side of each second staple driver.

Example 84

The surgical staple driver array of Examples 83, wherein each of the first surgical staples comprises a first crown and wherein the first crown of one of the first surgical staples that is supported on one of the first staple drivers is aligned on a first base axis and wherein another crown of another of the first surgical staples that is supported on the first staple driver is aligned on a second base axis that is parallel to the first base axis. Each of the second staples comprises a second crown that is aligned on a third base axis that is transverse to the first and second base axes.

Example 85

The surgical staple driver array of Examples 83 or 84, wherein one of the plurality of first staple drivers comprises a distal most first staple driver in the staple driver array and another one of the first staple drivers comprises a proximal most first staple driver in the staple driver array.

Example 86

The surgical staple driver array of Examples 83, 84 or 85, wherein each of the first staple drivers comprises a first camming surface and a second camming surface that is spaced from the first camming surface.

Example 87

The surgical staple driver array of Example 86, wherein each second staple driver comprises a primary camming surface and a secondary camming surface that is spaced from the primary camming surface. The first camming surface and the primary camming surface are aligned on a first camming axis and the second camming surface and the secondary camming surface are aligned on a second camming axis.

Example 88

The surgical staple driver array of Example 87, wherein the first and second camming axes are transverse to the first and second base axes.

Example 89

The surgical staple driver array of Example 83, wherein the third base axis is transverse to the first and second camming axes.

Example 90

The surgical staple driver array of Examples 83, 84, 85, 86, 87, 88 or 89, wherein a portion of each first staple driver is configured to be slidably supported in a first wall portion of the surgical staple cartridge and wherein another portion of each first staple driver is configured to be slidably supported in a second wall portion of the surgical staple cartridge.

Example 91

A surgical staple cartridge, comprising a cartridge body that comprises a proximal and a distal end. A plurality of first staple drivers is movably supported in the cartridge body. Each first staple driver is configured to support two, first surgical staples that are oriented in corresponding first directions. At least one second staple driver is slidably supported in the surgical staple cartridge adjacent to two corresponding first staple drivers. Each second staple driver supports a single, second surgical staple thereon. The second surgical staple extends in a second direction that is transverse to each of the corresponding first directions. The first and second staple drivers are oriented in a line in the cartridge body such that one first staple driver is located on each axial side of each second staple driver.

Example 92

The surgical staple cartridge of Example 91, wherein one of the first surgical staples that is supported on one of the first staple drivers comprises a first crown that is aligned on a first base axis. Another one of the first surgical staples that is supported on the first staple driver comprises another first crown that is aligned on another first base axis. The another first base axis is parallel with the first base axis. Each second staple comprises a second crown that is aligned on a second base axis that is transverse to the first base axis and the another first base axis.

Example 93

The surgical staple cartridge of Examples 91 or 92, wherein the first staple driver comprises a first staple support member that comprises a first distal support column that is configured to support a first distal leg of a corresponding first surgical staple thereon. The first staple support member further comprises a first proximal support column that is configured to support a first proximal leg of the corresponding first surgical staple thereon. The first staple driver further comprises another first staple support member that comprises another first distal support column that is configured to support another first distal leg of another corresponding first surgical staple thereon. The another first staple support member further comprises another first proximal support column that is configured to support another first proximal leg of the another corresponding first surgical staple thereon.

Example 94

The surgical staple cartridge of Example 93, wherein each first staple support member further comprises a first camming surface that is aligned on a first cam axis that extends transversely between the first distal and first proximal support columns. Each first staple support member further comprises a second camming surface that is aligned on a second cam axis that extends transversely between the another first distal and the another first proximal support columns.

Example 95

The surgical staple cartridge of Examples 93 or 94, wherein at least one second staple driver comprises a second staple support member that comprises a second distal support column that is configured to support a second distal leg of a corresponding second surgical staple thereon. The second staple support member further comprises a second proximal support column that is configured to support a second proximal leg of the corresponding second surgical staple thereon.

Example 96

The surgical staple cartridge of Example 95, wherein each second staple support member further comprises a primary first camming surface that is adjacent to the second proximal support column and is aligned on the first cam axis. The second staple support member further comprises a secondary camming surface that is adjacent to the second distal support column and is aligned on the second cam axis.

Example 97

The surgical staple cartridge of Examples 93, 94, 95 or 96, wherein the first distal support column is slidably supported in a corresponding first slot in a first wall portion of the cartridge body and wherein the another first proximal support column is slidably supported in a corresponding second slot in a second wall portion of the cartridge body.

Example 98

The surgical staple cartridge of Examples 93, 94, 95, 96 or 97, wherein each first staple driver further comprises a first camming surface that is aligned on a first cam axis that extends transversely between the first distal and first proximal support columns. Each first staple driver further comprises a second camming surface that is aligned on a second cam axis that extends transversely between the another first distal support column and the another first proximal support column.

Example 99

The surgical staple cartridge of Example 97, wherein the cartridge body defines a cartridge axis and wherein the first slot lies along a first slot axis that is transverse to the cartridge axis and wherein the second slot lies along a second axis that is transverse to the cartridge axis.

Example 100

The surgical staple cartridge of Example 98, wherein each second staple driver further comprises a primary camming surface aligned on the first cam axis and a secondary camming surface aligned on the second cam axis.

Example 101

A surgical instrument, comprising an axially movable sled that comprises first and second camming members. The surgical instrument further comprises a surgical staple cartridge and a plurality of first staple drivers that is movably supported in the surgical staple cartridge. Each first staple driver is configured to support two, first surgical staples that are oriented in corresponding first directions. Each first staple driver comprises a first camming surface that is aligned for camming contact with the first camming member and a second camming surface that is aligned for camming contact with the second camming member. The surgical instrument further comprises a plurality of second staple drivers that is slidably supported in the surgical staple cartridge adjacent to at least one corresponding first staple driver. Each second staple driver supports a single, second surgical staple thereon. The second surgical staple extends in a second direction that is transverse to each of the corresponding first directions. Each second staple driver comprises a primary camming surface that is aligned for camming contact with the first camming member and a secondary camming surface that is aligned for camming contact with the second camming member.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical staple driver array for operable use with a surgical staple cartridge comprising an axially movable sled, wherein the axially movable sled comprises first and second camming members, and wherein said surgical staple driver array comprises:
   a distal staple driver slidably supportable in the surgical staple cartridge and configured to operably support a single distal surgical staple thereon that is oriented in a distal direction;
   a plurality of intermediate staple drivers configured to be slidably supported in the surgical staple cartridge in series, wherein a distal most one of said intermediate staple drivers is adjacent to said distal staple driver, each of said intermediate staple drivers being configured to operably support a first surgical staple oriented in a first direction, a second surgical staple oriented in a second direction and a third surgical staple oriented in a third direction, wherein the first direction and the third direction are parallel to each other, wherein the second direction is transverse to the first direction and the third direction, wherein each said intermediate staple driver comprises a first camming surface extending transversely under a portion of the first surgical staple and being aligned for camming contact with said first camming member and a second camming surface extending transversely under a portion of the third surgical staple and being aligned for camming contact with the second camming member, and wherein each of said intermediate staple drivers is configured to hookingly engage corresponding portions of the surgical staple cartridge to slidably interlock each said intermediate staple driver to the surgical staple cartridge for slidable operable travel relative thereto in a direction that is transverse to an axis of the surgical staple cartridge; and
   a proximal staple driver slidably supported adjacent a proximal most one of said intermediate staple drivers, said proximal staple driver configured to operably support a proximal surgical staple oriented in a proximal direction.

2. The surgical staple driver array of claim 1, wherein said distal direction is parallel to at least one of said first, second and third directions.

3. The surgical staple driver array of claim 1, wherein said proximal direction is parallel to at least one of said first, second and third directions.

4. The surgical staple driver array of claim 1, wherein said distal direction, said first direction, said third direction and said proximal direction are parallel.

5. The surgical staple driver array of claim 1, wherein a distal crown of the distal surgical staple is supported along a distal base axis and a first crown of the first surgical staple is supported along a first base axis that is parallel to said distal base axis.

6. The surgical staple driver array of claim 5, wherein a second staple crown of the second surgical staple is supported along a second base axis that is transverse to said first base axis.

7. The surgical staple driver array of claim 6, wherein a third staple crown of the third surgical staple is supported along a third base axis that is parallel to said first base axis.

8. The surgical staple driver array of claim 7, wherein a proximal staple crown of the proximal surgical staple is supported along a proximal base axis that is parallel to said third base axis of the third surgical staple supported in said proximal most one of said intermediate staple drivers.

9. A surgical staple cartridge, comprising:
   an axially movable sled comprising first and second camming members;
   a cartridge body comprising a proximal end and a distal end;
   a distal staple driver movably supported in said cartridge body and configured to support a distal surgical staple thereon in a distal direction;
   a plurality of intermediate staple drivers movably supported in said cartridge body in series, wherein a distal most one of said intermediate staple drivers is adjacent to said distal staple driver, each said intermediate staple driver supporting a first surgical staple in a first direction, a second surgical staple in a second direction and a third surgical staple in a third direction, wherein the first direction and the third direction are parallel to each other, and wherein the second direction is transverse to the first direction and the third direction, wherein each said intermediate staple driver comprises a first camming surface extending transversely under a portion of the first surgical staple and being aligned for camming contact with said first camming member and a second camming surface extending transversely under a portion of the third surgical staple and being aligned for camming contact with the second camming member, and wherein each of said intermediate staple drivers is configured to hookingly engage corresponding portions of the surgical staple cartridge to slidably interlock each said intermediate staple driver to the surgical staple cartridge for slidable operable travel relative thereto in a direction that is transverse to an axis of the surgical staple cartridge; and
a proximal staple driver slidably supported adjacent a proximal most one of said intermediate staple drivers, said proximal staple driver configured to operably support a proximal surgical staple oriented in a proximal direction.

10. The surgical staple cartridge of claim 9, wherein:
a distal crown of the distal surgical staple is supported along a distal base axis and a first crown of the first surgical staple is supported along a first base axis that is parallel to said distal base axis;
a second staple crown of the second surgical staple is supported along a second base axis that is transverse to said first base axis;
a third staple crown of the third surgical staple is supported along a third base axis that is parallel to said first base axis; and
a proximal staple crown of the proximal surgical staple is supported along a proximal base axis that is parallel to said third base axis of the third surgical staple supported in said proximal most intermediate staple driver.

11. The surgical staple cartridge of claim 9, wherein said distal staple driver comprises a distal staple support member comprising:
a distal support column configured to support a distal leg of the distal surgical staple thereon; and
a proximal support column configured to support a proximal leg of the distal surgical staple thereon and wherein one of said distal and proximal support columns is slidably supported in one of a first wall portion and a second wall portion of said cartridge body.

12. The surgical staple cartridge of claim 11, wherein said distal staple driver further comprises a distal camming surface aligned on a first cam axis that extends transversely between said distal and proximal support columns.

13. The surgical staple cartridge of claim 12, wherein at least one of said intermediate staple drivers comprises:
a first staple support member comprising:
a first distal support column configured to support a first distal leg of a corresponding first surgical staple thereon; and
a first proximal support column configured to support a first proximal leg of the corresponding first surgical staple thereon and wherein said at least one of said intermediate staple drivers further comprises:
a second staple support member comprising:
a second distal support column configured to support a second distal leg of a corresponding second surgical staple thereon; and
a second proximal support column configured to support a second proximal leg of the corresponding second surgical staple thereon and wherein said at least one of said intermediate staple drivers further comprises:
a third staple support member comprising:
a third distal support column configured to support a third distal leg of a corresponding third surgical staple thereon; and
a third proximal support column configured to support a third proximal leg of the corresponding third surgical staple thereon and wherein one of said third distal support column and said third proximal support column is slidably supported in one of said first and second wall portions of said cartridge body.

14. The surgical staple cartridge of claim 13, wherein said proximal staple driver comprises:
a proximal staple support member comprising:
another distal support column configured to support another distal leg of the proximal surgical staple thereon; and
another proximal support column configured to support another proximal leg of the proximal surgical staple thereon and wherein one of said another distal and another proximal support columns is slidably supported in one of said first wall portion and said second wall portion of said cartridge body.

15. The surgical staple cartridge of claim 14, further comprising:
at least one distal camming surface on said distal staple support member;
at least one first camming surface on at least one of said first, second and third staple support members; and
at least one proximal camming surface on said proximal staple support member.

16. The surgical staple cartridge of claim 15, wherein said at least one distal camming surface, said at least one first camming surface and said at least one proximal camming surface are aligned on a common camming axis.

17. The surgical staple cartridge of claim 16, wherein said at least one distal camming surface comprises:
a first distal camming surface; and
a second distal camming surface spaced from said first distal camming surface and wherein said at least one first camming surface comprises:
a first camming surface; and
a second camming surface spaced from said first camming surface and wherein said at least one proximal camming surface comprises:
a first proximal camming surface and a second proximal camming surface.

18. The surgical staple cartridge of claim 17, wherein said first distal camming surface, said first camming surface and said first proximal camming surface are aligned on a first camming axis and wherein said second distal camming surface, said second camming surface and said second proximal camming surface are aligned on a second camming axis.

19. The surgical staple cartridge of claim 18, wherein said first camming surface is on said first staple support member and said second camming surface is on said third staple support member.

20. A surgical instrument, comprising:
an axially movable sled comprising first and second camming members;
a surgical staple cartridge;
a distal staple driver movably supported in said surgical staple cartridge, said distal staple driver configured to operably support a corresponding distal surgical staple thereon and comprising a first distal camming surface aligned for camming contact with said first camming member and a second distal camming surface aligned for camming contact with said second camming member;

a plurality of intermediate staple drivers movably supported in said surgical staple cartridge in series, wherein a distal most one of said intermediate staple drivers is adjacent to said distal staple driver, each said intermediate staple driver supporting a corresponding first surgical staple, a corresponding second surgical staple, and a corresponding third surgical staple on staple cradles defined in each intermediate staple driver, each said intermediate staple driver comprising a first camming surface extending transversely under a portion of the first surgical staple and being aligned for camming contact with said first camming member and a second camming surface extending transversely under a portion of the third surgical staple and being aligned for camming contact with the second camming member, and wherein said first surgical staple is oriented parallel to said third surgical staple, and wherein said second surgical staple is oriented transverse to said first surgical staple and said second surgical staple; and a proximal staple driver slidably supported adjacent a proximal most one of said intermediate staple drivers, said proximal staple driver configured to operably support a corresponding proximal surgical staple thereon and comprising a first proximal camming surface aligned for camming contact with said first camming member and a second proximal camming surface aligned for camming contact with said second camming member.

* * * * *